US012404533B2

(12) United States Patent
Jewett et al.

(10) Patent No.: US 12,404,533 B2
(45) Date of Patent: *Sep. 2, 2025

(54) BIOCONJUGATE VACCINES' SYNTHESIS IN PROKARYOTIC CELL LYSATES

(71) Applicants: Northwestern University, Evanston, IL (US); Cornell University, Ithaca, NY (US)

(72) Inventors: Michael Christopher Jewett, Evanston, IL (US); Jessica Carol Stark, Evanston, IL (US); Matthew P. DeLisa, Ithaca, NY (US); Thapakorn Jaroentomeechai, Ithaca, NY (US)

(73) Assignees: Northwestern University, Evanston, IL (US); Cornell University, Ithaca, NY (US)

( * ) Notice: Subject to any disclaimer, the term of this patent is extended or adjusted under 35 U.S.C. 154(b) by 1065 days.

This patent is subject to a terminal disclaimer.

(21) Appl. No.: 17/310,022

(22) PCT Filed: Jan. 10, 2020

(86) PCT No.: PCT/US2020/013207
§ 371 (c)(1),
(2) Date: Jul. 12, 2021

(87) PCT Pub. No.: WO2020/146814
PCT Pub. Date: Jul. 16, 2020

(65) Prior Publication Data
US 2022/0267821 A1 Aug. 25, 2022

Related U.S. Application Data

(60) Provisional application No. 62/791,425, filed on Jan. 11, 2019.

(51) Int. Cl.
| C12P 21/00 | (2006.01) |
| A61K 39/00 | (2006.01) |
| A61K 39/39 | (2006.01) |

(52) U.S. Cl.
CPC ............ *C12P 21/005* (2013.01); *A61K 39/00* (2013.01); *A61K 39/39* (2013.01)

(58) Field of Classification Search
None
See application file for complete search history.

(56) References Cited

U.S. PATENT DOCUMENTS

| 4,496,538 A | 1/1985 | Gordon |
| 4,727,136 A | 2/1988 | Jennings et al. |
| 5,478,730 A | 12/1995 | Alakhov et al. |
| 5,556,769 A | 9/1996 | Wu et al. |
| 5,623,057 A | 4/1997 | Marburg et al. |
| 5,665,563 A | 9/1997 | Beckler |
| 5,679,352 A | 10/1997 | Chong et al. |
| 6,168,931 B1 | 1/2001 | Swartz et al. |
| 6,248,334 B1 | 6/2001 | Lees et al. |
| 6,531,131 B1 | 3/2003 | Gu et al. |
| 6,869,774 B2 | 3/2005 | Endo |
| 6,994,986 B2 | 2/2006 | Swartz et al. |
| 7,118,883 B2 | 10/2006 | Inoue et al. |
| 7,189,528 B2 | 3/2007 | Higashide et al. |
| 7,338,789 B2 | 3/2008 | Swartz et al. |
| 7,387,884 B2 | 6/2008 | Suzuki et al. |
| 7,399,610 B2 | 7/2008 | Shikata et al. |
| 8,637,025 B2 * | 1/2014 | Robins-Browne ..... A61K 35/20 424/150.1 |
| 8,703,471 B2 | 4/2014 | Herrema et al. |
| 8,999,668 B2 | 4/2015 | DeLisa et al. |
| 2004/0209321 A1 | 10/2004 | Swartz et al. |
| 2005/0054044 A1 | 3/2005 | Swartz et al. |
| 2005/0170452 A1 | 8/2005 | Wildt et al. |
| 2006/0211085 A1 | 9/2006 | Bobrowicz |
| 2006/0234345 A1 | 10/2006 | Schwartz et al. |
| 2006/0252672 A1 | 11/2006 | Betenbaugh et al. |
| 2006/0257399 A1 | 11/2006 | Gerngross et al. |
| 2006/0286637 A1 | 12/2006 | Hamilton |
| 2007/0026485 A1 | 2/2007 | DeFrees et al. |

(Continued)

FOREIGN PATENT DOCUMENTS

| CN | 1767853 A | 5/2006 |
| CN | 101048175 A | 10/2007 |

(Continued)

OTHER PUBLICATIONS

Pichichero et al. Human Vaccines and Immunotherapeutics 9:12, 2505-2523, 2013.*
Smith et al. Biotechniques 56:186-193, Apr. 2014.*
Abu-Qarn, M., J. Eichler, and N. Sharon, Not just for Eukarya anymore: protein glycosylation in Bacteria and Archaea. Curr Opin Struct Biol, 2008. 18(5): p. 544-50.

(Continued)

*Primary Examiner* — Oluwatosin A Ogunbiyi
(74) *Attorney, Agent, or Firm* — Quarles & Brady LLP

(57) ABSTRACT

Disclosed are methods, systems, components, and compositions for cell-free synthesis of glycosylated proteins, which may be utilized in vaccines, including anti-bacterial vaccines. The glycosylated proteins may include a bacterial polysaccharide conjugated to a carrier, which may be utilized to generate an immune response in an immunized host against the polysaccharide conjugated to the carrier. Suitable carriers may include but are not limited to *Haemophilus influenzae* protein D (PD), *Neisseria meningitidis* porin protein (PorA), *Corynebacterium diphtheriae* toxin (CRM 197), *Clostridium tetani* toxin (TT), and *Escherichia coli* maltose binding protein, and variants thereof.

23 Claims, 37 Drawing Sheets
Specification includes a Sequence Listing.

(56) References Cited

U.S. PATENT DOCUMENTS

| | | |
|---|---|---|
| 2007/0154983 A1 | 7/2007 | Calhoun et al. |
| 2007/0178551 A1 | 8/2007 | Gerngross |
| 2008/0138857 A1 | 6/2008 | Swartz et al. |
| 2011/0274720 A1 | 11/2011 | Wacker et al. |
| 2012/0171720 A1 | 7/2012 | Church et al. |
| 2014/0045267 A1 | 2/2014 | Lajoie et al. |
| 2014/0255987 A1 | 9/2014 | Delisa |
| 2014/0295492 A1 | 10/2014 | Jewett et al. |
| 2015/0259757 A1 | 9/2015 | Jewett et al. |
| 2018/0016612 A1 | 1/2018 | Jewett |

FOREIGN PATENT DOCUMENTS

| | | | |
|---|---|---|---|
| CN | 104902931 A | 9/2015 | |
| EP | 1481057 A1 * | 12/2004 | ............ A61K 39/02 |
| JP | 2002540075 A | 11/2002 | |
| WO | 2003/056914 A1 | 7/2003 | |
| WO | 2004/013151 A1 | 2/2004 | |
| WO | 2004/035605 A2 | 4/2004 | |
| WO | 2006/102652 A2 | 9/2006 | |
| WO | 2006/119987 A2 | 11/2006 | |
| WO | 2007/120932 A2 | 10/2007 | |
| WO | 2017117539 A1 | 7/2017 | |

OTHER PUBLICATIONS

Adiga, R., Al-adhami, M., Andar, A., Borhani, S., Brown, S., Burgenson, D., Cooper, M.A., Deldari, S., Frey, D.D., Ge, X., et al. (2018). Point-of-care production of therapeutic proteins of good-manufacturing-practice quality. Nat Biomed Eng.

Albrecht, S., et al., Glycosylation as a marker for inflammatory arthritis. Cancer Biomark, 2014. 14(1): p. 17-28.

Anderson, P., Antibody responses to Haemophilus influenzae type b and diphtheria toxin induced by conjugates of oligosaccharides of the type b capsule with the nontoxic protein CRM197. Infect Immun, 1983. 39(1): p. 233-8.

Ashok, A., Brison, M., and LeTallec, Y. (2017). Improving cold chain systems: Challenges and solutions. Vaccine 35, 2217-2223.

Axford, J.S., Glycosylation and rheumatic disease. Biochim Biophys Acta, 1999. 1455(2-3): p. 219-29.

Bacon, D.J., et al., A phase-variable capsule is involved in virulence of Campylobacter jejuni 81-176. Mol Microbiol, 2001. 40(3): p. 769-77.

Baudoin, L. and T. Issad, O-GlcNAcylation and Inflammation: A Vast Territory to Explore. Front Endocrinol (Lausanne), 2014. 5: p. 235.

Bayburt, T.H., and Sligar, S.G. (2010). Membrane protein assembly into Nanodiscs. FEBS Lett 584, 1721-1727.

Bernhard, F. and Y. Tozawa, Cell-free expression—making a mark. Curr Opin Struct Biol, 2013. 23(3): p. 374-80.

Bhushan, R., Anthony, B.F., and Frasch, C.E. (1998). Estimation of group B streptococcus type III polysaccharide-specific antibody concentrations in human sera is antigen dependent. Infect Immun 66, 5848-5853.

Bogaert, D., Hermans, P.W., Adrian, P.V., Rumke, H.C., and de Groot, R. (2004). Pneumococcal vaccines: an update on current strategies. Vaccine 22, 2209-2220.

Boles, K.S., Kannan, K., Gill, J., Felderman, M., Gouvis, H., Hubby, B., Kamrud, K.I., Venter, J.C., and Gibson, D.G. (2017). Digital-to-biological converter for on-demand production of biologics. Nat Biotechnol 35, 672-675.

Brito, L.A., and Singh, M. (2011). Acceptable levels of endotoxin in vaccine formulations during preclinical research. J Pharm Sci 100, 34-37.

Brodel, A.K., D.A. Wustenhagen, and S. Kubick, Cell-free protein synthesis systems derived from cultured Mammalian cells. Methods Mol Biol, 2015. 1261: p. 129-40.

Bundy, B.C., M.J. Franciszkowicz, and J.R. Swartz, *Escherichia coli*-based cell-free synthesis of virus-like particles. Biotechnol Bioeng, 2008. 100(1): p. 28-37.

Calhoun, K.A. and J.R. Swartz, An economical method for cell-free protein synthesis using glucose and nucleoside monophosphates. Biotechnol Prog, 2005. 21(4): p. 1146-53.

Calhoun, K.A. and J.R. Swartz, Energizing cell-free protein synthesis with glucose metabolism. Biotechnol Bioeng, 2005. 90(5): p. 606-13.

Carlson, E.D., et al., Cell-free protein synthesis: applications come of age. Biotechnol Adv, 2012. 30(5): p. 1185-94.

Caschera, F. and V. Noireaux, Synthesis of 2.3 mg/ml of protein with an all *Escherichia coli* cell-free transcription-translation system. Biochimie, 2014. 99: p. 162-8.

Casella, C.R., and Mitchell, T.C. (2008). Putting endotoxin to work for us: monophosphoryl lipid A as a safe and effective vaccine adjuvant. Cell Mol Life Sci 65, 3231-3240.

CDC (2019). CDC Vaccine Price List.

Celik, E., Ollis, A.A., Lasanajak, Y., Fisher, A.C., Gur, G., Smith, D.F., and DeLisa, M.P. (2015). Glycoarrays with engineered phages displaying structurally diverse oligosaccharides enable high-throughput detection of glycan-protein interactions. Biotechnol J 10, 199-209.

Chambers, D.A. and G. Zubay, The stimulatory effect of cyclic adenosine 3'5'-monophosphate on DNA-directed synthesis of beta-galactosidase in a cell-free system. Proc Natl Acad Sci U S A, 1969. 63(1): p. 118-22.

Chauhan, J.S., A. Rao, and G.P. Raghava, In silico platform for prediction of N-, O- and C-glycosites in eukaryotic protein sequences. PLoS One, 2013. 8(6): p. e67008.

Chen, D.J., Osterrieder, N., Metzger, S.M., Buckles, E., Doody, A.M., DeLisa, M.P., and Putnam, D. (2010). Delivery of foreign antigens by engineered outer membrane vesicle vaccines. Proc Natl Acad Sci U S A 107, 3099-3104.

Chen, L., et al., Outer membrane vesicles displaying engineered glycotopes elicit protective antibodies. Proc Natl Acad Sci U S A, 2016. 113(26): p. E3609-18.

Chen, M.M., K.J. Glover, and B. Imperiali, From peptide to protein: comparative analysis of the substrate specificity of N-linked glycosylation in C. jejuni. Biochemistry, 2007. 46(18): p. 5579-85.

Chong, S., Overview of cell-free protein synthesis: historic landmarks, commercial systems, and expanding applications. Curr Protoc Mol Biol, 2014. 108: p. 16 30 1-11.

Crowell, L.E., Lu, A.E., Love, K.R., Stockdale, A., Timmick, S.M., Wu, D., Wang, Y.A., Doherty, W., Bonnyman, A., Vecchiarello, N., et al. (2018). On-demand manufacturing of clinical-quality biopharmaceuticals. Nat Biotechnol.

Cuccui, J., et al., Exploitation of bacterial N-linked glycosylation to develop a novel recombinant glycoconjugate vaccine against Francisella tularensis. Open Biol, 2013. 3(5): p. 130002.

Daniels, M.A., K.A. Hogquist, and S.C. Jameson, Sweet 'n' sour: the impact of differential glycosylation on T cell responses. Nat Immunol, 2002. 3(10): p. 903-10.

Datsenko, K.A., and Wanner, B.L. (2000). One-step inactivation of chromosomal genes in *Escherichia coli* K-12 using PCR products. Proc Natl Acad Sci U S A 97, 6640-6645.

Dennis, D.T., et al., Tularemia as a biological weapon: medical and public health management. Jama, 2001. 285(21): p. 2763-2773.

Dube, D.H. and A.R. Bertozzi, Glycans in cancer and inflammation—potential for therapeutics and diagnostics. Nat Rev Drug Discov, 2005. 4: p. 477-488.

Dudley, Q.M., A.S. Karim, and M.C. Jewett, Cell-free metabolic engineering: Biomanufacturing beyond the cell. Biotechnology Journal, 2015. 10(1): p. 69-82.

Duerr, C.U., et al., O-antigen delays lipopolysaccharide recognition and impairs antibacterial host defense in murine intestinal epithelial cells. PLoS Pathog, 2009. 5(9): p. e1000567.

Feldman, M.F., et al., Engineering N-linked protein glycosylation with diverse O antigen lipopolysaccharide structures in *Escherichia coli*. Proc Natl Acad Sci U S A, 2005. 102(8): p. 3016-3021.

Fernandez, S., Palmer, D.R., Simmons, M., Sun, P., Bisbing, J., McClain, S., Mani, S., Burgess, T., Gunther, V., and Sun, W. (2007). Potential role for Toll-like receptor 4 in mediating *Escherichia coli* maltose-binding protein activation of dendritic cells. Infect Immun 75, 1359-1363.

(56) References Cited

OTHER PUBLICATIONS

Figueiredo, D., Turcotte, C., Frankel, G., Li, Y., Dolly, O., Wilkin, G., Marriott, D., Fairweather, N., and Dougan, G. (1995). Characterization of recombinant tetanus toxin derivatives suitable for vaccine development. Infect Immun 63, 3218-3221.
Fisher, A.C., et al., Production of secretory and extracellular N-linked glycoproteins in *Escherichia coli*. Appl Environ Microbiol, 2011. 77(3): p. 871-881.
Frasch, C.E. (2009). Preparation of bacterial polysaccharide-protein conjugates: analytical and manufacturing challenges. Vaccine 27, 6468-6470.
Fulop, M., et al., Role of antibody to lipopolysaccharide in protection against low- and high-virulence strains of Francisella tularensis. Vaccine, 2001. 19(31): p. 4465-4472.
Garcia-Quintanilla, F., et al., Production of a recombinant vaccine candidate against Burkholderia pseudomallei exploiting the bacterial N-glycosylation machinery. Front Microbiol, 2014. 5: p. 381.
Gavel, Y. and G. von Heijne, Sequence differences between glycosylated and non-glycosylated Asn-X-Thr/Ser acceptor sites: implications for protein engineering. Protein Eng, 1990. 3(5): p. 433-442.
Glover, K.J., E. Weerapana, and B. Imperiali, In vitro assembly of the undecaprenylpyrophosphate-linked heptasaccharide for prokaryotic N-linked glycosylation. Proc Natl Acad Sci U S A, 2005. 102(40): p. 14255-14259.
Glover, K.J., et al., Direct biochemical evidence for the utilization of UDP-bacillosamine by PglC, an essential glycosyl-1-phosphate transferase in the Campylobacter jejuni N-linked glycosylation pathway. Biochemistry, 2006. 45 (16): p. 5343-5350.
Guarino, C. and M.P. DeLisa, A prokaryote-based cell-free translation system that efficiently synthesizes glycoproteins. Glycobiology, 2012. 22(5): p. 596-601.
Guerry, P., et al., Campylobacter polysaccharide capsules: virulence and vaccines. Front Cell Infect Microbiol, 2012. 2: p. 7.
Haghi, F., Peerayeh, S.N., Siadat, S.D., and Montajabiniat, M. (2011). Cloning, expression and purification of outer membrane protein PorA of Neisseria meningitidis serogroup B. J Infect Dev Ctries 5, 856-862.
Weerapana, E. and B. Imperiali, Asparagine-linked protein glycosylation: from eukaryotic to prokaryotic systems. Glycobiology, 2006. 16(6): p. 91R-101R.
Weintraub, A. (2003). Immunology of bacterial polysaccharide antigens. Carbohydr Res 338, 2539-2547.
Wetter, M., Kowarik, M., Steffen, M., Carranza, P., Corradin, G., and Wacker, M. (2013). Engineering, conjugation, and immunogenicity assessment of *Escherichia coli* O121 O antigen for its potential use as a typhoid vaccine component. Glycoconj J 30, 511-522.
WHO (2014). Temperature Sensitivity of Vaccines.
Wilson, I.B., Y. Gavel, and G. von Heijne, Amino acid distributions around O-linked glycosylation sites. Biochem J, 1991. 275 ( Pt 2): p. 529-534.
Xu, Y., et al. Production of bispecific antibodies in "Knobs-into-Holes" using a cell-free expression system. in mAbs. 2014. Taylor & Francis.
Young, N.M., et al., Structure of the N-linked glycan present on multiple glycoproteins in the Gram-negative bacterium, Campylobacter jejuni. Journal of Biological Chemistry, 2002. 277(45): p. 42530-42539.
Zalkin, H., C. Yanofsky, and C.L. Squires, Regulated in vitro synthesis of *Escherichia coli* tryptophan operon messenger ribonucleic acid and enzymes. J Biol Chem, 1974. 249(2): p. 465-475.
Zawada, J.F., et al., Microscale to manufacturing scale-up of cell-free cytokine production—a new approach for shortening protein production development timelines. Biotechnol Bioeng, 2011. 108(7): p. 1570-1578.
Zimmerman, E.S., et al., Production of Site-Specific Antibody-Drug Conjugates Using Optimized Non-Natural Amino Acids in a Cell-Free Expression System. Bioconjugate Chemistry, 2014. 25(2): p. 351-361.
Office Action, corresponding to JP 2021-540255, dated Dec. 12, 2023.
Novak, R.T., Kambou, J.L., Diomande, F.V., Tarbangdo, T.F., Ouedraogo-Traore, R., Sangare, L., Lingani, C., Martin, S.W., Hatcher, C., Mayer, L.W., et al. (2012). Serogroup A meningococcal conjugate vaccination in Burkina Faso: analysis of national surveillance data. Lancet Infect Dis 12, 757-764.
Ohtsubo, K. and J.D. Marth, Glycosylation in cellular mechanisms of health and disease. Cell, 2006. 126(5): p. 855-867.
Olivier, N.B., et al., In vitro biosynthesis of UDP-N, N'-diacetylbacillosamine by enzymes of the Campylobacter jejuni general protein glycosylation system. Biochemistry, 2006. 45(45): p. 13659-13669.
Ollis, A.A., et al., Engineered oligosaccharyltransferases with greatly relaxed acceptor-site specificity. Nat Chem Biol, 2014. 10(10): p. 816-822.
Ollis, A.A., et al., Substitute sweeteners: diverse bacterial oligosaccharyltransferases with unique N-glycosylation site preferences. Sci Rep, 2015. 5: p. 15237.
Dyston, P.C., A. Sjostedt, and R.W. Titball, Tularaemia: bioterrorism defence renews interest in Francisella tularensis. Nat Rev Microbiol, 2004. 2(12): p. 967-978.
Oza, J.P., et al., Robust production of recombinant phosphoproteins using cell-free protein synthesis. Nature Communications, 2015. 6: p. 8168.
Pardee, K., Slomovic, S., Nguyen, Peter Q., Lee, Jeong W., Donghia, N., Burrill, D., Ferrante, T., McSorley, Fern R., Furuta, Y., Vernet, A., et al. (2016). Portable, on-demand biomolecular manufacturing. Cell 167, 248-259.e212.
Perez, C., et al., Structure and mechanism of an active lipid-linked oligosaccharide flippase. Nature, 2015. 524(7566): p. 433-438.
Perez, J.G., J.C. Stark, and M.C. Jewett, Cell-free synthetic biology: Engineering beyond the cell. Cold Spring Harb. Perspect. Biol., 2016.
Perez-Pinera, P., Han, N., Cleto, S., Cao, J., Purcell, O., Shah, K.A., Lee, K., Ram, R., and Lu, T.K. (2016). Synthetic biology and microbioreactor platforms for programmable production of biologics at the point-of-care. Nat Commun 7, 12211.
Petsch, D. and F.B. Anspach, Endotoxin removal from protein solutions. J. Biotechnol., 2000. 76(2-3): p. 97-119.
Pinho, S.S. and C.A. Reis, Glycosylation in cancer: mechanisms and clinical implications. Nat Rev Cancer, 2015. 15 (9): p. 540-555.
Poehling, K.A., Talbot, T.R., Griffin, M.R., Craig, A.S., Whitney, C.G., Zell, E., Lexau, C.A., Thomas, A.R., Harrison, L. H., Reingold, A.L., et al. (2006). Invasive pneumococcal disease among infants before and after introduction of pneumococcal conjugate vaccine. JAMA 295, 1668-1674.
Prior, J.L., et al., Characterization of the O antigen gene cluster and structural analysis of the O antigen of Francisella tularensis subsp. tularensis. J Med Microbiol, 2003. 52(Pt 10): p. 845-851.
Qadri, F., Svennerholm, A.M., Faruque, A.S., and Sack, R.B. (2005). Enterotoxigenic *Escherichia coli* in developing countries: epidemiology, microbiology, clinical features, treatment, and prevention. Clin Microbiol Rev 18, 465-483.
Raetz, C.R., and Whitfield, C. (2002). Lipopolysaccharide endotoxins. Annu Rev Biochem 71, 635-700.
Raman, R., et al., Glycomics: an integrated systems approach to structure-function relationships of glycans. Nat Methods, 2005. 2(11): p. 817-824.
Ravenscroft, N., et al., Purification and characterization of a Shigella conjugate vaccine, produced by glycoengineering *Escherichia coli*. Glycobiology, 2015.
Riddle, M.S., Kaminski, R.W., Di Paolo, C., Porter, C.K., Gutierrez, R.L., Clarkson, K.A., Weerts, H.E., Duplessis, C., Castellano, A., Alaimo, C., et al. (2016). Safety and immunogenicity of a candidate bioconjugate vaccine against Shigella flexneri 2a administered to healthy adults: a single blind, randomized phase I study. Clin Vaccine Immunol.
Rietschel, E.T., et al., Bacterial endotoxin: molecular relationships of structure to activity and function. FASEB J., 1994. 3(2): p. 217-225.
Roush, S.W., Mcintyre, L., and Baldy, L.M. (2008). Manual for the surveillance of vaccine-preventable diseases. Atlanta: Centers for Disease Control and Prevention, 4.
Russell, J.A., Management of sepsis. N. Engl. J. Med., 2006. 355(16): p. 1699-1713.

(56) References Cited

OTHER PUBLICATIONS

Saldias, M.S., X. Ortega, and M.A. Valvano, Burkholderia cenocepacia O antigen lipopolysaccharide prevents phagocytosis by macrophages and adhesion to epithelial cells. J Med Microbiol, 2009. 58(Pt 12): p. 1542-1548.
Salehi, A.S., et al., Escherichia coli-based cell-free extract development for protein-based cancer therapeutic production. Int J Dev Biol, 2016. 60(7-8-9): p. 237-243.
Salehi, A.S., Smith, M.T., Bennett, A.M., Williams, J.B., Pitt, W.G., and Bundy, B.C. (2016). Cell-free protein synthesis of a cytotoxic cancer therapeutic: Onconase production and a just-add-water cell-free system. Biotechnol J 11, 274-281.
Schoborg, J.A., Hershewe, J.M., Stark, J.C., Kightlinger, W., Kath, J.E., Jaroentomeechai, T., Natarajan, A., DeLisa, M.P., and Jewett, M.C. (2017). A cell-free platform for rapid synthesis and testing of active oligosaccharyltransferases. Biotechnol Bioeng.
Schwarz, F., et al., A combined method for producing homogeneous glycoproteins with eukaryotic N-glycosylation. Nat Chem Biol, 2010. 6(4): p. 264-266.
Schwarz, F., et al., Relaxed acceptor site specificity of bacterial oligosaccharyltransferase in vivo. Glycobiology, 2011. 21(1): p. 45-54.
Sleytr, U.B., Heterologous reattachment of regular arrays of glycoproteins on bacterial surfaces. Nature, 1975. 257 (5525): p. 400-402.
Spiro, R.G., Protein glycosylation: nature, distribution, enzymatic formation, and disease implications of glycopeptide bonds. Glycobiology, 2002. 12(4): p. 43R-56R.
Stech, M., et al., A continuous-exchange cell-free protein synthesis system based on extracts from cultured insect cells. PLoS One, 2014. 9(5): p. e96635.
Stech, M., et al., Cell-free systems: functional modules for synthetic and chemical biology. Adv Biochem Eng Biotechnol, 2013. 137: p. 67-102.
Stefan, A., Conti, M., Rubboli, D., Ravagli, L., Presta, E., and Hochkoeppler, A. (2011). Overexpression and purification of the recombinant diphtheria toxin variant CRM197 in Escherichia coli. J Biotechnol 156, 245-252.
Stefanetti, G., et al., Glycoconjugate vaccine using a genetically modified O antigen induces protective antibodies to Francisella tularensis. Proc. Natl. Acad. Sci. U. S. A., 2019. 116(14): p. 7062-7070.
Szymanski, C.M., et al., Evidence for a system of general protein glycosylation in Campylobacter jejuni. Mol Microbiol, 1999. 32(5): p. 1022-1030.
Thanka Christlet, T.H. and K. Veluraja, Database analysis of O-glycosylation sites in proteins. Biophys J, 2001. 80(2): p. 952-960.
The Review on Antimicrobial Resistance, C.b.J.O.N. (2014). Antimicrobial Resistance: Tackling a crisis for the health and wealth of nations.
Theodoratou, E., et al., The role of glycosylation in IBD. Nat Rev Gastroenterol Hepatol, 2014. 11(10): p. 588-600.
Trotter, C.L., McVernon, J., Ramsay, M.E., Whitney, C.G., Mulholland, E.K., Goldblatt, D., Hombach, J., and Kieny, M. P. (2008). Optimising the use of conjugate vaccines to prevent disease caused by Haemophilus influenzae type b, Neisseria meningitidis and Streptococcus pneumoniae. Vaccine 26, 4434-4445.
Valderrama-Rincon, J.D., et al., An engineered eukaryotic protein glycosylation pathway in Escherichia coli. Nat Chem Biol, 2012. 8(5): p. 434-436.
Valvano, M.A., and Crosa, J.H. (1989). Molecular cloning and expression in Escherichia coli K-12 of chromosomal genes determining the O7 lipopolysaccharide antigen of a human invasive strain of E. coli O7:K1. Infect Immun 57, 937-943.
Varki, A., Biological roles of oligosaccharides: all of the theories are correct. Glycobiology, 1993. 3(2): p. 97-130.
Wacker, M., et al., N-linked glycosylation in Campylobacter jejuni and its functional transfer into E. coli. Science, 2002. 298(5599): p. 1790-1793.
Wacker, M., et al., Prevention of Staphylococcus aureus infections by glycoprotein vaccines synthesized in Escherichia coli. J Infect Dis, 2014. 209(10): p. 1551-1561.
Wahl, B., O'Brien, K.L., Greenbaum, A., Majumder, A., Liu, L., Chu, Y., Luksic, I., Nair, H., McAllister, D.A., Campbell, H., et al. (2018). Burden of Streptococcus pneumoniae and Haemophilus influenzae type b disease in children in the era of conjugate vaccines: global, regional, and national estimates for 2000-15. Lancet Glob Health 6, e744-e757.
Walt, D., et al., Transforming Glycoscience: A Roadmap for the Future. 2012: The National Academies Press.
Wang, J.Z., I. Grundke-Iqbal, and K. Iqbal, Glycosylation of microtubule-associated protein tau: an abnormal posttranslational modification in Alzheimer's disease. Nat Med, 1996. 2(8): p. 871-875.
Wang, L.X. and B.G. Davis, Realizing the Promise of Chemical Glycobiology. Chem Sci, 2013. 4(9): p. 3381-3394.
Wang, X., et al., Peptide surfactants for cell-free production of functional G protein-coupled receptors. Proc Natl Acad Sci U S A, 2011. 108(22): p. 9049-9054.
Hatz, C.F., Bally, B., Rohrer, S., Steffen, R., Kramme, S., Siegrist, C.A., Wacker, M., Alaimo, C., and Fonck, V.G. (2015). Safety and immunogenicity of a candidate bioconjugate vaccine against Shigella dysenteriae type 1 administered to healthy adults: A single blind, partially randomized Phase I study. Vaccine 33, 4594-4601.
Hodgman, C.E. and M.C. Jewett, Cell-free synthetic biology: thinking outside the cell. Metab Eng, 2012. 14(3): p. 261-269.
Hong, S.H., Ntai, I., Haimovich, A.D., Kelleher, N.L., Isaacs, F.J., and Jewett, M.C. (2014). Cell-free protein synthesis from a release factor 1 deficient Escherichia coli activates efficient and multiple site-specific nonstandard amino acid Incorporation. ACS Synth Biol 3, 398-409.
Humphreys, G. (2011). Vaccination: rattling the supply chain (Bulletin of the World Health Organization: World Health Organization).
Huttner, A., Hatz, C., van den Dobbelsteen, G., Abbanat, D., Hornacek, A., Frolich, R., Dreyer, A.M., Martin, P., Davies, T., Fae, K., et al. (2017). Safety, immunogenicity, and preliminary clinical efficacy of a vaccine against extraintestinal pathogenic Escherichia coli in women with a history of recurrent urinary tract infection: a randomised, single-blind, placebo-controlled phase 1b trial. Lancet Infect Dis.
Ihssen, J., et al., Increased efficiency of Campylobacter jejuni N-oligosaccharyltransferase PglB by structure-guided engineering. Open Biol, 2015. 5(4).
Ihssen, J., et al., Production of glycoprotein vaccines in Escherichia coli. Microb Cell Fact, 2010. 9: p. 61.
Imberty, A. and A. Varrot, Microbial recognition of human cell surface glycoconjugates. Curr Opin Struct Biol, 2008. 18 5): p. 567-576.
Iwashkiw, J.A., et al., Exploiting the Campylobacter jejuni protein glycosylation system for glycoengineering vaccines and diagnostic tools directed against brucellosis. Microb Cell Fact, 2012. 11: p. 13.
Jansson, P.E., et al., Structural studies of the Escherichia coli O78 O-antigen polysaccharide. Carbohydr Res, 1987. 165(1): p. 87-92.
Jaroentomeechai, T., et al., A Pipeline for Studying and Engineering Single-Subunit Oligosaccharyltransferases. Methods Enzymol, 2017. 597: p. 55-81.
Jaroentomeechai, T., et al., Single-pot glycoprotein biosynthesis using a cell-free transcription-translation system enriched with glycosylation machinery. Nat Commun, 2018. 9(1): p. 2686.
Jervis, A.J., et al., Characterization of the structurally diverse N-linked glycans of Campylobacter species. J Bacteriol, 2012. 194(9): p. 2355-2362.
Jewett, M.C. and J.R. Swartz, Mimicking the Escherichia coli cytoplasmic environment activates long-lived and efficient cell-free protein synthesis. Biotechnology and bioengineering, 2004. 86(1): p. 19-26.
Jin, C., Gibani, M.M., Moore, M., Juel, H.B., Jones, E., Meiring, J., Harris, V., Gardner, J., Nebykova, A., Kerridge, S. A., et al. (2017). Efficacy and immunogenicity of a Vi-tetanus toxoid conjugate vaccine in the prevention of typhoid fever using a controlled human infection model of Salmonella Typhi: a randomised controlled, phase 2b trial. Lancet 390, 2472-2480.

(56) References Cited

OTHER PUBLICATIONS

Johnson, J.R. (1991). Virulence factors in *Escherichia coli* urinary tract infection. Clin Microbiol Rev 4, 80-128.
Kaiser, L., et al., Efficient cell-free production of olfactory receptors: detergent optimization, structure, and ligand binding analyses. Proc Natl Acad Sci U S A, 2008. 105(41): p. 15726-15731.
Kalynych, S., R. Morona, and M. Cygler, Progress in understanding the assembly process of bacterial O-antigen. FEMS Microbiol Rev, 2014. 38(5): p. 1048-1065.
Kampf, M.M., et al., In vivo production of a novel glycoconjugate vaccine against Shigella flexneri 2a in recombinant *Escherichia coli:* identification of stimulating factors for in vivo glycosylation. Microb Cell Fact, 2015. 14: p. 12.
Karim, A.S. and M.C. Jewett, A cell-free framework for rapid biosynthetic pathway prototyping and enzyme discovery. Metab Eng, 2016. 36: p. 116-126.
Kim, D.M., and Swartz, J.R. (2001). Regeneration of adenosine triphosphate from glycolytic intermediates for cell-free protein synthesis. Biotechnol Bioeng 74, 309-316.
Knapp, K.G., Goerke, A.R., and Swartz, J.R. (2007). Cell-free synthesis of proteins that require disulfide bonds using glucose as an energy source. Biotechnol Bioeng 97, 901-908.
Kowarik, M., et al., Definition of the bacterial N-glycosylation site consensus sequence. The EMBO Journal, 2006. 25 (9): p. 1957-1966.
Kubick, S., et al., In vitro synthesis of posttranslationally modified membrane proteins. Current Topics in Membranes, 2009. 63(2): p. 25-49.
Kumru, O.S., et al., Vaccine instability in the cold chain: mechanisms, analysis and formulation strategies. Biologicals, 2014. 42(5): p. 237-259.
Kwon, Y.-C. and M.C. Jewett, High-throughput preparation methods of crude extract for robust cell-free protein synthesis. Scientific Reports, 2015. 5: p. 8663.
L'vov, V.L., Shashkov, A.S., Dmitriev, B.A., Kochetkov, N.K., Jann, B., and Jann, K. (1984). Structural studies of the O-specific side chain of the lipopolysaccharide from *Escherichia coli* O:7. Carbohydr Res 126, 249-259.
Laine, R.A., The Information-Storing Potential of the Sugar Code. Glycosciences: Status and Perspectives, 1997: p. 1-14.
Lehle, L. and W. Tanner, Glycosyl transfer from dolichyl phosphate sugars to endogenous and exogenous glycoprotein acceptors in yeast. Eur J Biochem, 1978. 83(2): p. 563-570.
Lesinski, G.B. and M.A. Westerink, Novel vaccine strategies to T-independent antigens. J Microbiol Methods, 2001. 47 (2): p. 135-149.
Lian, Q., H. Cao, and F. Wang, The cost-efficiency realization in the *Escherichia coli*-based cell-free protein synthesis systems. Appl Biochem Biotechnol, 2014. 174(7): p. 2351-2367.
Linton, D., et al., Identification of N-acetylgalactosamine-containing glycoproteins PEB3 and CgpA in Campylobacter ejuni. Mol Microbiol, 2002. 43(2): p. 497-508.
Lizak, C., et al., X-ray structure of a bacterial oligosaccharyltransferase. Nature, 2011. 474(7351): p. 350-355.
Lu, Y., J.P. Welsh, and J.R. Swartz, Production and stabilization of the trimeric influenza hemagglutinin stem domain for potentially broadly protective influenza vaccines. Proc Natl Acad Sci U S A, 2014. 111(1): p. 125-130.
Lu, Z., Madico, G., Roche, M.I., Wang, Q., Hui, J.H., Perkins, H.M., Zaia, J., Costello, C.E., and Sharon, J. (2012). Protective B-cell epitopes of Francisella tularensis O-polysaccharide in a mouse model of respiratory tularaemia. Immunology 136, 352-360.
Lydon, P., Zipursky, S., Tevi-Benissan, C., Djingarey, M.H., Gbedonou, P., Youssouf, B.O., and Zaffran, M. (2014). Economic benefits of keeping vaccines at ambient temperature during mass vaccination: the case of meningitis A vaccine in Chad. Bull World Health Organ 92, 86-92.
Ma, Z. and K. Vosseller, Cancer metabolism and elevated O-GlcNAc in oncogenic signaling. J Biol Chem, 2014. 289 (50): p. 34457-34465.
Ma, Z., et al., Glycoconjugate vaccine containing *Escherichia coli* O157:H7 O-antigen linked with maltose-binding protein elicits humoral and cellular responses. PLoS One, 2014. 9(8): p. e105215.
Marshall, L.E., Nelson, M., Davies, C.H., Whelan, A.O., Jenner, D.C., Moule, M.G., Denman, C., Cuccui, J., Atkins, T. P., Wren, B.W., et al. (2018). An O-antigen glycoconjugate vaccine produced using protein glycan coupling technology is protective in an inhalational rat model of tularemia. J Immunol Res 2018, 8087916.
Matthies, D., et al., Cell-free expression and assembly of ATP synthase. J Mol Biol, 2011. 413(3): p. 593-603.
Maue, A.C., F. Poly, and p. Guerry, A capsule conjugate vaccine approach to prevent diarrheal disease caused by Campylobacter jejuni. Hum Vaccin Immunother, 2014. 10(6): p. 1499-1504.
Mescher, M.F. and J.L. Strominger, Purification and characterization of a prokaryotic glucoprotein from the cell envelope of Halobacterium salinarium. J Biol Chem, 1976. 251(7): p. 2005-2014.
Murphy, T.W., Sheng, J., Naler, L.B., Feng, X., and Lu, C. (2019). On-chip manufacturing of synthetic proteins for point-of-care therapeutics. Microsyst Nanoeng 5, 13.
Murray, G.L., S.R. Attridge, and R. Morona, Altering the length of the lipopolysaccharide O antigen has an impact on the interaction of *Salmonella enterica* serovar Typhimurium with macrophages and complement. J Bacteriol, 2006. 188 (7): p. 2735-2739.
Murray, G.L., S.R. Attridge, and R. Morona, Regulation of *Salmonella typhimurium* lipopolysaccharide O antigen chain ength is required for virulence; identification of FepE as a second Wzz. Mol Microbiol, 2003. 47(5): p. 1395-1406.
Needham, B.D., et al., Modulating the innate immune response by combinatorial engineering of endotoxin. Proc. Natl. Acad. Sci. U. S. A., 2013. 110(4): p. 1464-1469.
Neuberger, A., Carbohydrates in protein: The carbohydrate component of crystalline egg albumin. Biochem J, 1938. 32 (9): p. 1435-1451.
Ng, P.P., et al., A vaccine directed to B cells and produced by cell-free protein synthesis generates potent antilymphoma immunity. Proc Natl Acad Sci U S A, 2012. 109(36): p. 14526-14531.
Nirenberg, M.W. and J.H. Matthaei, The dependence of cell-free protein synthesis in *E. coli* upon naturally occurring or synthetic polyribonucleotides. Proc Natl Acad Sci U S A, 1961. 47: p. 1588-1602.
Nothaft, H., et al., Study of free oligosaccharides derived from the bacterial N-glycosylation pathway. Proc Natl Acad Sci U S A, 2009. 106(35): p. 15019-15024.
Forsgren et al., Protein D of Haemophilus influenzae: A Protective Nontypeable H. influenzae Antigen and a Carrier for Pneumococcal Conjugate Vaccines, Clinical Infectious Diseases, vol. 46, n. 5,Mar. 1, 2008 (Mar. 1, 2008), pp. 726-731.
Extended European Search Report, corresponding to EP 20737951.2, dated Apr. 4, 2023.
First Office Action, corresponding to CN 202080015372.5, dated Dec. 11, 2023.

\* cited by examiner (A) →4)-α-D-GalNAcAN-(1→4)-α-D-GalNAcAN-(1→3)-β-D-QuiNAc-(1→2)-β-D-Qui4NFm-(1→

(B) →3)-β-D-GlcNAc-(1→4)-β-D-GlcNAc-(1→4)-β-D-Man-(1→4)-β-D-Man-α1→

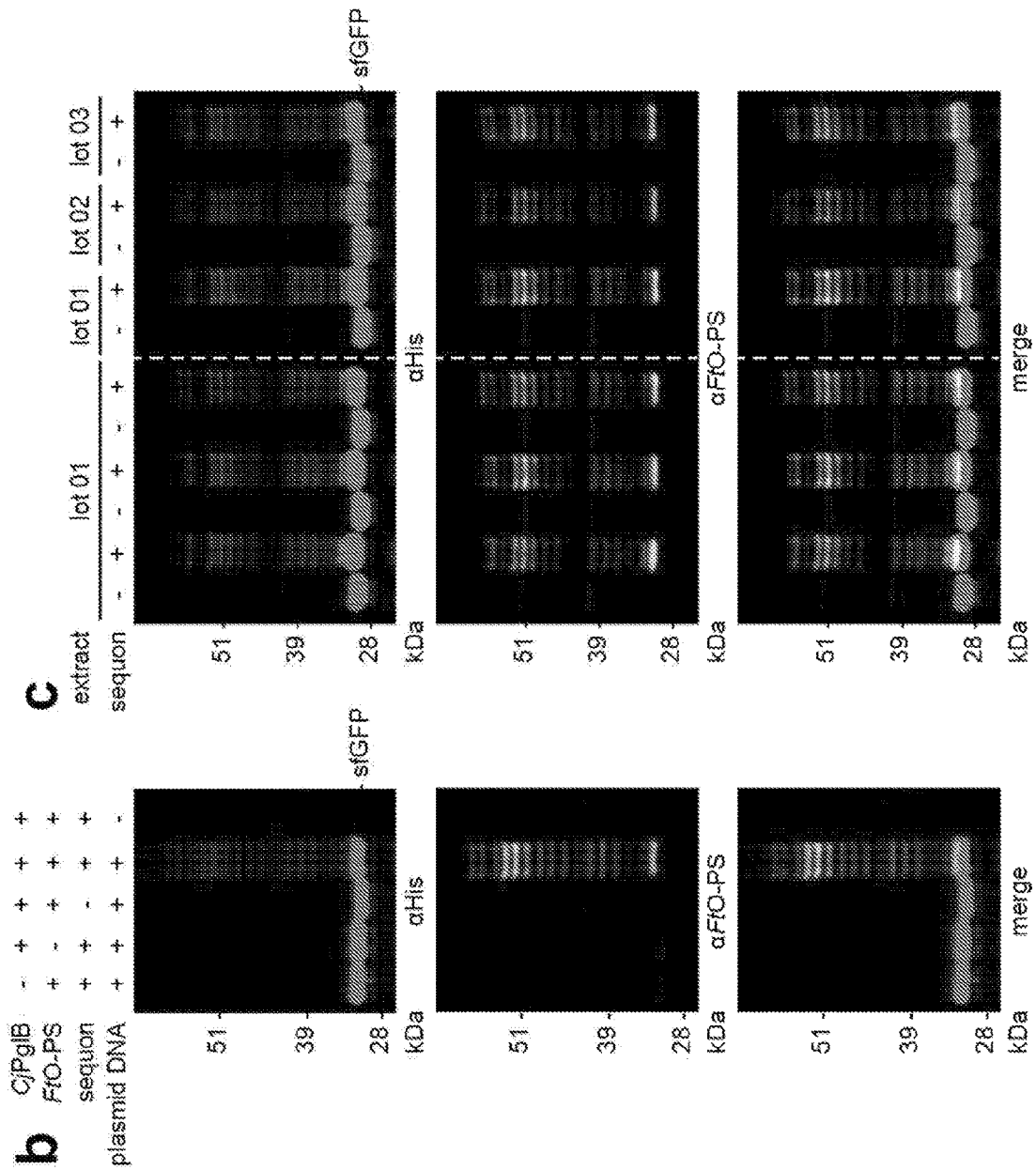
Figure 17, con't.

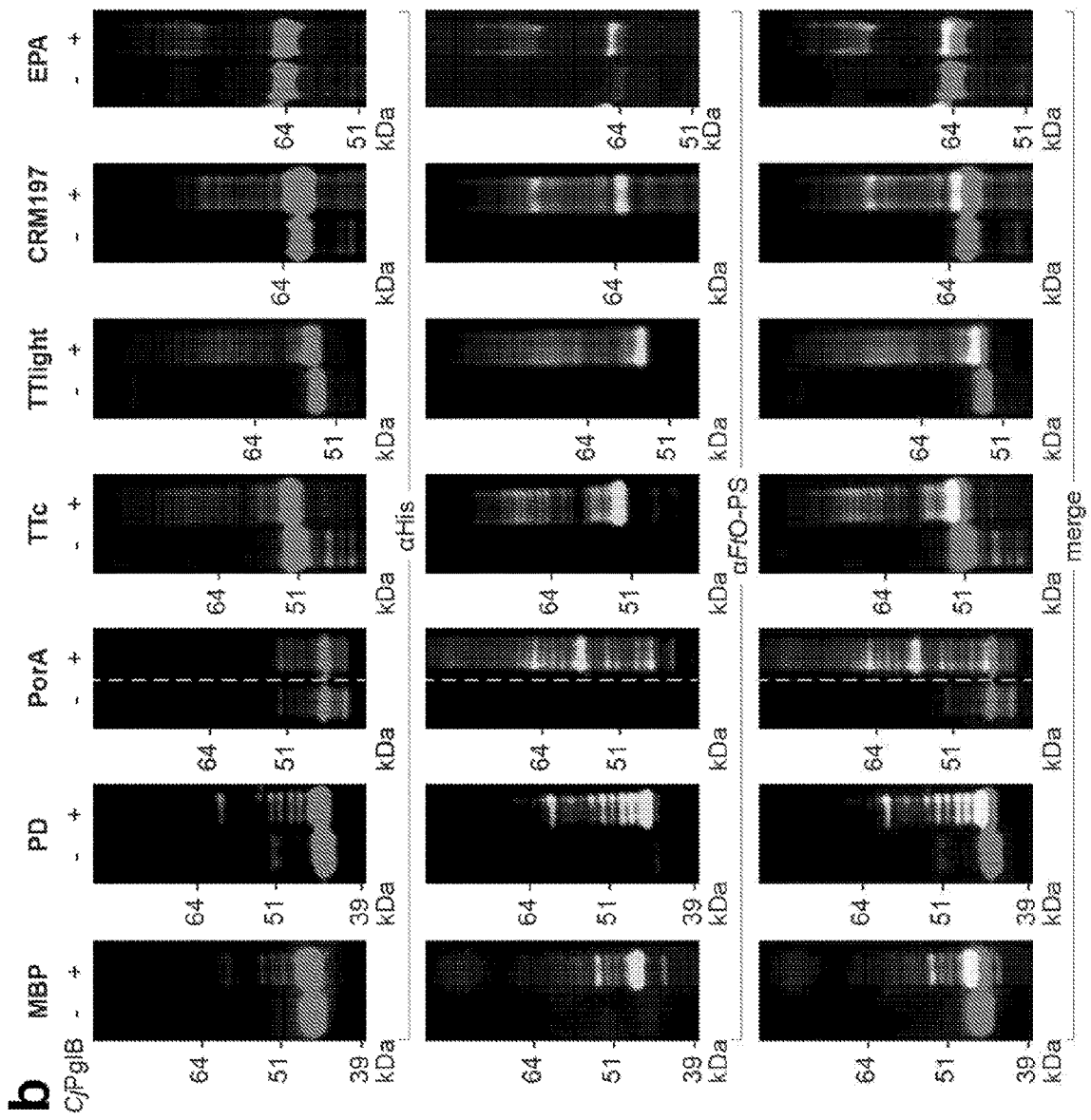
Figure 18, con't.

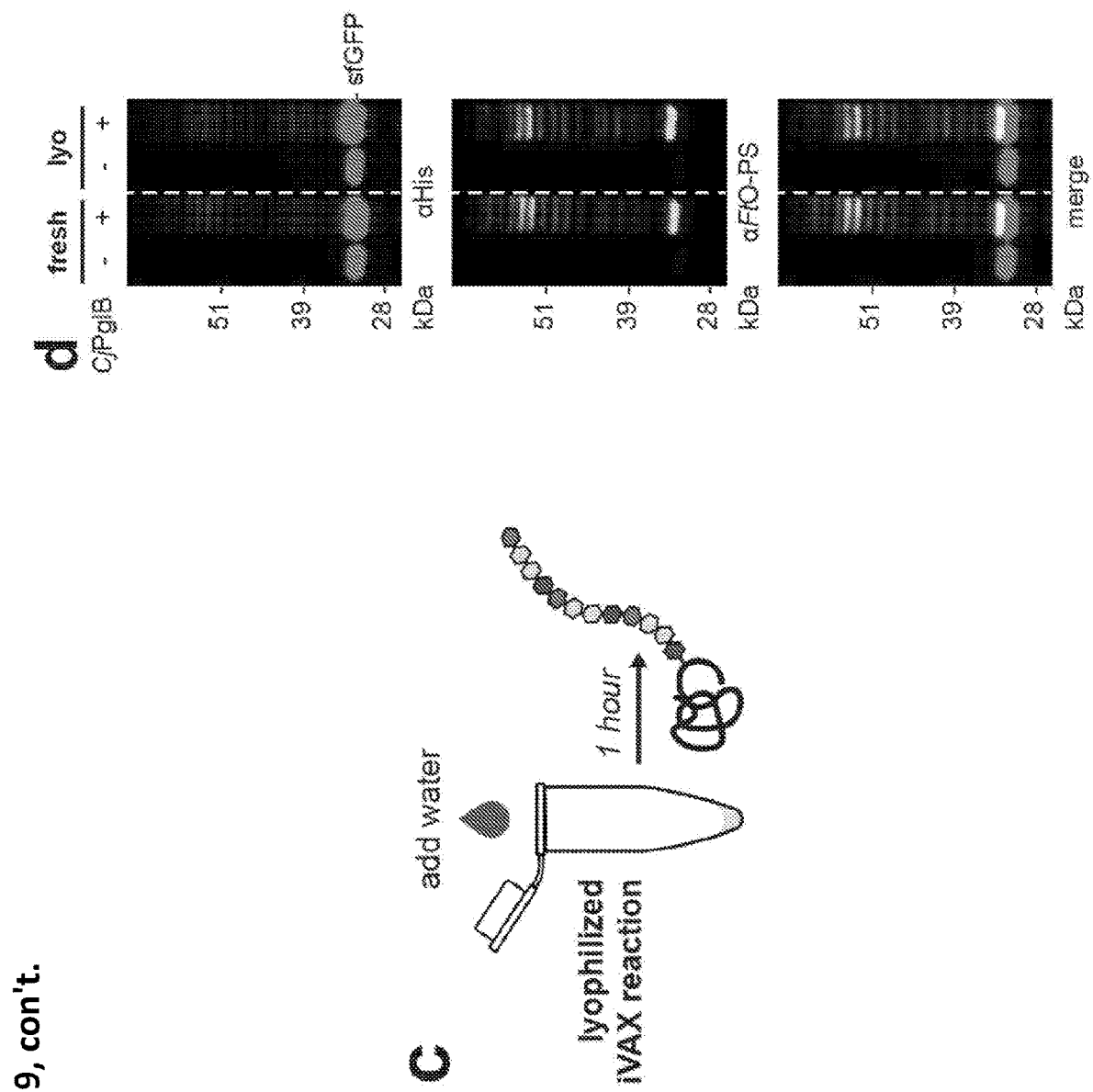
Figure 19, con't.

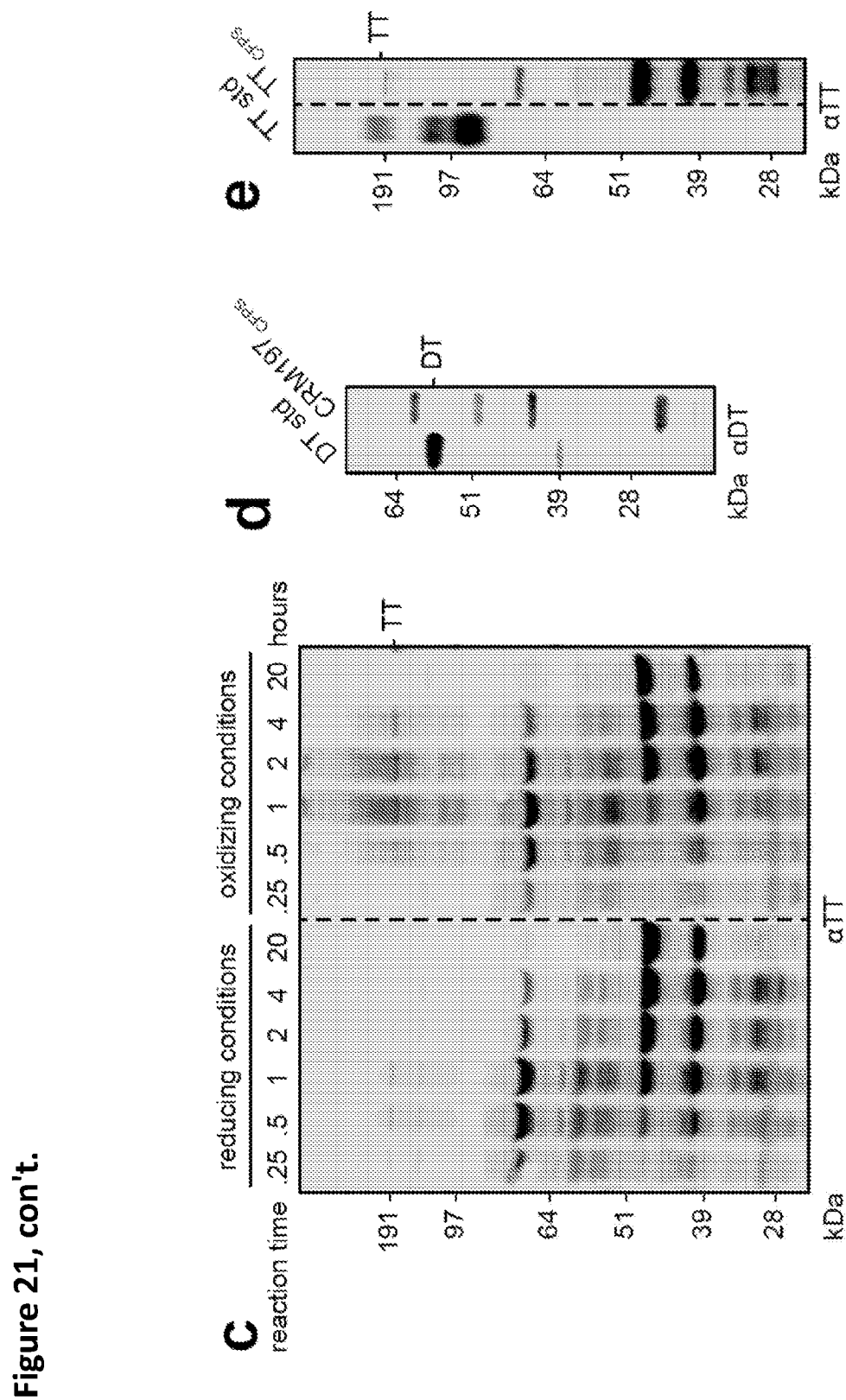
Figure 21, con't.

Figure 27

Table 1

| Component | Cost ($/mL rxn) | Supplier | Product No |
|---|---|---|---|
| Mg(Glu)$_2$ | <0.00 | Sigma | 49605 |
| NH$_4$Glu | <0.00 | MP | 02180595 |
| KGlu | <0.00 | Sigma | G1501 |
| ATP | 0.01 | Sigma | A2383 |
| GTP | 0.27 | Sigma | G8877 |
| UTP | 0.23 | Sigma | U6625 |
| CTP | 0.20 | Sigma | C1506 |
| Folinic acid | 0.02 | Sigma | 47612 |
| tRNA | 0.21 | Roche | 10109541001 |
| Amino acids | <0.00 | homemade | |
| PEP | 1.79 | Roche | 10108294001 |
| NAD | 0.07 | Sigma | N8535-15VL |
| CoA | 0.34 | Sigma | C3144 |
| Oxalic acid | <0.00 | Sigma | P0963 |
| Putrescine | <0.00 | Sigma | P5780 |
| Spermidine | <0.00 | Sigma | S2626 |
| HEPES | <0.00 | Sigma | H3375 |
| MnCl$_2$ | <0.00 | Sigma | 63535 |
| DDM | 0.36 | Anatrace | D310S |
| Plasmid | 0.88 | homemade | |
| Lysate | 7.37 | homemade | |
| Total | 11.75 | $/mL rxn | |
| | 5.88 | $/dose | |

Figure 28

Table 2

| Primer Name | DNA Sequence (5' to 3') |
|---|---|
| lpxM KO for | TACACTATCACCAGATTGATTTTGCCTTATCCGAAACTGGAAAAGCAT GGTGTAGGCTGGAGCTGCTTC |
| lpxM KO rev | GCGAAGGCCTCTCCTCGCGAGAGGCTTTTTATTTGATGGGATAAAGA TCCATATGAATATCCTCCTTAGTTCCTATTC |
| lpxM seq for | AGTACCGGCTTTTTTATTTGG |
| lpxM seq rev | CTAATACCACGCGTATTTTAACG |

Figure 29

Table 3

| Plasmid | Description | Source |
| --- | --- | --- |
| pSF-CjPglB | C. jejuni PglB with a C-terminal 1xFLAG epitope tag in pSF, a modified pBAD expression vector | (Ollis et al., 2014) |
| pGAB2 | F. tularensis O-PS antigen gene cluster in pLAFR1 | (Cuccui et al., 2013) |
| pMW07-O78 | E. coli O78 antigen gene cluster in pMW07 | (Celik et al., 2015) |
| pJHCV32 | E. coli O7 antigen gene cluster in pVK102 | (Valvano and Crosa, 1989) |
| pKD46 | Encodes λ red system for recombineering | (Datsenko and Wanner, 2000) |
| pKD4 | Encodes kanamycin resistance cassette with upstream and downstream FRT sites | (Datsenko and Wanner, 2000) |
| pCP20 | Encodes flp for Flp-FRT recombination | (Datsenko and Wanner, 2000) |
| pSF-CjPglB-LpxE | C. jejuni PglB with a C-terminal 1xFLAG epitope tag and F. tularensis LpxE in pSF | This work; Addgene 128389 |
| pJL1-sfGFP$^{217\text{-DQNAT}}$ | Superfolder green fluorescent protein variant modified after residue T216 with 21 amino acid insertion containing the C. jejuni AcrA N123 glycosylation site but with an optimal DQNAT glycosylation sequence and a C-terminal 6xHis tag | (Jaroentomeechai et al., 2018) |

Figure 29, con't.

Table 3, con't.

| Plasmid | Description | Source |
|---|---|---|
| pJL1-sfGFP[217-AQNAT] | Same as pJL1 sfGFP[217-DQNAT], but with an AQNAT glycosylation sequence that is not modified by CjPglB | (Jaroentomeechai et al., 2018) |
| pJL1-MBP[4xDQNAT] | E. coli maltose binding protein with a C-terminal 4xDQNAT glycosylation tag and a 6xHis tag in pJL1, a T7-driven in vitro expression vector | This work; Addgene 128390 |
| pJL1-PD[4xDQNAT] | H. influenzae protein D with a C-terminal 4xDQNAT glycosylation tag and a 6xHis tag in pJL1 | This work; Addgene 128391 |
| pJL1-PorA[4xDQNAT] | N. meningitidis PorA porin protein with a C-terminal 4xDQNAT glycosylation tag and a 6xHis tag in pJL1 | This work; Addgene 128392 |
| pJL1-TTc[4xDQNAT] | Fragment C domain of C. tetani toxin with a C-terminal 4xDQNAT glycosylation tag and a 6xHis tag in pJL1 | This work; Addgene 128393 |
| pJL1-TTlight[4xDQNAT] | Light chain variant of C. tetani toxin containing an inactivating E234A mutation in the enzyme active site with a C-terminal 4xDQNAT glycosylation tag and a 6xHis tag in pJL1 | This work; Addgene 128394 |
| pJL1-CRM197[4xDQNAT] | C. diphtheriae toxin variant with an inactivating G52E mutation in the enzyme active site with a C-terminal 4xDQNAT glycosylation tag and a 6xHis tag in pJL1 | This work; Addgene 128395 |
| pJL1-TT[4xDQNAT] | C. tetani toxin variant containing an inactivating E234A mutation in the enzyme active site with a C-terminal 4xDQNAT glycosylation tag and a 6xHis tag in pJL1 | This work; Addgene 128396 |
| pJL1-EPA[DNNNS-DQNRT] | P. aeruginosa exotoxin A containing a DNNNS glycosylation site at residue 242 and a DQNRT glycosylation site at residue 384 and a C-terminal 6xHis tag in pJL1 | This work; Addgene 128397 |

Figure 29, con't.

Table 3, con't.

| Plasmid | Description | Source |
|---|---|---|
| pTrc99s-ssDsbA-$MBP^{4xDQNAT}$ | *E. coli* maltose binding protein with an N-terminal DsbA signal sequence for periplasmic translocation and a C-terminal 4xDQNAT glycosylation tag and a 6xHis tag in pTrc99s | This work; Addgene 128398 |
| pTrc99s-ssDsbA-$PD^{4xDQNAT}$ | *H. influenzae* protein D with an N-terminal DsbA signal sequence for periplasmic translocation and a C-terminal 4xDQNAT glycosylation tag and a 6xHis tag in Trc99s | This work; Addgene 128399 |
| pTrc99s-ssDsbA-$PorA^{4xDQNAT}$ | *N. meningitidis* PorA porin protein with an N-terminal DsbA signal sequence for periplasmic translocation and a C-terminal 4xDQNAT glycosylation tag and a 6xHis tag in pTrc99s | This work; Addgene 128400 |
| pTrc99s-ssDsbA-$TTc^{4xDQNAT}$ | Fragment C domain of *C. tetani* toxin with an N-terminal DsbA signal sequence for periplasmic translocation and a C-terminal 4xDQNAT glycosylation tag and a 6xHis tag in pTrc99s | This work; Addgene 128401 |
| pTrc99s-ssDsbA-$TTlight^{4xDQNAT}$ | Light chain variant of *C. tetani* toxin containing an inactivating E234A mutation in the enzyme active site with an N-terminal DsbA signal sequence for periplasmic translocation and a C-terminal 4xDQNAT glycosylation tag and a 6xHis tag in pTrc99s | This work; Addgene 128402 |
| pTrc99s-ssDsbA-$CRM197^{4xDQNAT}$ | *C. diphtheriae* toxin variant with an inactivating G52E mutation in the enzyme active site with an N-terminal DsbA signal sequence for periplasmic translocation and a C-terminal 4xDQNAT glycosylation tag and a 6xHis tag in pTrc99s | This work; Addgene 128403 |
| pTrc99s-ssDsbA-$EPA^{DNNNS-DQNRT}$ | *P. aeruginosa* exotoxin A containing a DNNNS glycosylation site at residue 242 and a DQNRT glycosylation site at residue 384 with an N-terminal DsbA signal sequence for periplasmic translocation and a C-terminal 6xHis tag in pTrc99s | This work; Addgene 128404 |

Figure 30

Table 4

| Target | Source | Dilution |
|---|---|---|
| Rabbit pAb to 6xHis epitope tag | Abcam | 1:7500 |
| Mouse mAb FB11 to *F. tularensis* LPS | Abcam | 1:5000 |
| Rabbit pAb to *E. coli* O78 antigen | Abcam | 1:2500 |
| Rabbit pAb to *C. diphtheriae* toxin | Abcam | 1:2000 |
| Rabbit pAb to *C. tetani* toxin | Abcam | 1:2000 |
| Goat anti-rabbit IgG IR dye 680 | LI-COR | 1:15000-1:10000 |
| Goat anti-rabbit IgG IR dye 800 | LI-COR | 1:15000-1:10000 |
| Goat anti-mouse IgG IR dye 800 | LI-COR | 1:15000-1:10000 |
| Goat anti-mouse IgG HRP | Abcam | 1:25,000 |
| Goat anti-mouse IgG1 HRP | Abcam | 1:25,000 |
| Goat anti-mouse IgG2a HRP | Abcam | 1:25,000 |

BIOCONJUGATE VACCINES' SYNTHESIS IN PROKARYOTIC CELL LYSATES

CROSS REFERENCE TO RELATED PATENT APPLICATIONS

The present application is the U.S. National Stage of International Application PCT/US2020/013207, filed on Jan. 10, 2020, which application claims the benefit of priority under 35 U.S.C. § 119 (e) to U.S. Provisionals Patent Application No. 62/791,425, filed on Jan. 11, 2019, the contents of which applications are incorporated herein by reference in their entireties.

STATEMENT REGARDING FEDERALLY SPONSORED RESEARCH OR DEVELOPMENT

This invention was made with government support under MCB1413563 awarded by the National Science Foundation. The government has certain rights in the invention.

BACKGROUND

The field of the invention relates to in vitro synthesis of N-glycosylated protein in prokaryotic cell lysates. In particular, the field of the invention relates to the use of N-glycosylated proteins synthesized in vitro in prokaryotic cell lysates as vaccine conjugates against pathogens such as bacteria.

Conjugate vaccines are among the safest and most effective methods for prevention of life-threatening bacterial infections. Bioconjugate vaccines are a type of conjugate vaccine produced via protein glycan coupling technology (PGCT), in which polysaccharide antigens are conjugated via N-glycosylation to recombinant carrier proteins using a bacterial oligosaccharyltransferase (OST) in living *Escherichia coli* cells. Bioconjugate vaccines have the potential to greatly reduce the time and cost required to produce antibacterial vaccines. However, PGCT is limited by: i) the length of in vivo process development timelines; and ii) the fact that FDA-approved carrier proteins, such as the toxins from *Clostridium tetani* and *Corynebacterium diptheriae*, have not yet been demonstrated to be compatible with N-linked glycosylation in living *E. coli*. Here, we have applied cell-free glycoprotein synthesis (CFGpS) technology to enable rapid in vitro production of bioconjugate vaccines against pathogenic strains of *Escherichia coli* and *Franscicella tularensis* in reactions lasting 20 hours. Due to the modular nature of the CFGpS system, this cell-free strategy could be easily applied to produce bioconjugates using FDA-approved carrier proteins or additional vaccines against pathogenic bacteria whose surface antigen gene clusters are known. We further show that this system can be lyophilized and retain bioconjugate synthesis capability, demonstrating the potential for on-demand vaccine production and development in resource-poor settings. This work represents the first demonstration of bioconjugate vaccine production in *E. coli* lysates and has promising applications as a portable prototyping or production platform for anti-bacterial vaccine candidates.

SUMMARY

Disclosed are methods, systems, components, and compositions for cell-free synthesis of glycosylated proteins. The glycosylated proteins may be utilized in vaccines, including anti-bacterial vaccines. The glycosylated proteins may include a bacterial polysaccharide conjugated to a carrier, which may be utilized to generate an immune response in an immunized host against the polysaccharide conjugated to the carrier. Suitable carriers may include but are not limited to *Haemophilus influenzae* protein D (PD), *Neisseria meningitidis* porin protein (PorA), *Corynebacterium diphtheriae* toxin (CRM197), *Clostridium tetani* toxin (TT), and *Escherichia coli* maltose binding protein, or variants thereof. The glycosylated proteins may be synthesized in cell-free glycoprotein synthesis (CFGpS) systems using prokaryote cell lysates that are enriched in components for glycoprotein synthesis such as oligosaccharyltransferases (OSTs) and lipid-linked oligosaccharides (LLOs) including OSTs and LLOs associated with synthesis of bacterial O-antigens. As such, the prokaryote cell lysates may be prepared from recombinant prokaryotes that have been engineered to express heterologous OSTs and/or that have been engineered to express heterologous glycan synthesis pathways for production of LLOs. The disclosed lysates may be described as modular and may be combined to prepare glycosylated proteins in the disclosed CFGpS systems.

BRIEF DESCRIPTION OF THE FIGURES

FIG. 27. Table 1 shows the cost analysis for iVAX reactions. A 1 mL iVAX reaction produces two 10 μg vaccine doses and can be assembled for $11.75. In Table 1, amino acid cost accounts for 2 mM each of the 20 canonical amino acids purchased individually from Sigma. Lysate cost is based on a single employee making 50 mL lysate from a 10 L fermentation, assuming 30 lysate batches per year and a 5-year equipment lifetime. Component source is also included in the table if it is available to purchase directly from a supplier. Homemade components cannot be purchased directly and must be prepared according to procedures described in the Methods section.

FIG. 28. Table 2 shows the primers used to construct and verify the CLM24 ΔlpxM strain. KO primers were used for amplification of the kanamycin resistance cassette from pKD4 with homology to lpxM. Seq primers were used for colony PCRs and sequencing confirmation of knockout strains.

FIG. 29. Table 3 lists the plasmids used in the Examples.

FIG. 30. Table 4 lists the antibodies and antisera used in the Examples.

DETAILED DESCRIPTION

Figure 1:
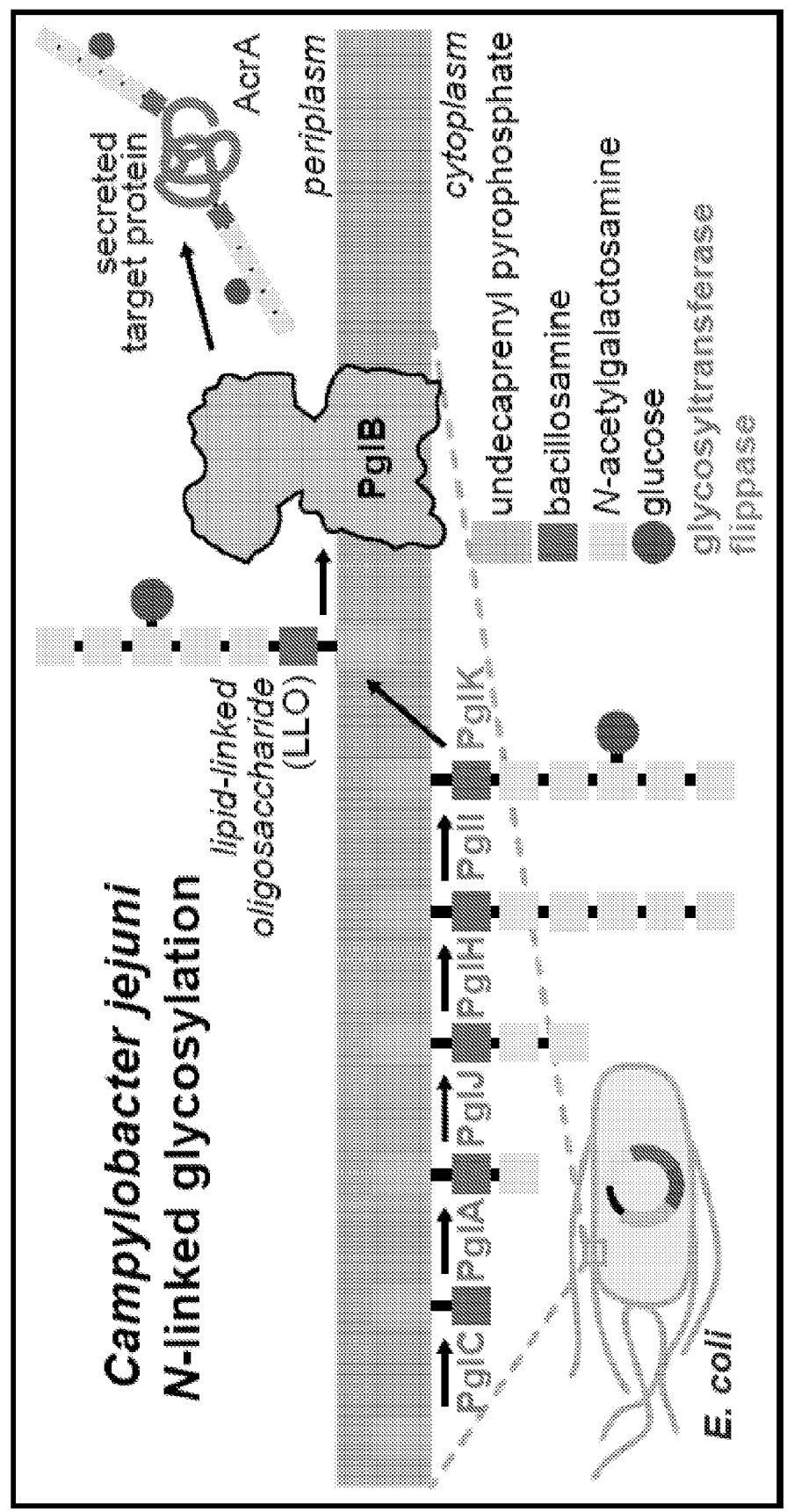
FIG. 1. Schematic depicting function of *C. jejuni* N-linked glycosylation pathway expressed in *E. coli* as adapted from Guarino C., and DeLisa M. P., Glycobiology, 2012 May 22(5):596-601, the content of which is incorporated herein by reference in its entirety.

The present invention is described herein using several definitions, as set forth below and throughout the application.

Definitions

The disclosed subject matter may be further described using definitions and terminology as follows. The definitions and terminology used herein are for the purpose of describing particular embodiments only, and are not intended to be limiting.

As used in this specification and the claims, the singular forms "a," "an," and "the" include plural forms unless the context clearly dictates otherwise. For example, the term "a gene" or "an oligosaccharide" should be interpreted to mean "one or more genes" and "one or more oligosaccharides," respectively, unless the context clearly dictates otherwise. As used herein, the term "plurality" means "two or more."

As used herein, "about", "approximately," "substantially," and "significantly" will be understood by persons of ordinary skill in the art and will vary to some extent on the context in which they are used. If there are uses of the term which are not clear to persons of ordinary skill in the art given the context in which it is used, "about" and "approximately" will mean up to plus or minus 10% of the particular term and "substantially" and "significantly" will mean more than plus or minus 10% of the particular term.

As used herein, the terms "include" and "including" have the same meaning as the terms "comprise" and "comprising." The terms "comprise" and "comprising" should be interpreted as being "open" transitional terms that permit the inclusion of additional components further to those components recited in the claims. The terms "consist" and "consisting of" should be interpreted as being "closed" transitional terms that do not permit the inclusion of additional components other than the components recited in the claims. The term "consisting essentially of" should be interpreted to be partially closed and allowing the inclusion only of additional components that do not fundamentally alter the nature of the claimed subject matter.

The phrase "such as" should be interpreted as "for example, including." Moreover the use of any and all exemplary language, including but not limited to "such as", is intended merely to better illuminate the invention and does not pose a limitation on the scope of the invention unless otherwise claimed.

Furthermore, in those instances where a convention analogous to "at least one of A, B and C, etc." is used, in general such a construction is intended in the sense of one having ordinary skill in the art would understand the convention (e.g., "a system having at least one of A, B and C" would include but not be limited to systems that have A alone, B alone, C alone, A and B together, A and C together, B and C together, and/or A, B, and C together.). It will be further understood by those within the art that virtually any disjunctive word and/or phrase presenting two or more alternative terms, whether in the description or figures, should be understood to contemplate the possibilities of including one of the terms, either of the terms, or both terms. For example, the phrase "A or B" will be understood to include the possibilities of "A" or "B" or "A and B."

All language such as "up to," "at least," "greater than," "less than," and the like, include the number recited and refer to ranges which can subsequently be broken down into ranges and subranges. A range includes each individual member. Thus, for example, a group having 1-3 members refers to groups having 1, 2, or 3 members. Similarly, a group having 6 members refers to groups having 1, 2, 3, 4, or 6 members, and so forth.

The modal verb "may" refers to the preferred use or selection of one or more options or choices among the several described embodiments or features contained within the same. Where no options or choices are disclosed regarding a particular embodiment or feature contained in the same, the modal verb "may" refers to an affirmative act regarding how to make or use and aspect of a described embodiment or feature contained in the same, or a definitive decision to use a specific skill regarding a described embodiment or feature contained in the same. In this latter context, the modal verb "may" has the same meaning and connotation as the auxiliary verb "can."

As used herein, the terms "bind," "binding," "interact," "interacting," "occupy" and "occupying" refer to covalent interactions, noncovalent interactions and steric interactions. A covalent interaction is a chemical linkage between two atoms or radicals formed by the sharing of a pair of electrons (a single bond), two pairs of electrons (a double bond) or three pairs of electrons (a triple bond). Covalent interactions are also known in the art as electron pair interactions or electron pair bonds. Noncovalent interactions include, but are not limited to, van der Waals interactions, hydrogen bonds, weak chemical bonds (via short-range noncovalent forces), hydrophobic interactions, ionic bonds and the like. A review of noncovalent interactions can be found in Alberts et al., in Molecular Biology of the Cell, 3d edition, Garland Publishing, 1994. Steric interactions are generally understood to include those where the structure of the compound is such that it is capable of occupying a site by virtue of its three dimensional structure, as opposed to any attractive forces between the compound and the site.

Polynucleotides and Synthesis Methods

The terms "nucleic acid" and "oligonucleotide," as used herein, refer to polydeoxyribonucleotides (containing 2-deoxy-D-ribose), polyribonucleotides (containing D-ribose), and to any other type of polynucleotide that is an N glycoside of a purine or pyrimidine base. There is no intended distinction in length between the terms "nucleic acid", "oligonucleotide" and "polynucleotide", and these terms will be used interchangeably. These terms refer only to the primary structure of the molecule. Thus, these terms include double- and single-stranded DNA, as well as double- and single-stranded RNA. For use in the present methods, an oligonucleotide also can comprise nucleotide analogs in which the base, sugar, or phosphate backbone is modified as well as non-purine or non-pyrimidine nucleotide analogs.

Oligonucleotides can be prepared by any suitable method, including direct chemical synthesis by a method such as the phosphotriester method of Narang et al., 1979, *Meth. Enzymol.* 68:90-99; the phosphodiester method of Brown et al., 1979, *Meth. Enzymol.* 68:109-151; the diethylphosphoramidite method of Beaucage et al., 1981, *Tetrahedron Letters* 22:1859-1862; and the solid support method of U.S. Pat. No. 4,458,066, each incorporated herein by reference. A review of synthesis methods of conjugates of oligonucleotides and modified nucleotides is provided in Goodchild, 1990, *Bioconjugate Chemistry* 1(3): 165-187, incorporated herein by reference.

The term "amplification reaction" refers to any chemical reaction, including an enzymatic reaction, which results in increased copies of a template nucleic acid sequence or results in transcription of a template nucleic acid. Amplification reactions include reverse transcription, the polymerase chain reaction (PCR), including Real Time PCR (see U.S. Pat. Nos. 4,683,195 and 4,683,202; PCR Protocols: A Guide to Methods and Applications (Innis et al., eds, 1990)), and the ligase chain reaction (LCR) (see Barany et al., U.S. Pat. No. 5,494,810). Exemplary "amplification reactions conditions" or "amplification conditions" typically comprise either two or three step cycles. Two-step cycles have a high temperature denaturation step followed by a hybridization/elongation (or ligation) step. Three step cycles comprise a denaturation step followed by a hybridization step followed by a separate elongation step.

The terms "target," "target sequence", "target region", and "target nucleic acid," as used herein, are synonymous and refer to a region or sequence of a nucleic acid which is to be amplified, sequenced, or detected.

The term "hybridization," as used herein, refers to the formation of a duplex structure by two single-stranded nucleic acids due to complementary base pairing. Hybridization can occur between fully complementary nucleic acid strands or between "substantially complementary" nucleic acid strands that contain minor regions of mismatch. Conditions under which hybridization of fully complementary nucleic acid strands is strongly preferred are referred to as "stringent hybridization conditions" or "sequence-specific hybridization conditions". Stable duplexes of substantially complementary sequences can be achieved under less stringent hybridization conditions; the degree of mismatch tolerated can be controlled by suitable adjustment of the hybridization conditions. Those skilled in the art of nucleic acid technology can determine duplex stability empirically considering a number of variables including, for example, the length and base pair composition of the oligonucleotides, ionic strength, and incidence of mismatched base pairs, following the guidance provided by the art (see, e.g., Sambrook et al., 1989, Molecular Cloning—A Laboratory Manual, Cold Spring Harbor Laboratory, Cold Spring Harbor, New York; Wetmur, 1991, Critical Review in Biochem. and Mol. Biol. 26(3/4):227-259; and Owczarzy et al., 2008, Biochemistry, 47: 5336-5353, which are incorporated herein by reference).

The term "primer," as used herein, refers to an oligonucleotide capable of acting as a point of initiation of DNA synthesis under suitable conditions. Such conditions include those in which synthesis of a primer extension product complementary to a nucleic acid strand is induced in the presence of four different nucleoside triphosphates and an agent for extension (for example, a DNA polymerase or reverse transcriptase) in an appropriate buffer and at a suitable temperature.

A primer is preferably a single-stranded DNA. The appropriate length of a primer depends on the intended use of the primer but typically ranges from about 6 to about 225 nucleotides, including intermediate ranges, such as from 15 to 35 nucleotides, from 18 to 75 nucleotides and from 25 to 150 nucleotides. Short primer molecules generally require cooler temperatures to form sufficiently stable hybrid complexes with the template. A primer need not reflect the exact sequence of the template nucleic acid, but must be sufficiently complementary to hybridize with the template. The design of suitable primers for the amplification of a given target sequence is well known in the art and described in the literature cited herein.

Primers can incorporate additional features which allow for the detection or immobilization of the primer but do not alter the basic property of the primer, that of acting as a point of initiation of DNA synthesis. For example, primers may contain an additional nucleic acid sequence at the 5' end which does not hybridize to the target nucleic acid, but which facilitates cloning or detection of the amplified product, or which enables transcription of RNA (for example, by inclusion of a promoter) or translation of protein (for example, by inclusion of a 5'-UTR, such as an Internal Ribosome Entry Site (IRES) or a 3'-UTR element, such as a poly(A)$_n$ sequence, where n is in the range from about 20 to about 200). The region of the primer that is sufficiently complementary to the template to hybridize is referred to herein as the hybridizing region.

As used herein, a primer is "specific," for a target sequence if, when used in an amplification reaction under sufficiently stringent conditions, the primer hybridizes primarily to the target nucleic acid. Typically, a primer is specific for a target sequence if the primer-target duplex stability is greater than the stability of a duplex formed between the primer and any other sequence found in the sample. One of skill in the art will recognize that various factors, such as salt conditions as well as base composition of the primer and the location of the mismatches, will affect the specificity of the primer, and that routine experimental confirmation of the primer specificity will be needed in many cases. Hybridization conditions can be chosen under which the primer can form stable duplexes only with a target sequence. Thus, the use of target-specific primers under suitably stringent amplification conditions enables the selective amplification of those target sequences that contain the target primer binding sites.

As used herein, a "polymerase" refers to an enzyme that catalyzes the polymerization of nucleotides. "DNA polymerase" catalyzes the polymerization of deoxyribonucleotides. Known DNA polymerases include, for example, *Pyrococcus furiosus* (Pfu) DNA polymerase, *E. coli* DNA polymerase I, T7 DNA polymerase and *Therms aquaticus* (Taq) DNA polymerase, among others. "RNA polymerase" catalyzes the polymerization of ribonucleotides. The foregoing examples of DNA polymerases are also known as DNA-dependent DNA polymerases. RNA-dependent DNA polymerases also fall within the scope of DNA polymerases. Reverse transcriptase, which includes viral polymerases encoded by retroviruses, is an example of an RNA-dependent DNA polymerase. Known examples of RNA polymerase ("RNAP") include, for example, T3 RNA polymerase, T7 RNA polymerase, SP6 RNA polymerase and *E. coli* RNA polymerase, among others. The foregoing examples of RNA polymerases are also known as DNA-dependent RNA polymerase. The polymerase activity of any of the above enzymes can be determined by means well known in the art.

The term "promoter" refers to a cis-acting DNA sequence that directs RNA polymerase and other trans-acting transcription factors to initiate RNA transcription from the DNA template that includes the cis-acting DNA sequence.

As used herein, the term "sequence defined biopolymer" refers to a biopolymer having a specific primary sequence. A sequence defined biopolymer can be equivalent to a genetically-encoded defined biopolymer in cases where a gene encodes the biopolymer having a specific primary sequence.

As used herein, "expression template" refers to a nucleic acid that serves as substrate for transcribing at least one RNA that can be translated into a sequence defined biopolymer (e.g., a polypeptide or protein). Expression templates include nucleic acids composed of DNA or RNA. Suitable sources of DNA for use a nucleic acid for an expression template include genomic DNA, cDNA and RNA that can be converted into cDNA. Genomic DNA, cDNA and RNA can be from any biological source, such as a tissue sample, a biopsy, a swab, sputum, a blood sample, a fecal sample, a urine sample, a scraping, among others. The genomic DNA, cDNA and RNA can be from host cell or virus origins and from any species, including extant and extinct organisms. As used herein, "expression template" and "transcription template" have the same meaning and are used interchangeably.

In certain exemplary embodiments, vectors such as, for example, expression vectors, containing a nucleic acid encoding one or more rRNAs or reporter polypeptides and/or proteins described herein are provided. As used herein, the term "vector" refers to a nucleic acid molecule capable of transporting another nucleic acid to which it has been linked. One type of vector is a "plasmid," which refers to a circular double stranded DNA loop into which additional DNA segments can be ligated. Such vectors are referred to herein as "expression vectors." In general, expression vectors of utility in recombinant DNA techniques are often in the form of plasmids. In the present specification, "plasmid" and "vector" can be used interchangeably. However, the disclosed methods and compositions are intended to include such other forms of expression vectors, such as viral vectors (e.g., replication defective retroviruses, adenoviruses and adeno-associated viruses), which serve equivalent functions.

In certain exemplary embodiments, the recombinant expression vectors comprise a nucleic acid sequence (e.g., a nucleic acid sequence encoding one or more rRNAs or reporter polypeptides and/or proteins described herein) in a form suitable for expression of the nucleic acid sequence in one or more of the methods described herein, which means that the recombinant expression vectors include one or more regulatory sequences which is operatively linked to the nucleic acid sequence to be expressed. Within a recombinant expression vector, "operably linked" is intended to mean that the nucleotide sequence encoding one or more rRNAs or reporter polypeptides and/or proteins described herein is linked to the regulatory sequence(s) in a manner which allows for expression of the nucleotide sequence (e.g., in an in vitro transcription and/or translation system). The term "regulatory sequence" is intended to include promoters, enhancers and other expression control elements (e.g., polyadenylation signals). Such regulatory sequences are described, for example, in Goeddel; Gene Expression Technology: Methods in Enzymology 185, Academic Press, San Diego, Calif (1990).

Oligonucleotides and polynucleotides may optionally include one or more non-standard nucleotide(s), nucleotide analog(s) and/or modified nucleotides. Examples of modified nucleotides include, but are not limited to diaminopurine, $S^2T$, 5-fluorouracil, 5-bromouracil, 5-chlorouracil, 5-iodouracil, hypoxanthine, xantine, 4-acetylcytosine, 5-(carboxyhydroxylmethyl)uracil, 5-carboxymethylaminomethyl-2-thiouridine, 5-carboxymethylaminomethyluracil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-methylthio-D46-isopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5-oxyacetic acid methylester, uracil-5-oxyacetic acid (v), 5-methyl-2-thiouracil, 3-(3-amino-3-N-2-carboxypropyl) uracil, (acp3)w, 2,6-diaminopurine and the like. Nucleic acid molecules may also be modified at the base moiety (e.g., at one or more atoms that typically are available to form a hydrogen bond with a complementary nucleotide and/or at one or more atoms that are not typically capable of forming a hydrogen bond with a complementary nucleotide), sugar moiety or phosphate backbone.

As utilized herein, a "deletion" means the removal of one or more nucleotides relative to the native polynucleotide sequence. The engineered strains that are disclosed herein may include a deletion in one or more genes (e.g., a deletion in gmd and/or a deletion in waaL). Preferably, a deletion results in a non-functional gene product. As utilized herein, an "insertion" means the addition of one or more nucleotides to the native polynucleotide sequence. The engineered strains that are disclosed herein may include an insertion in one or more genes (e.g., an insertion in gmd and/or an insertion in waaL). Preferably, a deletion results in a non-functional gene product. As utilized herein, a "substitution" means replacement of a nucleotide of a native polynucleotide sequence with a nucleotide that is not native to the polynucleotide sequence. The engineered strains that are disclosed herein may include a substitution in one or more genes (e.g., a substitution in gmd and/or a substitution in waaL). Preferably, a substitution results in a non-functional gene product, for example, where the substitution introduces a premature stop codon (e.g., TAA, TAG, or TGA) in the coding sequence of the gene product. In some embodiments, the engineered strains that are disclosed herein may include two or more substitutions where the substitutions introduce multiple premature stop codons (e.g., TAATAA, TAGTAG, or TGATGA).

In some embodiments, the engineered strains disclosed herein may be engineered to include and express one or more heterologous genes. As would be understood in the art, a heterologous gene is a gene that is not naturally present in the engineered strain as the strain occurs in nature. A gene that is heterologous to *E. coli* is a gene that does not occur in *E. coli* and may be a gene that occurs naturally in another microorganism (e.g. a gene from *C. jejuni*) or a gene that does not occur naturally in any other known microorganism (i.e., an artificial gene).

Peptides, Polypeptides, Proteins, and Synthesis Methods

As used herein, the terms "peptide," "polypeptide," and "protein," refer to molecules comprising a chain a polymer of amino acid residues joined by amide linkages. The term "amino acid residue," includes but is not limited to amino acid residues contained in the group consisting of alanine (Ala or A), cysteine (Cys or C), aspartic acid (Asp or D), glutamic acid (Glu or E), phenylalanine (Phe or F), glycine (Gly or G), histidine (His or H), isoleucine (Ile or I), lysine (Lys or K), leucine (Leu or L), methionine (Met or M), asparagine (Asn or N), proline (Pro or P), glutamine (Gln or Q), arginine (Arg or R), serine (Ser or S), threonine (Thr or T), valine (Val or V), tryptophan (Trp or W), and tyrosine (Tyr or Y) residues. The term "amino acid residue" also may include nonstandard or unnatural amino acids. The term "amino acid residue" may include alpha-, beta-, gamma-, and delta-amino acids.

In some embodiments, the term "amino acid residue" may include nonstandard or unnatural amino acid residues contained in the group consisting of homocysteine, 2-Aminoadipic acid, N-Ethylasparagine, 3-Aminoadipic acid, Hydroxylysine, β-alanine, β-Amino-propionic acid, allo-Hydroxylysine acid, 2-Aminobutyric acid, 3-Hydroxyproline, 4-Aminobutyric acid, 4-Hydroxyproline, piperidinic acid, 6-Aminocaproic acid, Isodesmosine, 2-Aminoheptanoic acid, allo-Isoleucine, 2-Aminoisobutyric acid, N-Methylglycine, sarcosine, 3-Aminoisobutyric acid, N-Methylisoleucine, 2-Aminopimelic acid, 6-N-Methyllysine, 2,4-Diaminobutyric acid, N-Methylvaline, Desmosine, Norvaline, 2,2'-Diaminopimelic acid, Norleucine, 2,3-Diaminopropionic acid, Ornithine, and N-Ethylglycine. The term "amino acid residue" may include L isomers or D isomers of any of the aforementioned amino acids.

Other examples of nonstandard or unnatural amino acids include, but are not limited to, a p-acetyl-L-phenylalanine, a p-iodo-L-phenylalanine, an O-methyl-L-tyrosine, a p-propargyloxyphenylalanine, a p-propargyl-phenylalanine, an L-3-(2-naphthyl)alanine, a 3-methyl-phenylalanine, an O-4-allyl-L-tyrosine, a 4-propyl-L-tyrosine, a tri-O-acetyl-GlcNAcpβ-serine, an L-Dopa, a fluorinated phenylalanine, an isopropyl-L-phenylalanine, a p-azido-L-phenylalanine, a p-acyl-L-phenylalanine, a p-benzoyl-L-phenylalanine, an L-phosphoserine, a phosphonoserine, a phosphonotyrosine, a p-bromophenylalanine, a p-amino-L-phenylalanine, an isopropyl-L-phenylalanine, an unnatural analogue of a tyrosine amino acid; an unnatural analogue of a glutamine amino acid; an unnatural analogue of a phenylalanine amino acid; an unnatural analogue of a serine amino acid; an unnatural analogue of a threonine amino acid; an unnatural analogue of a methionine amino acid; an unnatural analogue of a leucine amino acid; an unnatural analogue of a isoleucine amino acid; an alkyl, aryl, acyl, azido, cyano, halo, hydrazine, hydrazide, hydroxyl, alkenyl, alkynl, ether, thiol, sulfonyl, seleno, ester, thioacid, borate, boronate, phosphono, phosphine, heterocyclic, enone, imine, aldehyde, hydroxylamine, keto, or amino substituted amino acid, or a combination thereof; an amino acid with a photoactivatable cross-linker; a spin-labeled amino acid; a fluorescent amino acid; a metal binding amino acid; a metal-containing amino acid; a radioactive amino acid; a photocaged and/or photoisomerizable amino acid; a biotin or biotin-analogue containing amino acid; a keto containing amino acid; an amino acid comprising polyethylene glycol or polyether; a heavy atom substituted amino acid; a chemically cleavable or photocleavable amino acid; an amino acid with an elongated side chain; an amino acid containing a toxic group; a sugar substituted amino acid; a carbon-linked sugar-containing amino acid; a redox-active amino acid; an α-hydroxy containing acid; an amino thio acid; an α,α disubstituted amino acid; a β-amino acid; a γ-amino acid, a cyclic amino acid other than proline or histidine, and an aromatic amino acid other than phenylalanine, tyrosine or tryptophan.

As used herein, a "peptide" is defined as a short polymer of amino acids, of a length typically of 20 or less amino acids, and more typically of a length of 12 or less amino acids (Garrett & Grisham, Biochemistry, $2^{nd}$ edition, 1999, Brooks/Cole, 110). In some embodiments, a peptide as contemplated herein may include no more than about 2, 3, 4, 5, 6, 7, 8, 9, 10, 11, 12, 13, 14, 15, 16, 17, 18, 19, or 20 amino acids. A polypeptide, also referred to as a protein, is typically of length ≥100 amino acids (Garrett & Grisham, Biochemistry, $2^{nd}$ edition, 1999, Brooks/Cole, 110). A polypeptide, as contemplated herein, may comprise, but is not limited to, 100, 101, 102, 103, 104, 105, about 110, about 120, about 130, about 140, about 150, about 160, about 170, about 180, about 190, about 200, about 210, about 220, about 230, about 240, about 250, about 275, about 300, about 325, about 350, about 375, about 400, about 425, about 450, about 475, about 500, about 525, about 550, about 575, about 600, about 625, about 650, about 675, about 700, about 725, about 750, about 775, about 800, about 825, about 850, about 875, about 900, about 925, about 950, about 975, about 1000, about 1100, about 1200, about 1300, about 1400, about 1500, about 1750, about 2000, about 2250, about 2500 or more amino acid residues.

A peptide as contemplated herein may be further modified to include non-amino acid moieties. Modifications may include but are not limited to acylation (e.g., O-acylation (esters), N-acylation (amides), S-acylation (thioesters)), acetylation (e.g., the addition of an acetyl group, either at the N-terminus of the protein or at lysine residues), formylation lipoylation (e.g., attachment of a lipoate, a C8 functional group), myristoylation (e.g., attachment of myristate, a C14 saturated acid), palmitoylation (e.g., attachment of palmitate, a C16 saturated acid), alkylation (e.g., the addition of an alkyl group, such as an methyl at a lysine or arginine residue), isoprenylation or prenylation (e.g., the addition of an isoprenoid group such as farnesol or geranylgeraniol), amidation at C-terminus, glycosylation (e.g., the addition of a glycosyl group to either asparagine, hydroxylysine, serine, or threonine, resulting in a glycoprotein). Distinct from glycation, which is regarded as a nonenzymatic attachment of sugars, polysialylation (e.g., the addition of polysialic acid), glypiation (e.g., glycosylphosphatidylinositol (GPI) anchor formation, hydroxylation, iodination (e.g., of thyroid hormones), and phosphorylation (e.g., the addition of a phosphate group, usually to serine, tyrosine, threonine or histidine). Modifications may include the addition of a glycosylation tag (e.g., 4xDQNAT optionally at the C-terminus) and/or a histidine tag (e.g., 6xHis).

Reference may be made herein to peptides, polypeptides, proteins and variants thereof. Reference amino acid sequences may include, but are not limited to, the amino acid sequence of any of SEQ ID NOs:1-10. Variants as contemplated herein may have an amino acid sequence that includes conservative amino acid substitutions relative to a reference amino acid sequence. For example, a variant peptide, polypeptide, or protein as contemplated herein may include conservative amino acid substitutions and/or non-conservative amino acid substitutions relative to a reference peptide, polypeptide, or protein. "Conservative amino acid substitutions" are those substitutions that are predicted to interfere least with the properties of the reference peptide, polypeptide, or protein, and "non-conservative amino acid substitution" are those substitution that are predicted to interfere most with the properties of the reference peptide, polypeptide, or protein. In other words, conservative amino acid substitutions substantially conserve the structure and the function of the reference peptide, polypeptide, or protein. The following table provides a list of exemplary conservative amino acid substitutions.

TABLE 1

| Original Residue | Conservative Substitution |
|---|---|
| Ala | Gly, Ser |
| Arg | His, Lys |
| Asn | Asp, Gln, His |
| Asp | Asn, Glu |
| Cys | Ala, Ser |
| Gln | Asn, Glu, His |
| Glu | Asp, Gln, His |
| Gly | Ala |
| His | Asn, Arg, Gln, Glu |
| Ile | Leu, Val |
| Leu | Ile, Val |
| Lys | Arg, Gln, Glu |
| Met | Leu, Ile |
| Phe | His, Met, Leu, Trp, Tyr |
| Ser | Cys, Thr |
| Thr | Ser, Val |
| Trp | Phe, Tyr |
| Tyr | His, Phe, Trp |
| Val | Ile, Leu, Thr |

Conservative amino acid substitutions generally maintain: (a) the structure of the peptide, polypeptide, or protein backbone in the area of the substitution, for example, as a beta sheet or alpha helical conformation, (b) the charge or hydrophobicity of the molecule at the site of the substitution, and/or (c) the bulk of the side chain. Non-conservative amino acid substitutions generally disrupt: (a) the structure of the peptide, polypeptide, or protein backbone in the area of the substitution, for example, as a beta sheet or alpha helical conformation, (b) the charge or hydrophobicity of the molecule at the site of the substitution, and/or (c) the bulk of the side chain.

Variants comprising deletions relative to a reference amino acid sequence of peptide, polypeptide, or protein are contemplated herein. A "deletion" refers to a change in the amino acid or nucleotide sequence that results in the absence of one or more amino acid residues or nucleotides relative to a reference sequence. A deletion removes at least 1, 2, 3, 4, 5, 10, 20, 50, 100, or 200 amino acids residues or nucleotides. A deletion may include an internal deletion or a terminal deletion (e.g., an N-terminal truncation or a C-terminal truncation of a reference polypeptide or a 5'-terminal or 3'-terminal truncation of a reference polynucleotide).

Variants comprising fragment of a reference amino acid sequence of a peptide, polypeptide, or protein are contemplated herein. A "fragment" is a portion of an amino acid sequence which is identical in sequence to but shorter in length than a reference sequence. A fragment may comprise up to the entire length of the reference sequence, minus at least one amino acid residue. For example, a fragment may comprise from 5 to 1000 contiguous amino acid residues of a reference polypeptide, respectively. In some embodiments, a fragment may comprise at least 5, 10, 15, 20, 21, 22, 23, 24, 25, 26, 27, 28, 29, 30, 40, 50, 60, 70, 80, 90, 100, 150, 250, or 500 contiguous amino acid residues of a reference polypeptide. Fragments may be preferentially selected from certain regions of a molecule. The term "at least a fragment" encompasses the full length polypeptide.

Variants comprising insertions or additions relative to a reference amino acid sequence of a peptide, polypeptide, or protein are contemplated herein. The words "insertion" and "addition" refer to changes in an amino acid or sequence resulting in the addition of one or more amino acid residues. An insertion or addition may refer to 1, 2, 3, 4, 5, 10, 20, 30, 40, 50, 60, 70, 80, 90, 100, 150, or 200 amino acid residues.

Fusion proteins also are contemplated herein. A "fusion protein" refers to a protein formed by the fusion of at least one peptide, polypeptide, or protein or variant thereof as disclosed herein to at least one heterologous protein peptide, polypeptide, or protein (or fragment or variant thereof). The heterologous protein(s) may be fused at the N-terminus, the C-terminus, or both termini of the peptides or variants thereof.

"Homology" refers to sequence similarity or, interchangeably, sequence identity, between two or more polypeptide sequences. Homology, sequence similarity, and percentage sequence identity may be determined using methods in the art and described herein.

The phrases "percent identity" and "% identity," as applied to polypeptide sequences, refer to the percentage of residue matches between at least two polypeptide sequences aligned using a standardized algorithm. Methods of polypeptide sequence alignment are well-known. Some alignment methods take into account conservative amino acid substitutions. Such conservative substitutions, explained in more detail above, generally preserve the charge and hydrophobicity at the site of substitution, thus preserving the structure (and therefore function) of the polypeptide. Percent identity for amino acid sequences may be determined as understood in the art. (See, e.g., U.S. Pat. No. 7,396,664, which is incorporated herein by reference in its entirety). A suite of commonly used and freely available sequence comparison algorithms is provided by the National Center for Biotechnology Information (NCBI) Basic Local Alignment Search Tool (BLAST) (Altschul, S. F. et al. (1990) J. Mol. Biol. 215:403 410), which is available from several sources, including the NCBI, Bethesda, Md., at its website. The BLAST software suite includes various sequence analysis programs including "blastp," that is used to align a known amino acid sequence with other amino acids sequences from a variety of databases.

Percent identity may be measured over the length of an entire defined polypeptide sequence, for example, as defined by a particular SEQ ID number (e.g., any of SEQ ID NOs:1-10), or may be measured over a shorter length, for example, over the length of a fragment taken from a larger, defined polypeptide sequence, for instance, a fragment of at least 15, at least 20, at least 30, at least 40, at least 50, at least 70 or at least 150 contiguous residues. Such lengths are exemplary only, and it is understood that any fragment length supported by the sequences shown herein, in the tables, figures or Sequence Listing, may be used to describe a length over which percentage identity may be measured.

A "variant" of a particular polypeptide sequence may be defined as a polypeptide sequence having at least 50% sequence identity to the particular polypeptide sequence over a certain length of one of the polypeptide sequences using blastp with the "BLAST 2 Sequences" tool available at the National Center for Biotechnology Information's website. (See Tatiana A. Tatusova, Thomas L. Madden (1999), "Blast 2 sequences—a new tool for comparing protein and nucleotide sequences", FEMS Microbiol Lett. 174:247-250). Such a pair of polypeptides may show, for example, at least 60%, at least 70%, at least 80%, at least 90%, at least 91%, at least 92%, at least 93%, at least 94%, at least 95%, at least 96%, at least 97%, at least 98%, or at least 99% or greater sequence identity over a certain defined length of one of the polypeptides. A "variant" may have substantially the same functional activity as a reference polypeptide (e.g., glycosylase activity or other activity). "Substantially isolated or purified" amino acid sequences are contemplated herein. The term "substantially isolated or purified" refers to amino acid sequences that are removed from their natural environment, and are at least 60% free, preferably at least 75% free, and more preferably at least 90% free, even more preferably at least 95% free from other components with which they are naturally associated. Variant polypeptides as contemplated herein may include variant polypeptides of any of SEQ ID NOs:1-10).

As used herein, "translation template" refers to an RNA product of transcription from an expression template that can be used by ribosomes to synthesize polypeptides or proteins.

The term "reaction mixture," as used herein, refers to a solution containing reagents necessary to carry out a given reaction. A reaction mixture is referred to as complete if it contains all reagents necessary to perform the reaction. Components for a reaction mixture may be stored separately in separate container, each containing one or more of the total components. Components may be packaged separately for commercialization and useful commercial kits may contain one or more of the reaction components for a reaction mixture.

The steps of the methods described herein can be performed in any suitable order unless otherwise indicated herein or otherwise clearly contradicted by context. The steps may be repeated or reiterated any number of times to achieve a desired goal unless otherwise indicated herein or otherwise clearly contradicted by context.

Preferred aspects of this invention are described herein, including the best mode known to the inventors for carrying out the invention. Variations of those preferred aspects may become apparent to those of ordinary skill in the art upon reading the foregoing description. The inventors expect a person having ordinary skill in the art to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

Cell-Free Protein Synthesis (CFPS)

The strains and systems disclosed herein may be applied to cell-free protein synthesis methods as known in the art. See, for example, U.S. Pat. Nos. 4,496,538; 4,727,136; 5,478,730; 5,556,769; 5,623,057; 5,665,563; 5,679,352; 6,168,931; 6,248,334; 6,531,131; 6,869,774; 6,994,986; 7,118,883; 7,189,528; 7,338,789; 7,387,884; 7,399,610; 8,703,471; and 8,999,668. See also U.S. Published Application Nos. 2015-0259757, 2014-0295492, 2014-0255987, 2014-0045267, 2012-0171720, 2008-0138857, 2007-0154983, 2005-0054044, and 2004-0209321. See also U.S. Published Application Nos. 2005-0170452; 2006-0211085; 2006-0234345; 2006-0252672; 2006-0257399; 2006-0286637; 2007-0026485; 2007-0178551. See also Published PCT International Application Nos. 2003/056914; 2004/013151; 2004/035605; 2006/102652; 2006/119987; and 2007/120932. See also Jewett, M. C., Hong, S. H., Kwon, Y. C., Martin, R. W., and Des Soye, B. J. 2014, "Methods for improved in vitro protein synthesis with proteins containing non standard amino acids," U.S. Patent Application Ser. No. 62/044,221; Jewett, M. C., Hodgman, C. E., and Gan, R. 2013, "Methods for yeast cell-free protein synthesis," U.S. Patent Application Ser. No. 61/792,290; Jewett, M. C., J. A. Schoborg, and C. E. Hodgman. 2014, "Substrate Replenishment and Byproduct Removal Improve Yeast Cell-Free Protein Synthesis," U.S. Patent Application Ser. No. 61/953,275; and Jewett, M. C., Anderson, M. J., Stark, J. C., Hodgman, C. E. 2015, "Methods for activating natural energy metabolism for improved yeast cell-free protein synthesis," U.S. Patent Application Ser. No. 62/098,578. See also Guarino, C., & DeLisa, M. P. (2012). A prokaryote-based cell-free translation system that efficiently synthesizes glycoproteins. Glycobiology, 22(5), 596-601. The contents of all of these references are incorporated in the present application by reference in their entireties.

In certain exemplary embodiments, one or more of the methods described herein are performed in a vessel, e.g., a single, vessel. The term "vessel," as used herein, refers to any container suitable for holding on or more of the reactants (e.g., for use in one or more transcription, translation, and/or glycosylation steps) described herein. Examples of vessels include, but are not limited to, a microtitre plate, a test tube, a microfuge tube, a beaker, a flask, a multi-well plate, a cuvette, a flow system, a microfiber, a microscope slide and the like.

In certain exemplary embodiments, physiologically compatible (but not necessarily natural) ions and buffers are utilized for transcription, translation, and/or glycosylation, e.g., potassium glutamate, ammonium chloride and the like. Physiological cytoplasmic salt conditions are well-known to those of skill in the art.

The strains and systems disclosed herein may be applied to cell-free protein methods in order to prepare glycosylated macromolecules (e.g., glycosylated peptides, glycosylated proteins, and glycosylated lipids). Glycosylated proteins that may be prepared using the disclosed strains and systems may include proteins having N-linked glycosylation (i.e., glycans attached to nitrogen of asparagine and/or arginine side-chains) and/or O-linked glycosylation (i.e., glycans attached to the hydroxyl oxygen of serine, threonine, tyrosine, hydroxylysine, and/or hydroxyproline). Glycosylated lipids may include O-linked glycans via an oxygen atom, such as ceramide.

The glycosylated macromolecules disclosed herein may include unbranched and/or branched sugar chains composed of monomers as known in the art such as, but not limited to, glucose (e.g., β-D-glucose), galactose (e.g., β-D-galactose), mannose (e.g., β-D-mannose), fucose (e.g., α-L-fucose), N-acetyl-glucosamine (GlcNAc), N-acetyl-galactosamine (GalNAc), neuraminic acid, N-acetylneuraminic acid (i.e., sialic acid), and xylose, which may be attached to the glycosylated macromolecule, growing glycan chain, or donor molecule (e.g., a donor lipid and/or a donor nucleotide) via respective glycosyltransferases (e.g., oligosaccharyltransferases, GlcNAc transferases, GalNAc transferases, galactosyltransferases, and sialyltransferases). The glycosylated macromolecules disclosed herein may include glycans as known in the art.

The disclosed cell-free protein synthesis systems may utilize components that are crude and/or that are at least partially isolated and/or purified. As used herein, the term "crude" may mean components obtained by disrupting and lysing cells and, at best, minimally purifying the crude components from the disrupted and lysed cells, for example by centrifuging the disrupted and lysed cells and collecting the crude components from the supernatant and/or pellet after centrifugation. The term "isolated or purified" refers to components that are removed from their natural environment, and are at least 60% free, preferably at least 75% free, and more preferably at least 90% free, even more preferably at least 95% free from other components with which they are naturally associated.

Cell-Free Glycoprotein Synthesis (CFGpS) in Prokaryotic Cell Lysates Enriched with Components for Glycosylation Disclosed are compositions and methods for performing cell-free glycoprotein synthesis (CFGpS). In some embodiments, the composition and methods include or utilize prokaryotic cell lysates enriched with components for glycosylation and prepared from genetically modified strains of prokaryotes.

In some embodiments, the genetically modified prokaryote is a genetically modified strain of *Escherichia coli* or any other prokaryote suitable for preparing a lysate for CFGpS. Optionally, the modified strain of *Escherichia coli* is derived from rEc.C321. Preferably, the modified strain includes genomic modifications (e.g., deletions of genes rendering the genes inoperable) that preferably result in lysates capable of high-yielding cell-free protein synthesis. Also, preferably, the modified strain includes genomic modification (e.g., deletions of genes rendering the genes inoperable) that preferably result in lysates comprising sugar precursors for glycosylation at relatively high concentrations (e.g., in comparison to a strain not having the genomic modification). In some embodiments, a lysate prepared from the modified strain comprises sugar precursors at a concentration that is at least 20%, 30%, 40%, 50%, 60%, 70%, 80%, 90%, 100%, 150%, 200%, or higher than a lysate prepared from a strain that is not modified. By way of example, but not by way of limitation, bacterial source strains useful in the present methods, kits, and systems include recombinant strains of *E. coli*, such as recombinant strains of *E. coli* that are deficient in one or more gene products selected from prfA, endA, gor, rne, and lpxM. Suitable recombinant strains for the disclosed methods, kits, and systems may include, but are not limited to, r*E. coli* ΔprfA ΔendA Δgor Δrne (705), *E. coli* BL21(DE3), *E. coli* CLM24, *E. coli* CLM24 ΔlpxM, *E. coli* CLM24 ΔlpxM CH-IpxE, *E. coli* CLM24 ΔlpxM CH-IpxE TT-IpxE, *E. coli* CLM24 ΔlpxM CH-IpxE TT-IpxE KL-IpxE, and *E. coli* CLM24 ΔlpxM CH-IpxE TT-IpxE KL-IpxE KO-IpxE.

In some embodiments, the modified strain includes a modification that results in an increase in the concentration of a monosaccharide utilized in glycosylation (e.g., glucose, mannose, N-acetyl-glucosamine (GlcNAc), N-acetyl-galactosamine (GalNAc), galactose, sialic acid, neuraminic acid, fucose). As such, the modification may inactivate an enzyme that metabolizes a monosaccharide or polysaccharide utilized in glycosylation. In some embodiments, the modification inactivates a dehydratase or carbon-oxygen lyase enzyme (EC 4.2) (e.g., via a deletion of at least a portion of the gene encoding the enzyme). In particular, the modification may inactivate a GDP-mannose 4,6-dehydratase (EC 4.2.1.47). When the modified strain is *E. coli*, the modification may include an inactivating modification in the gmd gene (e.g., via a deletion of at least a portion of the gmd gene). The sequence of the *E. coli* gmd gene is provided herein as SEQ ID NO:1 and the amino acid sequence of *E. coli* GDP-mannose 4,6-dehydratase is provided as SEQ ID NO:2.

In some embodiments, the modified strain includes a modification that inactivates an enzyme that is utilized in the glycosyltransferase pathway. In some embodiments, the modification inactivates an oligosaccharide ligase enzyme (e.g., via a deletion of at least a portion of the gene encoding the enzyme). In particular, the modification may inactivate an O-antigen ligase that optionally conjugates an O-antigen to a lipid A core oligosaccharide. The modification may include an inactivating modification in the waaL gene (e.g., via a deletion of at least a portion of the waaL gene). The sequence of the *E. coli* waaL gene is provided herein as SEQ ID NO:3 and the amino acid sequence of *E. coli* O-antigen ligase is provided as SEQ ID NO:4.

In some embodiments, the modified strain includes a modification that inactivates a dehydratase or carbon-oxygen lyase enzyme (e.g., via a deletion of at least a portion of the gene encoding the enzyme) and also the modified strain includes a modification that inactivates an oligosaccharide ligase enzyme (e.g., via a deletion of at least a portion of the gene encoding the enzyme). The modified strain may include an inactivation or deletion of both gmd and waaL.

In some embodiments, the modified strain may be modified to express one or more orthogonal or heterologous genes. In particular, the modified strain may be genetically modified to express an orthogonal or heterologous gene that is associated with glycoprotein synthesis such as a glycosyltransferase (GT) which is involved in the lipid-linked oligosaccharide (LLO) pathway. In some embodiments, the modified strain may be modified to express an orthogonal or heterologous oligosaccharyltransferase (EC 2.4.1.119) (OST). Oligosaccharyltransferases or OSTs are enzymes that transfer oligosaccharides from lipids to proteins.

In particular, the modified strain may be genetically modified to express an orthogonal or heterologous gene in a glycosylation system (e.g., an N-linked glycosylation system and/or an O-linked glycosylation system). The N-linked glycosylation system of *Campylobacter jejuni* has been transferred to *E. coli*. (See Wacker et al., "N-linked glycosylation in *Campylobacter jejuni* and its functional transfer into *E. coli*," Science 2002, Nov. 29; 298(5599):1790-3, the content of which is incorporated herein by reference in its entirety). In particular, the modified strain may be modified to express one or more genes of the pgl locus of *C. jejuni* or one or more genes of a homologous pgl locus. The genes of the pgl locus include pglG, pglF, pglE, wlaJ, pglD, pglC, pglA, pglB, pglJ, pglI, pglH, pglK, and gne, and are used to synthesize lipid-linked oligosaccharides (LLOs) and transfer the oligosaccharide moieties of the LLOs to a protein via an oligosaccharyltransferase.

Suitable orthogonal or heterologous oligosaccharyltransferases (OST) which may be expressed in the genetically modified strains may include *Campylobacter jejuni* oligosaccharyltransferase PglB. The gene for the *C. jejuni* OST is referred to as pglB, which sequence is provided as SEQ ID NO:5 and the amino acid sequence of *C. jejuni* PglB is provided as SEQ ID NO:6. PglB catalyzes transfer of an oligosaccharide to a D/E-Y-N-X-S/T motif (Y, X≠P) present on a protein. Additional non-limiting examples of OST enzymes useful in the methods, kits, and systems disclosed herein may include, but are not limited to, *Campylobacter coli* PglB, *Campylobacter lari* PglB, *Desulfovibrio desulfuricans* PglB, *Desulfovibrio gigas* PglB, and *Desulfovibrio vulgaris* PglB.

Crude cell lysates may be prepared from the modified strains disclosed herein. The crude cell lysates may be prepared from different modified strains as disclosed herein and the crude cell lysates may be combined to prepare a mixed crude cell lysate. In some embodiments, one or more crude cell lysates may be prepared from one or more modified strains including a genomic modification (e.g., deletions of genes rendering the genes inoperable) that preferably result in lysates comprising sugar precursors for glycosylation at relatively high concentrations (e.g., in comparison to a strain not having the genomic modification). In some embodiments, one or more crude cell lysates may be prepared from one or more modified strains that have been modified to express one or more orthogonal or heterologous genes or gene clusters that are associated with glycoprotein synthesis. Preferably, the crude cell lysates or mixed crude cell lysates are enriched in glycosylation components, such as lipid-linked oligosaccharides (LLOs), glycosyltransferases (GTs), oligosaccharyltransferases (OSTs), or any combination thereof. More preferably, the crude cell lysates or mixed crude cell lysates are enriched in $Man_3GlcNAc_2$ LLOs representing the core eukaryotic glycan and/or $Man_3GlcNAc_4Gal_2Neu_5Ac_2$ LLOs representing the fully sialylated human glycan. By way of example, but not by way of limitation, glycan structures useful in the disclosed methods, kits and systems may include but are not limited to *Francisella tularensis* SchuS4 O-polysaccharides, *Escherichia coli* O78 O-polysaccharides, *Escherichia coli* O-7 O-polysaccharides, *Escherichia coli* O-9 O-polysaccharides primer, *Campylobacter jejuni* heptasaccharides N-glycan, *Campylobacter lari* PglB hexasaccharides N-glycan, engineered *Campylobacter lari* PglB hexasaccharides N-glycan, *Wolinella succinogenes* hexasaccharide N-glycan, and eukaryotic Man3GlcNac2 N-glycan structure.

The disclosed crude cell lysates may be used in cell-free glycoprotein synthesis (CFGpS) systems to synthesize a variety of glycoproteins. The glycoproteins synthesized in the CFGpS systems may include prokaryotic glycoproteins and eukaryotic proteins, including human proteins. The CFGpS systems may be utilized in methods for synthesizing glycoproteins in vitro by performing the following steps using the crude cell lysates or mixtures of crude cell lysates disclosed herein: (a) performing cell-free transcription of a gene for a target glycoprotein; (b) performing cell-free translation; and (c) performing cell-free glycosylation. The methods may be performed in a single vessel or multiple vessels. Preferably, the steps of the synthesis method may be performed using a single reaction vessel. The disclosed methods may be used to synthesis a variety of glycoproteins, including prokaryotic glycoproteins and eukaryotic glycoproteins.

Bioconjugate Vaccine Production

While protein-glycan coupling technology (PGCT) represents a simplified and cost-effective strategy for bioconjugate vaccine production, it has three main limitations. First, process development timelines, glycosylation pathway design-build-test (DBT) cycles, and bioconjugate production are all limited by cellular growth. Second, it has not yet been shown whether FDA-approved carrier proteins, such as the toxins from *Clostridium tetani* and *Corynebacterium diptheriae*, have not yet been demonstrated to be compatible with N-linked glycosylation in living *E. coli*. Third, select non-native glycans are known to be transferred with low efficiency by the *C. jejuni* oligosaccharyltransferase (OST), PglB.

A modular, in vitro platform for production of bioconjugates has the potential to address all of these limitations. Here, we demonstrate that bioconjugates against pathogenic strains of *Franciscella tualrensis* and *Escherichia coli* can be produced through coordinated in vitro transcription, translation, and N-glycosylation in cell-free glycoprotein synthesis (CFGpS) reactions lasting just 20 hours. This system has the potential to reduce process development and distribution timelines for novel antibacterial vaccines from weeks to days. Further, because of the modular nature of the CFGpS platform and the fact that cell-free systems have demonstrated advantages for production of membrane proteins compared to living cells, this method could be readily applied to produce bioconjugates using FDA-approved carrier proteins, such as the *Clostridium tetani* and *Corynebacterium diptheriae* toxins, which are membrane localized. This could be accomplished simply by supplying plasmid encoding these carrier proteins to CFGpS reactions. Additionally, because of the modular nature of CFGpS, the in vitro approach could be used to prototype other natural or engineered homologs of the archetypal *C. jejuni* OST to identify candidate OSTs with improved efficiency for transfer of O-antigen LLOs of interest. This can be accomplished by enriching lysates with OSTs of interest and mixing them with LLO lysates in mixed lysate CFGpS reactions, as we have described previously. (See WO 2017/117539, the content of which is incorporated herein by reference in its entirety). Finally, we demonstrate that cell-free bioconjugate synthesis reactions can be lyophilized and retain bioconjugate synthesis capability, demonstrating the potential of the CFGpS system for on-demand, portable, and low cost production or development efforts for novel vaccines. This novel method for in vitro bioconjugate vaccine production has demonstrated advantages for rapid, modular, and portable vaccine prototyping and production compared to existing methods. Our technology enables rapid production of bioconjugate vaccines directed against a user-specified bacterial target for therapeutic development or fundamental research.

The present inventors are not aware of any prokaryotic cell-free system with the capability to produce glycoproteins or bioconjugate vaccines. There are commercial eukaryotic cell lysate systems for cell-free glycoprotein production (Promega, ThermoFisher), but these systems do not involve overexpression of orthogonal glycosylation machinery and do not enable modular, user-specified glycosylation in the way our system can. For this reason, we feel that there is still substantial commercial promise for our invention.

The presently disclosed method for in vitro bioconjugate vaccine production has demonstrated advantages for rapid, modular, and portable vaccine prototyping and production compared to existing methods. This system addresses limitations of existing production approaches, making it an attractive alternative or complementary strategy for antibacterial vaccine production. In light of the growing healthcare concerns caused by antibiotic-resistant bacterial infections, this method has the potential to be extremely valuable for development, production, and distribution of novel vaccines against diverse pathogenic bacterial strains. Advantages of the disclosed method include: on demand expression of bioconjugate vaccines; prototyping novel bioconjugate vaccine candidates; prototyping novel bioconjugate vaccine production pathways; distribution of bioconjugate vaccines to resource-poor settings.

In summary, we disclose the first prokaryotic cell-free system capable of coordinated, cell-free transcription, translation, and glycosylation of glycoprotein vaccines. The disclosed system enables production of bioconjugate vaccines in 20 hours. The modularity of the system enables rapid prototyping of novel glycosylation pathways and vaccine candidates with various carrier proteins. Suitable carriers may include but are not limited to Haemophilus influenzae protein D (PD) (SEQ ID NO: 7), Neisseria meningitidis porin protein (PorA) (SEQ ID NO: 8), Corynebacterium diphtheriae toxin (CRM197) (SEQ ID NO: 9), Clostridium tetani toxin (TT) (SEQ ID NO: 10), fragment C of TT (TTc), the light chain domains of TT (TTlight), Escherichia coli maltose binding protein, human glucagon peptide fused with MBP, Superfolder Green Fluorescent Protein (GFP), single-chain variable antibody fragment (scFv), human erythropoietin variants, Campylobacter jejuni AcrA, and Pseudomonas aeruginosa exotoxin A (EPA), or variants thereof. The components and products of the system maybe lyophilized, which enables the potential for broad and rapid distribution of vaccine production technology. The disclosed system reduces the time required to produce bioconjugates in a prokaryotic cell lysate from weeks to days, which could provide competitive advantage in commercialization of the technology.

The disclosed bioconjugates may be formulated as vaccines which optionally may include additional agents for inducing and/or potentiating an immune response such as adjuvants. The term "adjuvant" refers to a compound or mixture that enhances an immune response. An adjuvant can serve as a tissue depot that slowly releases the antigen and also as a lymphoid system activator that non-specifically enhances the immune response. Examples of adjuvants which may be utilized in the disclosed compositions include but are not limited to, co-polymer adjuvants (e.g., Pluronic L121® brand poloxamer 401, CRL1005, or a low molecular weight co-polymer adjuvant such as Polygen® adjuvant), poly (I:C), R-848 (a Th1-like adjuvant), resiquimod, imiquimod, PAM3CYS, aluminum phosphates (e.g., $AlPO_4$), loxoribine, potentially useful human adjuvants such as BCG (Bacille Calmette-Guerin) and Corynebacterium parvum, CpG oligodeoxynucleotides (ODN), cholera toxin derived antigens (e.g., CTA1-DD), lipopolysaccharide adjuvants, complete Freund's adjuvant, incomplete Freund's adjuvant, saponin (e.g., Quil-A), mineral gels such as aluminum hydroxide, surface active substances such as lysolecithin, pluronic polyols, polyanions, peptides, oil or hydrocarbon emulsions in water (e.g., MF59 available from Novartis Vaccines or Montanide ISA 720), keyhole limpet hemocyanins, and dinitrophenol.

ILLUSTRATIVE EMBODIMENTS

The following embodiments are illustrative and are not intended to limit the scope of the claimed subject matter.

Embodiment 1. A method for synthesizing a N-glycosylated recombinant protein carrier which optionally may be utilized as a bioconjugate immunogen or vaccine, the method comprising performing coordinated transcription, translation, and N-glycosylation of the recombinant protein carrier thereby providing the N-glycosylated recombinant protein carrier which may be utilized as the bioconjugate immunogen or vaccine, wherein the N-glycosylated recombinant protein carrier comprises: (i) a consensus sequence (which optionally is inserted in the protein carrier), N-X-S/T, wherein X may be any natural or unnatural amino acid except proline; and (ii) at least one antigenic polysaccharide from at least one bacterium N-linked to the recombinant protein carrier, wherein the at least one antigenic polysaccharide optionally is at least one bacterial O-antigen, optionally from one or more strains of E. coli or Franciscella tularensis; and the bioconjugate vaccine optionally may include an adjuvant.

Embodiment 2. The method of embodiment 1, wherein the carrier protein is an engineered variant of E. coli maltose binding protein (MBP).

Embodiment 3. The method of embodiment 1, wherein the carrier protein is selected from a detoxified variant of the toxin from Clostridium tetani and a detoxified variant of the toxin from Corynebacterium diptheriae Embodiment 4. The method of embodiment 1, wherein the carrier protein is selected from Haemophilus influenzae protein D (PD) and Neisseria meningitidis porin protein (PorA), and variants thereof.

Embodiment 5. The method of any of the foregoing embodiments, wherein the method utilizes an oligosaccharyltransferase (OST) which is a naturally occurring bacterial homolog of C. jejuni PglB.

Embodiment 6. The method of any of embodiments 1-4, wherein the method utilizes an OST that is an engineered variant of C. jejuni PglB.

Embodiment 7. The method of any of embodiments 1-4, wherein the method utilizes an OST that is a naturally occurring archaeal OST.

Embodiment 8. The method of any of embodiments 1-4, wherein the method utilizes an OST which is a naturally occurring single-subunit eukaryotic OST, such as those found in Trypanosoma bruceii.

Embodiment 9. A method for crude cell lysate preparation in which orthogonal genes or gene clusters are expressed in a source strain for the crude cell lysate, which results in lysates enriched with glycosylation components (lipid-linked oligosaccharides (LLOs), oligosaccharyltransferases (OSTs), and/or both LLOs and OSTs), and optionally which results in a separate lysate enriched with LLOs (e.g., LLOs associated with O-antigen) and a separate lysate enriched with OSTs (e.g., for which the LLOs are a substrate), and optionally combining the separate lysates to perform cell-free protein synthesis of a carrier protein which is glycosylated with the glycan component of the LLOs via the OST's enzyme activity, and further optionally purifying the glycosylated carrier protein and optionally administering the glycosylated carrier protein as an immunogen.

Embodiment 10. The method of embodiment 9, in which the source strain overexpresses a gene encoding an oligosaccharyltransferase (OST).

Embodiment 11. The method of embodiment 9 or 10, in which the source strain overexpresses a synthetic glycosyltransferase pathway, resulting in the production of O-antigens, optionally O-antigens from *F. tularensis* Schu S4 lipid-linked oligosaccharides (FtLLOs).

Embodiment 12. The method of embodiment 9 or 10, in which the source strain overexpresses a synthetic glycosyltransferase pathway, resulting in the production of antigens, optionally O-antigens from enterotoxigenic *E. coli* O78 lipid-linked oligosaccharides (EcO78LLOs).

Embodiment 13. The method of any of embodiments 9-12, in which the source strain overexpresses a glycosyltransferase pathway and an OST, resulting in the production of LLOs and OST.

Embodiment 14. The method of embodiment 9 or 10, in which the source strain overexpresses an O-antigen glycosyltransferase pathway from a pathogenic bacterial strain, resulting in the production of O-antigen lipid-linked oligosaccharides (LLOs).

Embodiment 15. A method for cell-free production of a bioconjugate immunogen or vaccine that involves, as one or more steps, mixing crude cell lysates (e.g., any of the crude cell lysates of embodiments 9-14).

Embodiment 16. The method of embodiment 15, in which the bioconjugate immunogen or vaccine comprises an immunogenic carrier that is a protein or a peptide.

Embodiment 17. The method of embodiment 15, in which the bioconjugate immunogen or vaccine comprises an immunogenic carrier that is a protein or peptide comprising a protein or peptide thereof selected form *Haemophilus influenzae* protein D (PD), *Neisseria meningitidis* porin protein (PorA), *Corynebacterium diphtheriae* toxin (CRM197), *Clostridium tetani* toxin (TT), and *Escherichia coli* maltose binding protein, and variants thereof.

Embodiment 18. The method of any of embodiments 1-17 in which the components of the method may be lyophilized and retain bioconjugate synthesis capability when rehydrated.

Embodiment 19. The method of any of embodiments 15-18 where the goal is on-demand vaccine production.

Embodiment 20. The method of any of embodiments 15-19 where the goal is vaccine production in resource-limited settings.

Embodiment 21. A kit for synthesizing a N-glycosylated carrier protein in vitro, the kit comprising one or more of the following components: (i) a first component comprising a cell lysate that comprises an orthogonal oligosaccharyltransferase (OST); (ii) a second component comprising a cell lysate that comprises an O-antigen (e.g., lipid-linked oligosaccharides (LLOs) comprising O-antigen; (iii) a third component comprising a transcription template and optionally a polymerase for synthesizing an mRNA from the transcription template encoding a carrier protein, the carrier protein comprising an inserted and/or a naturally occurring consensus sequence, N-X-S/T, wherein X may be any natural or unnatural amino acid except proline.

Embodiment 22. The kit of embodiment 21, wherein one or more of the first component, the second component, and the third component are lyophilized and retain biological activity when rehydrated.

Embodiment 23. The kit of embodiment 21 or 22, wherein the first component cell lysate is produced from a source strain (e.g., *E. coli*) that overexpresses a gene encoding the orthogonal OST (e.g. *C. jejuni* PglB).

Embodiment 24. The kit of any of embodiments 21-23, wherein the second component cell lysate is produced from a source strain that overexpresses a synthetic glycosyltransferase pathway (e.g., the biosynthetic machinery to produce the *Franciscella tularensis* Schu S4 O-antigen (FtLLOs lysate) or the biosynthetic machinery to produce the enterotoxigenic *E. coli* O78 lipid-linked oligosaccharides (EcO78LLOs lysate).

Embodiment 25. A method for cell-free production of a glycoprotein which optionally may be a bioconjugate suitable for use as a bioconjugate immunogen or vaccine, the method comprising: (a) mixing a first cell lysate comprising an orthogonal oligosaccharyltransferase (OST) and a second cell lysate that comprises an O-antigen (e.g., as lipid-linked oligosaccharides (LLOs)) to prepare a cell-free protein synthesis reaction; (b) transcribing and translating a carrier protein in the cell-free protein synthesis reaction (e.g., optionally by adding a transcription template for the carrier protein and/or a polymerase to the cell-free protein synthesis reaction), the carrier protein comprising an inserted and/or naturally occurring consensus sequence, N-X-S/T, wherein X may be any natural or unnatural amino acid except proline; and (c) glycosylating the carrier protein in the cell-free protein synthesis reaction with the bacterial o-antigen.

Embodiment 25. The method of embodiment 24, wherein the second cell lysate comprises the O-antigen as part of lipid-linked oligosaccharides (LLOs).

Embodiment 26. The method of embodiment 24 or 25, further comprising formulating the glycoprotein as a vaccine composition optionally including an adjuvant.

Embodiment 27. A bioconjugate immunogen or vaccine prepared by any of the foregoing methods and/or kits.

Embodiment 28. A vaccination method comprising administering the vaccine of embodiment 27 to a subject in need thereof.

EXAMPLES

The following Examples are illustrative and are not intended to limit the scope of the claimed subject matter.

Example 1—Method for Rapid In Vitro Synthesis of Bioconjugate Vaccines Via Recombinant Production of N-Glycosylated Proteins in Prokaryotic Cell Lysates Abstract Conjugate vaccines are among the safest and most effective methods for prevention of life-threatening bacterial infections [1-10]. Bioconjugate vaccines are a type of conjugate vaccine produced via protein glycan coupling technology (PGCT), in which polysaccharide antigens are conjugated via N-glycosylation to recombinant carrier proteins using a bacterial oligosaccharyltransferase (OST) in living *Escherichia coli* cells [11]. Bioconjugate vaccines have the potential to greatly reduce the time and cost required to produce antibacterial vaccines. However, PGCT is limited by i) the length of in vivo process development timelines and ii) the fact that FDA-approved carrier proteins, such as the toxins from *Clostridium tetani* and *Corynebacterium diptheriae*, have not yet been demonstrated to be compatible with N-linked glycosylation in living *E. coli*. Here, we have applied cell-free glycoprotein synthesis (CFGpS) technology to enable rapid in vitro production of bioconjugate vaccines against pathogenic strains of *Escherichia coli* and *Franscicella tularensis* in reactions lasting 20 hours. Due to the modular nature of the CFGpS system, this cell-free strategy could be easily applied to produce bioconjugates using FDA-approved carrier proteins or additional vaccines against pathogenic bacteria whose surface antigen gene clusters are known [11] [9] [7, 10] [3, 5, 6, 8]. We further show that this system can be lyophilized and retain bioconjugate synthesis capability, demonstrating the potential for on-demand vaccine production and development in resource-poor settings. This work represents the first demonstration of bioconjugate vaccine production in *E. coli* lysates and has promising applications as a portable prototyping or production platform for antibacterial vaccine candidates.

Background and Significance

Glycosylation, or the attachment of glycans (sugars) to proteins, is the most abundant post-translational modification in nature and plays a pivotal role in protein folding and activity [1-4]. When it was first discovered in the 1930s [12], glycosylation was thought to be exclusive to eukaryotes. However, glycoproteins were also discovered in archaea in the 1970s [13, 14], and in bacteria in the late 1990s and early 2000s [15, 16], establishing glycosylation as a central post-translational modification in all domains of life. A vast diversity of glycan structures, including both linear and highly branched polysaccharide chains, have been described [17], giving rise to exponentially increased information content compared to other polypeptide modifications [18].

As a consequence of its role in protein structure and information storage, glycosylation is involved in a variety of biological processes. In eukaryotes, glycoproteins are involved in immune recognition and response, intracellular trafficking, and intercellular signaling [19-22]. Furthermore, changes in glycosylation have been shown to correlate with disease states, including cancer [23-25], inflammation [26-29], and Alzheimer's disease [30]. In prokaryotes, glycosylation is known to play important roles in virulence and host invasion [31-33]. Based on the vital role of glycosylation in numerous biological processes, it has been proposed that the central dogma of biology be adapted to include glycans as a central component [34].

The most common forms of glycosylation are asparagine linked (N-linked) and serine (Ser) or threonine (Thr) linked (O-linked) [35]. N-linked glycosylation is characterized by the addition of a glycan moiety to the side chain nitrogen of asparagine (Asn) residues by an oligosaccharyltransferase (OST) that recognizes the consensus sequence Asn-X-Ser/Thr, where X is any amino acid except proline [36, 37]. This process occurs in the endoplasmic reticulum and aids in protein folding, quality control, and trafficking [38]. O-linked glycosylation occurs in the Golgi apparatus following the attachment of N-glycans. Unlike N-linked glycosylation, there is no known consensus sequence for O-linked glycosylation [39, 40]. Despite the importance of glycans in biology, glycoscience was recently identified as an understudied field. A 2012 National Research Council of the U.S. National Academies report highlighted the critical need for transformational advances in glycoscience [41]. The discovery of glycosylation pathways in bacteria is enabling new discoveries about this important post-translational modification [42, 43], but new synthetic and analytical tools are needed to advance the field.

Since the recent discovery of bacterial glycosylation, proteins bearing N- and O-linked glycans have been found in a number of bacteria [44, 45]. The best-studied bacterial glycosylation system is the pgl pathway from *Campylobacter jejuni*, which has been shown to express functionally in *Escherichia coli* (FIG. 1) [46]. In *C. jejuni*, proteins are N-glycosylated with the 1.406 kDa GlcGalNAc$_5$Bac heptasaccharide (Glc: glucose, GalNAc: N-acetylgalactosamine, Bac: bacillosamine). GTs assemble the heptasaccharide onto the lipid anchor undecaprenol pyrophosphate (Und-PP), which is then used as a substrate for the OST (PglB) for N-linked glycosylation [47-49]. This pathway is significantly simpler than eukaryotic glycosylation pathways, and has been leveraged to increase our understanding of the mechanism of N-linked glycosylation [42, 43].

Though not all bacteria synthesize glycoproteins, glycosylation is often involved in the synthesis of the bacterial cell wall. Lipopolysaccharide (LPS) molecules are a major component of the outer membrane of many Gram-negative bacteria, and are made up of a lipid anchor, an oligosaccharide core, and a variable polysaccharide region known as the O-antigen [32]. Capsular polysaccharides (CPS) are another type of surface polysaccharide similar in structure to LPS, except that in this case the polysaccharide region is linked directly to lipid A or a phospholipid anchor [31]. LPS antigens (O-PS) and CPS are one of the main tools used by bacterial pathogens for survival in hostile host environments and for host invasion [50-53]. As a result, elucidation of CPS and O-PS biosynthesis mechanisms is of interest for antibiotic and antibacterial vaccine development.

Figure 2:
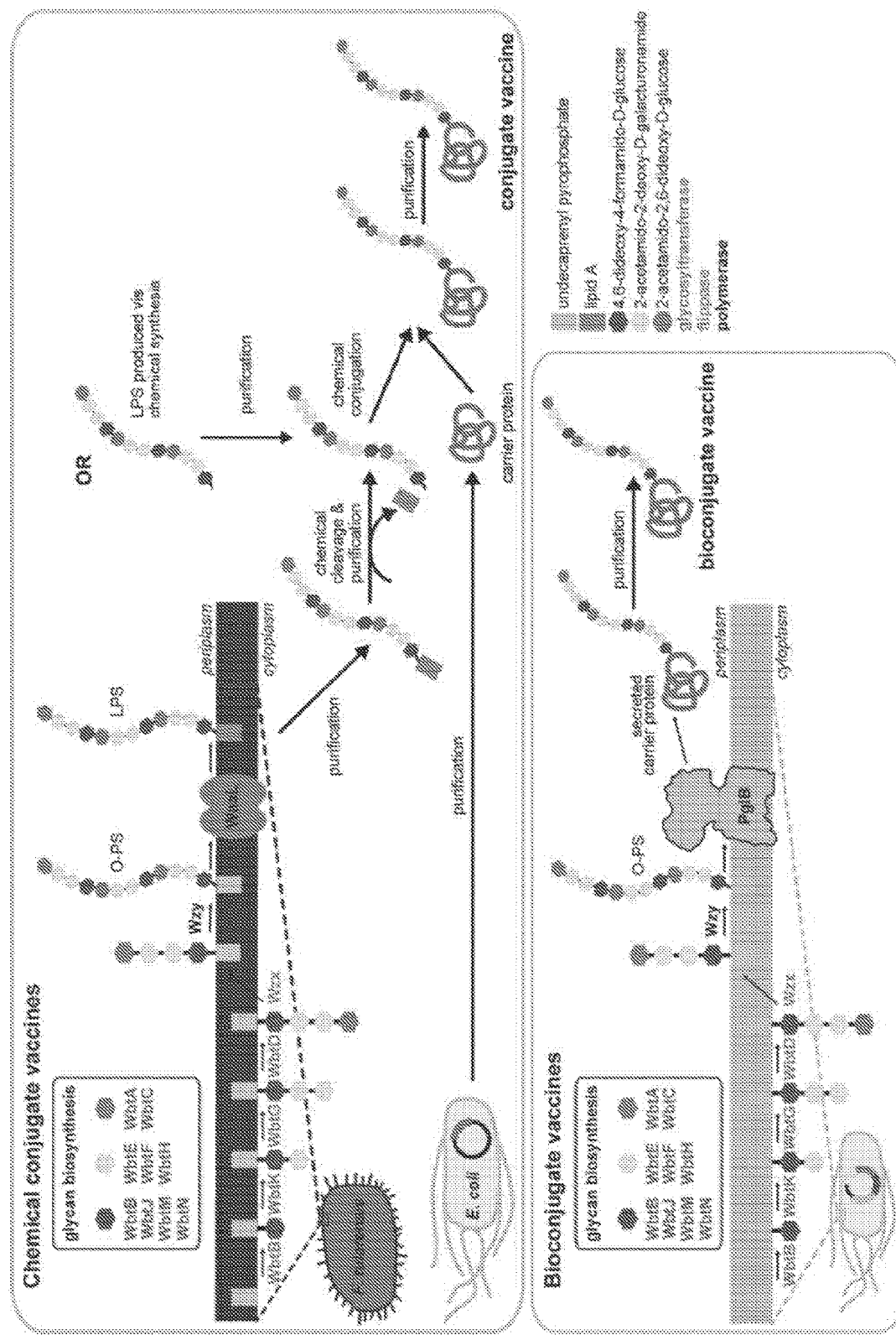
FIG. 2. Strategies for production of conjugate and bioconjugate vaccines as adapted from Ihssen et al., Microb. Cell. Fact. 2010 9:61, pages 1-13, the content of which is incorporated herein by reference in its entirety. The schematic illustrates production of an example vaccine against *Franciscella tularensis*.

The rise of antibiotic-resistant bacterial strains necessitates the development of novel strategies for treatment and prevention of life-threatening bacterial infections. In 2013, the Center for Disease Control and Prevention released a report citing antibiotic resistance as one of United States' most serious health threats. Conjugate vaccines, which consist of CPS or O-PS antigens covalently linked to carrier proteins, are among the safest and most effective preventative measures against bacterial infections and have been used to reduce the incidence of *Streptococcus pneumoniae*, *Neisseria meningitides*, and *Haemophilus influenza* infection [1-10]. Because polysaccharide antigens cannot directly activate naïve T cells, they must be conjugated to a carrier protein in order to induce long-lasting immunological memory [54]. However, existing technologies for producing conjugate vaccines are complex, involve multiple processing and purification steps, and the resulting products are ill-defined (FIG. 2, top) [2]. Additionally, these processes are time-consuming and can require large-scale fermentation of pathogenic bacteria, making conjugate vaccines prohibitively expensive for vaccination campaigns in developing nations.

The production of recombinant O antigen-protein conjugates in living *E. coli* cells was recently accomplished using bacterial N-glycosylation machinery (FIG. 2, bottom) [11]. These so-called bioconjugate vaccines have the potential to reduce the cost and time required for antibacterial vaccine production. Bioconjugates have been developed against several bacterial targets, including *Franciscella tularensis* [4], *Pseudomonas aeruginosa* [11], *Salmonella enterica* [9], *Shigella dynsenteriae* [7, 10], *Shigella flexneri* [8], *Staphylococcus aureus* [5], *Brucella abortus* [3], and *Burkholderia pseudomallei* [6]. An in vitro method for bioconjugate production could shorten process development timelines for novel antibacterial vaccines from months to weeks [55].

Cell-free protein synthesis (CFPS) is an emerging field that allows for the production of proteins in crude cell lysates [55, 56]. CFPS technology was first used over 50 years ago by Nirenberg and Matthaei to decipher the genetic code [57]. In the late 1960s and early 1970s, CFPS was employed to help elucidate the regulatory mechanisms of the *E. coli* lactose [58] and tryptophan [59] operons. In the last two decades, CFPS platforms have experienced a surge in development to meet the increasing demand for recombinant protein expression technologies [55].

CFPS offers several advantages for recombinant protein expression. In particular, the open reaction environment allows for addition or removal of substrates for protein synthesis, as well as precise, on-line reaction monitoring. Additionally, the CFPS reaction environment can be wholly directed toward and optimized for production of the protein product of interest. CFPS effectively decouples the cell's objectives (growth & reproduction) from the engineer's objectives (protein overexpression & simple product purification), which has proven advantageous for the production of complex proteins and protein assemblies, including membrane proteins [60-63], bispecific antibodies [64], antibody-drug conjugates [65], and virus-like particle vaccines [66-68]. Overall, CFPS technology allows for shortened protein synthesis timelines and increased flexibility for addition or removal of substrates compared to in vivo approaches. The E. coli CFPS system in particular has been widely adopted because of i) its high batch yields, with up to 2.3 g/L of green fluorescent protein (GFP) reported [69], ii) inexpensive required substrates [70-72], and iii) the ability to linearly scale reaction volumes over $10^6$ L [73].

Glycosylation is possible in some eukaryotic CFPS systems, including ICE, CHO extract, and a human leukemia cell line extract [74-77]. However, these platforms harness the endogenous machinery to carry out glycosylation, meaning that i) the possible glycans structures are restricted to those naturally synthesized by the host cells and ii) the glycosylation process is carried out in a "black box" and thus difficult to engineer or control. The development of a highly active E. coli CFPS platform has prompted recent efforts to enable glycoprotein production in E. coli lysates through the addition of orthogonal glycosylation components. In one study, Guarino and DeLisa demonstrated the ability to produce glycoproteins in E. coli CFPS by adding purified lipid-linked oligosaccharides (LLOs) and the C. jejuni OST to a CFPS reaction. Yields of between 50-100 μg/mL of AcrA, a C. jejuni glycoprotein, were achieved [78]. Despite these recent advances, bacterial cell-free glycosylation systems have been limited by their inability to co-activate efficient protein synthesis and glycosylation. We recently developed a cell-free glycoprotein synthesis (CFGpS) system that addresses this limitation by enabling modular, coordinated transcription, translation, and N-glycosylation of proteins in E. coli lysates selectively enriched with glycosylation enzymes (see WO 2017/117539, the content of which is incorporated herein by reference in its entirety). Here, we apply this technology platform to the production of bioconjugate vaccines to yield a methodology for rapid, modular in vitro expression of bioconjugates.

Results and Discussion

Cell-free Glycoprotein Synthesis (CFGpS) for Bioconjugate Vaccine Production. While protein-glycan coupling technology (PGCT) represents a simplified and cost-effective strategy for bioconjugate vaccine production, it has three main limitations. First, process development timelines, glycosylation pathway design-build-test (DBT) cycles, and bioconjugate production are all limited by cellular growth. Second, it has not yet been shown whether FDA-approved carrier proteins, such as the toxins from Clostridium tetani and Corynebacterium diptheriae, have not yet been demonstrated to be compatible with N-linked glycosylation in living E. coli. Third, select non-native glycans are known to be transferred with low efficiency by the C. jejuni OST, PglB [9].

A modular, in vitro platform for production of bioconjugates has the potential to address all of these limitations. Here, we demonstrate that bioconjugates against pathogenic strains of Franciscella tualrensis and Escherichia coli can be produced through coordinated in vitro transcription, translation, and N-glycosylation in cell-free glycoprotein synthesis (CFGpS) reactions lasting just 20 hours. This system has the potential to reduce process development and distribution timelines for novel antibacterial vaccines from weeks to days. Further, because of the modular nature of the CFGpS platform and the fact that cell-free systems have demonstrated advantages for production of membrane proteins compared to living cells [60-63], this method could be readily applied to produce bioconjugates using FDA-approved carrier proteins, such as the Clostridium tetani and Corynebacterium diptheriae toxins, which are membrane localized. This could be accomplished simply by supplying plasmid encoding these carrier proteins to CFGpS reactions. Additionally, because of the modular nature of CFGpS, the in vitro approach could be used to prototype other natural or engineered homologs of the archetypal C. jejuni OST, such as those described recently [9, 79, 80], to identify candidate OSTs with improved efficiency for transfer of O-antigen LLOs of interest. This can be accomplished by enriching lysates with OSTs of interest and mixing them with LLO lysates in mixed lysate CFGpS reactions, as we have described previously (Jewett lab, unpublished data; US Provisional Patent Application 62/273,124). Finally, we demonstrate that cell-free bioconjugate synthesis reactions can be lyophilized and retain bioconjugate synthesis capability, demonstrating the potential of the CFGpS system for on-demand, portable, and low-cost production or development efforts for novel vaccines. This novel method for in vitro bioconjugate vaccine production has demonstrated advantages for rapid, modular, and portable vaccine prototyping and production compared to existing methods.

Figure 3:
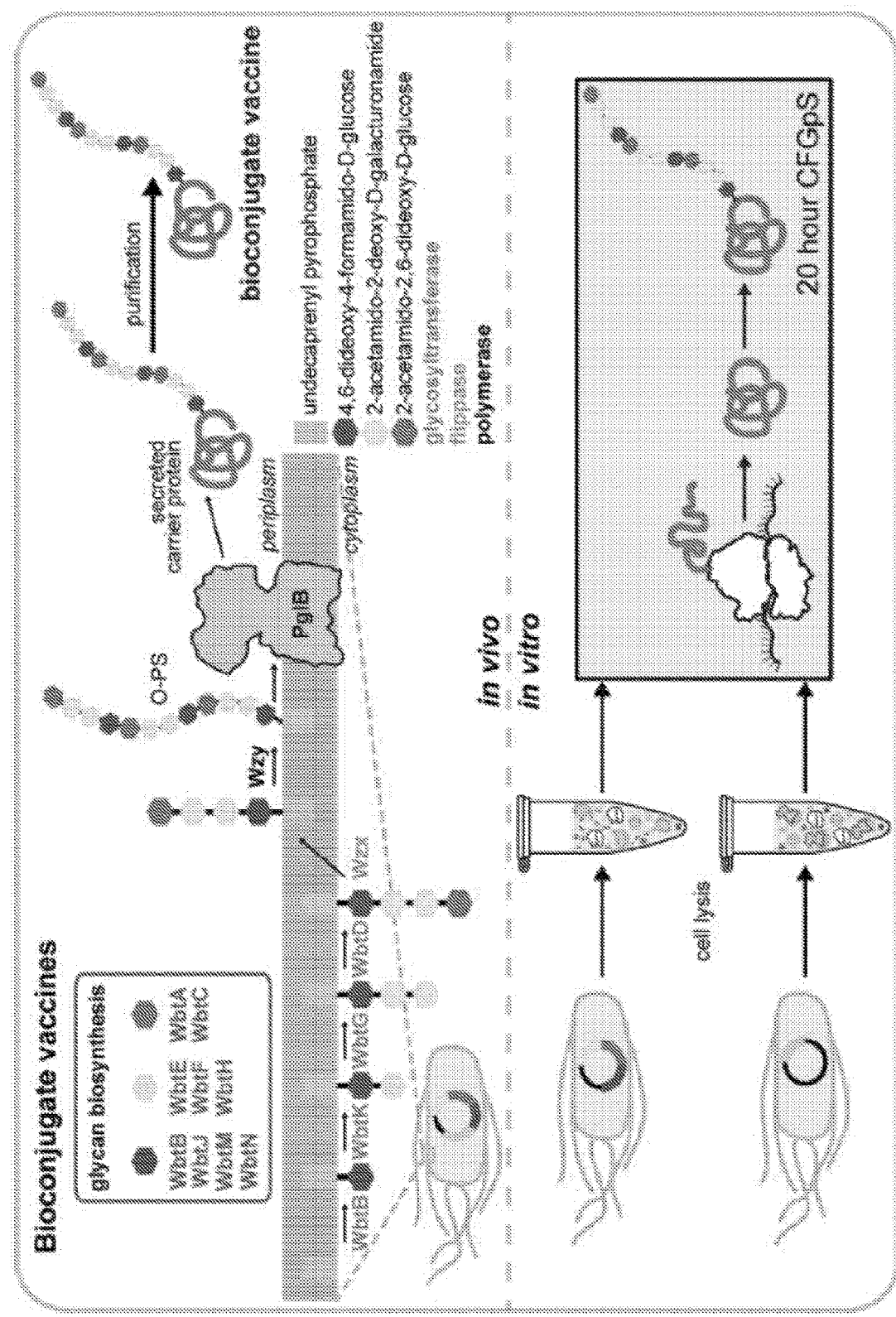
FIG. 3. Application of CFGpS technology for in vitro production of bioconjugate vaccines. Example of in vivo and in vitro workflows for production of anti-*F. tularensis* bioconjugates. The ability to produce bioconjugates in vitro will enable rapid prototyping of novel vaccine candidates.
Figure 4:
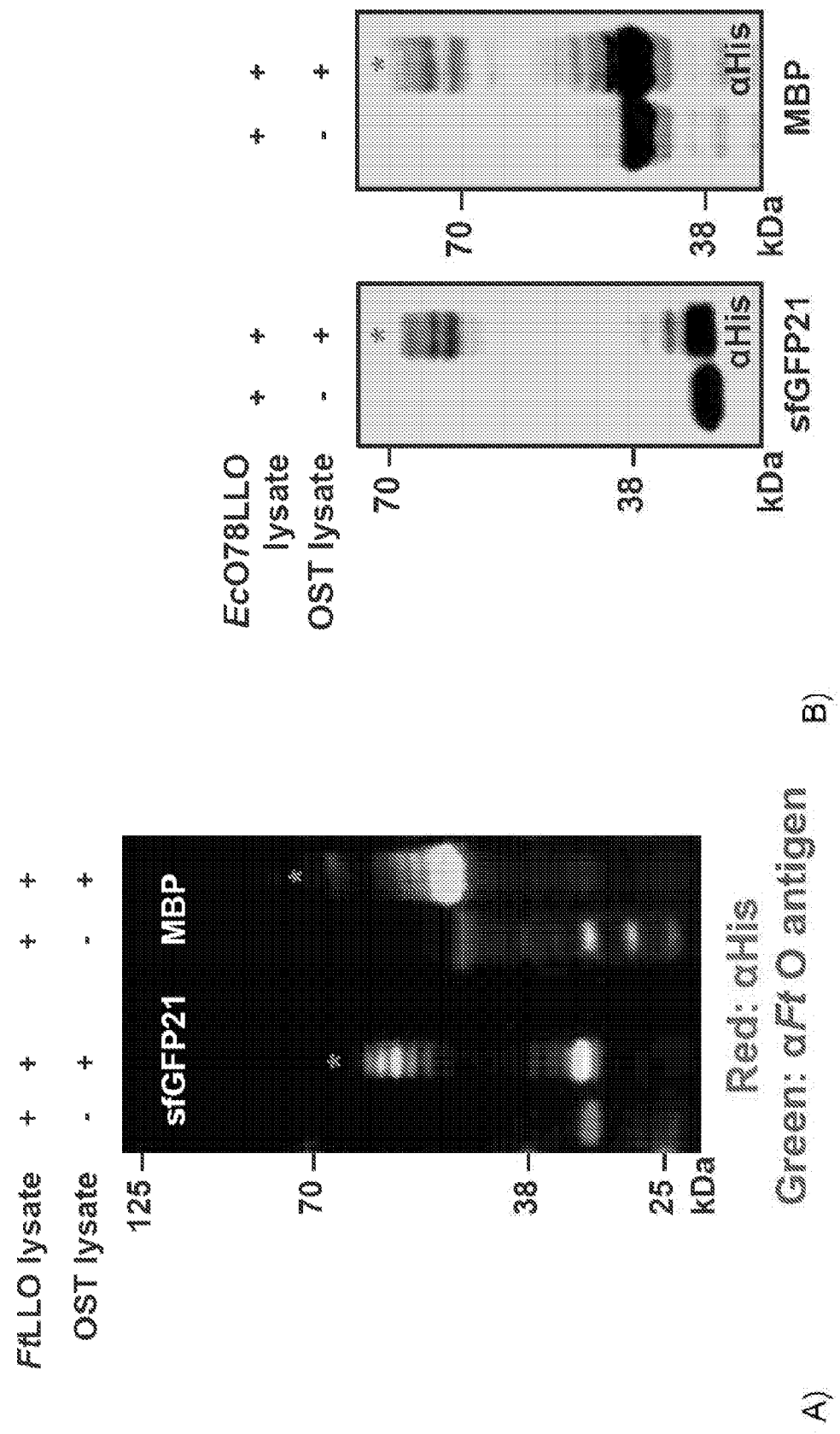
FIG. 4. Rapid synthesis of glycoproteins bearing diverse bacterial O-antigens in mixed lysate CFGpS. S30 lysates were prepared from CLM24 cells expressing the *C. jejuni* OST (CjOST lysate), the *Franciscella tularensis* O-antigen (FtO-PS) biosynthesis pathway (FtLLO lysate), or the *Escherichia coli* O78 antigen (EcO78-PS) biosynthesis pathway (EcO78LLO lysate). (A) FtLLO lysate was mixed with CjOST lysate in CFGpS reactions containing DNA template for either sfGFP21-DQNAT-6xHis or MBP-4xDQNAT-6xHis. The FtO-PS is covalently attached to R4-DQNAT and MBP-4xDQNAT when both the CcOST and FtLLO lysate are present in the CFGpS reaction, indicated by the ladder-like pattern observed in the Western blot assay (lanes 2, 4). (B) EcO78LLO lysate was mixed with CjOST lysate in CFGpS reactions containing DNA template for either sfGFP21-DQNAT-6xHis, or MBP-4xDQNAT-6xHis. The EcO78-PS is covalently attached to sfGFP-21-DQNAT and MBP-4xDQNAT when both the CjOST and EcO78LLO lysate are present in the CFGpS reaction, indicated by the ladder-like pattern observed in the Western blot assay (lanes 2, 4). The bioconjugates were also cross-reactive with a commercial antiserum against the *E. coli* O78 strain (data not shown). These results demonstrate the modularity of LLOs in mixed lysate CFGpS and the potential of CFGpS technology for rapid synthesis of antibacterial vaccines. Abbreviations: CLM24 pSF CjOST; FtLLO lysate: CLM24 pGAB2; α-FtO antigen: FB11 mAb specific for *F. tularensis* O-antigen glycan.
Figure 5:
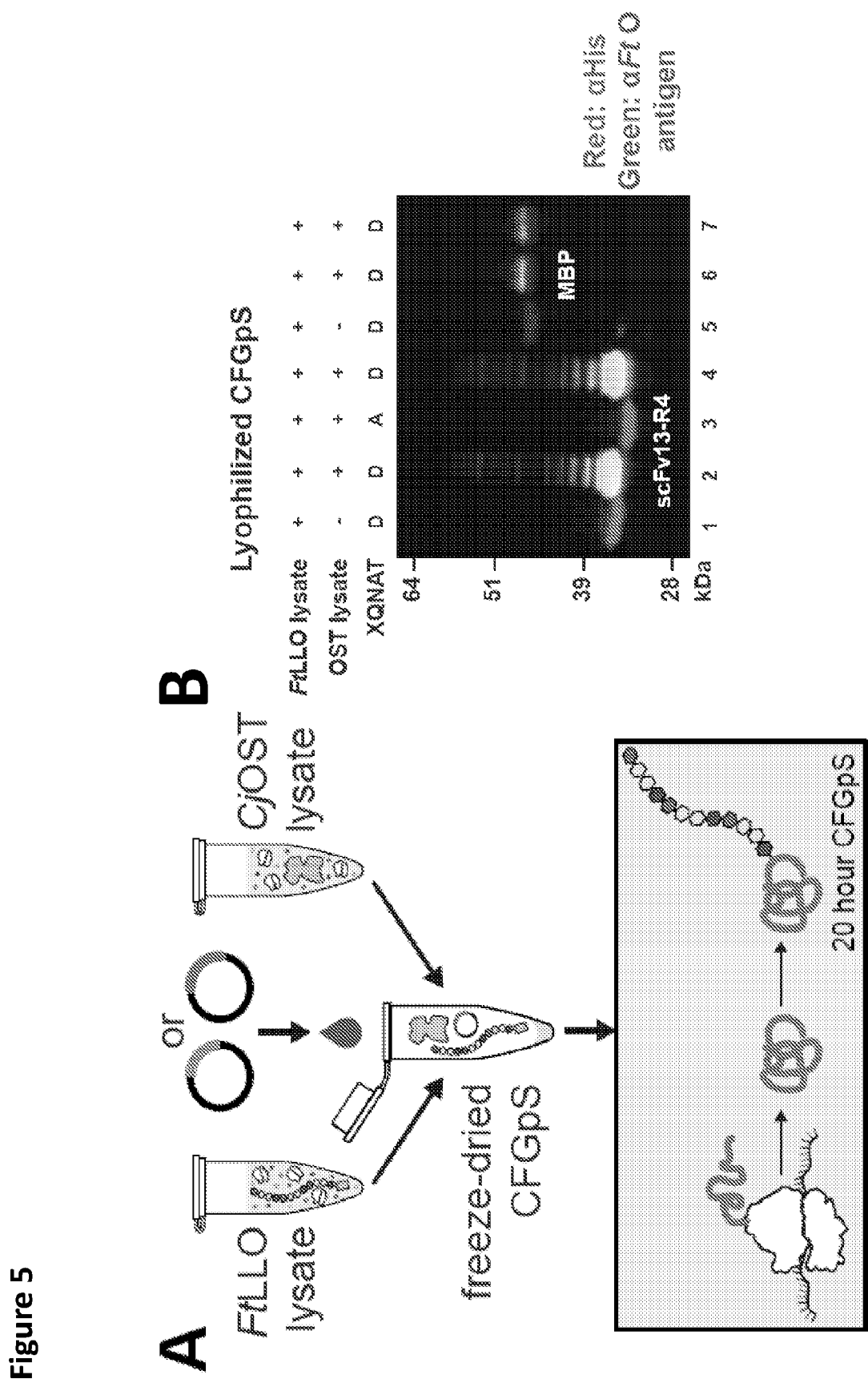
FIG. 5. Freeze-dried CFGpS reactions for point-of-use vaccine manufacturing. (A) Scheme for portable bioconjugate production and distribution in resource-limited settings. (B) Lyophilized CFGpS reactions retain bioconjugate synthesis activity. CFGpS reactions were prepared containing either CjOST lysate or FtLLO lysate alone, or a mixture of both CjOST and FtLLO lysates. These reactions were then lyophilized and reconstituted with 15 µL nuclease-free water. Pre-mixed reactions (lanes 1, 2, 5, 6) were run directly following reconstitution, while reactions containing CjOST lysate or FtLLO lysate alone were mixed following reconstitution (lanes 3, 4, 7). The FtO-PS is attached to the target protein when the DQNAT sequon is synthesized and both CjOST lysate or FtLLO lysate are present in the reaction (lanes 2, 4, 6, 7). Bioconjugate synthesis capability is preserved following lyophilization, demonstrating the potential of CFGpS for portable bioconjugate production and distribution in resource-poor areas. Abbreviations: CjOST lysate: CLM24 pSF CjOST; FtLLO lysate: CLM24 pGAB2; α-FtO antigen: FB11 mAb specific for *F. tularensis* O-antigen glycan. Red (e.g., lanes 1, 3 and 5): αHis.

Bioconjugate vaccines against F. tularensis can be synthesized in vitro via CFGpS. Franciscella tularensis is a gram-negative bacterium that causes tularemia. F. tularensis is considered one of the most infectious bacteria known to man: a single inhaled bacillus results in infection of 40-50% of individuals, with a mortality rate of up to 30% [81]. The gene locus for O-antigen biosynthesis was recently characterized [82] and used to create a bioconjugate vaccine in living E. coli cells [4]. We decided to use this pathway to produce an anti-F. tularensis bioconjugate vaccine using CFGpS. We hypothesized that anti-F. tularensis bioconjugate vaccines can be synthesized in vitro using CFGpS technology (FIG. 3).

Figure 6:
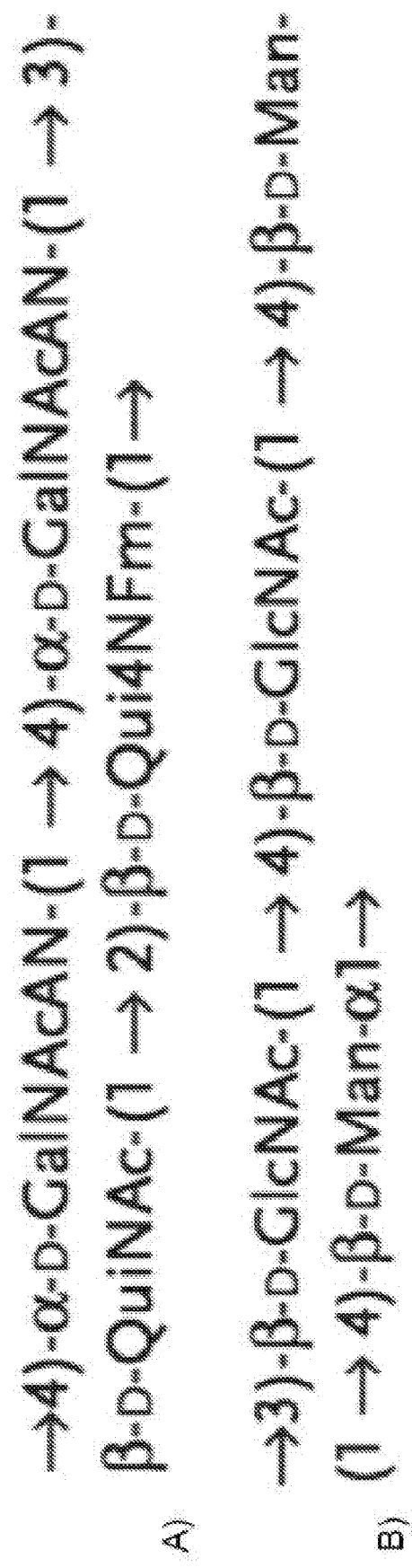
FIG. 6. Structures of O-antigens produced in selectively enriched S30 lysates. (A) Structure of the *F. tularensis* Schu S4 O-antigen. (B) Structure of the enterotoxigenic *E. coli* O78 antigen.

We hypothesized that Und-PP-linked polysaccharide antigens can be enriched in S30 lysates via overexpression of orthogonal glycosylation machinery in an E. coli CFGpS chassis strain lacking the WaaL O-antigen ligase. To test this hypothesis, we produced lysates from CLM24 cells overexpressing the C. jejuni OST, PglB (CjOST lysate) and the biosynthetic machinery to produce the Franciscella tularensis Schu S4 O antigen (FtLLO lysate). This 17 kb gene cluster from F. tularensis Schu S4 contains 15 predicted open reading frames (ORFS) and produces oligosaccharides comprised of the repeating unit GalNAcAN$_2$QuiNAcQui4NFm (GalNAcAN: 2-acetamido-2-deoxy-D-galacturonamide, QuiNAc: 2-acetamido-2,6-dideoxy-D-glucose, Qui4NFm: 4,6-dideoxy-4-formamido-D-glucose) (FIG. 6A) [82]. Lysates were prepared via high-pressure homogenization, to encourage formation of soluble inverted membrane vesicles, which carry membrane-bound components, such as FtLLOs and CjOST, into the crude lysate.

We hypothesized that anti-*F. tularensis* bioconjugate vaccines can be synthesized in vitro using CFGpS technology. To produce bioconjugates bearing the *F. tularensis* O polysaccharide (FtO-PS), CjPglB lysate was mixed with FtLLO lysate in CFGpS reactions lasting 20 hours at 30° C. These reactions contained plasmid encoding either i) super-folder green fluorescent protein engineered to include a DQNAT sequon in a flexible linker inserted at residue T216 and a C-terminal His tag (sfGFP-21-DQNAT-6xHis) or ii) an engineered maltose binding protein construct with four C-terminal repeats of the DQNAT sequon and a C-terminal His tag (MBP-4xDQNAT-6xHis). Bioconjugates composed of *E. coli* O-antigens conjugated to MBP-4xDQNAT-6xHis were recently shown to elicit humoral and cellular immunity in mice [83]. Within the first hour of the CFGpS reaction, reaction mixtures were spiked with manganese chloride ($MnCl_2$) and n-dodecyl-β-D-maltopyranoside (DDM) detergent at final concentrations of 25 mM $MnCl_2$, 0.1% w/v DDM to optimize CjPglB activity (Jewett lab, unpublished data). After the CFGpS reactions were allowed to proceed for a total of 20 hours at 30° C., glycosylation activity was assayed via immunoblotting with anti-His antibody and a commercial monoclonal antibody specific to FtO-PS. The ladder-like pattern observed when the FtLLO and CjPglB lysates are mixed is indicative of FtLLO attachment and results from O-PS chain length variability through the action of the Wzy polymerase (FIG. 4A) [4, 11]. These results demonstrate the integration of coordinated cell-free carrier protein synthesis and O-antigen attachment for the first time. Furthermore, we show that cell-free bioconjugate synthesis occurs in just 20 hours, making this cell-free platform an attractive option for rapid production and prototyping of bioconjugate vaccine candidates.

Bioconjugate vaccines against *E. coli* O78 and other pathogenic strains can be readily synthesized due to the modular nature of CFGpS platform. To demonstrate the generality and modularity of the CFGpS approach for bioconjugate production, we sought to produce bioconjugates against an additional pathogenic bacterium. We decided to synthesize bioconjugates against enterotoxigenic *E. coli* strain O78, since its biosynthetic pathway has been described previously [84] and there exists a commercial antiserum specific to this strain. The *E. coli* O78 gene cluster was cloned and is encoded in plasmid pMW07-O78. Expression of the *E. coli* O78 gene cluster results in production of an O-antigen with the repeating unit $GlcNAc_2Man_2$ (GlcNAC: N-acetylglucosamine; Man: mannose) (FIG. 6B)

We prepared lysates enriched with *E. coli* O78 antigen LLOs (EcO78LLO lysate) from CLM24 cells expressing pMW07-O78 using the same method described above. We then mixed the EcO78LLO lysate with CjOST lysate in CFGpS reactions containing plasmid encoding either sfGFP21-DQNAT-6xHis or MBP-4xDQNAT-6xHis. CFGpS reactions were run as described above. Glycosylation activity was assayed via immunoblotting with an anti-His antibody and a commercial antiserum against the *E. coli* O78 strain. Again, a ladder-like pattern is observed when both EcO78LLO lysate and CjOST lysates are present in the reaction, indicating successful conjugation of the EcO78-PS (FIG. 4B). The bioconjugates were also cross-reactive with the anti-EcO78 serum (data not shown). These results demonstrate the modular nature of the in vitro approach, and provide evidence that the CFGpS platform could be used to produce bioconjugate vaccines targeting many different pathogenic bacterial strains. Attractive candidates include pathogenic bacteria whose surface antigen gene clusters are known, including *Pseudomonas aeruginosa* [11], *Salmonella enterica* [9], *Shigella dynsenteriae* [7, 10], *Shigella flexneri* [8], *Staphylococcus aureus* [5], *Brucella abortus* [3], and *Burkholderia pseudomallei* [6]. These results demonstrate the potential of the in vitro system for rapid production or prototyping of vaccine candidates directed against diverse pathogenic bacteria. Moreover, because synthesis can be achieved in just 20 h with different O-PS antigens, this cell-free platform represents an attractive option for rapid production and prototyping of novel bioconjugate vaccine candidates.

Lyophilized CFGpS reactions retain bioconjugate synthesis capability. A major limitation of traditional conjugate vaccines is their high cost, due to their time consuming production process. By comparison, bioconjugate vaccines are less expensive to produce, however, production time is dictated by the time required to ferment and purify proteins from living cells. We wanted to test whether our CFGpS reactions could be freeze-dried for potential room-temperature storage and distribution to enable faster production and broader-reaching vaccination campaigns and development efforts compared to in vivo approaches. To test whether this was possible, CFGpS reactions were prepared containing either CjOST lysate or FtLLO lysate alone, or a mixture of both CjOST and FtLLO lysates. These reactions were then lyophilized and reconstituted with 15 μL nuclease-free water. The reactions contained plasmid encoding either a short chain antibody fragment with a C-termnal DQNAT sequon followed by a His tag (scFv13-R4-DQNAT-6xHis) or MBP-4xDQNAT-6xHis. Pre-mixed reactions (lanes 1, 2, 5, 6) were run directly following reconstitution, while reactions containing CjOST lysate or FtLLO lysate alone were mixed following reconstitution (lanes 3, 4, 7). The FtO-PS is attached to the target protein when the DQNAT sequon is synthesized and both CjOST lysate or FtLLO lysate are present in the reaction (lanes 2, 4, 6, 7). These results confirm that the CFGpS reaction mixture can be lyophilized without loss of bioconjugate synthesis capability, highlighting the potential of our technology for portable, on-demand vaccine production and long-term, refrigeration-free storage.

Conclusions

We describe here a novel method for coordinated in vitro transcription, translation, and conjugation of vaccine antigens to carrier proteins. This in vitro approach uniquely (i) decouples cell viability from glycosylation activity and enables reduction of cellular metabolic burden through in vitro reconstitution of glycosylation components, (ii) permits design-build-test (DBT) iterations on individual glycosylation components, and (iii) allows for assembly of glycosylation pathways within well-defined experimental conditions including chemical and physical manipulations not possible in cells. Further, the system has obvious and commercially attractive applications to producing bioconjugates using FDA-approved carrier proteins, such as the toxins from *Clostridium tetani* and *Corynebacterium diptheriae*. This novel method for in vitro bioconjugate vaccine production has demonstrated advantages for rapid, modular, and portable vaccine prototyping and production compared to existing methods.

REFERENCES FOR EXAMPLE 1

1. Maue, A. C., F. Poly, and P. Guerry, A capsule conjugate vaccine approach to prevent diarrheal disease caused by *Campylobacter jejuni*. Hum Vaccin Immunother, 2014. 10(6): p. 1499-504.

2. Anderson, P., Antibody responses to *Haemophilus influenzae* type b and diphtheria toxin induced by conjugates of oligosaccharides of the type b capsule with the nontoxic protein CRM197. Infect Immun, 1983. 39(1): p. 233-8.

3. Iwashkiw, J. A., et al., Exploiting the *Campylobacter jejuni* protein glycosylation system for glycoengineering vaccines and diagnostic tools directed against brucellosis. Microb Cell Fact, 2012. 11: p. 13.

4. Cuccui, J., et al., Exploitation of bacterial N-linked glycosylation to develop a novel recombinant glycoconjugate vaccine against *Francisella tularensis*. Open Biol, 2013. 3(5): p. 130002.

5. Wacker, M., et al., Prevention of *Staphylococcus aureus* infections by glycoprotein vaccines synthesized in *Escherichia coli*. J Infect Dis, 2014. 209(10): p. 1551-61.

6. Garcia-Quintanilla, F., et al., Production of a recombinant vaccine candidate against *Burkholderia pseudomallei* exploiting the bacterial N-glycosylation machinery. Front Microbiol, 2014. 5: p. 381.

7. Ravenscroft, N., et al., Purification and characterization of a *Shigella* conjugate vaccine, produced by glycoengineering *Escherichia coli*. Glycobiology, 2015.

8. Kampf, M. M., et al., In vivo production of a novel glycoconjugate vaccine against *Shigella flexneri* 2a in recombinant *Escherichia coli*: identification of stimulating factors for in vivo glycosylation. Microb Cell Fact, 2015. 14: p. 12.

9. Ihssen, J., et al., Increased efficiency of *Campylobacter jejuni* N-oligosaccharyltransferase PglB by structure-guided engineering. Open Biol, 2015. 5(4).

10. Ihssen, J., et al., Production of glycoprotein vaccines in *Escherichia coli*. Microb Cell Fact, 2010. 9: p. 61.

11. Feldman, M. F., et al., Engineering N-linked protein glycosylation with diverse O antigen lipopolysaccharide structures in *Escherichia coli*. Proc Natl Acad Sci USA, 2005. 102(8): p. 3016-21.

12. Neuberger, A., Carbohydrates in protein: The carbohydrate component of crystalline egg albumin. Biochem J, 1938. 32(9): p. 1435-51.

13. Mescher, M. F. and J. L. Strominger, Purification and characterization of a prokaryotic glucoprotein from the cell envelope of *Halobacterium salinarium*. J Biol Chem, 1976. 251(7): p. 2005-14.

14. Sleytr, U. B., Heterologous reattachment of regular arrays of glycoproteins on bacterial surfaces. Nature, 1975. 257(5525): p. 400-2.

15. Szymanski, C. M., et al., Evidence for a system of general protein glycosylation in *Campylobacter jejuni*. Mol Microbiol, 1999. 32(5): p. 1022-30.

16. Linton, D., et al., Identification of N-acetylgalactosamine-containing glycoproteins PEB3 and CgpA in *Campylobacter jejuni*. Mol Microbiol, 2002. 43(2): p. 497-508.

17. Spiro, R. G., Protein glycosylation: nature, distribution, enzymatic formation, and disease implications of glycopeptide bonds. Glycobiology, 2002. 12(4): p. 43R-56R.

18. Laine, R. A., The Information-Storing Potential of the Sugar Code. Glycosciences: Status and Perspectives, 1997: p. 1-14.

19. Raman, R., et al., Glycomics: an integrated systems approach to structure-function relationships of glycans. Nat Methods, 2005. 2(11): p. 817-24.

20. Ohtsubo, K. and J. D. Marth, Glycosylation in cellular mechanisms of health and disease. Cell, 2006. 126(5): p. 855-67.

21. Imberty, A. and A. Varrot, Microbial recognition of human cell surface glycoconjugates. Curr Opin Struct Biol, 2008. 18(5): p. 567-76.

22. Daniels, M. A., K. A. Hogquist, and S. C. Jameson, Sweet 'n' sour: the impact of differential glycosylation on T cell responses. Nat Immunol, 2002. 3(10): p. 903-10.

23. Dube, D. H. and A. R. Bertozzi, Glycans in cancer and inflammation-potential for therapeutics and diagnostics. Nat Rev Drug Discov, 2005. 4: p. 477-88.

24. Pinho, S. S. and C. A. Reis, Glycosylation in cancer: mechanisms and clinical implications. Nat Rev Cancer, 2015. 15(9): p. 540-55.

25. Ma, Z. and K. Vosseller, Cancer metabolism and elevated O-GlcNAc in oncogenic signaling. J Biol Chem, 2014. 289(50): p. 34457-65.

26. Theodoratou, E., et al., The role of glycosylation in IBD. Nat Rev Gastroenterol Hepatol, 2014. 11(10): p. 588-600.

27. Albrecht, S., et al., Glycosylation as a marker for inflammatory arthritis. Cancer Biomark, 2014. 14(1): p. 17-28.

28. Axford, J. S., Glycosylation and rheumatic disease. Biochim Biophys Acta, 1999. 1455(2-3): p. 219-29.

29. Baudoin, L. and T. Issad, O-GlcNAcylation and Inflammation: A Vast Territory to Explore. Front Endocrinol (Lausanne), 2014. 5: p. 235.

30. Wang, J. Z., I. Grundke-Iqbal, and K. Iqbal, Glycosylation of microtubule-associated protein tau: an abnormal posttranslational modification in Alzheimer's disease. Nat Med, 1996. 2(8): p. 871-5.

31. Guerry, P., et al., Campylobacter polysaccharide capsules: virulence and vaccines. Front Cell Infect Microbiol, 2012. 2: p. 7.

32. Kalynych, S., R. Morona, and M. Cygler, Progress in understanding the assembly process of bacterial O-antigen. FEMS Microbiol Rev, 2014. 38(5): p. 1048-65.

33. Bacon, D. J., et al., A phase-variable capsule is involved in virulence of *Campylobacter jejuni* 81-176. Mol Microbiol, 2001. 40(3): p. 769-77.

34. Wang, L. X. and B. G. Davis, Realizing the Promise of Chemical Glycobiology. Chem Sci, 2013. 4(9): p. 3381-3394.

35. Chauhan, J. S., A. Rao, and G. P. Raghava, In silico platform for prediction of N-, O- and C-glycosites in eukaryotic protein sequences. PLoS One, 2013. 8(6): p. e67008.

36. Gavel, Y. and G. von Heijne, Sequence differences between glycosylated and non-glycosylated Asn-X-Thr/Ser acceptor sites: implications for protein engineering. Protein Eng, 1990. 3(5): p. 433-42.

37. Lehle, L. and W. Tanner, Glycosyl transfer from dolichyl phosphate sugars to endogenous and exogenous glycoprotein acceptors in yeast. Eur J Biochem, 1978. 83(2): p. 563-70.

38. Varki, A., Biological roles of oligosaccharides: all of the theories are correct. Glycobiology, 1993. 3(2): p. 97-130.

39. Wilson, I. B., Y. Gavel, and G. von Heijne, Amino acid distributions around 0-linked glycosylation sites. Biochem J, 1991. 275 (Pt 2): p. 529-34.

40. Thanka Christlet, T. H. and K. Veluraja, Database analysis of O-glycosylation sites in proteins. Biophys J, 2001. 80(2): p. 952-60.

41. Walt, D., et al., Transforming Glycoscience: A Roadmap for the Future. 2012: The National Academies Press.

42. Lizak, C., et al., X-ray structure of a bacterial oligosaccharyltransferase. Nature, 2011. 474(7351): p. 350-355.

43. Perez, C., et al., Structure and mechanism of an active lipid-linked oligosaccharide flippase. Nature, 2015. 524 (7566): p. 433-8.

44. Abu-Qarn, M., J. Eichler, and N. Sharon, Not just for Eukarya anymore: protein glycosylation in Bacteria and Archaea. Curr Opin Struct Biol, 2008. 18(5): p. 544-50.

45. Weerapana, E. and B. Imperiali, Asparagine-linked protein glycosylation: from eukaryotic to prokaryotic systems. Glycobiology, 2006. 16(6): p. 91R-101R.

46. Wacker, M., et al., N-linked glycosylation in *Campylobacter jejuni* and its functional transfer into *E. coli*. Science, 2002. 298(5599): p. 1790-3.

47. Glover, K. J., et al., Direct biochemical evidence for the utilization of UDP-bacillosamine by PglC, an essential glycosyl-1-phosphate transferase in the *Campylobacter jejuni* N-linked glycosylation pathway. Biochemistry, 2006. 45(16): p. 5343-50.

48. Glover, K. J., E. Weerapana, and B. Imperiali, In vitro assembly of the undecaprenylpyrophosphate-linked heptasaccharide for prokaryotic N-linked glycosylation. Proc Natl Acad Sci USA, 2005. 102(40): p. 14255-9.

49. Olivier, N. B., et al., In vitro biosynthesis of UDP-N,N'-diacetylbacillosamine by enzymes of the *Campylobacter jejuni* general protein glycosylation system. Biochemistry, 2006. 45(45): p. 13659-69.

50. Murray, G. L., S. R. Attridge, and R. Morona, Regulation of Salmonella typhimurium lipopolysaccharide O antigen chain length is required for virulence; identification of FepE as a second Wzz. Mol Microbiol, 2003. 47(5): p. 1395-406.

51. Murray, G. L., S. R. Attridge, and R. Morona, Altering the length of the lipopolysaccharide O antigen has an impact on the interaction of *Salmonella enterica* serovar Typhimurium with macrophages and complement. J Bacteriol, 2006. 188(7): p. 2735-9.

52. Duerr, C. U., et al., O-antigen delays lipopolysaccharide recognition and impairs antibacterial host defense in murine intestinal epithelial cells. PLoS Pathog, 2009. 5(9): p. e1000567.

53. Saldias, M. S., X. Ortega, and M. A. Valvano, Burkholderia cenocepacia O antigen lipopolysaccharide prevents phagocytosis by macrophages and adhesion to epithelial cells. J Med Microbiol, 2009. 58(Pt 12): p. 1542-8.

54. Lesinski, G. B. and M. A. Westerink, Novel vaccine strategies to T-independent antigens. J Microbiol Methods, 2001. 47(2): p. 135-49.

55. Carlson, E. D., et al., Cell-free protein synthesis: applications come of age. Biotechnol Adv, 2012. 30(5): p. 1185-94.

56. Hodgman, C. E. and M. C. Jewett, Cell-free synthetic biology: thinking outside the cell. Metab Eng, 2012. 14(3): p. 261-9.

57. Nirenberg, M. W. and J. H. Matthaei, The dependence of cell-free protein synthesis in *E. coli* upon naturally occurring or synthetic polyribonucleotides. Proc Natl Acad Sci USA, 1961. 47: p. 1588-602.

58. Chambers, D. A. and G. Zubay, The stimulatory effect of cyclic adenosine 3'5'-monophosphate on DNA-directed synthesis of beta-galactosidase in a cell-free system. Proc Natl Acad Sci USA, 1969. 63(1): p. 118-22.

59. Zalkin, H., C. Yanofsky, and C. L. Squires, Regulated in vitro synthesis of *Escherichia coli* tryptophan operon messenger ribonucleic acid and enzymes. J Biol Chem, 1974. 249(2): p. 465-75.

60. Matthies, D., et al., Cell-free expression and assembly of ATP synthase. J Mol Biol, 2011. 413(3): p. 593-603.

61. Kaiser, L., et al., Efficient cell-free production of olfactory receptors: detergent optimization, structure, and ligand binding analyses. Proc Natl Acad Sci USA, 2008. 105(41): p. 15726-31.

62. Wang, X., et al., Peptide surfactants for cell-free production of functional G protein-coupled receptors. Proc Natl Acad Sci USA, 2011. 108(22): p. 9049-54.

63. Bernhard, F. and Y. Tozawa, Cell-free expression—making a mark. Curr Opin Struct Biol, 2013. 23(3): p. 374-80.

64. Xu, Y., et al. Production of bispecific antibodies in "Knobs-into-Holes" using a cell-free expression system. in mAbs. 2014. Taylor & Francis.

65. Zimmerman, E. S., et al., Production of Site-Specific Antibody-Drug Conjugates Using Optimized Non-Natural Amino Acids in a Cell-Free Expression System. Bioconjugate Chemistry, 2014. 25(2): p. 351-361.

66. Ng, P. P., et al., A vaccine directed to B cells and produced by cell-free protein synthesis generates potent antilymphoma immunity. Proc Natl Acad Sci USA, 2012. 109(36): p. 14526-31.

67. Lu, Y., J. P. Welsh, and J. R. Swartz, Production and stabilization of the trimeric influenza hemagglutinin stem domain for potentially broadly protective influenza vaccines. Proc Natl Acad Sci USA, 2014. 111(1): p. 125-30.

68. Bundy, B. C., M. J. Franciszkowicz, and J. R. Swartz, *Escherichia coli*-based cell-free synthesis of virus-like particles. Biotechnol Bioeng, 2008. 100(1): p. 28-37.

69. Caschera, F. and V. Noireaux, Synthesis of 2.3 mg/ml of protein with an all *Escherichia coli* cell-free transcription-translation system. Biochimie, 2014. 99: p. 162-8.

70. Calhoun, K. A. and J. R. Swartz, An economical method for cell-free protein synthesis using glucose and nucleoside monophosphates. Biotechnol Prog, 2005. 21(4): p. 1146-53.

71. Calhoun, K. A. and J. R. Swartz, Energizing cell-free protein synthesis with glucose metabolism. Biotechnol Bioeng, 2005. 90(5): p. 606-13.

72. Lian, Q., H. Cao, and F. Wang, The cost-efficiency realization in the *Escherichia coli*-based cell-free protein synthesis systems. Appl Biochem Biotechnol, 2014. 174(7): p. 2351-67.

73. Zawada, J. F., et al., Microscale to manufacturing scale-up of cell-free cytokine production—a new approach for shortening protein production development timelines. Biotechnol Bioeng, 2011. 108(7): p. 1570-8.

74. Stech, M., et al., Cell-free systems: functional modules for synthetic and chemical biology. Adv Biochem Eng Biotechnol, 2013. 137: p. 67-102.

75. Brodel, A. K., D. A. Wustenhagen, and S. Kubick, Cell-free protein synthesis systems derived from cultured Mammalian cells. Methods Mol Biol, 2015. 1261: p. 129-40.

76. Stech, M., et al., A continuous-exchange cell-free protein synthesis system based on extracts from cultured insect cells. PLoS One, 2014. 9(5): p. e96635.

77. Kubick, S., et al., In vitro synthesis of posttranslationally modified membrane proteins. Current Topics in Membranes, 2009. 63(2): p. 25-49.

78. Guarino, C. and M. P. DeLisa, A prokaryote-based cell-free translation system that efficiently synthesizes glycoproteins. Glycobiology, 2012. 22(5): p. 596-601.

79. Ollis, A. A., et al., Substitute sweeteners: diverse bacterial oligosaccharyltransferases with unique N-glycosylation site preferences. Sci Rep, 2015. 5: p. 15237.

80. Ollis, A. A., et al., Engineered oligosaccharyltransferases with greatly relaxed acceptor-site specificity. Nat Chem Biol, 2014. 10(10): p. 816-22.

81. Dennis, D. T., et al., Tularemia as a biological weapon: medical and public health management. Jama, 2001. 285(21): p. 2763-73.

82. Prior, J. L., et al., Characterization of the O antigen gene cluster and structural analysis of the O antigen of *Francisella tularensis* subsp. *tularensis*. J Med Microbiol, 2003. 52(Pt 10): p. 845-51.

83. Ma, Z., et al., Glycoconjugate vaccine containing *Escherichia coli* O157:H7 O-antigen linked with maltose-binding protein elicits humoral and cellular responses. PLoS One, 2014. 9(8): p. e105215.

84. Jansson, P. E., et al., Structural studies of the *Escherichia coli* O78 O-antigen polysaccharide. Carbohydr Res, 1987. 165(1): p. 87-92.

85. Nothaft, H., et al., Study of free oligosaccharides derived from the bacterial N-glycosylation pathway. Proc Natl Acad Sci USA, 2009. 106(35): p. 15019-24.

86. Young, N. M., et al., Structure of the N-linked glycan present on multiple glycoproteins in the Gram-negative bacterium, *Campylobacter jejuni*. Journal of Biological Chemistry, 2002. 277(45): p. 42530-9.

87. Fisher, A. C., et al., Production of secretory and extracellular N-linked glycoproteins in *Escherichia coli*. Appl Environ Microbiol, 2011. 77(3): p. 871-81.

88. Oyston, P. C., A. Sjostedt, and R. W. Titball, Tularaemia: bioterrorism defence renews interest in *Francisella tularensis*. Nat Rev Microbiol, 2004. 2(12): p. 967-78.

89. Chen, L., et al., Outer membrane vesicles displaying engineered glycotopes elicit protective antibodies. Proc Natl Acad Sci USA, 2016. 113(26): p. E3609-18.

90. Kumru, O. S., et al., Vaccine instability in the cold chain: mechanisms, analysis and formulation strategies. Biologicals, 2014. 42(5): p. 237-59.

Example 2Broad Applicability of Cell-Free Glycoprotein Synthesis Platform

The emerging discipline of bacterial glycoengineering has made it possible to produce designer glycans and glycoconjugates for use as vaccines and therapeutics. Herein, we describe a novel cell-free glycoprotein synthesis technology that seamlessly integrates protein biosynthesis with asparagine-linked protein glycosylation. This technology leverages several *Escherichia coli* strains to source cell lysates that are selectively enriched with glycosylation components, including oligosaccharyltransferases (OSTs) and lipid-linked oligosaccharides (LLOs). The resulting extracts enable a one-pot reaction scheme for efficient and site-specific glycosylation of target proteins. The platform is highly modular, allowing the use of multiple distinct OSTs to decorate structurally diverse glycans, including several bacterial O-polysaccharides, onto many glycoprotein therapeutics and glycoconjugate vaccine carriers. The following table summarizes unique glycosylation components, namely *E. coli* source strains, OSTs, and LLOs, as well as glycoprotein acceptors that have been characterized in the disclosed cell-free glycoprotein synthesis system.

Summary Table: Generality of Cell-Free Glycoprotein Synthesis Platform with Regards to OST Enzymes, Glycan Structures, Acceptor Proteins, and Bacterial Source Strains.

| Cell-free glycoprotein synthesis components | List of samples being characterized in the system |
| --- | --- |
| 1. OST enzymes | *Campylobacter jejuni* PglB |
| | *Campylobacter coli* PglB |
| | *Campylobacter lari* PglB |
| | *Desulfovibrio desulfuricans* PglB |
| | *Desulfovibrio gigas* PglB |
| | *Desulfovibrio vulgaris* PglB |
| 2. Glycan structures | *Francisella tularensis* SchuS4 O-polysaccharides |
| | *Escherichia coli* O78 O-polysaccharides |
| | *Escherichia coli* O-7 O-polysaccharides |
| | *Escherichia coli* O-9 O-polysaccharides primer |
| | *Campylobacter jejuni* heptasaccharides N-glycan |
| | *Campylobacter lari* PglB hexasaccharides N-glycan |
| | Engineered *Campylobacter lari* PglB hexasaccharides N-glycan |
| | *Wolinella succinogenes* hexasaccharide N-glycan |
| | Eukaryotic Man$_3$GlcNAc$_2$ N-glycan structure |
| 3. Acceptor proteins | Superfolder GFP |
| | Single-chain variable antibody fragment (scFv) |
| | Maltose-binding protein (MBP) |
| | Human erythropoietin variants |
| | Human glucagon peptide fused with MBP |
| | *Campylobacter jejuni* AcrA |
| | *Haemophilus influenzae* protein D (PD) |
| | *Neisseria meningitidis* porin protein (PorA) |
| | *Pseudomonas aeruginosa* exotoxin A (EPA) |
| | Detoxified variants of the *Corynebacterium diphtheriae* toxin (CRM197) |
| | Detoxified variants of the *Clostridium tetani* toxin (TT). |
| | Fragment C (TTc) of TT |
| | Light chain (TTlight) domains of TT |

| Cell-free glycoprotein synthesis components | List of samples being characterized in the system |
|---|---|
| 4. Bacterial source strains created | rEcoli ΔprfA ΔendA Δgor Δrne (705)<br>E. coli BL21(DE3)<br>E. coli CLM24<br>E. coli CLM24 ΔlpxM<br>E. coli CLM24 ΔlpxM CH-lpxE<br>E. coli CLM24 ΔlpxM CH-lpxE TT-lpxE<br>E. coli CLM24 ΔlpxM CH-lpxE TT-lpxE KL-lpxE<br>E. coli CLM24 ΔlpxM CH-lpxE TT-lpxE KL-lpxE KO-lpxE |

Multiple distinct oligosaccharyltransferases (OSTs) can be enriched within E. coli lysates to activate cell-free protein glycosylation. For initial development of our cell-free glycoprotein synthesis technology, we selected the well-studied bacterial protein glycosylation locus (pgl) from the Gram-negative bacterium Campylobacter jejuni as our model glycosylation system [1]. This gene cluster encodes an asparagine-linked (N-linked) glycosylation pathway that is functionally similar to that of eukaryotes and archaea [2], involving a single-subunit OST, CjPglB, that catalyzes the en bloc transfer of a preassembled GlcGalNAc$_5$Bac heptasaccharide (where Bac is bacillosamine) from the lipid carrier undecaprenyl pyrophosphate (Und-PP) onto asparagine residues in a conserved motif (D/E-$X_{-1}$-N-$X_{+1}$-S/T, where $X_{-1}$ and $X_{+1}$ are any residues except proline) within acceptor proteins [3].

Figure 7:
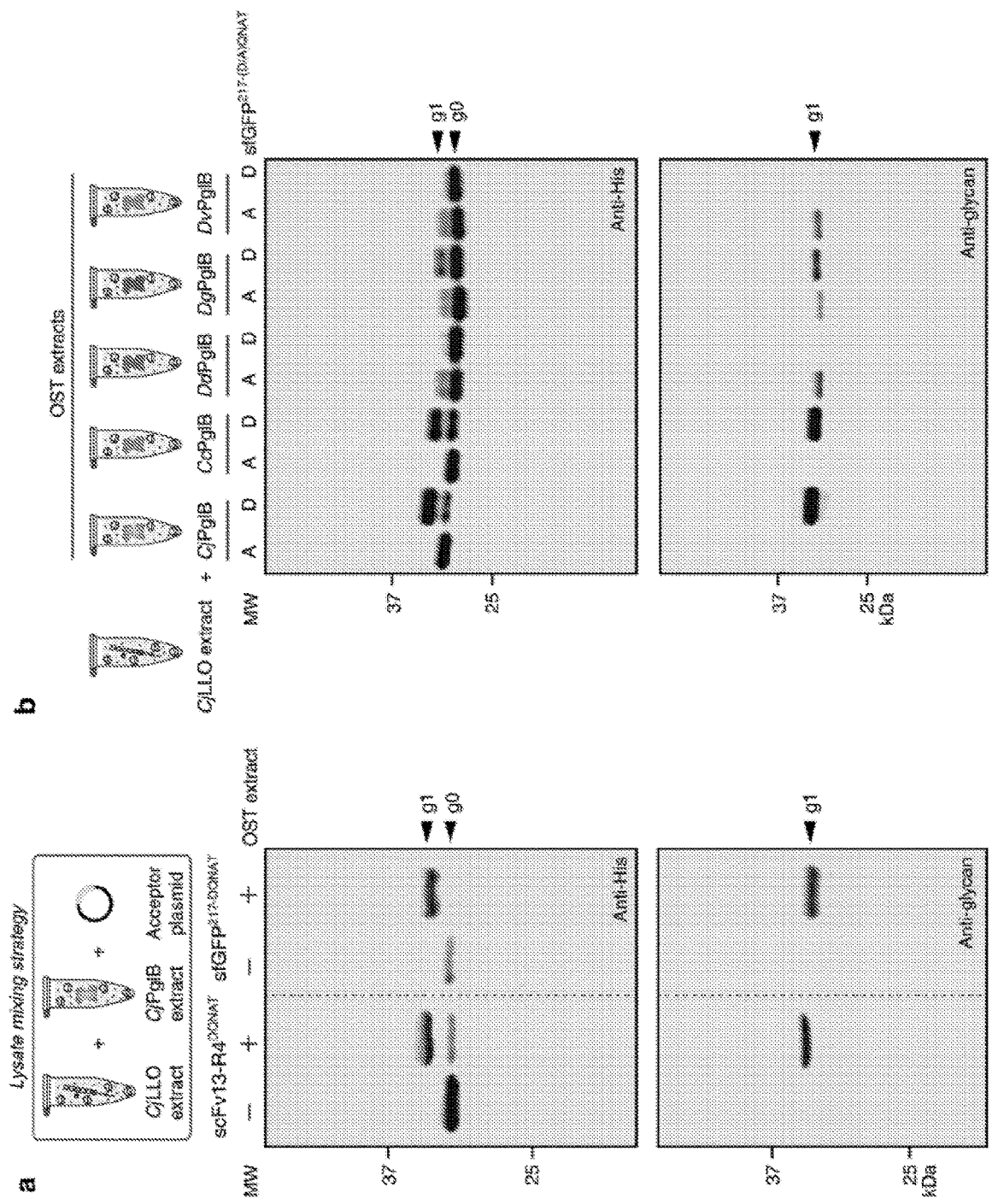
FIG. 7. Mixing of *E. coli* lysate enables rapid prototyping of different OST enzymes. (A) immunoblot analysis of cell-free glycoprotein synthesis reactions performed using lysate mixing strategy whereby CjLLO lysate derived from cells expressing glycan biosynthesis pathway was mixed with CjPglB lysate derived from cells expressing CjPglB, and the resulting lysate mixture was primed with plasmid DNA encoding either scFv13-R4$^{DQNAT}$ or sfGFP$^{217\text{-}DQNAT}$. (B) Immunoblot analysis of reactions performed using CjLLO lysate mixed with extract derived from cells expressing one of the following OSTs: CjPglB, CcPglB, DdPglB, DgPglB, or DvPglB. Mixed lysates were primed with plasmid DNA encoding either sfGFP$^{217\text{-}DQNAT}$ (D) or sfGFP$^{217\text{-}AQNAT}$ (A). Blots were probed with anti-His antibody to detect the acceptor proteins (top panels) and hR6 serum against the *C. jejuni* glycan (bottom panels). Arrows denote aglycosylated (g0) and singly glycosylated (g1) forms of the acceptor proteins. Molecular weight (MW) markers are indicated at left. Results are representative of at least three biological replicates. Figure taken from doi.org/10.1038/s41467-018-05110-x FIG. 8. Mixing of *E. coli* lysate can be used to synthesize conjugate vaccines. Cell-free reactions performed using lysate mixing strategy whereby LLO lysate derived from cells expressing the *E. coli* O78 polysaccharide antigen (EcO78-PS) biosynthesis pathway was mixed with OST lysate derived from cells expressing either PglB from *C. jejuni* or *C. coli*. The resulting lysate mixture was primed with plasmid DNA encoding either sfGFP$^{217\text{-}DQNAT}$. Blots were probed with anti-His antibody to detect the acceptor proteins (left) and anti-EcO78-PS antiserum (right). We observed that either CjPglB or CcPglB successfully conjugated EcO78-PS to sfGFP$^{217\text{-}DQNAT}$. Molecular weight (MW) markers are indicated at left. Asterisk (*) indicates nonspecific binding of the EcO78-PS antiserum. Results are representative of at least three biological replicates.

Given the open nature of cell-free system, it is possible to functionally interchange and prototype alternative biochemical reaction components. One straightforward way that this can be accomplished is by combining separately prepared lysates, each of which is selectively enriched with a given enzyme [4, 5]. As proof of this concept, separately prepared CjLLO and CjPglB lysates were mixed and then primed with DNA encoding the scFv13-R4$^{DQNAT}$, an anti-β-galactosidase (β-gal) single-chain variable fragment (scFv) antibody modified C-terminally with a single DQNAT motif [6], acceptor. The resulting mixture promoted efficient glycosylation of scFv13-R4$^{DQNAT}$ as observed in immunoblots probed with anti-His antibody and hR6 serum detecting C. jejuni glycan (FIG. 7a). In addition to scFv13-R4$^{DQNAT}$, we also expressed a different model acceptor protein that was created by grafting a 21-amino acid sequence from the C. jejuni glycoprotein AcrA, which was further modified with an optimized DQNAT glycosylation site, into a flexible loop of superfolder GFP (sfGFP$^{217-DQNAT}$). The mixed lysate reaction scheme was able to glycosylate the sfGFP$^{217-DQNAT}$ acceptor protein with 100% conversion (FIG. 7a).

Next, we sought to demonstrate that the mixed lysate approach could be used to rapidly prototype the activity of four additional bacterial OSTs. Crude lysates were separately prepared from E. coli CLM24 source strains heterologously overexpressing one of the following bacterial OSTs: Campylobacter coli PglB (CcPglB), Desulfovibrio desulfuricans PglB (DdPglB), Desulfovibrio gigas PglB (DgPglB), or Desulfovibrio vulgaris PglB (DvPglB). Each OST lysate was mixed with the CjLLO-enriched lysate and then supplemented with plasmid DNA encoding sfGFP$^{217-DQNAT}$ or a modified version of this target protein sfGFP$^{217-AQNAT}$. Upon completion of cell-free glycoprotein synthesis reactions, the expression and glycosylation status of both sfGFPs was followed by immunoblot analysis, which revealed information about the sequon preferences for these homologous enzymes. For example, the mixed lysate containing CcPglB was observed to efficiently glycosylate sfGFP$^{217-DQNAT}$ but not sfGFP$^{217-AQNAT}$ (FIG. 7b). This activity profile for CcPglB was identical to that observed for CjPglB, which was not surprising based on its high sequence similarity (~81%) to CjPglB [7]. In contrast, lysate mixtures containing OSTs from Desulfovibrio sp., which have low sequence identity (~15-20%) to CjPglB, showed more relaxed sequon preferences (FIG. 7b). Specifically, DgPglB-enriched extract mixtures modified both (D/A)QNAT motifs with nearly equal efficiency while mixed lysates containing DdOST and DvOST preferentially glycosylated the AQNAT sequon. Taken together, these results suggest that diverse oligosaccharyltransferase enzymes (OSTs) can be functionally enriched in our cell-free lysate to produce targeted glycoproteins. We postulate that the range of OSTs used in our cell-free system could be broadened to include those originate from organism such as protozoa, yeast, and mammalian.

Figure 8:
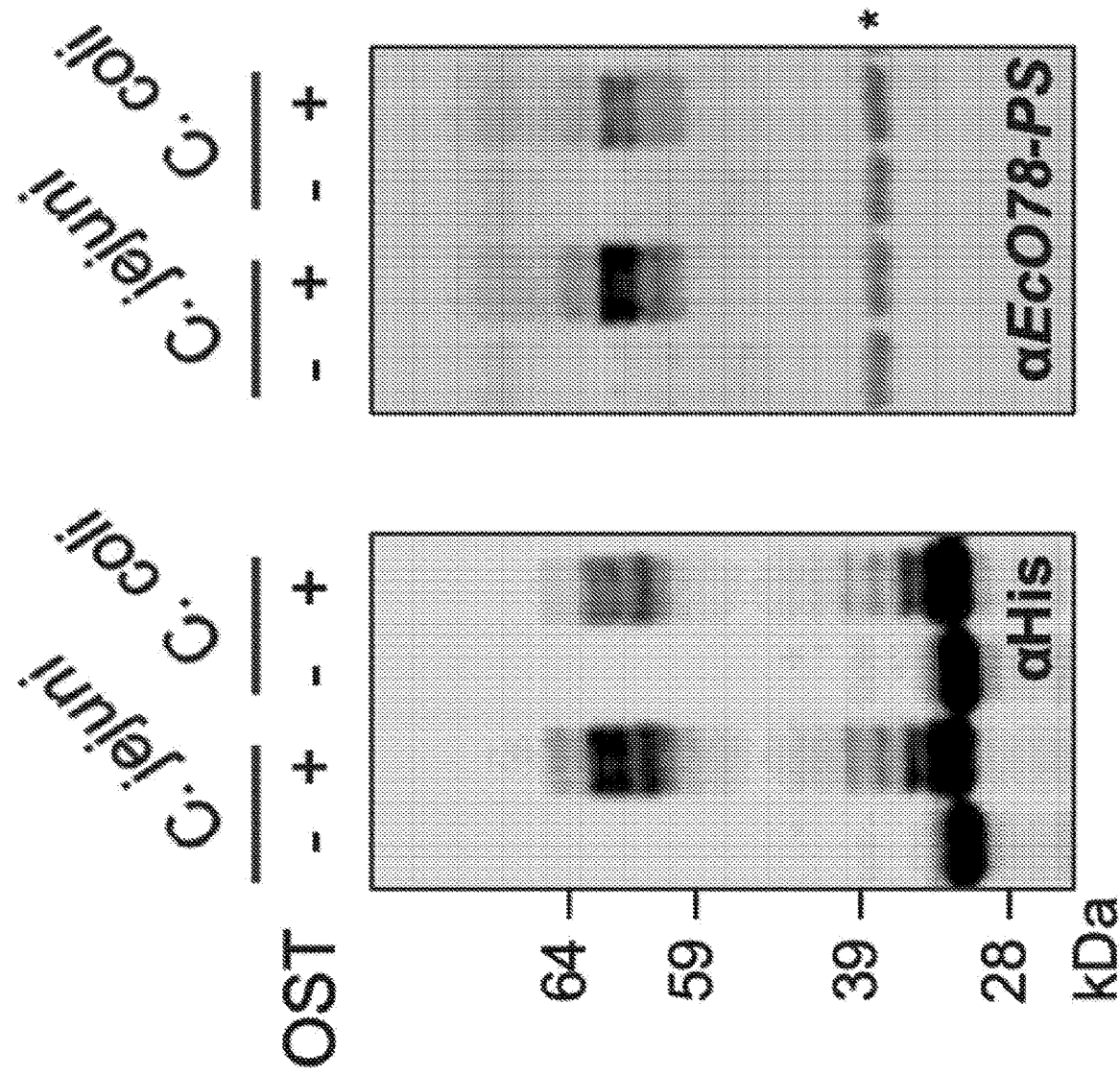

Finally, we have shown that O-antigen polysaccharides that represent clinically relevant vaccine antigens can be transferred to proteins using our lysate mixing approach with multiple OST enzymes. Here, we focused on conjugation of the E. coli O78 polysaccharide antigen (EcO78-PS) to inform development of an antibacterial vaccine, as the O78 strain is a leading cause of traveler's diarrhea in the developing world. Crude lysates enriched with CjPglB or CcPglB described above were mixed with an LLO lysate prepared from cells expressing the biosynthetic pathway for synthesis of EcO78-PS. These lysate mixtures were then supplemented with plasmid DNA encoding sfGFP$^{217-DQNAT}$. Immunoblot analysis revealed that both CjPglB and CcPglB can transfer EcO78-PS to proteins (FIG. 8). These data indicate that diverse oligosaccharyltransferase enzymes (OSTs) can be used to synthesize conjugate vaccine candidates in our cell-free platform. We have further developed this platform to enable on-demand and decentralized production of conjugate vaccines, described below.

Figure 9:
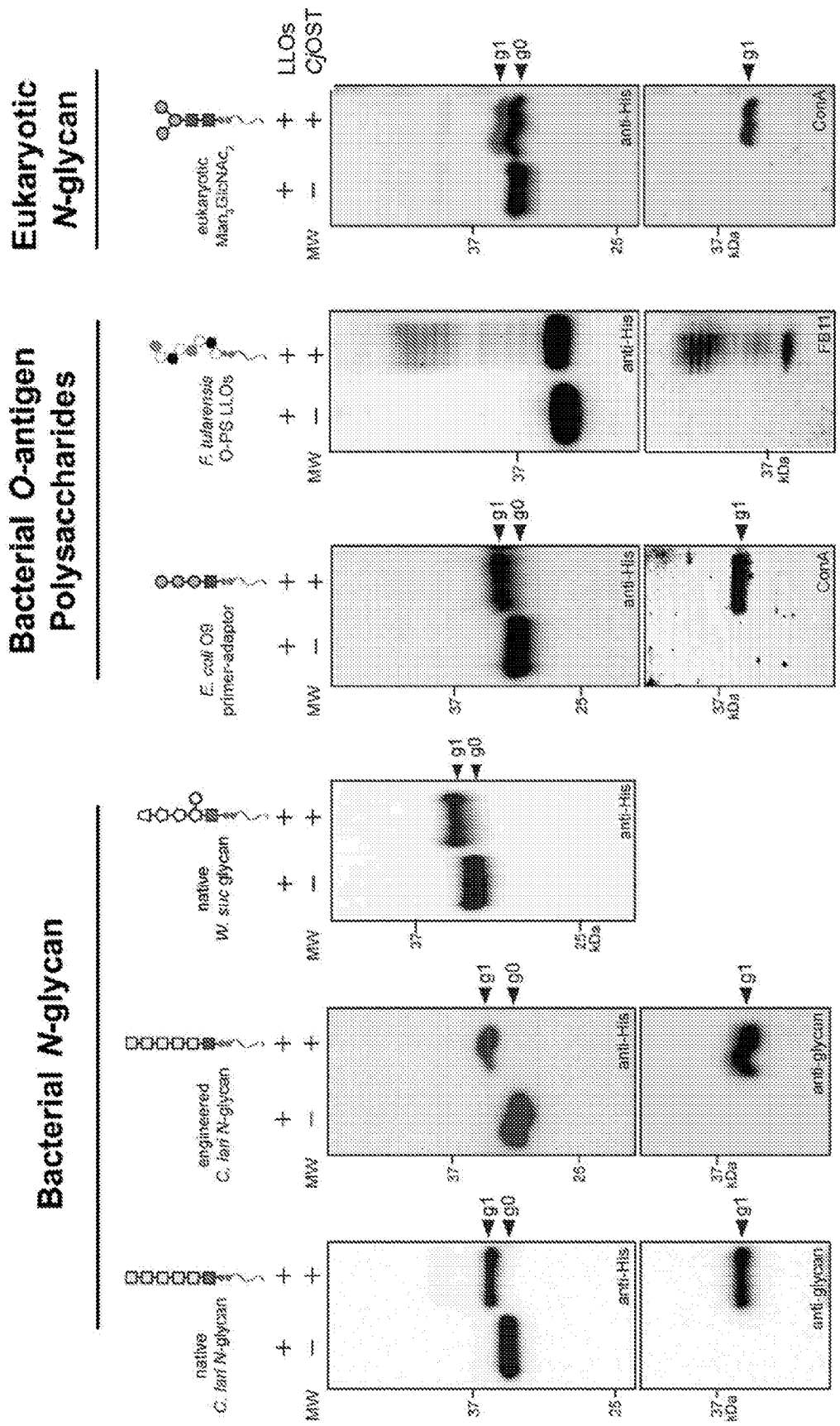
FIG. 9. Expanding cell-free glycosylation with different oligosaccharide structures. Immunoblot analysis of in vitro glycosylation reaction products generated with purified scFv13-R4$^{DQNAT}$ acceptor protein, purified CjPglB, and organic solvent-extracted LLOs from cells expressing biosynthesis pathway of the following glycan: a. the native *C. lari* hexasaccharide N-glycan; b. the engineered *C. lari* hexasaccharide N-glycan; c. the native *W. succinogenes* hexasaccharide N-glycan; d. the *E. coli* O9 'primer-adaptor' Man$_3$GlcNAc structure; e. the *F. tularensis* O-PS Qui4NFm-(GalNAcAN)$_2$-QuiNAc structures; and f. the eukaryotic Man$_3$GlcNAc$_2$ N-glycan structure. Blots were probed with anti-His antibody to detect the acceptor protein and one of the following: hR6 serum that cross-reacts with the native and engineered *C. lari* glycans or ConA lectin that binds internal and non-reducing terminal α-mannosyl groups in the Man$_3$GlcNAc and Man$_3$GlcNAc$_2$ glycans. FB11 antibody that specifically reacts with Ft-OPS structure. Because structural determination of the *W. succinogenes* N-glycan is currently incomplete, and because there are no available antibodies, the protein product bearing this N-glycan was only probed with the anti-His antibody. Arrows denote aglycosylated (g0) and singly glycosylated (g1) forms of the scFv13-R4DQNAT protein. Molecular weight (MW) markers are indicated at left. Results are representative of at least three biological replicates. Figure adapted from doi.org/10.1038/s41467-018-05110-x FIG. 10. The cell-free glycoprotein synthesis platform is modular and can be used to synthesize bioconjugates using diverse bacterial O-polysaccharides. *E. coli* lysates were prepared from cells expressing CjPglB and biosynthesis pathways for either (A) *F. tularensis* SchuS4 O antigen, (B) *E. coli* O78 antigen, or (C) *E. coli* O7 antigen and used to synthesize sfGFP$^{217\text{-}DQNAT}$ bioconjugate. In (A), anti-His signal is shown in red and anti-*F. tularensis* O antigen signal is in green. (B) and (C), blot images are anti-His. Images are representative of at least three biological replicates. Dashed lines indicate samples are from the same blot with the same exposure FIG. 11. One-pot cell-free protein synthesis using extracts selectively enriched with OSTs and LLOs. (a) Western blot analysis of scFv13-R4$^{DQNAT}$ or sfGFP$^{217\text{-}DQNAT}$ produced by cell-free glycosylation lysate selectively enriched with CjPglB and CjLLOs. (b) Top—Ribbon representation of human erythropoietin (PDB code 1BUY) with α-helices and flexible loops colored in red and green, respectively. Glycosylation sites modeled by mutating the native sequons at N24 (22-AENIT-26), N38 (36-NENIT-40), or N83 (81-LVNSS-85) to DQNAT, with asparagine residues in each sequon colored in blue. Glycoengineered hEPO variants in which the native sequons at N24 (22-AENIT-26), N38 (36-NENIT-40), or N83 (81-LVNSS-85) were individually mutated to an optimal bacterial sequon, DQNAT (shown in blue). Bottom—Western blot analysis of hEPO glycovariants produced by cell-free glycosylation lysate. Reactions were primed with plasmid pJL1-hEPO$^{22\text{-}DQNAT\text{-}26}$ (N24), pJL1-hEPO$^{36\text{-}DQNAT\text{-}40}$ (N38), or pJL1-hEPO$^{81\text{-}DQNAT\text{-}85}$ (N83) as indicated. All control reactions (lane 1 in each panel) were performed using CjLLO-enriched lysate that lacked CjPglB. Blots were probed with anti-hexa-histidine antibody (anti-His) to detect the acceptor proteins or hR6 serum (anti-glycan) to detect the N-glycan. Arrows denote aglycosylated (g0) and singly glycosylated (g1) forms of the protein targets. Asterisks denote bands corresponding to non-specific serum antibody binding. Molecular weight (MW) markers are indicated at left. Figure taken from Jaroentomeechai et al., Nat. Comm., Jul. 12, 2018, doi.org/10.1038/s41467-018-05110-x, the content of which is incorporated herein by reference in its entirety.

To date, only the C. jejuni glycosylation pathway has been reconstituted in vitro [8, 9], and it remains an open question whether our system can be reconfigured with different LLOs. Therefore, to extend the range of glycan structures beyond the C. jejuni heptasaccharide, we performed in vitro glycosylation reactions using lipid-linked oligosaccharide donors extracted from E. coli cells carrying alternative glycan biosynthesis pathways. These included LLOs bearing the following glycan structures: (i) native C. lari hexasaccharide N-glycan [10]; (ii) engineered GalNAc$_5$GlcNAc based on the C. lari hexasaccharide N-glycan [11]; (iii) native Wolinella succinogenes hexasaccharide N-glycan [12]; (iv) engineered E. coli O9 primer-adaptor O-PS glycan, Man$_3$GlcNAc; (v) F. tularensis O-PS, Qui4NFm-(GalNAcAN)$_2$-QuiNAc structures [13] and (vi) eukaryotic trimannosyl core N-glycan, Man$_3$GlcNAc$_2$ [6]. Glycosylation of scFv13-R4$^{DQNAT}$ with each of these different glycans was observed to occur only in the presence of CjPglB (FIG. 9). Taken together, these results demonstrate that structurally diverse glycans, including those that resemble eukaryotic structures and O-antigen polysaccharides, can be modularly interchanged in cell-free glycosylation reactions.

Figure 10:
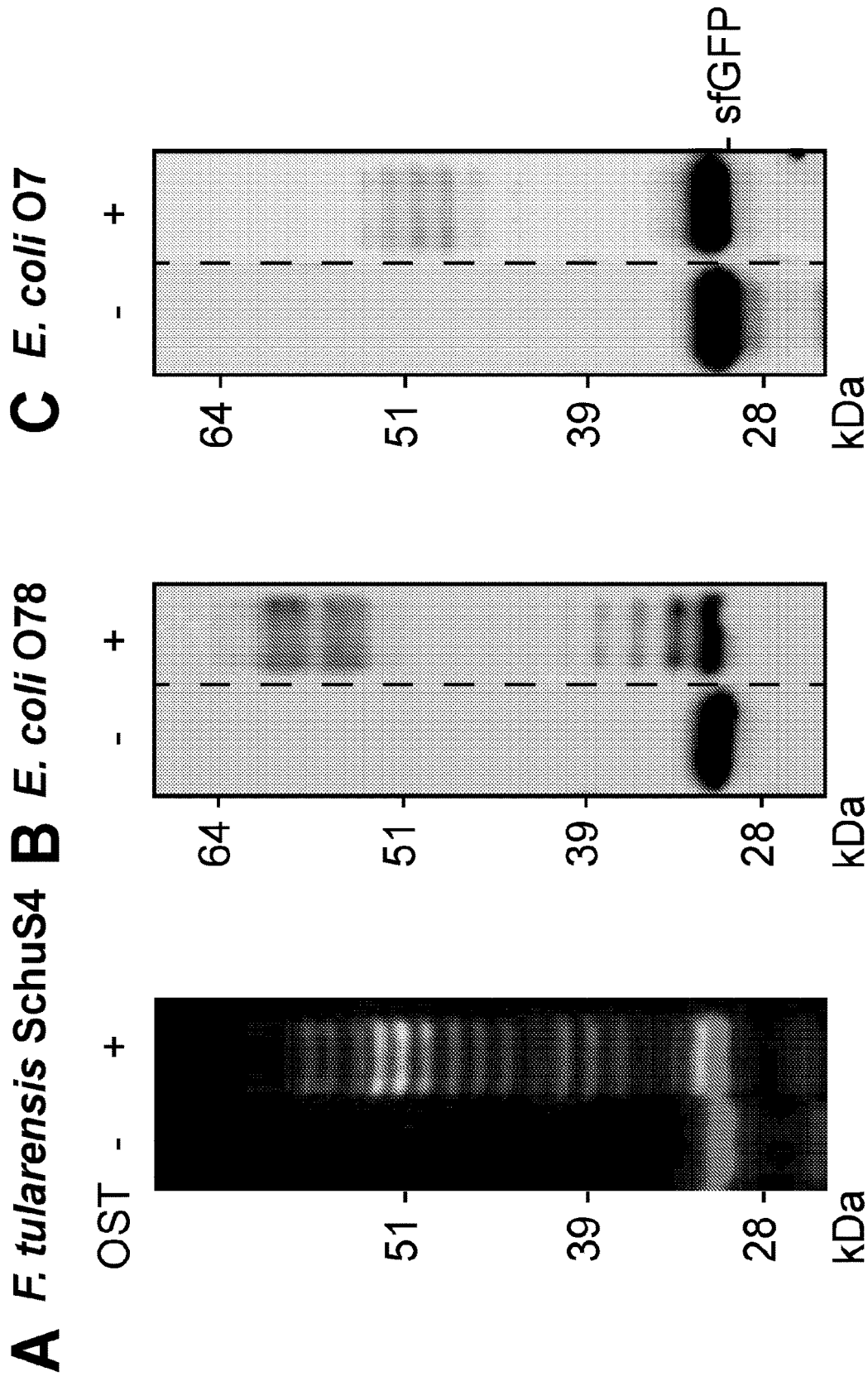

Building upon the successful introduction of several glycan structures into cell-free glycoprotein synthesis platform, we turned our interest to a particular group of glycan, bacterial O-polysaccharides. As antibacterial resistance is a growing problem worldwide, strategies to accelerate the production of new antibiotics and vaccines become necessary. In particular, conjugate vaccines, composed of a bacterial O-polysaccharide antigen conjugated to an immunogenic carrier protein, are over 90% effective at preventing bacterial infections with extremely rare instances of resistance. We hypothesized we could use our cell-free glycoprotein synthesis technology to prepare bioconjugate vaccine candidates in the context of a pathogen-specific polysaccharide. As proof-of-concept, we attempted to express and site-specifically glycosylate sfGFP-$^{DQNAT}$ with the O-PS structure from the Gram-negative pathogen *Franciscella tularensis* subsp. tularensis (type A) strain Schu S4, a facultative coccobacillus and the causative agent of tularemia. Glycosylation activity was assayed via immunoblotting with anti-His antibody and a monoclonal antibody specific to FtO-PS (FIG. 10A). The ladder-like pattern observed when the FtLLO and CjPglB lysates are mixed is indicative of FtLLO attachment and results from O-PS chain length variability through the action of the Wzy polymerase.

To demonstrate the generality and modularity of our cell-free approach for production of diverse conjugate vaccines, we sought to produce vaccines against two pathogenic strains of *E. coli*, namely enterotoxigenic *E. coli* strains O7 and O78. *E. coli* strain O7 is a leading cause of urinary tract infections and strain O78 is a leading cause of travelers' diarrhea and a major cause of diarrheal disease in lower-income countries. One-pot lysates were prepared from cells expressing CjPglB and the biosynthetic pathways for either the *E. coli* O78 antigen or O7 antigen. Cell-free reactions containing these lysates resulted in ladder-like glycosylation of our sfGFP variant by immunoblotting with an anti-His antibody (FIG. 10B, C) and antiserum against the *E. coli* O78 and O7 antigens (data not shown). Importantly, these results demonstrate the potential of our integrated technology for coordinated carrier protein synthesis and pathogen-specific O antigen attachment. Moreover, our cell-free platform represents an attractive option for rapid production and prototyping of novel conjugate vaccine candidates from diverse structure of bacterial O-polysaccharides.

Figure 11:
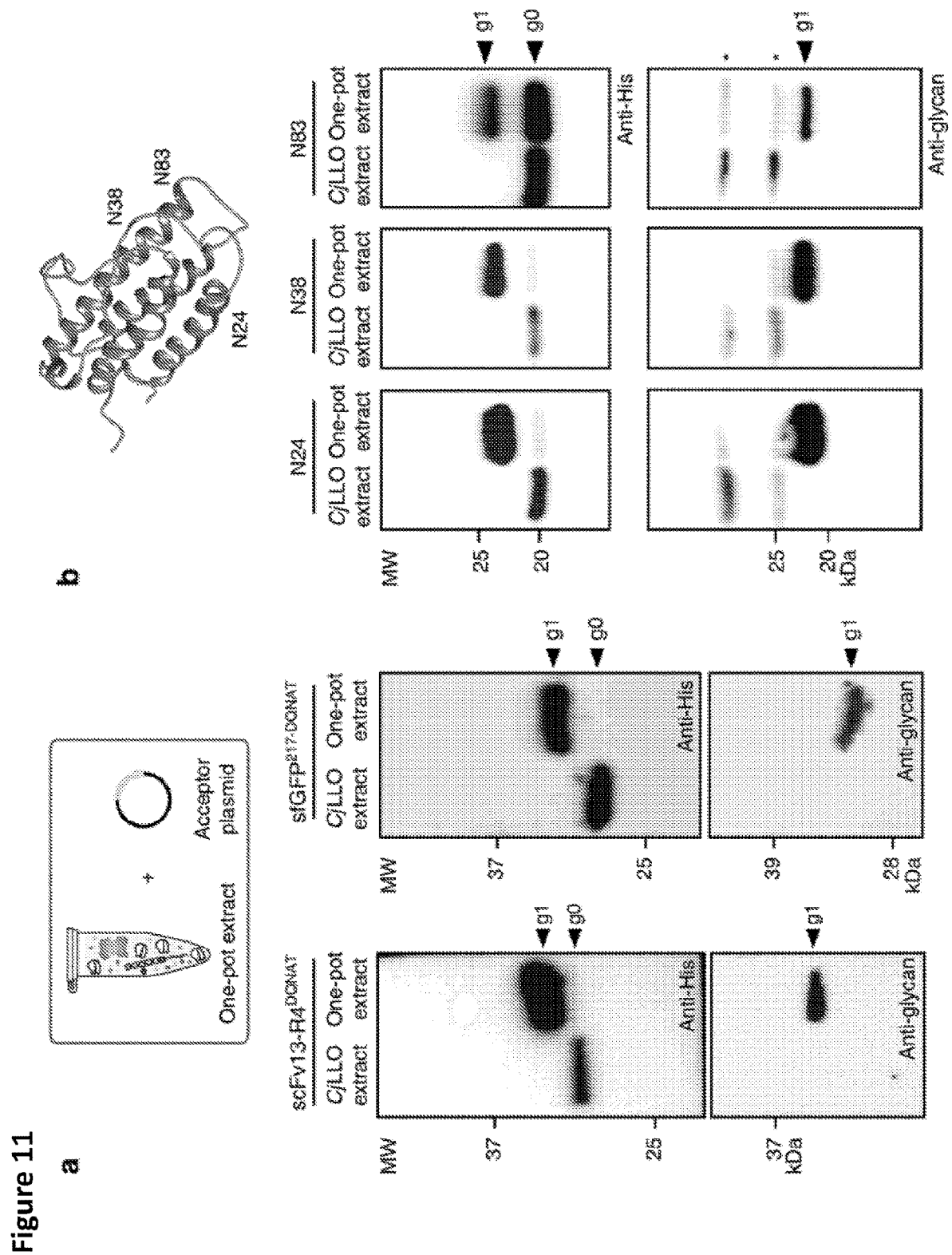

Our fully integrated cell-free glycoprotein synthesis platform has been demonstrated to permit one-pot synthesis of diverse N-glycoproteins. Using this system, reactions primed with plasmid DNA encoding either scFv13-R4$^{DQNAT}$ or sfGFP$^{217-DQNAT}$, led to a production of targeted protein with 100% protein glycosylation (FIG. 11a). Importantly, the in vitro synthesized scFv13-R4$^{DQNAT}$ and sfGFp$^{217-DQNAT}$ proteins retained biological activity, measured by the ability to bind antigen substrate in an ELISA format for scFv and by fluorescent signal for sfGFP, that was unaffected by N-glycan addition (data not shown). More importantly, our one-pot cell-free glycosylation system performed similarly in the reactions primed with plasmid DNA encoding several human erythropoietin (hEPO) glycovariants including those with native sequons at residue N24 (22-AENIT-26), N38 (36-NENIT-40) or N83 (81-LVNSS-85) were individually mutated to the optimal bacterial sequon, DQNAT (FIG. 11b). Western blot analysis revealed clearly detectable glycosylation of each hEPO glycovariant with 100% glycosylated product for the N24 and N38 sites and ~30-40% for the N83 site (FIG. 11b). All three glycosylated hEPO variants retained biological activity that was indistinguishable from the activity measured for the corresponding aglycosylated counterparts (data not shown). Collectively, these findings establish that one-pot lysate are capable of co-activating protein synthesis and N-glycosylation in a manner that yields efficiently glycosylated proteins including those of human origin.

Next, we sought to extend the capability of our cell-free system to synthesize authentic glycoprotein acceptors beyond model-targets like sfGFP or small cytokine glycoproteins such as hEPO. Specifically, we turned our effort to the expression of glycoconjugate vaccine carriers. Expressing conjugate vaccines in vivo in *E. coli* have been limited by the use of carrier proteins that are not yet approved by the FDA for use as protein adjuvants in the context of conjugate vaccines. FDA-approved carrier proteins, such as the tetanus or diphtheria toxin proteins, have not yet been demonstrated to be compatible with N-linked glycosylation in the periplasm of living *E. coli* cells. In fact, these FDA-approved carriers have proven difficult to express in vivo in *E. coli*, often requiring purification and refolding of insoluble product from inclusion bodies, fusion of expression partners to increase soluble expression, or expression of protein fragments in favor of the full-length protein. In contrast, cell-free protein synthesis approaches have recently shown promise for difficult-to-express proteins [14]. The carrier proteins that we focused on here included nonacylated *H. influenzae* protein D (PD), the *N. meningitidis* porin protein (PorA), and genetically detoxified variants of the *Corynebacterium diphtheriae* toxin (CRM197) and the *Clostridium tetani* toxin (TT). We also tested expression of the fragment C (TTc) and light chain (TTlight) domains of TT as well as *E. coli* MBP. To enable glycosylation, all carriers were modified at their C-termini with 4 tandem repeats of an optimal bacterial glycosylation motif, DQNAT [15]. A variant of superfolder green fluorescent protein that contained an internal DQNAT glycosylation site (sfGFP$^{217-DQNAT}$) [16] was used as a model protein to facilitate system development. All eight carriers were synthesized in vitro with soluble yields of ~50-650 µg mL$^{-1}$ as determined by $^{14}$C-leucine incorporation (data not shown).

Figure 12:
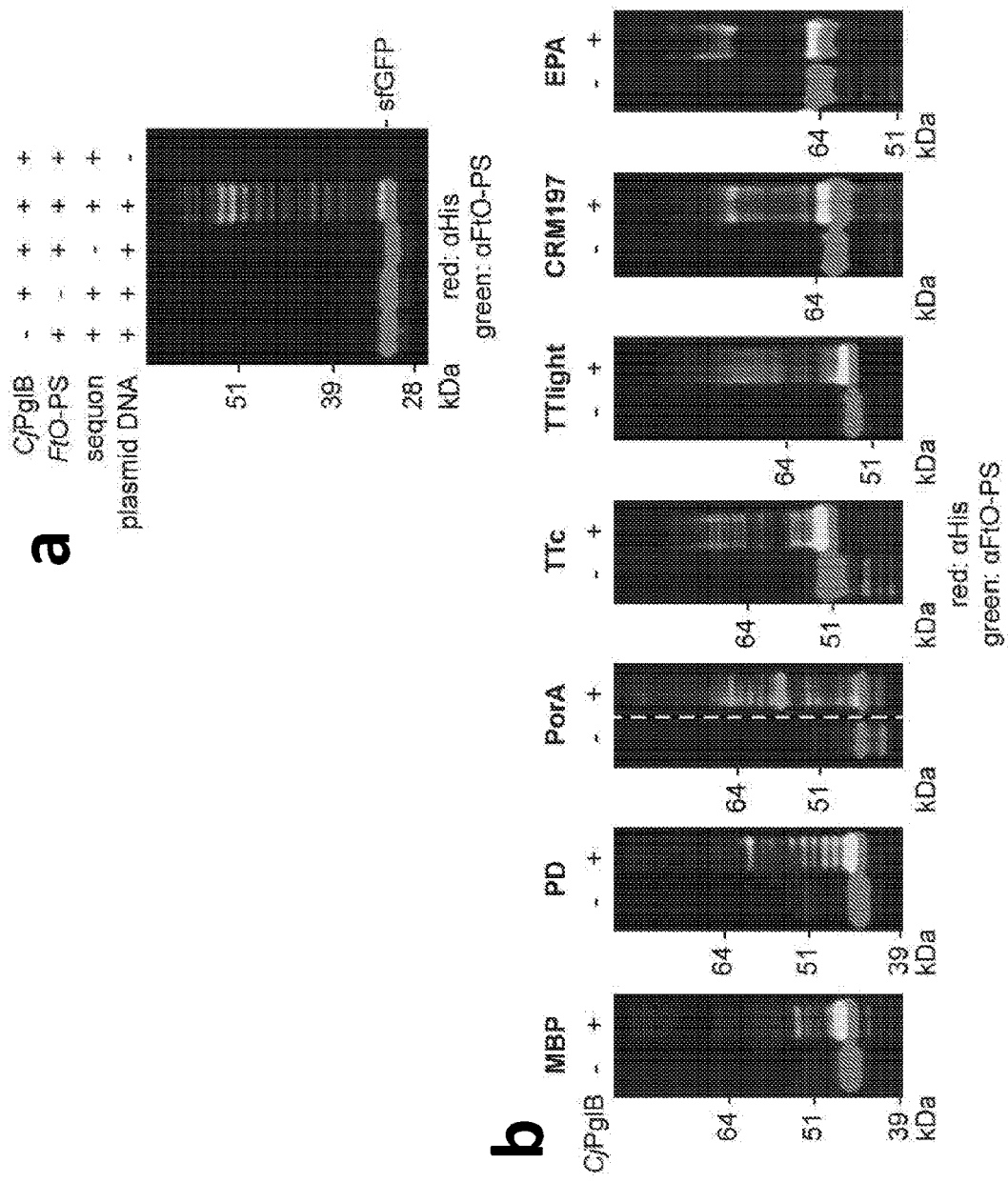
FIG. 12. On-demand and reproducible production of bioconjugates against *F. tularensis* using cell-free glycoprotein synthesis lysate. (a) Glycosylation of sfGFP$^{217\text{-}DQNAT}$ with FtO-PS was only observed when CjPglB, FtO-PS, and the preferred sequon were present in the reaction (lane 3). When plasmid DNA was omitted, sfGFP$^{217\text{-}DQNAT}$ synthesis was not observed. (b) On-demand synthesis of bioconjugate vaccines with immunostimulatory carriers including carriers used in licensed vaccines. Bioconjugates were purified using Ni-NTA agarose from 1 mL cell-free glycoprotein synthesis reactions lasting ~1 h at 30° C. Dashed lines indicate samples are from the same blot with the same exposure. Molecular weight ladders are shown at the left of each image. Figure adapted from Stark et al., bioRxiv, Jun. 24, 2019, doi.org/10.1101/681841, the content of which is incorporated herein by reference in its entirety.
Figure 13:
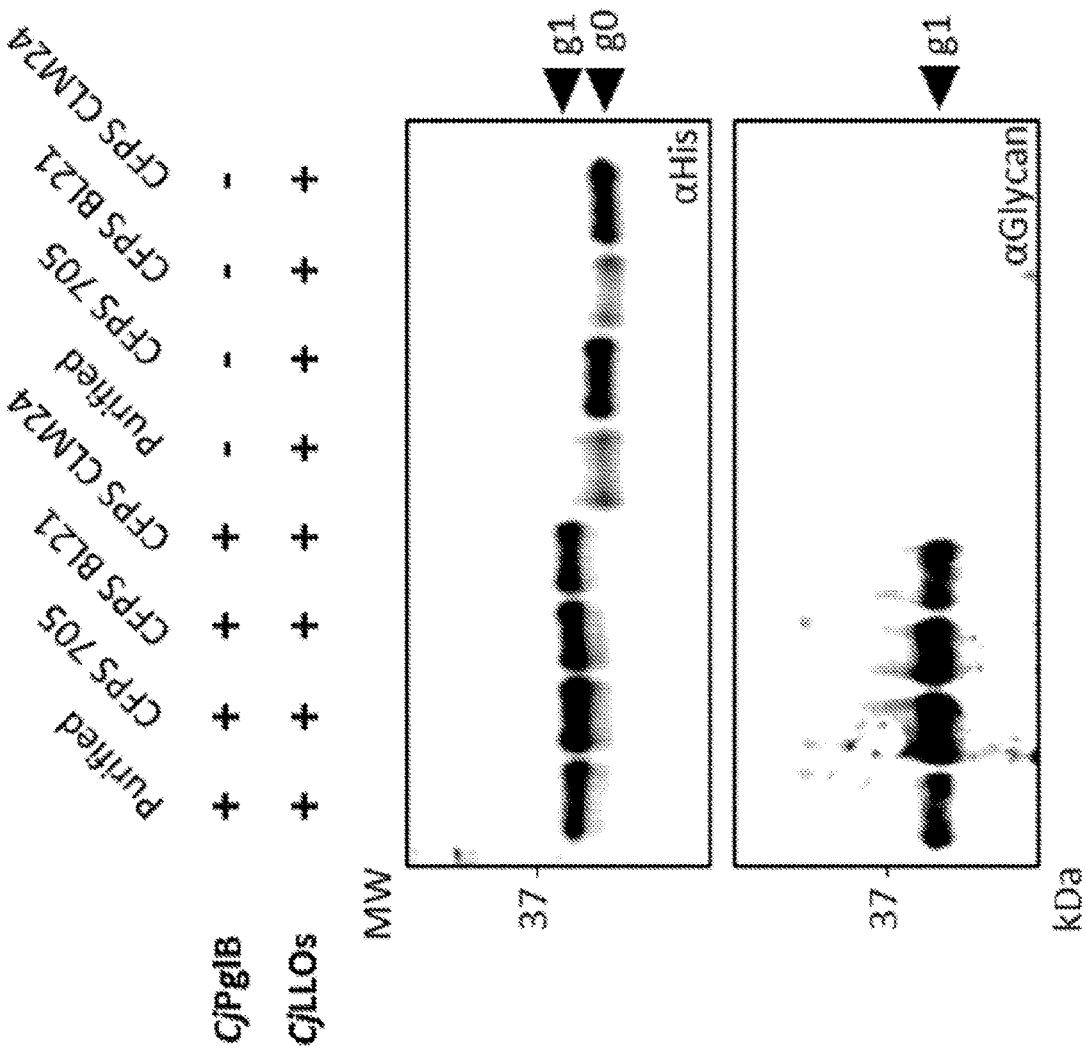
FIG. 13. Crude lysates prepared from diverse *E. coli* strains are amenable to in vitro protein glycosylation. Lysates prepared from several chassis strains including r *E. coli* 705, BL21(DE3), and CLM24 were used in reactions supplemented with purified CjPglB, organic solvent-extracted CjLLOs, and primed with plasmid pJL1-scFv13-R4$^{DQNAT}$. Efficient glycosylation was observed in the reactions lasting 16 hours. Blots were probed with anti-hexa-histidine antibody (anti-His) to detect the acceptor protein or hR6 serum (anti-glycan) to detect the N-glycan. Arrows denote aglycosylated (g0) and singly glycosylated (g1) forms of scFv13-R4$^{DQNAT}$. Molecular weight (MW) markers are indicated at left.
Figure 14:
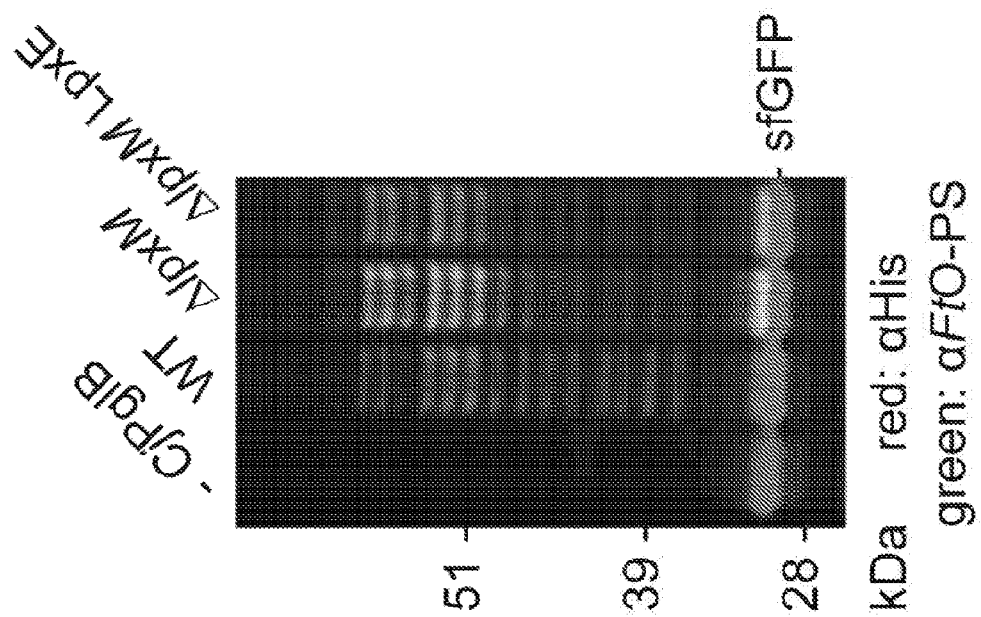
FIG. 14. Detoxified cell-free reactions produce bioconjugates. Lipid A remodeling does not affect glycosylation activity in cell-free glycoprotein synthesis reactions. Lysates were prepared from either wild-type CLM24, CLM24 ΔlpxM, or CLM24 ΔlpxM expressing FtLpxE cells also expressing CjPglB and FtO-PS. Nearly identical glycosylation activities were observed for each of the lysates derived from the engineered strains. Images are representative of at least three biological replicates. Figure adapted from Stark et al., bioRxiv, Jun. 24, 2019, doi.org/10.1101/681841, the content of which is incorporated herein by reference in its entirety.

We next sought to synthesize conjugated versions of these carrier proteins by merging their in vitro expression with one-pot, cell-free glycosylation. For the vaccine target, we focused on the highly virulent *Francisella tularensis* strain Schu S4. To glycosylate proteins with FtO-PS, we produced a one-pot lysate from glycoengineered *E. coli* cells expressing the FtO-PS biosynthetic pathway and the CjPglB enzyme. This lysate, which contained lipid-linked FtO-PS and catalytically active CjPglB, was used to catalyze reactions primed with plasmid DNA encoding sfGFP$^{217-DQNAT}$. Efficient synthesis of glycosylated sfGFP$^{217-DQNAT}$ decorated with FtO-PS was observed via immunoblotting with anti-His antibody or a monoclonal antibody specific to FtO-PS (FIG. 12a). Glycosylation of sfGFP$^{217-DQNAT}$ was observed only in reactions containing a complete glycosylation pathway and the preferred DQNAT glycosylation sequence (FIG. 12a).

Next, we investigated whether FDA-approved carriers could be similarly conjugated with FtO-PS in our cell-free reactions. Following addition of plasmid DNA encoding MBP$^{4xDQNAT}$, PD$^{4xDQNAT}$, PorA$^{4xDQNAT}$, TTc$^{4xDQNAT}$, TTlight$^{4xDQNAT}$, and CRM197$^{4xDQNAT}$, glycosylation of each with FtO-PS was observed for the reactions enriched with lipid-linked FtO-PS and CjPglB but not with control reactions lacking CjPglB (FIG. 12b). We 16. Jaroentomeechai, T., et al., Single-pot glycoprotein biosynthesis using a cell-free transcription-translation system enriched with glycosylation machinery. Nat. Commun., 2018. 9(1): p. 2686.

17. Stefanetti, G., et al., Glycoconjugate vaccine using a genetically modified O antigen induces protective antibodies to *Franciscella tularensis*. Proc. Natl. Acad. Sci. U.S.A., 2019. 116(14): p. 7062-7070.

18. Carlson, E. D., et al., Cell-free protein synthesis: Applications come of age. Biotechnology Advances, 2011. 30(5).

19. Salehi, A. S., et al., *Escherichia coli*-based cell-free extract development for protein-based cancer therapeutic production. Int J Dev Biol, 2016. 60(7-8-9): p. 237-243.

20. Chong, S., Overview of cell-free protein synthesis: historic landmarks, commercial systems, and expanding applications. Curr Protoc Mol Biol, 2014. 108: p. 16 30 1-11.

21. Oza, J. P., et al., Robust production of recombinant phosphoproteins using cell-free protein synthesis. Nature Communications, 2015. 6: p. 8168.

22. Kwon, Y.-C. and M. C. Jewett, High-throughput preparation methods of crude extract for robust cell-free protein synthesis. Scientific Reports, 2015. 5: p. 8663.

23. Jewett, M. C. and J. R. Swartz, Mimicking the *Escherichia coli* cytoplasmic environment activates long-lived and efficient cell-free protein synthesis. Biotechnology and bioengineering, 2004. 86(1): p. 19-26.

24. Jaroentomeechai, T., et al., A Pipeline for Studying and Engineering Single-Subunit Oligosaccharyltransferases. Methods Enzymol, 2017. 597: p. 55-81.

25. Rietschel, E. T., et al., Bacterial endotoxin: molecular relationships of structure to activity and function. FASEB J., 1994. 8(2): p. 217-25.

26. Russell, J. A., Management of sepsis. N. Engl. J. Med., 2006. 355(16): p. 1699-1713.

27. Petsch, D. and F. B. Anspach, Endotoxin removal from protein solutions. J. Biotechnol., 2000. 76(2-3): p. 97-119.

28. Chen, L., et al., Outer membrane vesicles displaying engineered glycotopes elicit protective antibodies. Proc. Natl. Acad. Sci. U.S.A., 2016.

29. Needham, B. D., et al., Modulating the innate immune response by combinatorial engineering of endotoxin. Proc. Natl. Acad. Sci. U.S.A., 2013. 110(4): p. 1464-9.

Example 3 On-Demand, Cell-Free Biomanufacturing of Conjugate Vaccine at the Point-of-Care Summary Conjugate vaccines are among the most effective methods for preventing bacterial infections, representing a promising strategy to combat drug-resistant pathogens. As noted previously, however, existing manufacturing approaches limit access to conjugate vaccines due to centralized production and cold chain distribution requirements. To address these limitations, a modular technology for in vitro bioconjugate vaccine expression (iVAX) is described below. iVAX includes portable, freeze-dried lysates from detoxified, non-pathogenic *Escherichia coli*. Upon rehydration, iVAX reactions synthesize clinically relevant doses of bioconjugate vaccines against diverse bacterial pathogens in one hour. This Example shows that, surprisingly and unexpectedly, iVAX synthesized vaccines against the highly virulent pathogen *Franciscella tularensis* subsp. *tularensis* (type A) strain Schu S4 elicited pathogen-specific antibodies in mice at significantly higher levels compared to vaccines produced using engineered bacteria. The iVAX platform promises to accelerate development of new bioconjugate vaccines with increased access through refrigeration-independent distribution and point-of-care production.

Introduction

Drug-resistant bacteria are predicted to threaten up to 10 million lives per year by 2050 (The Review on Antimicrobial Resistance, 2014), necessitating new strategies to develop and distribute antibiotics and vaccines. Conjugate vaccines, typically composed of a pathogen-specific capsular (CPS) or O-antigen polysaccharide (O-PS) linked to an immunostimulatory protein carrier, are among the safest and most effective methods for preventing life-threatening bacterial infections (Jin et al., 2017; Trotter et al., 2008; Weintraub, 2003). In particular, implementation of meningococcal and pneumococcal conjugate vaccines have significantly reduced the occurrence of bacterial meningitis and pneumonia worldwide (Novak et al., 2012; Poehling et al., 2006), in addition to reducing antibiotic resistance in targeted strains (Roush et al., 2008). However, despite their proven safety and efficacy, global childhood vaccination rates for conjugate vaccines remain as low as ~30%, with lack of access or low immunization coverage accounting for the vast majority of remaining disease burden (Wahl et al., 2018). In addition, the 2018 WHO prequalification of Typhbar-TCV® to prevent typhoid fever represents the first conjugate vaccine approval in nearly a decade. In order to address emerging drug-resistant pathogens, new technologies to accelerate the development and global distribution of conjugate vaccines are needed.

Contributing to the slow pace of conjugate vaccine development and distribution is the fact that these molecules are particularly challenging and costly to manufacture. The conventional process to produce conjugate vaccines involves chemical conjugation of carrier proteins with polysaccharide antigens purified from large-scale cultures of pathogenic bacteria. Large-scale fermentation of pathogens results in high manufacturing costs due to associated biosafety hazards and process development challenges. In addition, chemical conjugation can alter the structure of the polysaccharide, resulting in loss of the protective epitope (Bhushan et al., 1998). To address these challenges, it was recently demonstrated that polysaccharide-protein "bioconjugates" can be made in *Escherichia coli* using protein-glycan coupling technology (PGCT) (Feldman et al., 2005). In this approach, engineered *E. coli* cells covalently attach heterologously expressed CPS or O-PS antigens to carrier proteins via an asparagine-linked glycosylation reaction catalyzed by the *Campylobacter jejuni* oligosaccharyltransferase enzyme PglB (CjPglB) (Cuccui et al., 2013; Garcia-Quintanilla et al., 2014; Ihssen et al., 2010; Ma et al., 2014; Marshall et al., 2018; Wacker et al., 2014; Wetter et al., 2013). Despite this advance, both chemical conjugation and PGCT approaches rely on living bacterial cells, requiring centralized production facilities from which vaccines are distributed via a refrigerated supply chain. Refrigeration is critical to avoid conjugate vaccine spoilage due to precipitation and significant loss of the pathogen-specific polysaccharide upon both heating and freezing (Frasch, 2009; WHO, 2014). Only one conjugate vaccine, MenAfriVac™, is known to remain active outside of the cold chain for up to 4 days, which enabled increased vaccine coverage and an estimated 50% reduction in costs during vaccination in the meningitis belt of sub-Saharan Africa (Lydon et al., 2014). However, this required significant investment in the development and validation of a thermostable vaccine. Broadly, the need for cold chain refrigeration creates economic and logistical challenges that limit the reach of vaccination campaigns and present barriers to the eradication of disease, especially in the developing world (Ashok et al., 2017; Wahl et al., 2018).

Cell-free protein synthesis (CFPS) offers opportunities to both accelerate vaccine development and enable decentralized, cold chain-independent biomanufacturing by using cell lysates, rather than living cells, to synthesize proteins in vitro (Carlson et al., 2012). Importantly, CFPS platforms (i) enable point-of-care protein production, as relevant amounts of protein can be synthesized in vitro in just a few hours, (ii) can be freeze-dried for distribution at ambient temperature and reconstituted by just adding water (Adiga et al., 2018; Pardee et al., 2016), and (iii) circumvent biosafety concerns associated with the use of living cells outside of a controlled laboratory setting. CFPS has recently been used to enable on-demand and portable production of aglycosylated protein vaccines (Adiga et al., 2018; Pardee et al., 2016). Moreover, we recently described a cell-free glycoprotein synthesis technology that enables one-pot production of glycosylated proteins, including human glycoproteins and eukaryotic glycans (Jaroentomeechai et al., 2018). Despite these advances, cell-free systems and even decentralized manufacturing systems have historically been limited by their inability to synthesize glycosylated proteins at relevant titers and bearing diverse glycan structures, such as the polysaccharide antigens needed for bioconjugate vaccine production (Perez et al., 2016).

Figure 15:
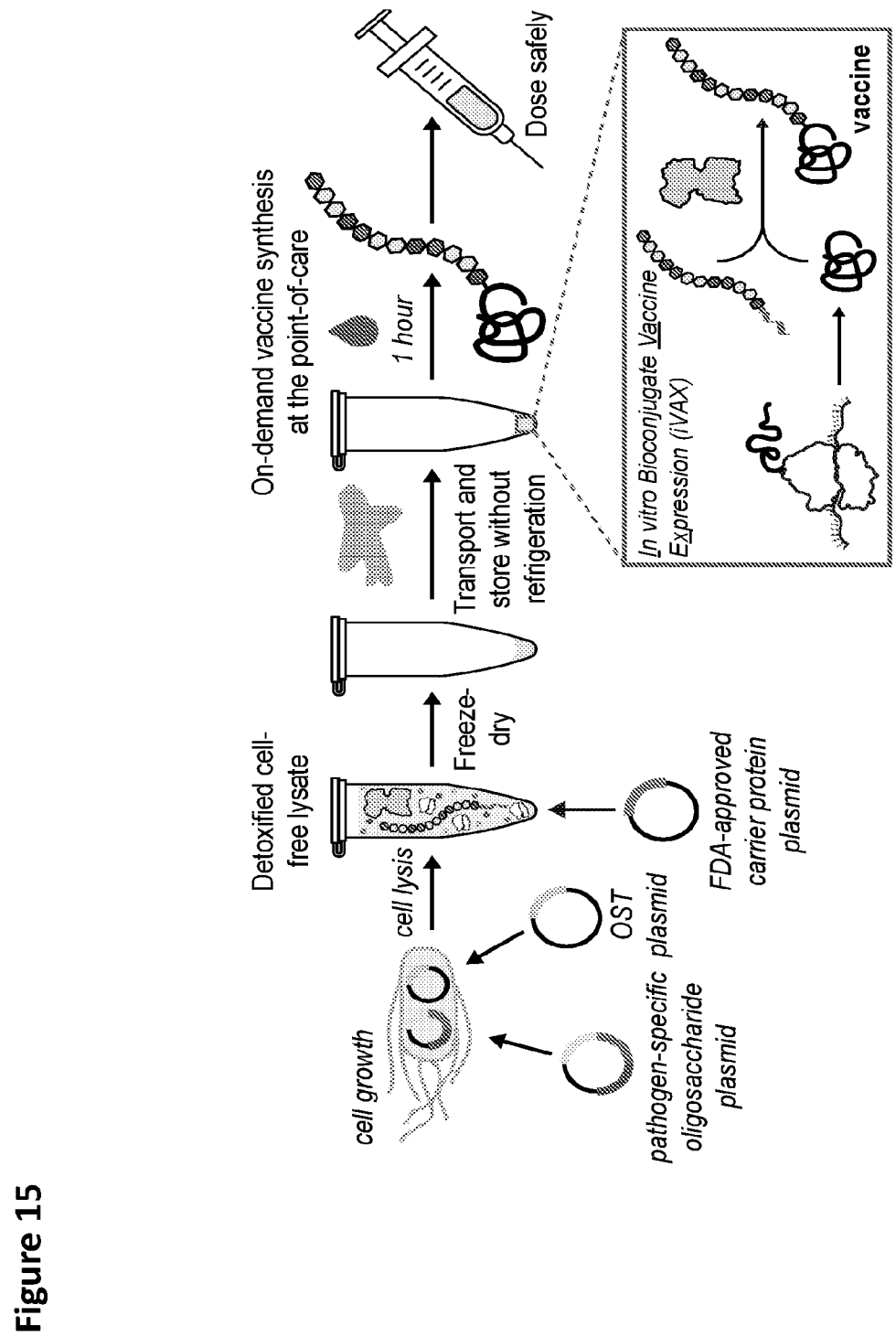
FIG. 15. Schematic showing an embodiment of the iVAX platform that enables on-demand and portable production of antibacterial vaccines. The in vitro bioconjugate vaccine expression (iVAX) platform provides a rapid means to develop and distribute vaccines against bacterial pathogens. Expression of pathogen-specific polysaccharides (e.g., CPS, O-PS) and a bacterial oligosaccharyltransferase enzyme in engineered nonpathogenic *E. coli* with detoxified lipid A yields low-endotoxin lysates containing all of the machinery required for synthesis of bioconjugate vaccines. Reactions catalyzed by iVAX lysates can be used to produce bioconjugates containing licensed carrier proteins and can be freeze-dried without loss of activity for refrigeration-free transportation and storage. Freeze-dried reactions can be activated at the point-of-care via simple rehydration and used to reproducibly synthesize immunologically active bioconjugates in ~1 h.

To address these limitations, described below is the iVAX (in vitro bioconjugate vaccine expression) platform that enables rapid development and cold chain-independent biosynthesis of conjugate vaccines in cell-free reactions (FIG. 15). iVAX was designed to have the following features. First, iVAX is fast, with the ability to produce multiple individual doses of bioconjugates in one hour. Second, iVAX is robust, yielding equivalent amounts of bioconjugate over a range of operating temperatures. Third, iVAX is modular, offering the ability to rapidly interchange carrier proteins, including those used in licensed conjugate vaccines, as well as conjugated polysaccharide antigens. As described in this example, this modularity was leveraged to create an array of vaccine candidates targeted against diverse bacterial pathogens, including the highly virulent *Franciscella tularensis* subsp. tularensis (type A) strain Schu S4, enterotoxigenic (ETEC) *E. coli* O78, and uropathogenic (UPEC) *E. coli* O7. Fourth, iVAX is shelf-stable, derived from freeze-dried cell-free reactions that operate in a just-add-water strategy. Fifth, iVAX is safe, leveraging lipid A remodeling that effectively avoids the high levels of endotoxin present in non-engineered *E. coli* manufacturing platforms. These results demonstrate that anti-*F. tularensis* bioconjugates derived from freeze-dried, low-endotoxin iVAX reactions elicit pathogen-specific antibody responses in mice and outperform a bioconjugate produced using the established PGCT approach in living cells. Overall, the iVAX platform offers a new way to deliver the protective benefits of an important class of antibacterial vaccines to both the developed and developing world.

Results

In Vitro Synthesis of Licensed Vaccine Carrier Proteins

To demonstrate proof-of-principle for cell-free bioconjugate vaccine production, a set of carrier proteins that are currently used in FDA-approved conjugate vaccines was expressed in vitro. Producing these carrier proteins in soluble conformations in vitro represented an important benchmark because their expression in living *E. coli* has proven challenging, often requiring purification and refolding of insoluble product from inclusion bodies (Haghi et al., 2011; Stefan et al., 2011), fusion of expression partners such as maltose-binding protein (MBP) to increase soluble expression (Figueiredo et al., 1995; Stefan et al., 2011), or expression of truncated protein variants in favor of the full-length proteins (Figueiredo et al., 1995). In contrast, cell-free protein synthesis approaches have recently shown promise for difficult-to-express proteins (Perez et al., 2016). The carrier proteins expressed in the in vitro system described herein included nonacylated *H. influenzae* protein D (PD), the *N. meningitidis* porin protein (PorA), and genetically detoxified variants of the *Corynebacterium diphtheriae* toxin (CRM197) and the *Clostridium tetani* toxin (TT). Also tested were the expression of the fragment C (TTc) and light chain (TTlight) domains of TT as well as *E. coli* MBP. While MBP is not a licensed carrier, it has demonstrated immunostimulatory properties (Fernandez et al., 2007) and when linked to O-PS was found to elicit polysaccharide-specific humoral and cellular immune responses in mice (Ma et al., 2014). Similarly, the TT domains, TTlight and TTc, have not been used in licensed vaccines, but are immunostimulatory and individually sufficient for protection against *C. tetani* challenge in mice (Figueiredo et al., 1995). To enable glycosylation, all carriers were modified at their C-termini with 4 tandem repeats of an optimal bacterial glycosylation motif, DQNAT (Chen et al., 2007). A C-terminal 6xHis tag was also included to enable purification and detection via Western blot analysis. A variant of superfolder green fluorescent protein that contained an internal DQNAT glycosylation site (sfGFP$^{217\text{-}DQNAT}$) (Jaroentomeechai et al., 2018) was used as a model protein to facilitate system development.

All eight carriers were synthesized in vitro with soluble yields of ~50-650 μg mL$^{-1}$ as determined by $^{14}$C-leucine incorporation (FIG. 16a). In particular, the MBP$^{4xDQNAT}$ and PD$^{4xDQNAT}$ variants were nearly 100% soluble, with yields of 500 μg mL$^{-1}$ and 200 μg mL$^{-1}$, respectively, and expressed as exclusively full-length products according to Western blot analysis (FIG. 16b). Similar soluble yields were observed for all carriers at 25° C., 30° C., and 37° C., with the exception of CRM197$^{4xDQNAT}$ (FIG. 21a), which is known to be heat sensitive (WHO, 2014). These results show that the described method of cell-free carrier biosynthesis is robust over a 13° C. range in temperature and could be used in settings where precise temperature control is not feasible.

Figure 21:
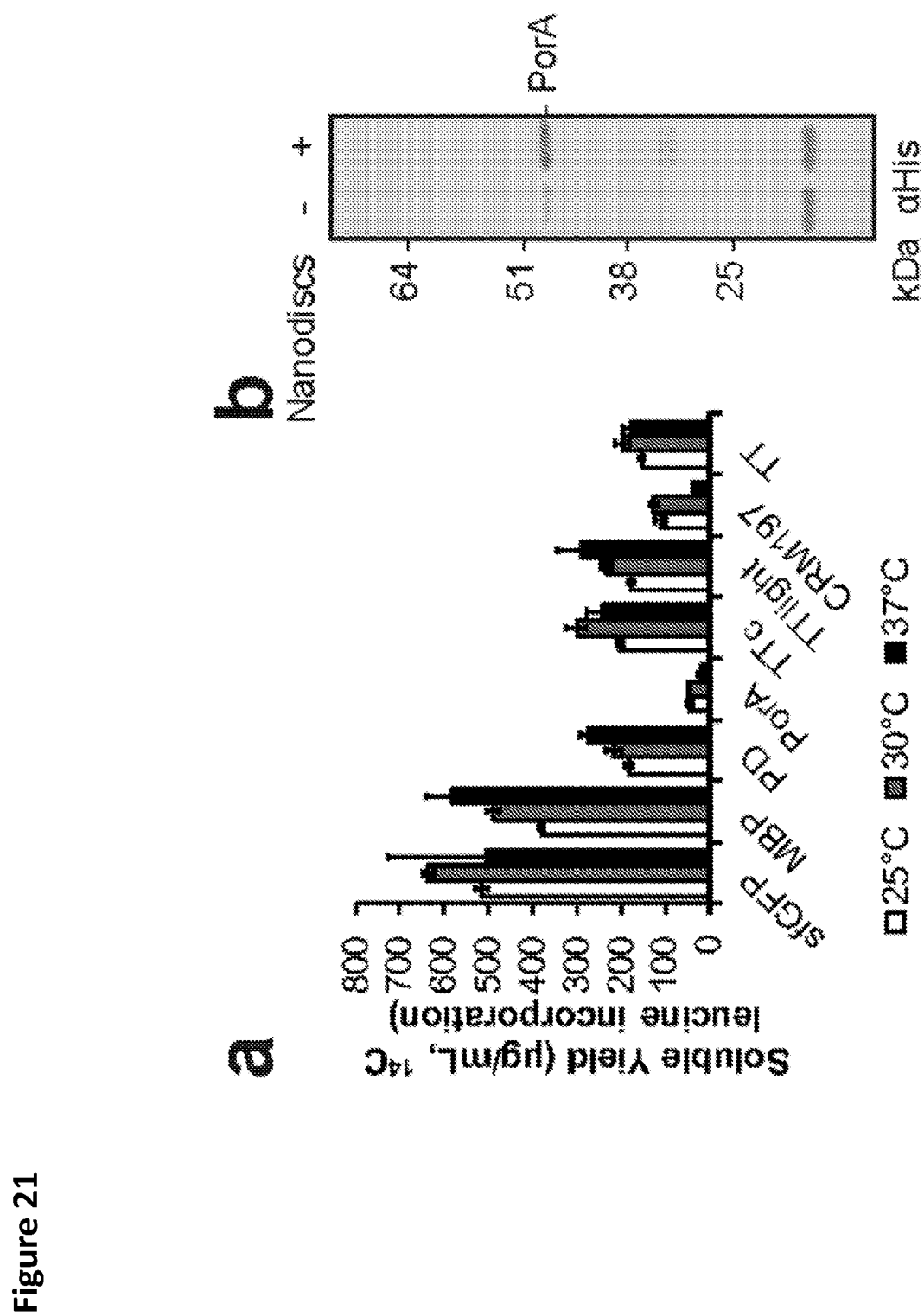
FIG. 21. In vitro synthesis of licensed conjugate vaccine carrier proteins is possible over a range of temperatures and can be readily optimized. See also FIG. 16. (a) With the exception of CRM197, all carriers expressed with similar soluble yields at 25° C., 30° C., and 37° C., as measured by $^{14}$C-leucine incorporation. Values represent means and error bars represent standard deviations of biological replicates (n=3). (b) Soluble expression of PorA was improved through the addition of lipid nanodiscs to the reaction. (c) Expression of full-length TT was enhanced by (i) performing in vitro protein synthesis in oxidizing conditions to improve assembly of the disulfide-bonded heavy and light chains into full-length TT and (ii) allowing reactions to run for only 2 h to minimize protease degradation. (d) CRM197 and (e) TT produced in CFPS reactions are detected with α-DT and α-TT antibodies, respectively, and are comparable in size to commercially available purified DT and TT protein standards (50 ng standard loaded). Images are representative of at least three biological replicates. Dashed line indicates samples are from the same blot with the same exposure. Molecular weight ladders are shown at the left of each image.

The open reaction environment of these cell-free reactions enabled facile manipulation of the chemical and reaction environment to improve production of more complex carriers. For example, in the case of the membrane protein PorA$^{4xDQNAT}$, lipid nanodiscs were added to increase soluble expression (FIG. 21b). Nanodiscs provide a cellular membrane mimic to co-translationally stabilize hydrophobic regions of membrane proteins (Bayburt and Sligar, 2010). For expression of TT, which contains an intermolecular disulfide bond, expression was carried out for 2 hours in oxidizing conditions (Knapp et al., 2007), which improved assembly of the heavy and light chains into full-length product and minimized protease degradation of full-length TT (FIG. 21c). In vitro synthesized CRM197$^{4xDQNAT}$ and TT$^{4xDQNAT}$ were comparable in size to commercially available purified diphtheria toxin (DT) and TT protein standards and were reactive with α-DT and α-TT antibodies, respectively (FIG. 21d, e), indicating that both were produced in immunologically relevant conformations. This is notable as CRM197 and TT are FDA-approved vaccine antigens for diphtheria and tetanus, respectively, when they are administered without conjugated polysaccharides. Together, these results highlight the ability of CFPS to express licensed conjugate vaccine carrier proteins in soluble conformations over a range of temperatures.

On-Demand Synthesis of Bioconjugate Vaccines

Next, polysaccharide-conjugated versions of these carrier proteins were synthesized by merging their in vitro expression with one-pot, cell-free glycosylation. As a model vaccine target, the highly virulent *Francisella tularensis* subsp. *tularensis* (type A) strain Schu S4, a gram-negative, facultative coccobacillus and the causative agent of tularemia, was used. This bacterium is categorized as a class A bioterrorism agent due to its high fatality rate, low dose of infection, and ability to be aerosolized (Oyston et al., 2004). Although there are currently no licensed vaccines against *F. tularensis*, several studies have independently confirmed the important role of antibodies directed against *F. tularensis* LPS, specifically the O-PS repeat unit, in providing protection against the Schu S4 strain (Fulop et al., 2001; Lu et al., 2012). More recently, a bioconjugate vaccine comprising the *F. tularensis* Schu S4 O-PS (FtO-PS) conjugated to the *Pseudomonas aeruginosa* exotoxin A (EPA$^{DNNNS\text{-}DQNRT}$) carrier protein produced using PGCT (Cuccui et al., 2013; Marshall et al., 2018) was shown to be protective against challenge with the Schu S4 strain in a rat inhalation model of tularemia (Marshall et al., 2018). In light of these earlier findings, the ability of the iVAX platform to produce anti-*F. tularensis* bioconjugate vaccine candidates on-demand by conjugating the FtO-PS structure to diverse carrier proteins in vitro was tested.

Figure 17:
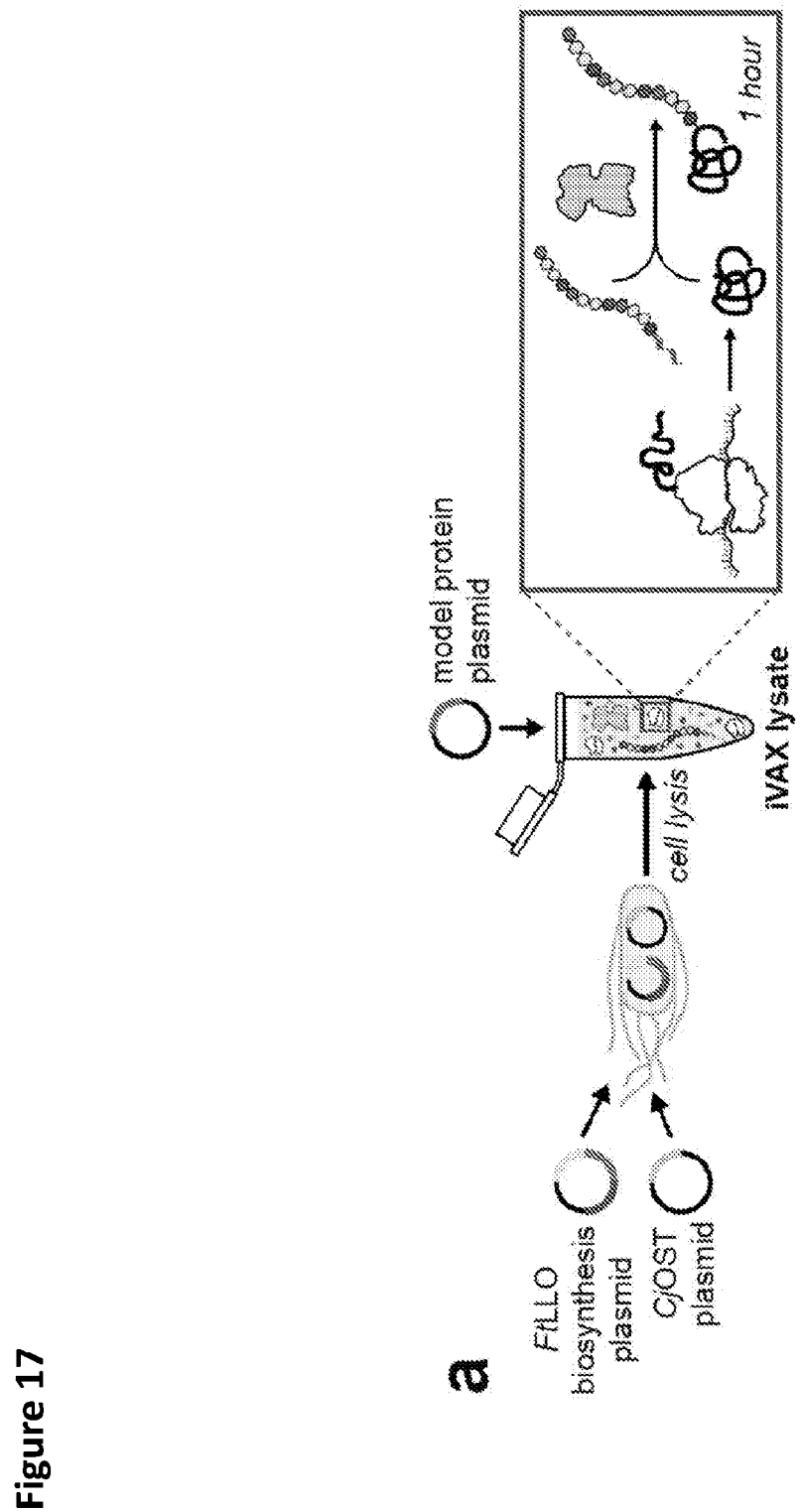
FIG. 17. Reproducible glycosylation of proteins with FtO-PS in iVAX lysates. (a) iVAX lysates were prepared from cells expressing CjPglB and a biosynthetic pathway encoding FtO-PS. (b) Glycosylation of sfGFP$^{217\text{-}DQNAT}$ with FtO-PS was only observed when CjPglB, FtO-PS, and the preferred sequon were present in the reaction (lane 3). When plasmid DNA was omitted, sfGFP$^{217\text{-}DQNAT}$ synthesis was not observed. (c) Biological replicates of iVAX reactions producing sfGFP$^{217\text{-}DQNAT}$ using the same lot (left) or different lots (right) of iVAX lysates demonstrated reproducibility of reactions and lysate preparation. Top panels show signal from probing with anti-hexa-histidine antibody (αHis) to detect the carrier protein, middle panels show signal from probing with commercial anti-FtO-PS antibody (αFtO-PS), and bottom panels show αHis and αFtO-PS signals merged. Unless replicates are explicitly shown, images are representative of at least three biological replicates. Dashed lines indicate samples are from the same blot with the same exposure. Molecular weight ladders are shown at the left of each image. See also FIG. 22.

The FtO-PS is composed of the 826-Da repeating tetrasaccharide unit Qui4NFm-(GalNAcAN)$_2$-QuiNAc (Qui4NFm: 4,6-dideoxy-4-formamido-D-glucose; GalNAcAN: 2-acetamido-2-deoxy-D-galacturonamide; QuiNAc: 2-acetamido-2,6-dideoxy-D-glucose) (Prior et al., 2003). To glycosylate proteins with FtO-PS, an iVAX lysate from glycoengineered *E. coli* cells expressing the FtO-PS biosynthetic pathway and the oligosaccharyltransferase enzyme CjPglB (FIG. 17a) was produced. This lysate, which contained lipid-linked FtO-PS and active CjPglB, was used to catalyze iVAX reactions primed with plasmid DNA encoding sfGFP$^{217\text{-}DQNAT}$. Control reactions in which attachment of the FtO-PS was not expected were performed with lysates from cells that lacked either the FtO-PS pathway or the CjPglB enzyme. Reactions that lacked plasmid encoding the target protein sfGFP$^{217\text{-}DQNAT}$ or were primed with plasmid encoding sfGFP$^{217\text{-}AQNAT}$, which contained a mutated glycosylation site (AQNAT) that is not modified by CjPglB (Kowarik et al., 2006) were also tested. In reactions containing the iVAX lysate and primed with plasmid encoding sfGFP$^{217\text{-}DQNAT}$, immunoblotting with anti-His antibody or a commercial monoclonal antibody specific to FtO-PS revealed a ladder-like banding pattern (FIG. 17b). This ladder is characteristic of FtO-PS attachment, resulting from O-PS chain length variability through the action of the Wzy polymerase (Cuccui et al., 2013; Feldman et al., 2005; Prior et al., 2003). Glycosylation of sfGFP$^{217\text{-}DQNAT}$ was observed only in reactions containing a complete glycosylation pathway and the preferred DQNAT glycosylation sequence (FIG. 17b). This glycosylation profile was reproducible across biological replicates from the same lot of lysate (FIG. 17c, left) and using different lots of lysate (FIG. 17c, right). In vitro protein synthesis and glycosylation was observed after 1 hour, with the amount of conjugated polysaccharide reaching a maximum between 0.75 and 1.25 hours (FIG. 22).

Figure 22:
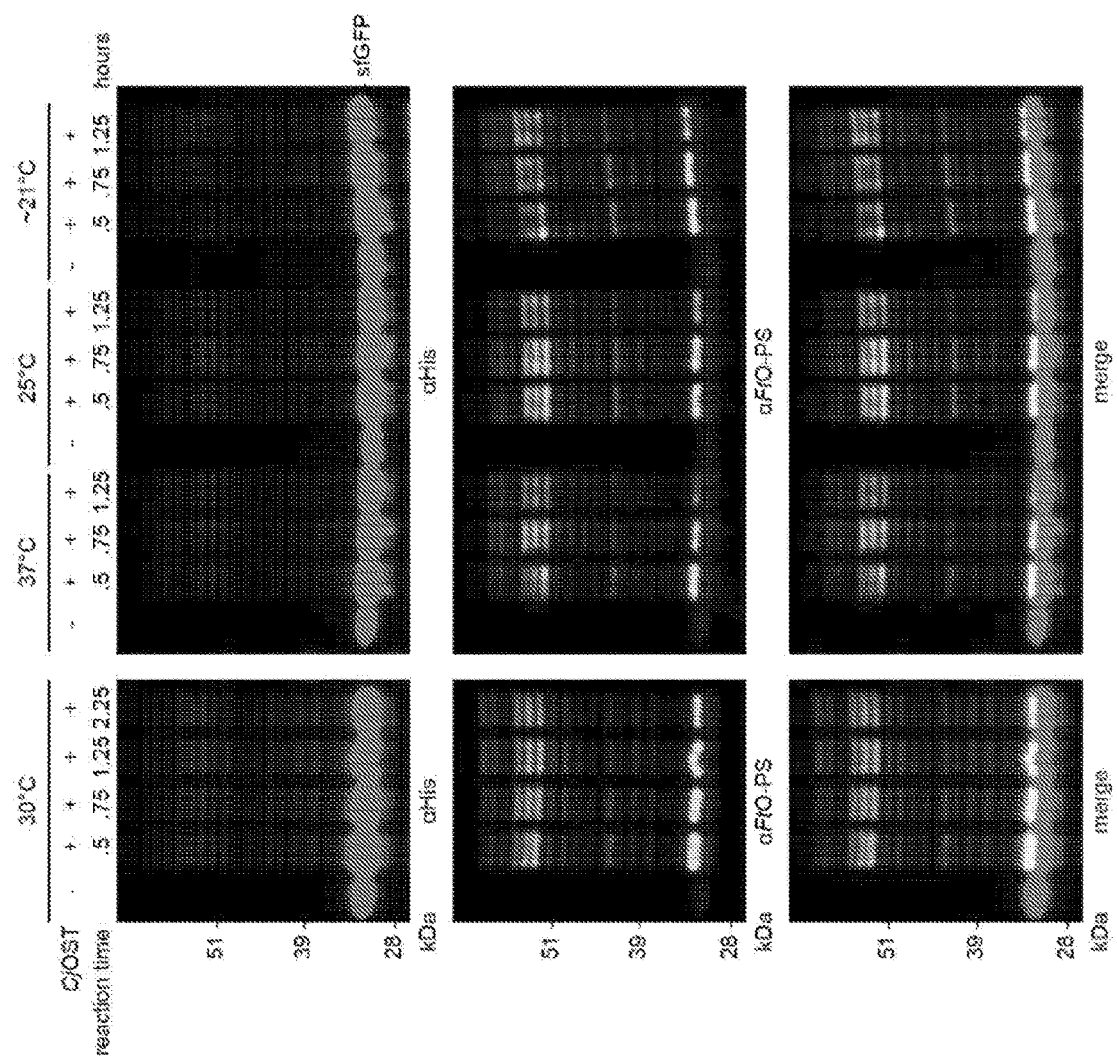
FIG. 22. Glycosylation in iVAX reactions occurs in 1 h over a range of temperatures. See also FIG. 17. Kinetics of FtO-PS glycosylation at 30° C. (left), 37° C., 25° C., and room temperature (~21° C.) (right) are comparable and show that protein synthesis and glycosylation occur in the first hour of the iVAX reaction. These results demonstrate that the iVAX platform can synthesize bioconjugates over a range of permissible temperatures. Top panels show signal from probing with anti-hexa-histidine antibody (αHis) to detect the carrier protein, middle panels show signal from probing with commercial anti-FtO-PS antibody (αFtO-PS), and bottom panels show αHis and αFtO-PS signals merged. Images are representative of at least three biological replicates. Molecular weight ladders are shown at the left of each image.

Similar glycosylation reaction kinetics were observed at 37° C., 30° C., 25° C., and room temperature (~21° C.), indicating that iVAX reactions are robust over a range of temperatures (FIG. 22).

Figure 18:
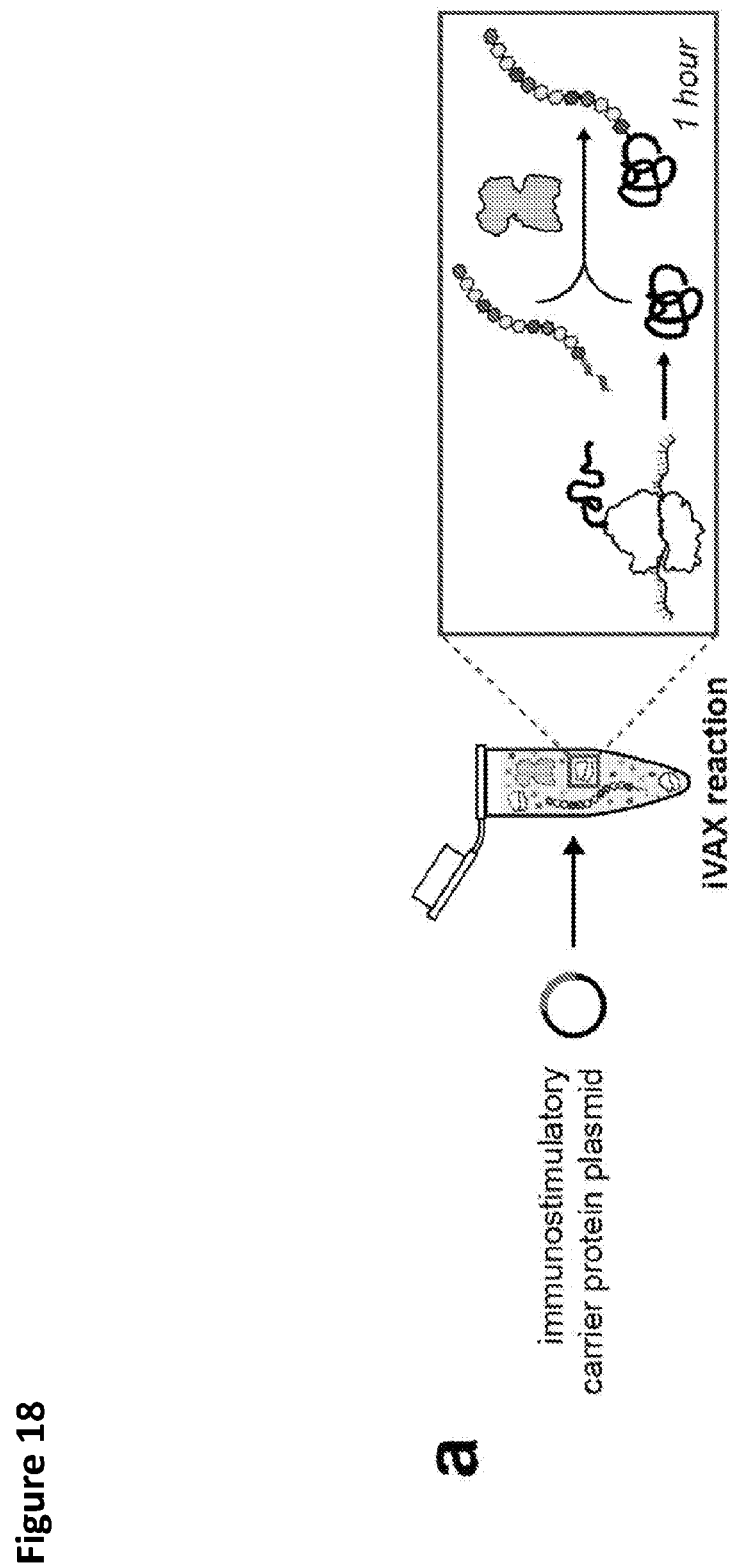
FIG. 18. On-demand production of bioconjugates against *F. tularensis* using iVAX. (a) iVAX reactions were prepared from lysates containing CjPglB and FtO-PS and primed with plasmid encoding immunostimulatory carriers, including those used in licensed vaccines. (b) On-demand synthesis of anti-*F. tularensis* bioconjugate vaccines for all carrier proteins tested was observed. Bioconjugates were purified using Ni-NTA agarose from 1 mL iVAX reactions lasting ~1 h. Top panels show signal from probing with anti-hexa-histidine antibody (αHis) to detect the carrier protein, middle panels show signal from probing with commercial anti-FtO-PS antibody (αFtO-PS), and bottom panels show αHis and αFtO-PS signals merged. Images are representative of at least three biological replicates. Dashed lines indicate samples are from the same blot with the same exposure. Molecular weight ladders are shown at the left of each image. See also FIGS. 23 and 24.
Figure 23:
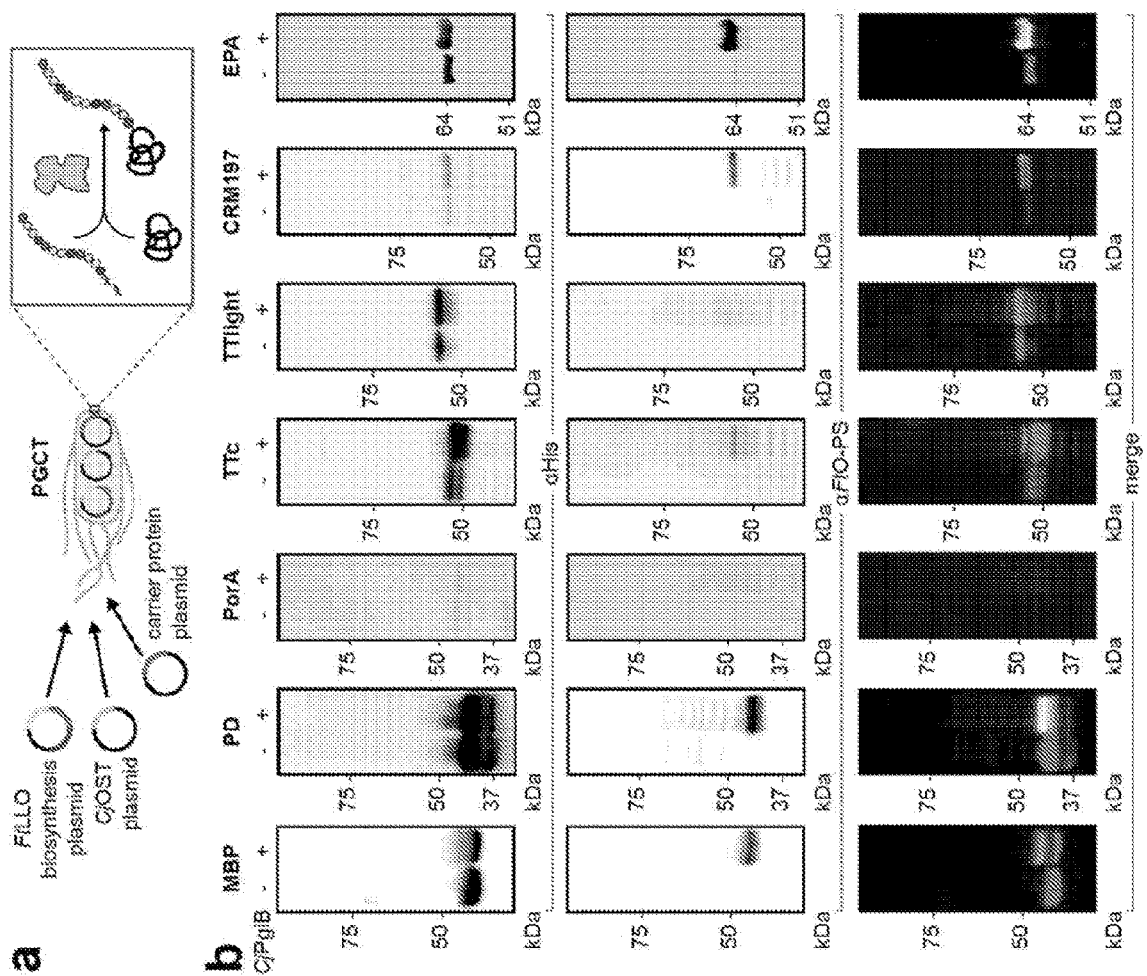
FIG. 23. Production of bioconjugates against F. tularensis using PGCT in living E. coli. See also FIG. 18. (a) Bioconjugates were produced via PGCT in CLM24 cells expressing CjPglB, the biosynthetic pathway for FtO-PS, and a panel of immunostimulatory carriers including those used in licensed vaccines. (b) We observed low expression of PorA, a membrane protein, as well as reduced glycan loading and conjugation of high molecular weight FtO-PS species in all carriers compared to iVAX-derived samples. Top panels show signal from probing with anti-hexa-histidine antibody (αHis) to detect the carrier protein, middle panels show signal from probing with commercial anti-FtO-PS antibody (αFtO-PS), and bottom panels show αHis and αFtO-PS signals merged. Images are representative of at least three biological replicates. Molecular weight ladders are shown at the left of each image.

Next, it was determined whether FDA-approved carriers could be similarly conjugated with FtO-PS in iVAX reactions. Following addition of plasmid DNA encoding MBP$^{4xDQNAT}$, PD$^{4xDQNAT}$, PorA$^{4xDQNAT}$, TTc$^{4xDQNAT}$, TTlight$^{4xDQNAT}$ and CRM197$^{4xDQNAT}$, glycosylation of each with FtO-PS was observed for iVAX reactions enriched with lipid-linked FtO-PS and CjPglB but not control reactions lacking CjPglB (FIG. 18). Conjugation of high molecular weight FtO-PS species (on the order of ~10-20 kDa) to all protein carriers tested was observed, which is important as longer glycan chain length has been shown to increase the efficacy of conjugate vaccines against *F. tularensis* (Stefanetti et al., 2019). Notably, attempts to synthesize the same panel of bioconjugates using the established PGCT approach in living *E. coli* yielded less promising results. Specifically, low levels of FtO-PS glycosylation and lower molecular weight conjugated FtO-PS species for all PGCT-derived bioconjugates compared to their iVAX-derived counterparts were observed (FIG. 23). The same trend was observed for PGCT- versus iVAX-derived bioconjugates involving the most common PGCT carrier protein, EPA$^{DNNNS\text{-}DQNRT}$ (Cuccui et al., 2013; Ihssen et al., 2010; Marshall et al., 2018; Wacker et al., 2014; Wetter et al., 2013) (FIG. 18; FIG. 23). In addition, only limited expression of the PorA membrane protein was achieved in vivo (FIG. 23). Collectively, these data show that iVAX provides advantages over PGCT for production of bioconjugate vaccine candidates with high molecular weight O-PS antigens conjugated efficiently to diverse and potentially membrane-bound carrier proteins.

Figure 16:
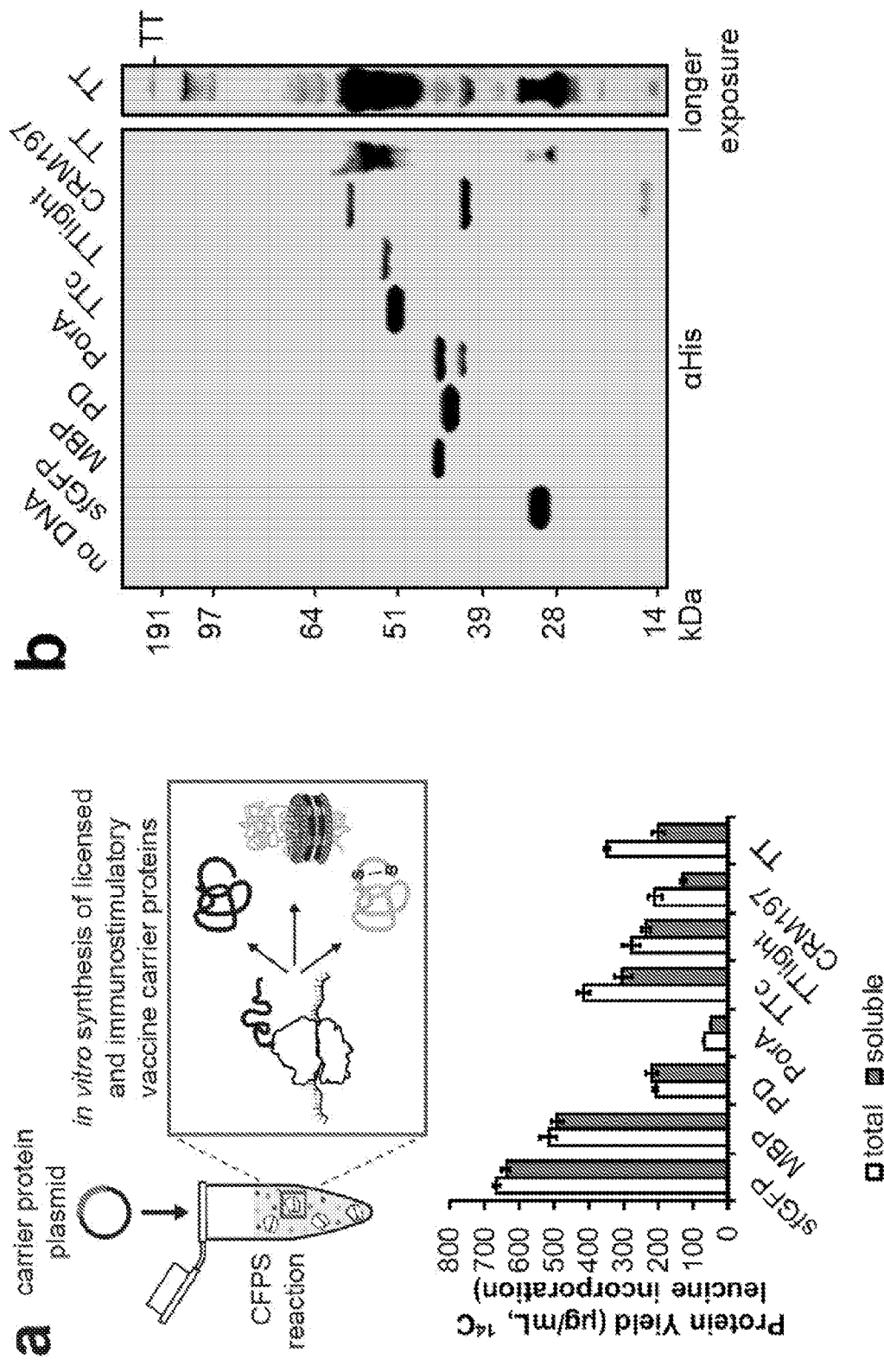
FIG. 16. In vitro synthesis of licensed conjugate vaccine carrier proteins. (a) All four carrier proteins used in FDA-approved conjugate vaccines were synthesized solubly in vitro, as measured via $^{14}$C-leucine incorporation. These include *H. influenzae* protein D (PD), the *N. meningitidis* porin protein (PorA), and genetically detoxified variants of the *C. diphtheriae* toxin (CRM197) and the *C. tetani* toxin (TT). Additional immunostimulatory carriers were also synthesized solubly, including *E. coli* maltose binding protein (MBP) and the fragment C (TTc) and light chain (TTlight) domains of TT. Values represent means and error bars represent standard deviations of biological replicates (n=3). (b) Full length product was observed for all proteins tested via Western blot. Different exposures are indicated with solid lines. Molecular weight ladder is shown at left. See also FIG. 21.
Figure 24:
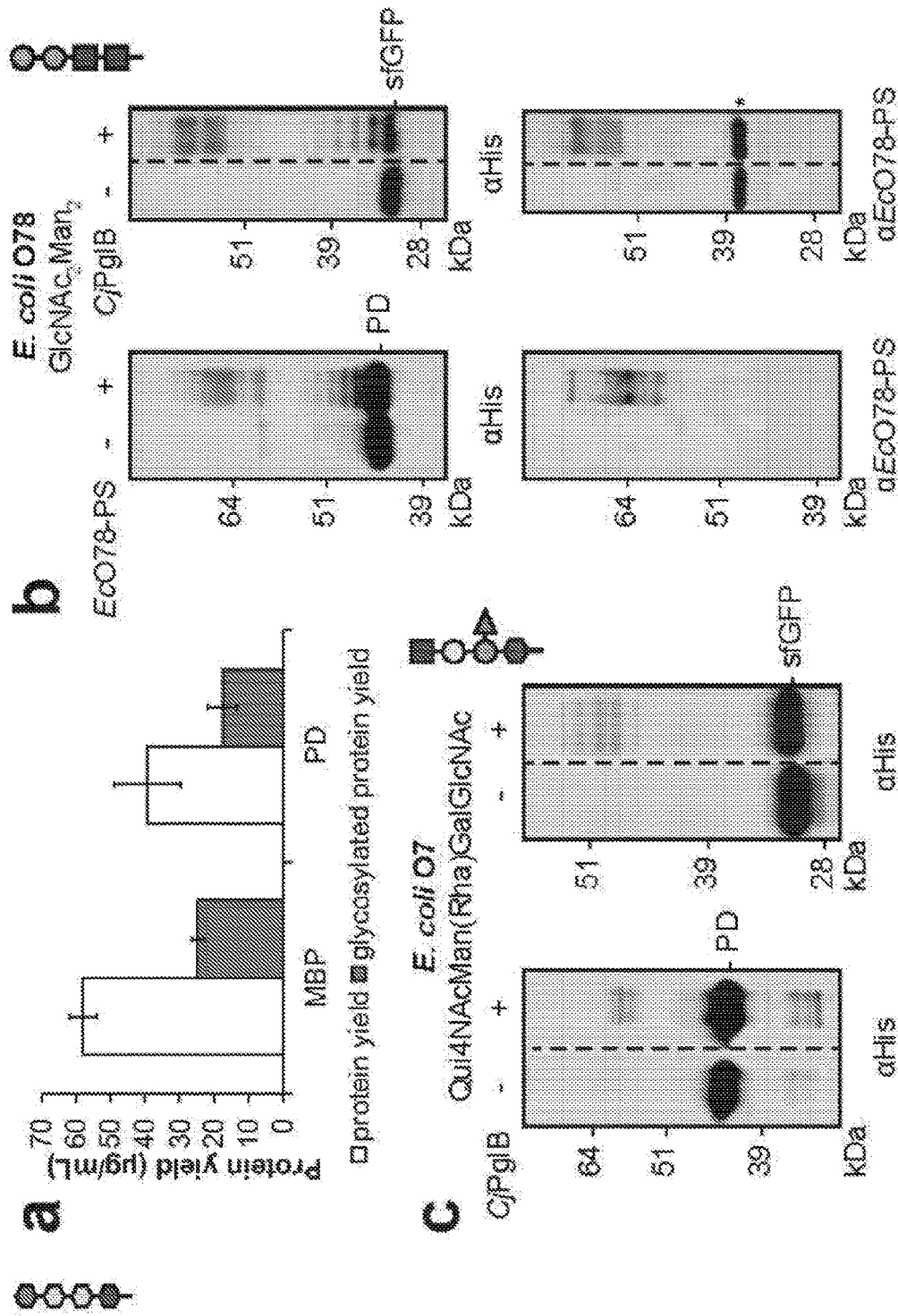
FIG. 24. The iVAX platform is modular and can be used to synthesize clinically relevant yields of diverse bioconjugates. See also FIG. 18. (a) Protein synthesis and glycosylation with FtO-PS were measured in iVAX reactions producing MBP$^{4xDQNAT}$ and PD$^{4xDQNAT}$. After ~1 h, reactions produced ~40 µg mL$^{-1}$ protein, as measured via $^{14}$C-leucine incorporation, of which ~20 µg mL$^{-1}$ was glycosylated with Ft0-PS, as determined by densitometry. Values represent means and error bars represent standard errors of biological replicates (n=2). To demonstrate modularity, iVAX lysates were prepared from cells expressing CjPglB and biosynthetic pathways for either (b) the E. coli O78 antigen or (c) the E. coli O7 antigen and used to synthesize PD$^{4xDQNAT}$ (left) or sfGFP$^{217-DQNAT}$ (right) bioconjugates. The structure and composition of the repeating monomer unit for each antigen is shown. Both polysaccharide antigens are compositionally and, in the case of the O7 antigen, structurally distinct compared to the F. tularensis O antigen. Blots show signal from probing with anti-hexa-histidine antibody (αHis) to detect the carrier protein. If a commercial anti-O-PS serum or antibody was available, it was used to confirm the identity of the conjugated O antigen (α-EcO78 blots, panel b). Asterisk denotes bands resulting from non-specific serum antibody binding. Images are representative of at least three biological replicates. Dashed lines indicate samples are from the same blot with the same exposure. Molecular weight ladders are shown at the left of each image.

Next, it was determined whether the yields of bioconjugates produced using iVAX were sufficient to enable production of relevant vaccine doses. Recent clinical data show 1-10 µg doses of bioconjugate vaccine candidates are well-tolerated and effective in stimulating the production of antibacterial IgGs (Hatz et al., 2015; Huttner et al., 2017; Riddle et al., 2016). To assess expression titers and for future experiments, MBP$^{4xDQNAT}$ and PD$^{4xDQNAT}$ were texted because these carriers expressed in vitro with high soluble titers and without truncation products (FIG. 16). It was found that reactions lasting ~1 hour produced ~20 µg mL$^{-1}$ of glycosylated MBP$^{4xDQNAT}$ and PD$^{4xDQNAT}$ as determined by $^{14}$C-leucine incorporation and densitometry analysis (FIG. 24a). It should be noted that vaccines are currently distributed in vials containing 1-20 doses of vaccine to minimize wastage (Humphreys, 2011). Thus, these yield results suggest that multiple doses per mL can be synthesized in 1 hour using the iVAX platform.

To demonstrate the modularity of the iVAX approach for bioconjugate production, bioconjugates bearing O-PS antigens from additional pathogens including ETEC *E. coli* strain O78 and UPEC *E. coli* strain O7 were produced. *E. coli* O78 is a major cause of diarrheal disease in developing countries, especially among children, and a leading cause of traveler's diarrhea (Qadri et al., 2005), while the O7 strain is a common cause of urinary tract infections (Johnson, 1991). Like the FtO-PS, the biosynthetic pathways for EcO78-PS and EcO-PS have been described previously and confirmed to produce O-PS antigens with the repeating units GlcNAc$_2$Man$_2$ (Jansson et al., 1987) and Qui4NAcMan (Rha)GalGlcNAc (L'vov et al., 1984) (GlcNAc: N-acetyl-glucosamine; Man: mannose; Qui4NAc: 4-acetamido-4,6-dideoxy-D-glucopyranose; Rha: rhamnose; Gal: galactose), respectively. Using iVAX lysates from cells expressing CjPglB and either the EcO78-PS and EcO7-PS pathways in reactions that were primed with PD$^{4xDQNAT}$ or sfGFP$^{217\text{-}DQNAT}$ plasmids, carrier glycosylation was observed only when both lipid-linked O-PS and CjPglB were present in the reactions (FIG. 24b, c). These results demonstrate modular production of bioconjugates against multiple bacterial pathogens, enabled by compatibility of multiple heterologous O-PS pathways with in vitro carrier protein synthesis and glycosylation.

Endotoxin Editing and Freeze-Drying Yield iVAX Reactions that are Safe and Portable A key challenge inherent in using any *E. coli*-based system for biopharmaceutical production is the presence of lipid A, or endotoxin, which is known to contaminate protein products and can cause lethal septic shock at high levels (Russell, 2006). As a result, the amount of endotoxin in formulated biopharmaceuticals is regulated by the United States Pharmacopeia (USP), US Food and Drug Administration (FDA), and the European Medicines Agency (EMEA) (Brito and Singh, 2011). Because the iVAX reactions rely on lipid-associated components, such as CjPglB and FtO-PS, standard detoxification approaches involving the removal of lipid A (Petsch and Anspach, 2000) could compromise the activity or concentration of the glycosylation components in addition to increasing cost and processing complexities.

Figure 19:
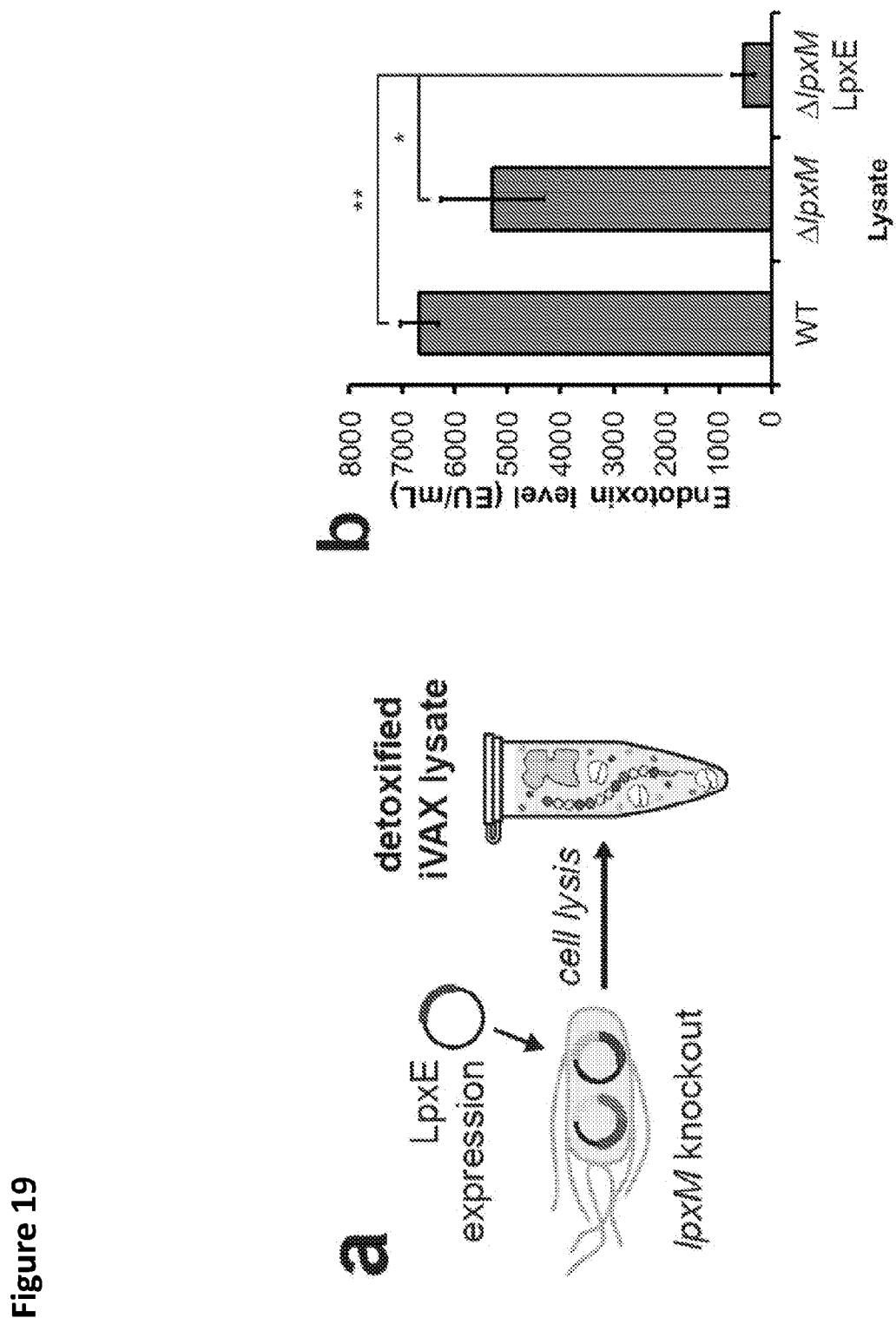
FIG. 19. Detoxified, lyophilized iVAX reactions produce bioconjugates. (a) iVAX lysates were detoxified via deletion of lpxM and expression of *F. tularensis* LpxE in the source strain for lysate production. (b) The resulting lysates exhibited significantly reduced endotoxin activity. *p=0.019 and **p=0.003, as determined by two-tailed t-test. (c) iVAX reactions producing sfGFP$^{217\text{-}DQNAT}$ were run immediately or following lyophilization and rehydration. (d) Glycosylation activity was preserved following lyophilization, demonstrating the potential of iVAX reactions for portable biosynthesis of bioconjugate vaccines. Top panel shows signal from probing with anti-hexa-histidine antibody (αHis) to detect the carrier protein, middle panel shows signal from probing with commercial anti-FtO-PS antibody (αFtO-PS), and bottom panel shows αHis and αFtO-PS signals merged. Images are representative of at least three biological replicates. Molecular weight ladder is shown at the left of each image. See also FIG. 25.
Figure 25:
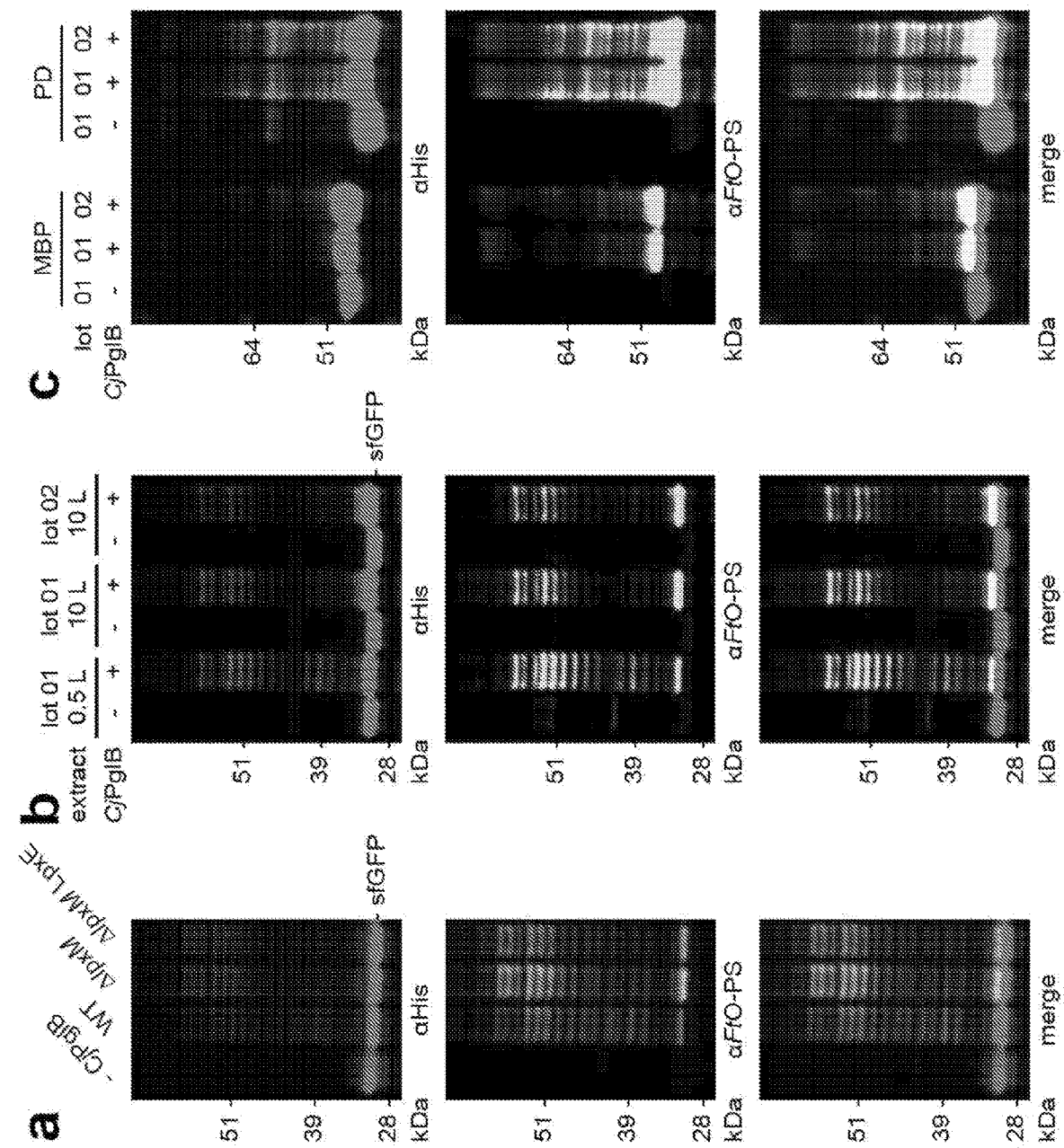
FIG. 25. Detoxified iVAX lysates synthesize bioconjugates and both lysate production and freeze-dried reactions scale reproducibly. See also FIG. 19. (a) iVAX lysates containing CjPglB and FtO-PS were prepared from wild-type CLM24, CLM24 ΔlpxM, or CLM24 ΔlpxM cells expressing FtLpxE. Nearly identical sfGFP$^{217-DQNAT}$ glycosylation was observed for each of the lysates derived from the engineered strains. (b) To generate material for immunizations, fermentations to produce endotoxin-edited iVAX lysates were scaled from 0.5 L to 10 L. We observed similar levels of sfGPP$^{217-DQNAT}$ glycosylation for lysates derived from 0.5 L and 10 L cultures, and across different batches of lysate produced from 10 L fermentations. (c) For immunizations, we prepared two lots of FtO-PS-conjugated MBP$^{4xDQNAT}$ and PD$^{4xDQNAT}$ from 5 mL freeze-dried iVAX reactions. We observed similar levels of purified protein (~200 µg) and FtO-PS modification (>50%, measured by densitometry) across both carriers and lots of material. Top panels show signal from probing with anti-hexa-histidine antibody (αHis) to detect the carrier protein, middle panels show signal from probing with commercial anti-FtO-PS antibody (αFtO-PS), and bottom panels show αHis and αFtO-PS signals merged. Images are representative of at least three biological replicates. Molecular weight ladders are shown at left.

To address this issue, a previously reported strategy to detoxify the lipid A molecule through strain engineering (Chen et al., 2016; Needham et al., 2013) was tested. In particular, the deletion of the acyltransferase gene lpxM and the overexpression of the *F. tularensis* phosphatase LpxE in *E. coli* has been shown to result in the production of nearly homogenous pentaacylated, monophosphorylated lipid A with significantly reduced toxicity but retained activity as an adjuvant (Chen et al., 2016). This pentaacylated, monophosphorylated lipid A was structurally identical to the primary component of monophosphoryl lipid A (MPL) from *Salmonella minnesota* R595, an approved adjuvant composed of a mixture of monophosphorylated lipids (Casella and Mitchell, 2008). To generate detoxified lipid A structures in the context of iVAX, lysates from a ΔlpxM derivative of CLM24 that co-expressed FtLpxE and the FtO-PS glycosylation pathway were produced (FIG. 19a). Lysates derived from this strain exhibited significantly decreased levels of toxicity compared to wild type CLM24 lysates expressing CjPglB and FtO-PS (FIG. 19b) as measured by human TLR4 activation in HEK-Blue hTLR4 reporter cells (Needham et al., 2013). Importantly, the structural remodeling of lipid A did not affect the activity of the membrane-bound CjPglB and FtO-PS components in iVAX reactions (FIG. 25a). By engineering the chassis strain for lysate production, iVAX lysates with endotoxin levels <1,000 EU mL$^{-1}$, within the range of reported values for commercial protein-based vaccine products were produced (0.288-180,000 EU mL$^{-1}$) (Brito and Singh, 2011).

A major limitation of traditional conjugate vaccines is that they must be refrigerated (WHO, 2014), making it difficult to distribute these vaccines to remote or resource-limited settings. The ability to freeze-dry iVAX reactions for ambient temperature storage and distribution could alleviate the logistical challenges associated with refrigerated supply chains that are required for existing vaccines. To investigate this possibility, detoxified iVAX lysates were used to produce FtO-PS bioconjugates in two different ways: either by running the reaction immediately after priming with plasmid encoding the sfGFP$^{217\text{-}DQNAT}$ target protein or by running after the same reaction mixture was lyophilized and rehydrated (FIG. 19c). In both cases, conjugation of FtO-PS to sfGFP$^{217\text{-}DQNAT}$ was observed when CjPglB was present, with modification levels that were nearly identical (FIG. 19d). In addition, detoxified, freeze-dried iVAX reactions were scaled to 5 mL for production of FtO-PS-conjugated MBP$^{4xDQNAT}$ and PD$^{4xDQNAT}$ in a manner that is reproducible from lot to lot and indistinguishable from production without freeze-drying (FIG. 25b, c). The ability to lyophilize iVAX reactions and manufacture bioconjugates without specialized equipment highlights the potential for portable, on-demand vaccine production.

In Vitro Synthesized Bioconjugates Elicit Pathogen-Specific Antibodies in Mice

Figure 26:
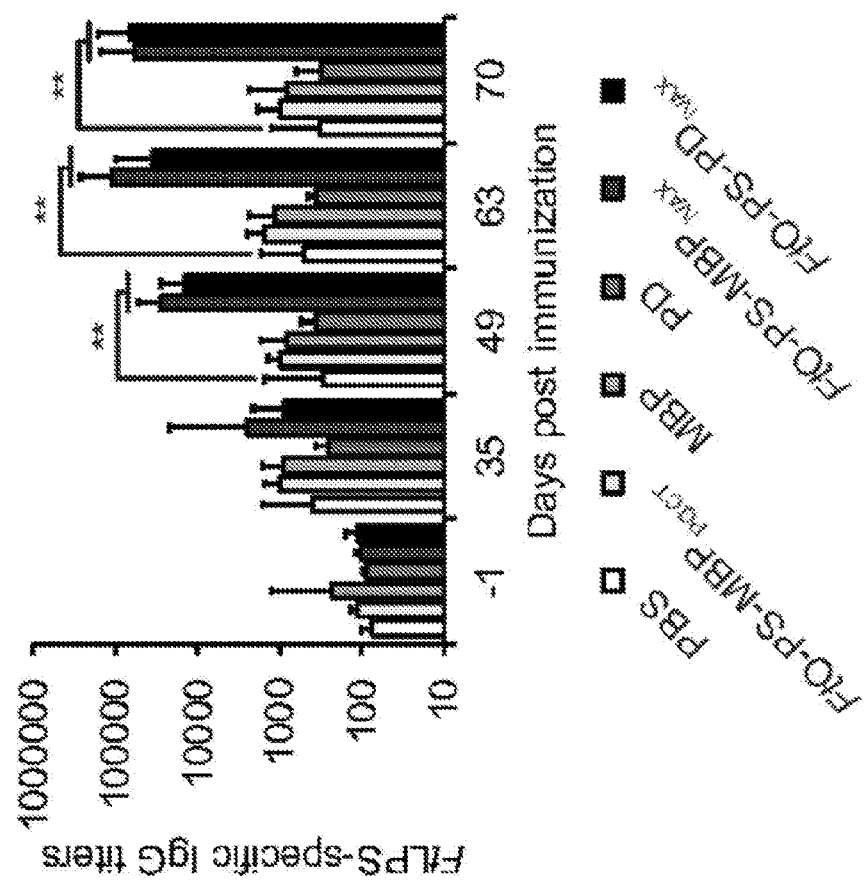
FIG. 26. FtLPS-specific antibody titers in vaccinated mice over time. See also FIG. 20. Six groups of BALB/c mice were immunized subcutaneously with PBS or 7.5 µg of purified, cell-free synthesized aglycosylated MBP$^{4xDQNAT}$, FtO-PS-conjugated MBP$^{4xDQNAT}$, aglycosylated PD$^{4xDQNAT}$, or FtO-PS-conjugated PD$^{4xDQNAT}$. FtO-PS-conjugated MBP$^{4xDQNAT}$ prepared in living *E. coli* cells using PCGT was used as a positive control. Each group was composed of six mice except for the PBS control group, which was composed of five mice. Mice were boosted on days 21 and 42 with identical doses of antigen. FtLPS-specific IgG titers were measured by ELISA in serum collected on day -1, 35, 49, 63, and 70 following initial immunization. iVAX-derived bioconjugates elicited significantly higher levels of FtLPS-specific IgG compared to compared to the PBS control group in serum collected on day 35, 49, and 70 of the study (**p<0.01, Tukey-Kramer HSD). Values represent means and error bars represent standard errors of FtLPS-specific IgGs detected by ELISA.

To validate the efficacy of bioconjugates produced using the iVAX platform, the ability of iVAX-derived bioconjugates to elicit anti-FtLPS antibodies in mice was tested (FIG. 20a). It was found that BALB/c mice receiving iVAX-derived FtO-PS-conjugated MBP$^{4xDQNAT}$ or PD$^{4xDQNAT}$ produced high titers of FtLPS-specific IgG antibodies, which were significantly elevated compared to the titers measured in the sera of control mice receiving PBS or aglycosylated versions of each carrier protein (FIG. 20b, FIG. 26). The IgG titers measured in sera from mice receiving glycosylated MBP$^{4xDQNAT}$ derived from PGCT were similar to the titers observed in the control groups (FIG. 20b, FIG. 26), in line with the markedly weaker glycosylation of this candidate relative to its iVAX-derived counterpart (FIG. 23). Both MBP$^{4xDQNAT}$ and PD$^{4xDQNAT}$ bioconjugates produced using iVAX elicited similar levels of IgG production and neither resulted in any observable adverse events in mice, confirming the modularity and safety of the technology for production of bioconjugate vaccine candidates.

IgG titers were characterized by analysis of IgG1 and IgG2a subtypes and found that both iVAX-derived FtO-PS-conjugated MBP$^{4xDQNAT}$ and PD$^{4xDQNAT}$ boosted production of IgG1 antibodies by >2 orders of magnitude relative to all control groups as well as to glycosylated MBP$^{4xDQNAT}$ derived from PGCT (FIG. 20c). This analysis also revealed that both iVAX-derived bioconjugates elicited a strongly Th2-biased (IgG1«IgG2a) response, which is characteristic of most conjugate vaccines (Bogaert et al., 2004). Taken together, these results provide evidence that the iVAX platform supplies vaccine candidates that are capable of eliciting strong, pathogen-specific humoral immune responses and recapitulate the Th2 bias that is characteristic of licensed conjugate vaccines.

Discussion

In this example, it has been established that iVAX, is a cell-free platform for portable, on-demand production of bioconjugate vaccines. It was shown that iVAX reactions can be detoxified to ensure the safety of bioconjugate vaccine products, freeze-dried for cold chain-independent distribution, and re-activated for high-yielding bioconjugate production by simply adding water. As a model vaccine candidate, it was shown that anti-*F. tularensis* bioconjugates derived from freeze-dried, endotoxin-edited iVAX reactions elicited pathogen-specific IgG antibodies in mice as part of a Th2-biased immune response characteristic of licensed conjugate vaccines.

The iVAX platform includes several novel features. First, iVAX is modular, which has been demonstrated herein through the interchangeability of (i) carrier proteins, including those used in licensed conjugate vaccines, and (ii) bacterial O-PS antigens from *F. tularensis* subsp. *tularensis* (type A) Schu S4, ETEC *E. coli* O78, and UPEC *E. coli* O7. This represents the first demonstration of oligosaccharytransferase-mediated O-PS conjugation to authentic FDA-approved carrier proteins, likely due to historical challenges associated with the expression of licensed carriers in living *E. coli* (Figueiredo et al., 1995; Haghi et al., 2011; Stefan et al., 2011). Further expansion of the O-PS pathways used in iVAX should be possible given the commonly observed clustering of polysaccharide biosynthesis genes in the genomes of pathogenic bacteria (Raetz and Whitfield, 2002). This feature could make iVAX an attractive option for rapid, de novo development of bioconjugate vaccine candidates in response to a disease outbreak or against emerging drug-resistant bacteria.

Second, iVAX reactions are inexpensive, costing ~$12 $mL^{-1}$ (FIG. 27, Table 1) with the ability to synthesize ~20 µg bioconjugate $mL^{-1}$ in one hour (FIG. 24a). Assuming a dose size of 10 µg, the iVAX reactions can produce a vaccine dose for ~$6. For comparison, the CDC cost per dose for conjugate vaccines ranges from ~$9.50 for the *H. influenzae* vaccine ActHIB® to ~$75 and ~$118 for the meningococcal vaccine Menactra® and pneumococcal vaccine Prevnar 13®, respectively (CDC, 2019).

Figure 20:
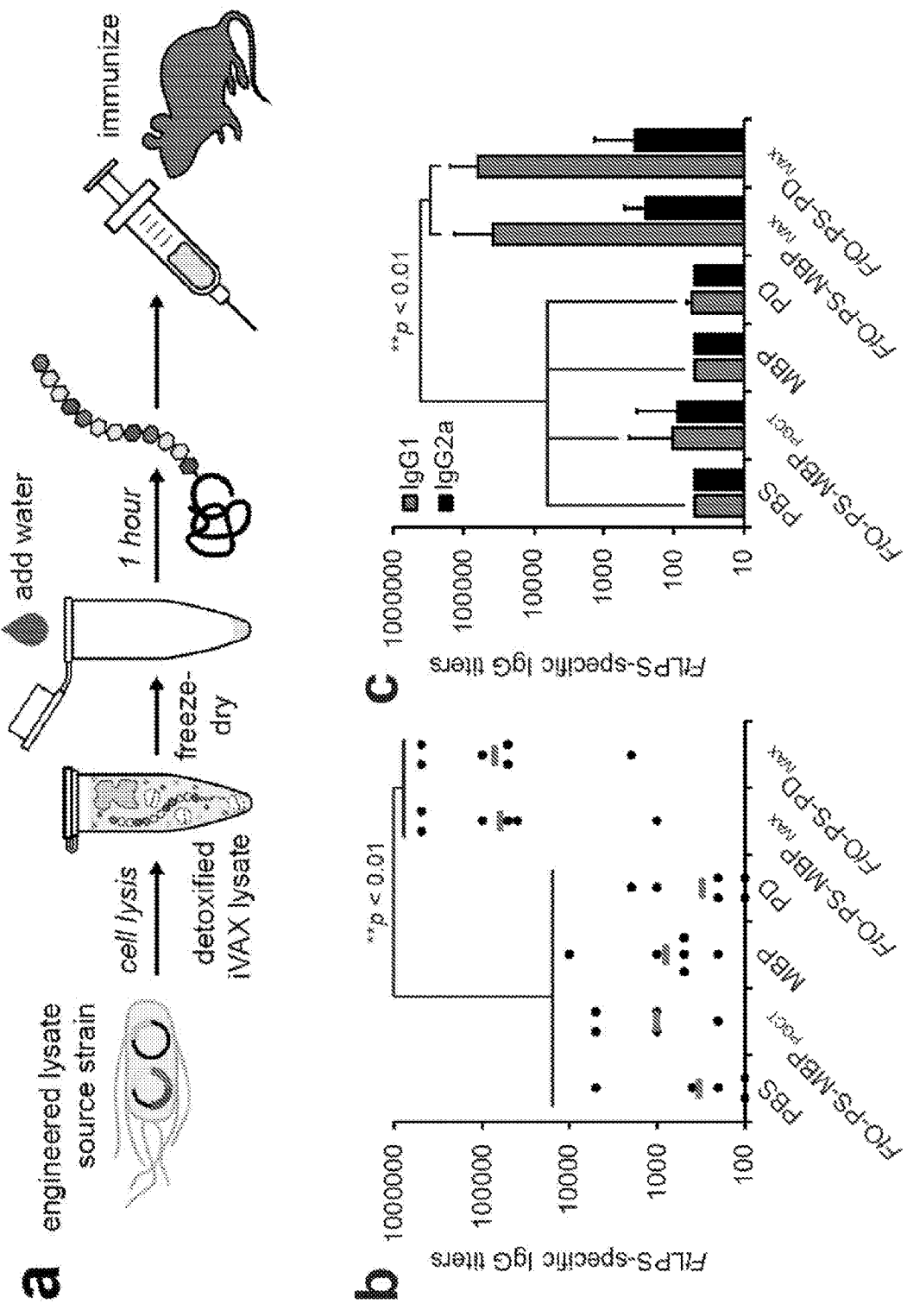
FIG. 20. iVAX-derived bioconjugates elicit FtLPS-specific antibodies in mice. (a) Freeze-dried iVAX reactions assembled using detoxified lysates were used to synthesize anti-*F. tularensis* bioconjugates for immunization studies. (b) Six groups of BALB/c mice were immunized subcutaneously with PBS or 7.5 µg of purified, cell-free synthesized aglycosylated MBP$^{4xDQNAT}$, FtO-PS-conjugated MBP$^{4xDQNAT}$, aglycosylated PD$^{4xDQNAT}$, or FtO-PS-conjugated PD$^{4xDQNAT}$. FtO-PS-conjugated MBP$^{4xDQNAT}$ prepared in living E. coli cells using PCGT was used as a positive control. Each group was composed of six mice except for the PBS control group, which was composed of five mice. Mice were boosted on days 21 and 42 with identical doses of antigen. FtLPS-specific IgG titers were measured by ELISA in endpoint (day 70) serum of individual mice (black dots) with F. tularensis LPS immobilized as antigen. Mean titers of each group are also shown (red lines). iVAX-derived bioconjugates elicited significantly higher levels of FtLPS-specific IgG compared to all other groups (p<0.01, Tukey-Kramer HSD). (c) IgG1 and IgG2a subtype titers measured by ELISA from endpoint serum revealed that iVAX-derived bioconjugates boosted production of FtO-PS-specific IgG1 compared to all other groups tested (p<0.01, Tukey-Kramer HSD). These results indicate that iVAX bioconjugates elicited a Th2-biased immune response typical of most conjugate vaccines. Values represent means and error bars represent standard errors of FtLPS-specific IgGs detected by ELISA. See also FIG. 26.

Third, it was shown that the iVAX-derived bioconjugates were significantly more effective at eliciting FtLPS-specific IgGs than a bioconjugate derived from living *E. coli* cells using PGCT (FIG. 20). Without wishing to be bound by theory, one possible explanation for this increased effectiveness is the more extensive glycosylation that was observed for the in vitro expressed bioconjugates, with greater carbohydrate loading and decoration with higher molecular weight FtO-PS species compared to their PGCT-derived counterparts. The reduced presence of high molecular weight O-PS species observed on bioconjugates produced using PGCT could be due to competition between the O-antigen polymerase Wzy and PglB in vivo. In contrast, the in vitro approach of the present disclosure decouples O-PS synthesis, which occurs in vivo before lysate production, from glycosylation, which occurs in vitro as part of iVAX reactions. These results are consistent with previous reports of PGCT-derived anti-*F. tularensis* bioconjugates which show that increasing the ratio of conjugated FtO-PS to protein in bioconjugates yields enhanced protection against *F. tularensis* Schu S4 in a rat inhalation model of tularemia (Marshall et al., 2018). In addition, a recent study showed that a conjugate vaccine made with a high molecular weight (80 kDa) FtO-PS coupled to TT conferred better protection against intranasal challenge with *F. tularensis* live vaccine strain compared to a conjugate made with a low molecular weight (25 kDa) polysaccharide (Stefanetti et al., 2019).

By enabling portable production of bioconjugate vaccines, iVAX addresses a key gap in both cell-free and decentralized biomanufacturing technologies. Production of glycosylated products has not yet been demonstrated in cell-based decentralized biomanufacturing platforms (Crowell et al., 2018; Perez-Pinera et al., 2016) and existing cell-free platforms using *E. coli* lysates lack the ability to synthesize glycoproteins (Boles et al., 2017; Murphy et al., 2019; Pardee et al., 2016; Salehi et al., 2016). While glycosylated human erythropoietin has been produced in a cell-free biomanufacturing platform based on freeze-dried Chinese hamster ovary cell lysates (Adiga et al., 2018), this and the vast majority of other eukaryotic cell-free and cell-based systems rely on endogenous protein glycosylation machinery. As a result, these expression platforms offer little control over the glycan structures produced or the underlying glycosylation reactions, and significant optimization is often required to achieve acceptable glycosylation profiles (Adiga et al., 2018). In contrast, the iVAX platform is enabled by lysates derived from *E. coli* that lack endogenous protein glycosylation pathways, allowing for bottom-up engineering of desired glycosylation activity (Jaroentomeechai et al., 2018). The ability to engineer desired glycosylation activity in iVAX uniquely enables the production of an important class of antibacterial vaccines at the point-of-care.

iVAX provides a new approach for rapid development and portable, on-demand biomanufacturing of bioconjugate vaccines. The iVAX platform alleviates cold chain requirements, which could enhance delivery of medicines to regions with limited infrastructure and minimize vaccine losses due to spoilage. In addition, the ability to rapidly produce vaccine candidates in vitro provides a unique means for rapidly responding to pathogen outbreaks and emergent threats.

Experimental Model and Subject Details

Bacteria

*E. coli* strains were grown in Luria Bertani (LB), LB-Lennox, or 2xYTP media at 30-37° C. in shaking incubators, as specified in the Method Details section below. *E. coli* NEB 5-alpha (NEB) was used for plasmid cloning and purification. *E. coli* CLM24 or CLM24 ΔlpxM strains were used for preparing cell-free lysates. *E. coli* CLM24 was used as the chassis for expressing bioconjugates in vivo using PGCT. CLM24 is a glyco-optimized derivative of W3110 that carries a deletion in the gene encoding the WaaL ligase, facilitating the accumulation of preassembled glycans on undecaprenyl diphosphate (Feldman et al., 2005). CLM24 ΔlpxM has an endogenous acyltransferase deletion and serves as the chassis strain for production of detoxified cell-free lysates.

Human Cell Culture

HEK-Blue hTLR4 cells (Invivogen) were cultured in DMEM media high glucose/L-glutamine supplement with 10% fetal bovine serum, 50 U $mL^{-1}$ penicillin, 50 mg $mL^{-1}$ streptomycin, and 100 μg $mL^{-1}$ Normacin™ in a humidified incubator at 37° C. with 5% $CO_2$, per manufacturer's specifications.

Mice

Six-week old female BALB/c mice obtained from Harlan Sprague Dawley were randomly assigned to experimental groups. Mice were housed in groups of three to five animals and cages were changed weekly. All animals were observed daily for behavioral and physical health such as visible signs of injury and abnormal grooming habits. Mice were also observed 24 and 48 hours after each injection and no abnormal responses were reported. This study was performed at Cornell University in facilities accredited by the Association for Assessment and Accreditation of Laboratory Animal Care International. All procedures were done in accordance with Protocol 2012-0132 approved by the Cornell University Institutional Animal Care and Use Committee under relevant university, state, and federal regulations including the Animal Welfare Act, Public Health Service Policy on Humane Care and Use of Laboratory Animals, New York State Health Law Article 5, Section 504, and Cornell University Policy 1.4.

Method Details

Construction of CLM24 ΔlpxM Strain

*E. coli* CLM24 ΔlpxM was generated using the Datsenko-Wanner gene knockout method (Datsenko and Wanner, 2000). Briefly, CLM24 cells were transformed with the pKD46 plasmid encoding the λ red system. Transformants were grown to an OD600 of 0.5-0.7 in 25 mL LB-Lennox media (10 g $L^{-1}$ tryptone, 5 g $L^{-1}$ yeast extract and 5 g $L^{-1}$ NaCl) with 50 μg $mL^{-1}$ carbenicillin at 30° C., harvested and washed three times with 25 mL ice-cold 10% glycerol to make them electrocompetent, and resuspended in a final volume of 100 μL 10% glycerol. In parallel, a lpxM knockout cassette was generated by PCR amplifying the kanamycin resistance cassette from pKD4 with forward and reverse primers with homology to lpxM. Electrocompetent cells were transformed with 400 ng of the lpxM knockout cassette and plated on LB agar with 30 μg mL$^{-1}$ kanamycin for selection of resistant colonies. Plates were grown at 37° C. to cure cells of the pKD46 plasmid. Colonies that grew on kanamycin were confirmed to have acquired the knockout cassette via colony PCR and DNA sequencing. These confirmed colonies were then transformed with pCP20 to remove the kanamycin resistance gene via Flp-FRT recombination. Transformants were plated on LB agar with 50 μg mL$^{-1}$ carbenicillin. Following selection, colonies were grown in liquid culture at 42° C. to cure cells of the pCP20 plasmid. Colonies were confirmed to have lost both lpxM and the knockout cassette via colony PCR and DNA sequencing and confirmed to have lost both kanamycin and carbenicillin resistance via replica plating on LB agar plates with 50 μg mL$^{-1}$ carbenicillin or kanamycin. All primers used for construction and validation of this strain are listed in FIG. 28, Table 2.

All plasmids used in the study are listed in FIG. 29, Table 3. Plasmids pJL1-MBP$^{4xDQNAT}$, pJL1-PD$^{4xDQNAT}$, pJL1-PorA$^{4xDQNAT}$, pJL1-TTc$^{4xDQNAT}$, pJL1-TTlight$^{4xDQNAT}$, pJL1-CRM197$^{4xDQNAT}$, and pJL1-TT$^{4xDQNAT}$ were generated via PCR amplification and subsequent Gibson Assembly of a codon optimized gene construct purchased from IDT with a C-terminal 4xDQNAT-6xHis tag (Fisher et al., 2011) between the NdeI and SalI restriction sites in the pJL1 vector. Plasmid pJL1-EPA$^{DNNNS-DQNRT}$ was constructed using the same approach, but without the addition of a C-terminal 4xDQNAT-6xHis tag. Plasmids pTrc99s-ssDsbA-MBP$^{4xDQNAT}$, pTrc99s-ssDsbA-PD$^{4xDQNAT}$, pTrc99s-ssDsbA-PorA$^{4xDQNAT}$, pTrc99s-ssDsbA-TTc$^{4xDQNAT}$, pTrc99s-ssDsbA-TTlight$^{4xDQNAT}$, and pTrc99s-ssDsbA-EPA$^{DNNNS-DQNRT}$ were created via PCR amplification of each carrier protein gene and insertion into the pTrc99s vector between the NcoI and HindIII restriction sites via Gibson Assembly. Plasmid pSF-CjPglB-LpxE was constructed using a similar approach, but via insertion of the lpxE gene from pE (Needham et al., 2013) between the NdeI and NsiI restriction sites in the pSF vector. Inserts were amplified via PCR using Phusion® High-Fidelity DNA polymerase (NEB) with forward and reverse primers designed using the NEBuilder® Assembly Tool (nebuilder.neb.com) and purchased from IDT. The pJL1 vector (Addgene 69496) was digested using restriction enzymes NdeI and SalI-HF® (NEB). The pSF vector was digested using restriction enzymes NdeI and NotI (NEB). PCR products were gel extracted using an EZNA Gel Extraction Kit (Omega Bio-Tek), mixed with Gibson assembly reagents and incubated at 50° C. for 1 hour. Plasmid DNA from the Gibson assembly reactions were transformed into E. coli NEB 5-alpha cells and circularized constructs were selected using kanamycin at 50 μg mL$^{-1}$ (Sigma). Sequence-verified clones were purified using an EZNA Plasmid Midi Kit (Omega Bio-Tek) for use in CFPS and iVAX reactions.

Cell-Free Lysate Preparation

E. coli CLM24 source strains were grown in 2xYTP media (10 g/L yeast extract, 16 g/L tryptone, 5 g/L NaCl, 7 g/L K$_2$HPO$_4$, 3 g/L KH$_2$PO$_4$, pH 7.2) in shake flasks (1 L scale) or a Sartorius Stedim BIOSTAT Cplus bioreactor (10 L scale) at 37° C. Protein synthesis yields and glycosylation activity were reproducible across different batches of lysate at both small and large scale. To generate CjPglB-enriched lysate, CLM24 cells carrying plasmid pSF-CjPglB (Ollis et al., 2015) was used as the source strain. To generate FtO-PS-enriched lysates, CLM24 carrying plasmid pGAB2 (Cuccui et al., 2013) was used as the source strain. To generate one-pot lysates containing both CjPglB and FtO-PS, EcO78-PS, or EcO7-PS, CLM24 carrying pSF-CjPglB and one of the following bacterial O-PS biosynthetic pathway plasmids was used as the source strain: pGAB2 (FtO-PS), pMW07-078 (EcO78-PS), and pJHCV32 (EcO7-PS). CjPglB expression was induced at an OD$_{600}$ of 0.8-1.0 with 0.02% (w/v) L-arabinose and cultures were moved to 30° C. Cells were grown to a final OD$_{600}$ of ~3.0, at which point cells were pelleted by centrifugation at 5,000×g for 15 min at 4° C. Cell pellets were then washed three times with cold S30 buffer (10 mM Tris-acetate pH 8.2, 14 mM magnesium acetate, 60 mM potassium acetate) and pelleted at 5000×g for 10 min at 4° C. After the final wash, cells were pelleted at 7000×g for 10 min at 4° C., weighed, flash frozen in liquid nitrogen, and stored at -80° C. To make cell lysate, cell pellets were resuspended to homogeneity in 1 mL of S30 buffer per 1 g of wet cell mass. Cells were disrupted via a single passage through an Avestin EmulsiFlex-B15 (1 L scale) or EmulsiFlex-C3 (10 L scale) high-pressure homogenizer at 20,000-25,000 psi. The lysate was then centrifuged twice at 30,000×g for 30 min to remove cell debris. Supernatant was transferred to clean microcentrifuge tubes and incubated at 37° C. with shaking at 250 rpm for 60 min. Following centrifugation (15,000×g) for 15 min at 4° C., supernatant was collected, aliquoted, flash-frozen in liquid nitrogen, and stored at -80° C. S30 lysate was active for about 3 freeze-thaw cycles and contained ~40 g/L total protein as measured by Bradford assay.

Cell-Free Protein Synthesis

CFPS reactions were carried out in 1.5 mL microcentrifuge tubes (15 μL scale), 15 mL conical tubes (1 mL scale), or 50 mL conical tubes (5 mL scale) with a modified PANOx-SP system (Jewett and Swartz, 2004). The CFPS reaction mixture consists of the following components: 1.2 mM ATP; 0.85 mM each of GTP, UTP, and CTP; 34.0 μg mL$^{-1}$ L-5-formyl-5, 6, 7, 8-tetrahydrofolic acid (folinic acid); 170.0 μg mL$^{-1}$ of E. coli tRNA mixture; 130 mM potassium glutamate; 10 mM ammonium glutamate; 12 mM magnesium glutamate; 2 mM each of 20 amino acids; 0.4 mM nicotinamide adenine dinucleotide (NAD); 0.27 mM coenzyme-A (CoA); 1.5 mM spermidine; 1 mM putrescine; 4 mM sodium oxalate; 33 mM phosphoenolpyruvate (PEP); 57 mM HEPES; 13.3 μg mL$^{-1}$ plasmid; and 27% v/v of cell lysate. For reaction volumes mL, plasmid was added at 6.67 μg mL$^{-1}$, as this lower plasmid concentration conserved reagents with no effect on protein synthesis yields or kinetics. For expression of PorA, reactions were supplemented with nanodiscs at 1 μg mL$^{-1}$, which were prepared as previously described (Schoborg et al., 2017) or purchased (Cube Biotech). For expression of CRM197$^{4xDQNAT}$, CFPS was carried out at 25° C. for 20 hours, unless otherwise noted. For all other carrier proteins, CFPS was run at 30° C. for 20 hours, unless otherwise noted.

For expression of TT$^{4xDQNAT}$, which contains intermolecular disulfide bonds, CFPS was carried out under oxidizing conditions. For oxidizing conditions, lysate was pre-conditioned with 750 μM iodoacetamide at room temperature for 30 min to covalently bind free sulfhydryls (-SH) and the reaction mix was supplemented with 200 mM glutathione at a 4:1 ratio of oxidized and reduced forms and 10 μM recombinant E. coli DsbC (Knapp et al., 2007).

In Vitro Bioconjugate Vaccine Expression (iVAX)

For in vitro expression and glycosylation of carrier proteins in crude lysates, a two-phase scheme was implemented. In the first phase, CFPS was carried out for 15 min at 25-30° C. as described above. In the second phase, protein glycosylation was initiated by the addition of $MnCl_2$ and DDM at a final concentration of 25 mM and 0.1% (w/v), respectively, and allowed to proceed at 30° C. for a total reaction time of 1 hour. Protein synthesis yields and glycosylation activity were reproducible across biological replicates of iVAX reactions at both small and large scale. Reactions were then centrifuged at 20,000×g for 10 min to remove insoluble or aggregated protein products and the supernatant was analyzed by SDS-PAGE and Western blotting.

Purification of aglycosylated and glycosylated carriers from iVAX reactions was carried out using Ni-NTA agarose (Qiagen) according to manufacturer's protocols. Briefly, 0.5 mL Ni-NTA agarose per 1 mL cell-free reaction mixture was equilibrated in Buffer 1 (300 mM NaCl 50 mM $NaH_2PO_4$) with 10 mM imidazole. Soluble fractions from iVAX reactions were loaded on Ni-NTA agarose and incubated at 4° C. for 2-4 hours to bind 6xHis-tagged protein. Following incubation, the cell-free reaction/agarose mixture was loaded onto a polypropylene column (BioRad) and washed twice with 6 column volumes of Buffer 1 with 20 mM imidazole. Protein was eluted in 4 fractions, each with 0.3 mL Buffer 1 with 300 mM imidazole per mL of cell-free reaction mixture. All buffers were used and stored at 4° C. Protein was stored at a final concentration of 1-2 mg $mL^{-1}$ in sterile 1×PBS (137 mM NaCl, 2.7 mM KCl, 10 mM $Na_2HPO_4$, 1.8 mM $KH_2PO_4$, pH 7.4) at 4° C.

Expression of Bioconjugates In Vivo Using Protein Glycan Coupling Technology (PGCT)

Plasmids encoding bioconjugate carrier protein genes preceded by the DsbA leader sequence for translocation to the periplasm were transformed into CLM24 cells carrying pGAB2 and pSF-CjPglB. CLM24 carrying only pGAB2 was used as a negative control. Transformed cells were grown in 5 mL LB media (10 g $L^{-1}$ yeast extract, 5 g $L^{-1}$ tryptone, 5 g $L^{-1}$ NaCl) overnight at 37° C. The next day, cells were subcultured into 100 mL LB and allowed to grow at 37° C. for 6 hours after which the culture was supplemented with 0.2% arabinose and 0.5 mM IPTG to induce expression of CjPglB and the bioconjugate carrier protein, respectively. Protein expression was then carried out for 16 hours at 30° C., at which point cells were harvested. Cell pellets were resuspended in 1 mL sterile PBS (137 mM NaCl, 2.7 mM KCl, 10 mM $Na_2HPO_4$, 1.8 mM $KH_2PO_4$, pH 7.4) and lysed using a Q125 Sonicator (Qsonica, Newtown, CT) at 40% amplitude in cycles of 10 sec on/10 sec off for a total of 5 min. Soluble fractions were isolated following centrifugation at 15,000 rpm for 30 min at 4° C. Protein was purified from soluble fractions using Ni-NTA spin columns (Qiagen), following the manufacturer's protocol.

Western Blot Analysis

Samples were run on 4-12% Bis-Tris SDS-PAGE gels (Invitrogen). Following electrophoretic separation, proteins were transferred from gels onto Immobilon-P polyvinylidene difluoride (PVDF) membranes (0.45 µm) according to the manufacturer's protocol. Membranes were washed with PBS (80 g $L^{-1}$ NaCl, 0.2 g $L^{-1}$ KCl, 1.44 g $L^{-1}$ $Na_2HPO_4$, 0.24 g $L^{-1}$ $KH_2PO_4$, pH 7.4) followed by incubation for 1 hour in Odyssey® Blocking Buffer (LI-COR). After blocking, membranes were washed 6 times with PBST (80 g $L^{-1}$ NaCl, 0.2 g $L^{-1}$ KCl, 1.44 g $L^{-1}$ $Na_2HPO_4$, 0.24 g $L^{-1}$ $KH_2PO_4$, 1 mL $L^{-1}$ Tween-20, pH 7.4) with a 5 min incubation between each wash. For iVAX samples, membranes were probed with both an anti-6xHis tag antibody and an anti-O-PS antibody or antisera specific to the O antigen of interest, if commercially available. Probing of membranes was performed for at least 1 hour with shaking at room temperature, after which membranes were washed with PBST in the same manner as described above and probed with fluorescently labeled secondary antibodies. Membranes were imaged using an Odyssey® Fc imaging system (LI-COR). CRM197 and TT production were compared to commercial DT and TT standards (Sigma) and orthogonally detected by an identical SDS-PAGE procedure followed by Western blot analysis with a polyclonal antibody that recognizes diphtheria or tetanus toxin, respectively. All antibodies and dilutions used are listed in FIG. 30, Table 4.

TLR4 Activation Assay

HEK-Blue hTLR4 cells (Invivogen) were maintained in DMEM media, high glucose/L-glutamine supplement with 10% fetal bovine serum, 50 U $mL^{-1}$ penicillin, 50 mg $mL^{-1}$ streptomycin, and 100 µg $mL^{-1}$ Normacin™ at 37° C. in a humidified incubator containing 5% $CO_2$. After reaching ~50-80% confluency, cells were plated into 96-well plates at a density of $1.4 \times 10^5$ cells per mL in HEK-Blue detection media (Invivogen). Antigens were added at the following concentrations: 100 ng $µL^{-1}$ purified protein; and 100 ng $µL^{-1}$ total protein in lysate. Purified E. coli O55:B5 LPS (Sigma-Aldrich) and detoxified E. coli O55:B5 (Sigma-Aldrich) were added at 1.0 ng $mL^{-1}$ and served as positive and negative controls, respectively. Plates were incubated at 37° C., 5% $CO_2$ for 10-16 h before measuring absorbance at 620 nm. Statistical significance was determined using paired t-tests.

Mouse Immunization

Six groups of six-week old female BALB/c mice (Harlan Sprague Dawley) were injected subcutaneously with 100 µL PBS (pH 7.4) alone or containing purified aglycosylated MBP, FtO-PS-conjugated MBP, aglycosylated PD, or FtO-PS-conjugated PD, as previously described (Chen et al., 2010). Groups were composed of six mice except for the PBS control group, which was composed of five mice. The amount of antigen in each preparation was normalized to 7.5 µg to ensure that an equivalent amount of aglycosylated protein or bioconjugate was administered in each case. Purified protein groups formulated in PBS were mixed with an equal volume of incomplete Freund's Adjuvant (Sigma-Aldrich) before injection. Prior to immunization, material for each group (5 µL) was streaked on LB agar plates and grown overnight at 37° C. to confirm sterility and endotoxin activity was measured by TLR4 activation assay. Each group of mice was boosted with an identical dosage of antigen 21 days and 42 days after the initial immunization. Blood was obtained on day −1, 21, 35, 49, and 63 via submandibular collection and at study termination on day 70 via cardiac puncture. Mice were observed 24 and 48 hours after each injection for changes in behavior and physical health and no abnormal responses were reported. This study and all procedures were done in accordance with Protocol 2012-0132 approved by the Cornell University Institutional Animal Care and Use Committee.

Enzyme-Linked Immunosorbent Assay

F. tularensis LPS-specific antibodies elicited by immunized mice were measured via indirect ELISA using a modification of a previously described protocol (Chen et al., 2010). Briefly, sera were isolated from the collected blood draws after centrifugation at 5000×g for 10 min and stored at −20° C.; 96-well plates (Maxisorp; Nunc Nalgene) were coated with *F. tularensis* LPS (BEI resources) at a concentration of 5 µg mL$^{-1}$ in PBS and incubated overnight at 4° C. The next day, plates were washed three times with PBST (PBS, 0.05% Tween-20, 0.3% BSA) and blocked overnight at 4° C. with 5% nonfat dry milk (Carnation) in PBS. Samples were serially diluted by a factor of two in triplicate between 1:100 and 1:12,800,000 in blocking buffer and added to the plate for 2 hours at 37° C. Plates were washed three times with PBST and incubated for 1 hour at 37° C. in the presence of one of the following HRP-conjugated antibodies (all from Abcam and used at 1:25,000 dilution): goat anti-mouse IgG, anti-mouse IgG1, and anti-mouse IgG2a. After three additional washes with PBST, 3,3'-5,5'-tetramethylbenzidine substrate (1-Step Ultra TMB-ELISA; Thermo-Fisher) was added, and the plate was incubated at room temperature in the dark for 30 min. The reaction was halted with 2 M $H_2SO_4$, and absorbance was quantified via microplate spectrophotometer (Tecan) at a wavelength of 450 nm. Serum antibody titers were determined by measuring the lowest dilution that resulted in signal 3 SDs above no serum background controls. Statistical significance was determined in RStudio 1.1.463 using one-way ANOVA and the Tukey-Kramer post hoc honest significant difference test.

Quantification and Statistical Analysis

Quantification of Cell-Free Protein Synthesis Yields

To quantify the amount of protein synthesized in iVAX reactions, two approaches were used. Fluorescence units of sfGFP were converted to concentrations using a previously reported standard curve (Hong et al., 2014). Yields of all other proteins were assessed via the addition of 10 µM L-$^{14}$C-leucine (11.1 GBq mmol$^{-1}$, PerkinElmer) to the CFPS mixture to yield trichloroacetic acid-precipitable radioactivity that was measured using a liquid scintillation counter as described previously (Kim and Swartz, 2001).

Statistical Analysis

Statistical parameters including the definitions and values of n, p-values, standard deviations, and standard errors are reported in the Figures and corresponding Figure Legends. Analytical techniques are described in the corresponding Method Details section.

Data and Software Availability

All plasmid constructs used in this study including complete DNA sequences are deposited on Addgene (constructs 128389-128404).

REFERENCES FOR EXAMPLE 3

Adiga, R., Al-adhami, M., Andar, A., Borhani, S., Brown, S., Burgenson, D., Cooper, M. A., Deldari, S., Frey, D. D., Ge, X., et al. (2018). Point-of-care production of therapeutic proteins of good-manufacturing-practice quality. Nat Biomed Eng.

Ashok, A., Brison, M., and LeTallec, Y. (2017). Improving cold chain systems: Challenges and solutions. Vaccine 35, 2217-2223.

Bayburt, T. H., and Sligar, S. G. (2010). Membrane protein assembly into Nanodiscs. FEBS Lett 584, 1721-1727.

Bhushan, R., Anthony, B. F., and Frasch, C. E. (1998). Estimation of group B streptococcus type III polysaccharide-specific antibody concentrations in human sera is antigen dependent. Infect Immun 66, 5848-5853.

Bogaert, D., Hermans, P. W., Adrian, P. V., Rumke, H. C., and de Groot, R. (2004). Pneumococcal vaccines: an update on current strategies. Vaccine 22, 2209-2220.

Boles, K. S., Kannan, K., Gill, J., Felderman, M., Gouvis, H., Hubby, B., Kamrud, K. I., Venter, J. C., and Gibson, D. G. (2017). Digital-to-biological converter for on-demand production of biologics. Nat Biotechnol 35, 672-675.

Brito, L. A., and Singh, M. (2011). Acceptable levels of endotoxin in vaccine formulations during preclinical research. J Pharm Sci 100, 34-37.

Carlson, E. D., Gan, R., Hodgman, C. E., and Jewett, M. C. (2012). Cell-free protein synthesis: Applications come of age. Biotechnol Adv 30, 1185-1194.

Casella, C. R., and Mitchell, T. C. (2008). Putting endotoxin to work for us: monophosphoryl lipid A as a safe and effective vaccine adjuvant. Cell Mol Life Sci 65, 3231-3240.

CDC (2019). CDC Vaccine Price List.

Chen, D. J., Osterrieder, N., Metzger, S. M., Buckles, E., Doody, A. M., DeLisa, M. P., and Putnam, D. (2010). Delivery of foreign antigens by engineered outer membrane vesicle vaccines. Proc Natl Acad Sci USA 107, 3099-3104.

Chen, L., Valentine, J. L., Huang, C.-J., Endicott, C. E., Moeller, T. D., Rasmussen, J. A., Fletcher, J. R., Boll, J. M., Rosenthal, J. A., Dobruchowska, J., et al. (2016). Outer membrane vesicles displaying engineered glycotopes elicit protective antibodies. Proc Natl Acad Sci USA.

Chen, M. M., Glover, K. J., and Imperiali, B. (2007). From peptide to protein: comparative analysis of the substrate specificity of N-linked glycosylation in *C. jejuni*. Biochemistry 46, 5579-5585.

Crowell, L. E., Lu, A. E., Love, K. R., Stockdale, A., Timmick, S. M., Wu, D., Wang, Y. A., Doherty, W., Bonnyman, A., Vecchiarello, N., et al. (2018). On-demand manufacturing of clinical-quality biopharmaceuticals. Nat Biotechnol.

Cuccui, J., Thomas, R. M., Moule, M. G., D'Elia, R. V., Laws, T. R., Mills, D. C., Williamson, D., Atkins, T. P., Prior, J. L., and Wren, B. W. (2013). Exploitation of bacterial N-linked glycosylation to develop a novel recombinant glycoconjugate vaccine against *Francisella tularensis*. Open Biol 3, 130002.

Datsenko, K. A., and Wanner, B. L. (2000). One-step inactivation of chromosomal genes in *Escherichia coli* K-12 using PCR products. Proc Natl Acad Sci USA 97, 6640-6645.

Feldman, M. F., Wacker, M., Hernandez, M., Hitchen, P. G., Marolda, C. L., Kowarik, M., Morris, H. R., Dell, A., Valvano, M. A., and Aebi, M. (2005). Engineering N-linked protein glycosylation with diverse O antigen lipopolysaccharide structures in *Escherichia coli*. Proc Natl Acad Sci USA 102, 3016-3021.

Fernandez, S., Palmer, D. R., Simmons, M., Sun, P., Bisbing, J., McClain, S., Mani, S., Burgess, T., Gunther, V., and Sun, W. (2007). Potential role for Toll-like receptor 4 in mediating *Escherichia coli* maltose-binding protein activation of dendritic cells. Infect Immun 75, 1359-1363.

Figueiredo, D., Turcotte, C., Frankel, G., Li, Y., Dolly, O., Wilkin, G., Marriott, D., Fairweather, N., and Dougan, G. (1995). Characterization of recombinant tetanus toxin derivatives suitable for vaccine development. Infect Immun 63, 3218-3221.

Fisher, A. C., Haitjema, C. H., Guarino, C., Celik, E., Endicott, C. E., Reading, C. A., Merritt, J. H., Ptak, A. C., Zhang, S., and DeLisa, M. P. (2011). Production of secretory and extracellular N-linked glycoproteins in *Escherichia coli*. Appl Environ Microbiol 77, 871-881.

Frasch, C. E. (2009). Preparation of bacterial polysaccharide-protein conjugates: analytical and manufacturing challenges. Vaccine 27, 6468-6470.

Fulop, M., Mastroeni, P., Green, M., and Titball, R. W. (2001). Role of antibody to lipopolysaccharide in protection against low- and high-virulence strains of *Francisella tularensis*. Vaccine 19, 4465-4472.

Garcia-Quintanilla, F., Iwashkiw, J. A., Price, N. L., Stratilo, C., and Feldman, M. F. (2014). Production of a recombinant vaccine candidate against *Burkholderia pseudomallei* exploiting the bacterial N-glycosylation machinery. Front Microbiol 5, 381.

Haghi, F., Peerayeh, S. N., Siadat, S. D., and Montajabiniat, M. (2011). Cloning, expression and purification of outer membrane protein PorA of *Neisseria meningitidis* serogroup B. J Infect Dev Ctries 5, 856-862.

Hatz, C. F., Bally, B., Rohrer, S., Steffen, R., Kramme, S., Siegrist, C. A., Wacker, M., Alaimo, C., and Fonck, V. G. (2015). Safety and immunogenicity of a candidate bioconjugate vaccine against *Shigella dysenteriae* type 1 administered to healthy adults: A single blind, partially randomized Phase I study. Vaccine 33, 4594-4601.

Hong, S. H., Ntai, I., Haimovich, A. D., Kelleher, N. L., Isaacs, F.J., and Jewett, M. C. (2014). Cell-free protein synthesis from a release factor 1 deficient *Escherichia coli* activates efficient and multiple site-specific nonstandard amino acid incorporation. ACS Synth Biol 3, 398-409.

Humphreys, G. (2011). Vaccination: rattling the supply chain (Bulletin of the World Health Organization: World Health Organization).

Huttner, A., Hatz, C., van den Dobbelsteen, G., Abbanat, D., Hornacek, A., Frolich, R., Dreyer, A. M., Martin, P., Davies, T., Fae, K., et al. (2017). Safety, immunogenicity, and preliminary clinical efficacy of a vaccine against extraintestinal pathogenic *Escherichia coli* in women with a history of recurrent urinary tract infection: a randomised, single-blind, placebo-controlled phase 1b trial. Lancet Infect Dis.

Ihssen, J., Kowarik, M., Dilettoso, S., Tanner, C., Wacker, M., and Thony-Meyer, L. (2010). Production of glycoprotein vaccines in *Escherichia coli*. Microb Cell Fact 9, 61.

Jansson, P. E., Lindberg, B., Widmalm, G., and Leontein, K. (1987). Structural studies of the *Escherichia coli* O78 O-antigen polysaccharide. Carbohydr Res 165, 87-92.

Jaroentomeechai, T., Stark, J. C., Natarajan, A., Glasscock, C. J., Yates, L. E., Hsu, K. J., Mrksich, M., Jewett, M.C., and DeLisa, M. P. (2018). Single-pot glycoprotein biosynthesis using a cell-free transcription-translation system enriched with glycosylation machinery. Nat Commun 9, 2686.

Jewett, M. C., and Swartz, J. R. (2004). Mimicking the *Escherichia coli* cytoplasmic environment activates long-lived and efficient cell-free protein synthesis. Biotechnol Bioeng 86, 19-26.

Jin, C., Gibani, M. M., Moore, M., Juel, H. B., Jones, E., Meiring, J., Harris, V., Gardner, J., Nebykova, A., Kerridge, S. A., et al. (2017). Efficacy and immunogenicity of a Vi-tetanus toxoid conjugate vaccine in the prevention of typhoid fever using a controlled human infection model of *Salmonella typhi*: a randomised controlled, phase 2b trial. Lancet 390, 2472-2480.

Johnson, J. R. (1991). Virulence factors in *Escherichia coli* urinary tract infection. Clin Microbiol Rev 4, 80-128.

Kim, D. M., and Swartz, J. R. (2001). Regeneration of adenosine triphosphate from glycolytic intermediates for cell-free protein synthesis. Biotechnol Bioeng 74, 309-316.

Knapp, K. G., Goerke, A. R., and Swartz, J. R. (2007). Cell-free synthesis of proteins that require disulfide bonds using glucose as an energy source. Biotechnol Bioeng 97, 901-908.

Kowarik, M., Young, N. M., Numao, S., Schulz, B. L., Hug, I., Callewaert, N., Mills, D. C., Watson, D. C., Hernandez, M., Kelly, J. F., et al. (2006). Definition of the bacterial N-glycosylation site consensus sequence. EMBO J 25, 1957-1966.

L'vov, V. L., Shashkov, A. S., Dmitriev, B. A., Kochetkov, N. K., Jann, B., and Jann, K. (1984). Structural studies of the O-specific side chain of the lipopolysaccharide from *Escherichia coli* O:7. Carbohydr Res 126, 249-259.

Lu, Z., Madico, G., Roche, M. I., Wang, Q., Hui, J. H., Perkins, H. M., Zaia, J., Costello, C. E., and Sharon, J. (2012). Protective B-cell epitopes of *Francisella tularensis* O-polysaccharide in a mouse model of respiratory tularaemia. Immunology 136, 352-360.

Lydon, P., Zipursky, S., Tevi-Benissan, C., Djingarey, M. H., Gbedonou, P., Youssouf, B. O., and Zaffran, M. (2014). Economic benefits of keeping vaccines at ambient temperature during mass vaccination: the case of meningitis A vaccine in Chad. Bull World Health Organ 92, 86-92.

Ma, Z., Zhang, H., Shang, W., Zhu, F., Han, W., Zhao, X., Han, D., Wang, P. G., and Chen, M. (2014). Glycoconjugate vaccine containing *Escherichia coli* O157:H7 O-antigen linked with maltose-binding protein elicits humoral and cellular responses. PloS One 9, e105215.

Marshall, L. E., Nelson, M., Davies, C. H., Whelan, A. O., Jenner, D. C., Moule, M. G., Denman, C., Cuccui, J., Atkins, T. P., Wren, B. W., et al. (2018). An O-antigen glycoconjugate vaccine produced using protein glycan coupling technology is protective in an inhalational rat model of tularemia. J Immunol Res 2018, 8087916.

Murphy, T. W., Sheng, J., Naler, L. B., Feng, X., and Lu, C. (2019). On-chip manufacturing of synthetic proteins for point-of-care therapeutics. Microsyst Nanoeng 5, 13.

Needham, B. D., Carroll, S. M., Giles, D. K., Georgiou, G., Whiteley, M., and Trent, M. S. (2013). Modulating the innate immune response by combinatorial engineering of endotoxin. Proc Natl Acad Sci USA 110, 1464-1469.

Novak, R. T., Kambou, J. L., Diomande, F. V., Tarbangdo, T. F., Ouedraogo-Traore, R., Sangare, L., Lingani, C., Martin, S. W., Hatcher, C., Mayer, L. W., et al. (2012). Serogroup A meningococcal conjugate vaccination in Burkina Faso: analysis of national surveillance data. Lancet Infect Dis 12, 757-764.

Ollis, A. A., Chai, Y., Natarajan, A., Perregaux, E., Jaroentomeechai, T., Guarino, C., Smith, J., Zhang, S., and DeLisa, M. P. (2015). Substitute sweeteners: Diverse bacterial oligosaccharyltransferases with unique N-glycosylation site preferences. Sci Rep 5, 15237.

Oyston, P. C., Sjostedt, A., and Titball, R. W. (2004). Tularaemia: bioterrorism defence renews interest in *Francisella tularensis*. Nat Rev Microbiol 2, 967-978.

Pardee, K., Slomovic, S., Nguyen, Peter Q., Lee, Jeong W., Donghia, N., Burrill, D., Ferrante, T., McSorley, Fern R., Furuta, Y., Vernet, A., et al. (2016). Portable, on-demand biomolecular manufacturing. Cell 167, 248-259.e212.

Perez, J. G., Stark, J. C., and Jewett, M. C. (2016). Cell-free synthetic biology: Engineering beyond the cell. Cold Spring Harb Perspect Biol.

Perez-Pinera, P., Han, N., Cleto, S., Cao, J., Purcell, O., Shah, K. A., Lee, K., Ram, R., and Lu, T. K. (2016). Synthetic biology and microbioreactor platforms for programmable production of biologics at the point-of-care. Nat Commun 7, 12211.

Petsch, D., and Anspach, F. B. (2000). Endotoxin removal from protein solutions. J Biotechnol 76, 97-119.

Poehling, K. A., Talbot, T. R., Griffin, M. R., Craig, A. S., Whitney, C. G., Zell, E., Lexau, C. A., Thomas, A. R., Harrison, L. H., Reingold, A. L., et al. (2006). Invasive pneumococcal disease among infants before and after introduction of pneumococcal conjugate vaccine. JAMA 295, 1668-1674.

Prior, J. L., Prior, R. G., Hitchen, P. G., Diaper, H., Griffin, K. F., Morris, H. R., Dell, A., and Titball, R. W. (2003). Characterization of the O antigen gene cluster and structural analysis of the O antigen of *Francisella tularensis* subsp. *tularensis*. J Med Microbiol 52, 845-851.

Qadri, F., Svennerholm, A. M., Faruque, A. S., and Sack, R. B. (2005). Enterotoxigenic *Escherichia coli* in developing countries: epidemiology, microbiology, clinical features, treatment, and prevention. Clin Microbiol Rev 18, 465-483.

Raetz, C. R., and Whitfield, C. (2002). Lipopolysaccharide endotoxins. Annu Rev Biochem 71, 635-700.

Riddle, M. S., Kaminski, R. W., Di Paolo, C., Porter, C. K., Gutierrez, R. L., Clarkson, K. A., Weerts, H. E., Duplessis, C., Castellano, A., Alaimo, C., et al. (2016). Safety and immunogenicity of a candidate bioconjugate vaccine against *Shigella flexneri* 2a administered to healthy adults: a single blind, randomized phase I study. Clin Vaccine Immunol.

Roush, S. W., McIntyre, L., and Baldy, L. M. (2008). Manual for the surveillance of vaccine-preventable diseases. Atlanta: Centers for Disease Control and Prevention, 4.

Russell, J. A. (2006). Management of sepsis. N Engl J Med 355, 1699-1713.

Salehi, A. S., Smith, M. T., Bennett, A. M., Williams, J. B., Pitt, W. G., and Bundy, B. C. (2016). Cell-free protein synthesis of a cytotoxic cancer therapeutic: Onconase production and a just-add-water cell-free system. Biotechnol J 11, 274-281.

Schoborg, J. A., Hershewe, J. M., Stark, J. C., Kightlinger, W., Kath, J. E., Jaroentomeechai, T., Natarajan, A., DeLisa, M. P., and Jewett, M. C. (2017). A cell-free platform for rapid synthesis and testing of active oligosaccharyltransferases. Biotechnol Bioeng.

Stefan, A., Conti, M., Rubboli, D., Ravagli, L., Presta, E., and Hochkoeppler, A. (2011). Overexpression and purification of the recombinant diphtheria toxin variant CRM197 in *Escherichia coli*. J Biotechnol 156, 245-252.

Stefanetti, G., Okan, N., Fink, A., Gardner, E., and Kasper, D. L. (2019). Glycoconjugate vaccine using a genetically modified O antigen induces protective antibodies to *Francisella tularensis*. Proc Natl Acad Sci USA 116, 7062-7070.

The Review on Antimicrobial Resistance, C.b.J.O.N. (2014). Antimicrobial Resistance: Tackling a crisis for the health and wealth of nations.

Trotter, C. L., McVernon, J., Ramsay, M. E., Whitney, C. G., Mulholland, E. K., Goldblatt, D., Hombach, J., and Kieny, M. P. (2008). Optimising the use of conjugate vaccines to prevent disease caused by *Haemophilus influenzae* type b, *Neisseria meningitidis* and *Streptococcus pneumoniae*. Vaccine 26, 4434-4445.

Wacker, M., Wang, L., Kowarik, M., Dowd, M., Lipowsky, G., Faridmoayer, A., Shields, K., Park, S., Alaimo, C., Kelley, K. A., et al. (2014). Prevention of *Staphylococcus aureus* infections by glycoprotein vaccines synthesized in *Escherichia coli*. J Infect Dis 209, 1551-1561.

Wahl, B., O'Brien, K. L., Greenbaum, A., Majumder, A., Liu, L., Chu, Y., Luksic, I., Nair, H., McAllister, D. A., Campbell, H., et al. (2018). Burden of *Streptococcus pneumoniae* and *Haemophilus influenzae* type b disease in children in the era of conjugate vaccines: global, regional, and national estimates for 2000-15. Lancet Glob Health 6, e744-e757.

Weintraub, A. (2003). Immunology of bacterial polysaccharide antigens. Carbohydr Res 338, 2539-2547.

Wetter, M., Kowarik, M., Steffen, M., Carranza, P., Corradin, G., and Wacker, M. (2013). Engineering, conjugation, and immunogenicity assessment of *Escherichia coli* O121 O antigen for its potential use as a typhoid vaccine component. Glycoconj J 30, 511-522.WHO (2014). Temperature Sensitivity of Vaccines.

Celik, E., Ollis, A. A., Lasanajak, Y., Fisher, A. C., Gur, G., Smith, D. F., and DeLisa, M. P. (2015). Glycoarrays with engineered phages displaying structurally diverse oligosaccharides enable high-throughput detection of glycan-protein interactions. Biotechnol J 10, 199-209.

Cuccui, J., Thomas, R. M., Moule, M. G., D'Elia, R. V., Laws, T. R., Mills, D. C., Williamson, D., Atkins, T. P., Prior, J. L., and Wren, B. W. (2013). Exploitation of bacterial N-linked glycosylation to develop a novel recombinant glycoconjugate vaccine against *Francisella tularensis*. Open Biol 3, 130002.

Datsenko, K. A., and Wanner, B. L. (2000). One-step inactivation of chromosomal genes in *Escherichia coli* K-12 using PCR products. Proc Natl Acad Sci USA 97, 6640-6645.

Jaroentomeechai, T., Stark, J. C., Natarajan, A., Glasscock, C. J., Yates, L. E., Hsu, K. J., Mrksich, M., Jewett, M. C., and DeLisa, M. P. (2018). Single-pot glycoprotein biosynthesis using a cell-free transcription-translation system enriched with glycosylation machinery. Nat Commun 9, 2686.

Ollis, A. A., Zhang, S., Fisher, A. C., and DeLisa, M. P. (2014). Engineered oligosaccharyltransferases with greatly relaxed acceptor-site specificity. Nat Chem Biol 10, 816-822.

Valvano, M. A., and Crosa, J. H. (1989). Molecular cloning and expression in *Escherichia coli* K-12 of chromosomal genes determining the O7 lipopolysaccharide antigen of a human invasive strain of *E. coli* O7:K1. Infect Immun 57, 937-943.

Figure 31:
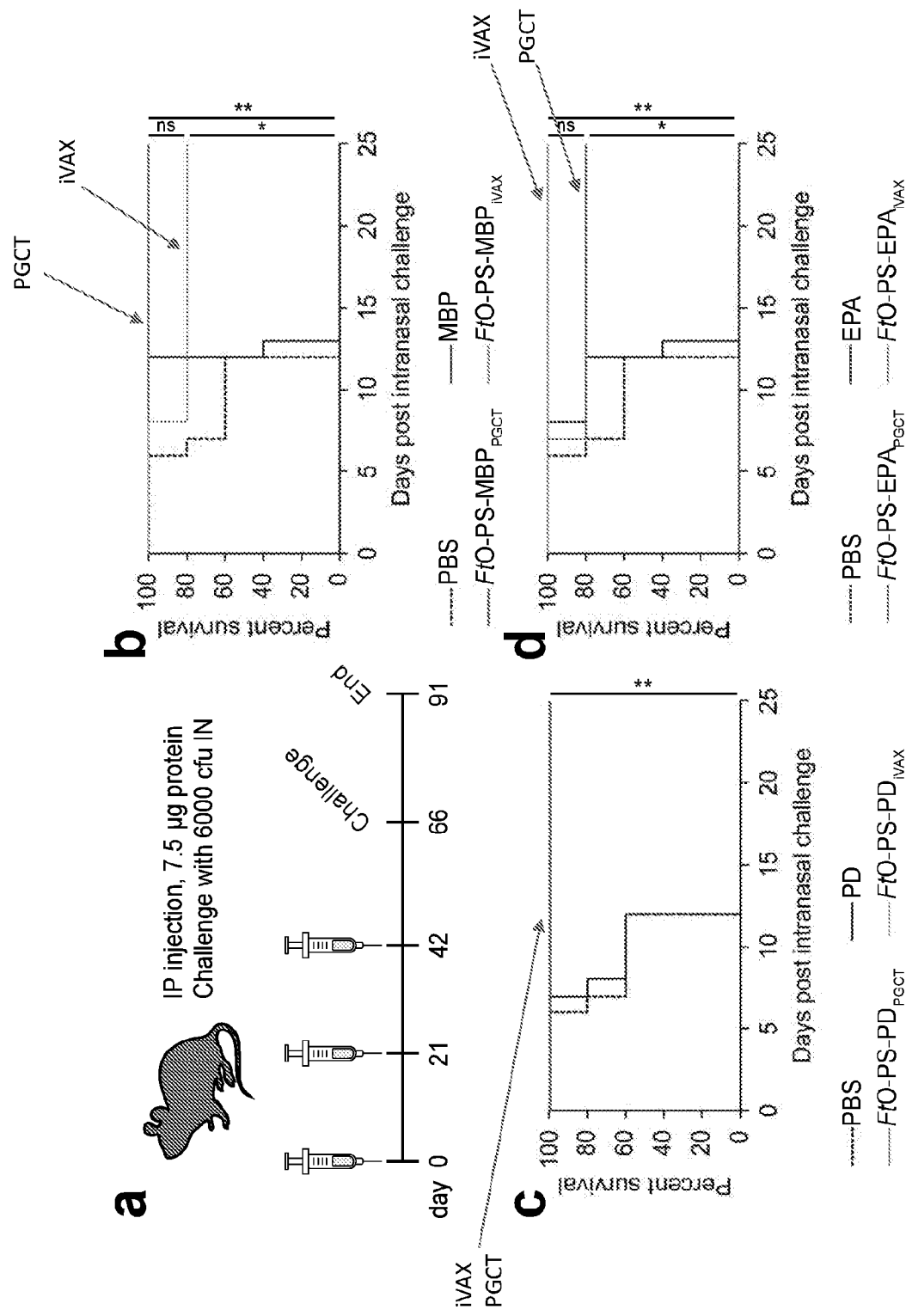
FIG. 31. iVAX-derived vaccines protect against lethal *F. tularensis* challenge. (a) Groups of five BALB/c mice were immunized intraperitoneally with PBS or 7.5 μg of purified, cell-free synthesized aglycosylated MBP$^{4xDQNAT}$, PD$^{4xDQNAT}$, or EPA$^{DNNNS-DQNRT}$, or FtO-PS-conjugated MBP$^{4xDQNAT}$, PD$^{4xDQNAT}$, or EPA$^{DNNNS-DQNRT}$. FtO-PS-conjugated MBP$^{4xDQNAT}$, PD$^{4xDQNAT}$, and EPA$^{DNNNS-DQNRT}$ prepared in living *E. coli* cells using PCGT were used as positive controls. Mice were boosted on days 21 and 42 with identical doses of antigen. On Day 66 mice were challenged intranasally with 6000 cfu (50 times the intranasal LD$_{50}$) *F. tularensis* subsp. *holarctica* live vaccine strain Rocky Mountain Laboratories and monitored for survival for an additional 25 days. Kaplan-Meier curves for immunizations with (b) MBP$^{4xDQNAT}$ (c) PD$^{4xDQNAT}$ and (d) EPA$^{DNNNS-DQNRT}$ as the carrier protein are shown. These results show that iVAX-derived vaccines protect mice from lethal pathogen challenge as effectively as vaccines synthesized using the state-of-the-art PGCT approach. (*p=0.0476; **p=0.0079, Fisher's exact test; ns: not significant).

Example 3 iVAX-Derived Vaccines Protect Against Lethal *F. tularensis* Challenge Groups of five BALB/c mice were immunized intraperitoneally with PBS or 7.5 µg of purified, cell-free synthesized aglycosylated $MBP^{4xDQNAT}$, $PD^{4xDQNAT}$ or $EPA^{DNNNS-DQNRT}$, or FtO-PS-conjugated $MBP^{4xDQNAT}$, $PD^{4xDQNAT}$ or $EPA^{DNNNS-DQNRT}$. FtO-PS-conjugated $MBP^{4xDQNAT}$, $PD^{4xDQNAT}$ and $EPA^{DNNNS-DQNRT}$ prepared in living *E. coli* cells using PCGT were used as positive controls. Mice were boosted on days 21 and 42 with identical doses of antigen. On Day 66 mice were challenged intranasally with 6000 cfu (50 times the intranasal $LD_{50}$) *F. tularensis* subsp. *holarctica* live vaccine strain Rocky Mountain Laboratories and monitored for survival for an additional 25 days. (FIG. 31a). Kaplan-Meier curves for immunizations with (FIG. 31b) $MBP^{4xDQNAT}$ (FIG. 31c) $PD^{4xDQNAT}$ and (FIG. 31d) $EPA^{DNNNS-DQNRT}$ as the carrier protein are shown. These results show that iVAX-derived vaccines protect mice from lethal pathogen challenge as effectively as vaccines synthesized using the state-of-the-art PGCT approach. (*p=0.0476; **p=0.0079, Fisher's exact test; ns: not significant).

In the foregoing description, it will be readily apparent to one skilled in the art that varying substitutions and modifications may be made to the invention disclosed herein without departing from the scope and spirit of the invention. The invention illustratively described herein suitably may be practiced in the absence of any element or elements, limitation or limitations which is not specifically disclosed herein. The terms and expressions which have been employed are used as terms of description and not of limitation, and there is no intention that in the use of such terms and expressions of excluding any equivalents of the features shown and described or portions thereof, but it is recognized that various modifications are possible within the scope of the invention. Thus, it should be understood that although the present invention has been illustrated by specific embodiments and optional features, modification and/or variation of the concepts herein disclosed may be resorted to by those skilled in the art, and that such modifications and variations are considered to be within the scope of this invention.

Citations to a number of patent and non-patent references are made herein. The cited references are incorporated by reference herein in their entireties. In the event that there is an inconsistency between a definition of a term in the specification as compared to a definition of the term in a cited reference, the term should be interpreted based on the definition in the specification.

We claim:

1. A method for synthesizing an N-glycosylated carrier protein for a polysaccharide via coordinated transcription, translation, and N-glycosylation in vitro, the method comprising:
   (i) transcribing and translating a carrier protein in a cell-free protein synthesis reaction, the carrier protein comprising an inserted consensus sequence, N—X—S/T, wherein X may be any natural or unnatural amino acid except proline;
   (ii) glycosylating the carrier protein in the cell-free protein synthesis reaction with at least one polysaccharide, wherein the at least one polysaccharide is at least one bacterial O-antigen;
   wherein the cell-free protein synthesis reaction comprises:
   (i) lysate derived from one or more genetically modified Escherichia coli (E. coli) strains, wherein the genetically modified E. coli strains (a) are deficient in lpxM gene product, (b) comprise an orthogonal or heterologous LpxE gene that is expressed in the engineered E. coli strains and is present in the lysate, and (c) comprise an inactivating modification in the waaL gene;
   (ii) transcription and translation machinery;
   (iii) at least one bacterial O-antigen as part of lipid-linked oligosaccharides (LLOs);
   (iii) an oligosaccharide transferase which recognizes the inserted consensus sequence;
   (iv) a transcription template encoding the carrier protein.

2. The method of claim 1, wherein the carrier protein is selected from Haemophilus influenzae protein D (PD), Neisseria meningitidis porin protein (PorA), and variants thereof.

3. The method of claim 1, wherein the bacterial O-antigen is from E. coli.

4. The method of claim 1, wherein the bacterial O-antigen is from Franciscella tularensis.

5. The method of claim 1, further comprising formulating the N-glycosylated carrier protein as a vaccine composition comprising the N-glycosylated carrier protein.

6. The method of claim 1, wherein the vaccine composition further comprises an adjuvant.

7. The method of claim 1, wherein the glycosylating step utilizes an oligosaccharyltransferase (OST) which is a naturally occurring or engineered bacterial OST.

8. The method of claim 1, wherein the glycosylating step utilizes an oligosaccharyltransferase (OST) which is a naturally occurring or engineered archaeal OST.

9. The method of claim 1, wherein the glycosylating step utilizes an oligosaccharyltransferase (OST) which is a naturally occurring bacterial homolog of C. jejuni PglB.

10. The method of claim 1, wherein the glycosylating step utilizes an OST that is an engineered variant of C. jejuni PglB.

11. The method of claim 1 wherein the glycosylating step utilizes an OST which is a naturally occurring single-subunit eukaryotic OST.

12. The method of claim 5, further comprising administering the vaccine composition to subject in need thereof.

13. A kit for synthesizing a N-glycosylated carrier protein in vitro, the kit comprising:
   (i) a first component comprising a cell lysate that comprises an orthogonal oligosaccharyltransferase (OST);
   (ii) a second component comprising a cell lysate that comprises an O-antigen; and
   (iii) a third component comprising a transcription template and a polymerase for synthesizing an mRNA from the transcription template encoding a carrier protein, the carrier protein comprising an inserted consensus sequence, N—X—S/T, wherein X may be any natural or unnatural amino acid except proline;
   wherein the cell lysate of (i) and/or (ii) is derived from one or more genetically modified Escherichia coli (E. coli) strains, wherein the genetically modified E. coli strains (a) are deficient in lpxM gene product; and (b) comprise an orthogonal or heterologous LpxE gene that is expressed in the engineered E. coli strains and is present in the lysate.

14. A kit for synthesizing a N-glycosylated carrier protein in vitro, the kit comprising:
   (i) a first component comprising a cell lysate that comprises an orthogonal oligosaccharyltransferase (OST) and an O-antigen; and
   (ii) a second component comprising a transcription template and a polymerase for synthesizing an mRNA from the transcription template encoding a carrier protein, the carrier protein comprising an inserted consensus sequence, N—X—S/T, wherein X may be any natural or unnatural amino acid except proline;
   wherein the cell lysate of (i) is derived from one or more genetically modified Escherichia coli (E. coli) strains, wherein the genetically modified E. coli strains (a) are deficient in lpxM gene product; and (b) comprise an orthogonal or heterologous LpxE gene that is expressed in the engineered E. coli strains and is present in the lysate.

15. The kit of claim 13, wherein one or more of the first component, the second component, and the third component, if present, are lyophilized.

16. The kit of claim 13, wherein the first component cell lysate is produced from a source strain that overexpresses a gene encoding the orthogonal OST.

17. The kit of claim 13, wherein the second component cell lysate is produced from a source strain that overexpresses a synthetic glycosyltransferase pathway.

18. The kit of claim 14, wherein the first component cell lysate is produced from a source strain that overexpresses one or both of (a) a gene encoding the orthogonal OST, and (b) a synthetic glycosyltransferase pathway.

19. The kit of claim 13, wherein the second component cell lysate or the first component cell lysate comprises O-antigen from F. tularensis Schu S4 lipid-linked oligosaccharides (FtLLOs) or O-antigens from enterotoxigenic *E. coli* O78 lipid-linked oligosaccharides (EcO78LLOs).

20. A method for cell-free production of a glycoprotein, the method comprising:
  i) forming a cell-free protein synthesis reaction mixture, the reaction mixture comprising:
    (a) a first cell lysate comprising an orthogonal oligosaccharyltransferase (OST) that recognizes consensus sequence N—X—S/T, wherein X may be any natural or unnatural amino acid except proline and a second cell lysate that comprises an O-antigen, wherein the first cell lysate and/or the second cell lysate is derived from one or more genetically modified *Escherichia coli* (*E. coli*) strains, wherein the genetically modified *E. coli* strains (a) are deficient in lpxM gene product, (b) comprise an orthogonal or heterologous LpxE gene that is expressed in the engineered *E. coli* strains and is present in the lysate, and (c) comprise an inactivating modification in the waaL gene; wherein the second cell lysate comprises the O-antigen as part of lipid-linked oligosaccharides (LLOs);
    (b) a transcription template encoding a carrier protein selected from *Haemophilus influenzae* protein D (PD), *Neisseria meningitidis* porin protein (PorA), and variants thereof, the carrier protein comprising an inserted consensus sequence, N—X—S/T, wherein X may be any natural or unnatural amino acid except proline;
    (c) transcription and translation machinery;
  ii) transcribing and translating the carrier protein in the cell-free protein synthesis reaction; and
  iii) glycosylating the carrier protein in the cell-free protein synthesis reaction with the bacterial O-antigen.

21. A method for cell-free production of a glycoprotein, the method comprising: (a) mixing a first cell lysate comprising (i) an orthogonal oligosaccharyltransferase (OST) that recognizes consensus sequence, N—X—S/T, wherein X may be any natural or unnatural amino acid except proline, and (ii) an O-antigen to prepare a cell-free protein synthesis reaction; (b) transcribing and translating a carrier protein from a transcription template encoding the carrier protein, wherein the carrier protein is selected from *Haemophilus influenzae* protein D (PD), *Neisseria meningitidis* porin protein (PorA), and variants thereof, in the cell-free protein synthesis reaction, the carrier protein comprising an inserted consensus sequence, N—X—S/T, wherein X may be any natural or unnatural amino acid except proline; and (c) glycosylating the carrier protein in the cell-free protein synthesis reaction with the bacterial O-antigen; wherein the first cell lysate is derived from one or more genetically modified *Escherichia coli* (*E. coli*) strains, wherein the genetically modified *E. coli* strains (a) are deficient in lpxM gene product, (b) comprise an orthogonal or heterologous LpxE gene that is expressed in the engineered *E. coli* strains and is present in the lysate, and (c) comprise an inactivating modification in the waaL gene; wherein the first cell lysate comprises the O-antigen as part of lipid-linked oligosaccharides (LLOs).

22. The method of claim 20, further comprising formulating the glycoprotein as a vaccine composition.

23. The method of claim 22, further comprising administering the vaccine composition to subject in need thereof.

* * * * *

SEQUENCE LISTING

<160> NUMBER OF SEQ ID NOS: 10

<210> SEQ ID NO 1
<211> LENGTH: 1122
<212> TYPE: DNA
<213> ORGANISM: Escherichia coli

<400> SEQUENCE: 1

```
atgtcaaaag tcgctctcat caccggtgta accggacaag acggttctta cctggcagag      60
tttctgctgg aaaaaggtta cgaggtgcat ggtattaagc gtcgcgcatc gtcattcaac     120
accgagcgcg tggatcacat ttatcaggat ccgcacacct gcaacccgaa attccatctg     180
cattatggcg acctgagtga tacctctaac ctgacgcgca ttttgcgtga agtacagccg     240
gatgaagtgt acaacctggg cgcaatgagc cacgttgcgg tctcttttga gtcaccagaa     300
tataccgctg acgtcgacgc gatgggtacg ctgcgcctgc tggaggcgat ccgcttcctc     360
ggtctggaaa agaaaactcg tttctatcag gcttccacct ctgaactgta tggtctggtg     420
caggaaattc gcagaaaga gaccacgccg ttctacccgc gatctccgta tgcggtcgcc     480
aaactgtacg cctactggat caccgttaac taccgtgaat cctacggcat gtacgcctgt     540
aacggaattc tcttcaacca tgaatccccg cgccgcggcg aaaccttcgt tacccgcaaa     600
atcacccgcg caatcgccaa catcgcccag gggctggagt cgtgcctgta cctcggcaat     660
atggattccc tgcgtgactg gggccacgcc aaagactacg taaaaatgca gtggatgatg     720
ctgcagcagg aacagccgga agatttcgtt atcgcgaccg gcgttcagta ctccgtgcgt     780
cagttcgtgg aaatggcggc agcacagctg ggcatcaaac tgcgctttga aggcacgggc     840
gttgaagaga agggcattgt ggtttccgtc accgggcatg acgcgccggg cgttaaaccg     900
ggtgatgtga ttatcgctgt tgacccgcgt tacttccgtc cggctgaagt tgaaacgctg     960
ctcggcgacc cgaccaaagc gcacgaaaaa ctgggctgga aaccggaaat cacccctcaga   1020
gagatggtgt ctgaaatggt ggctaatgac ctcgaagcgg cgaaaaaaca ctctctgctg    1080
aaatctcacg gctacgacgt ggcgatcgcg ctggagtcat aa                       1122
```

<210> SEQ ID NO 2
<211> LENGTH: 373
<212> TYPE: PRT
<213> ORGANISM: Escherichia coli

<400> SEQUENCE: 2

```
Met Ser Lys Val Ala Leu Ile Thr Gly Val Thr Gly Gln Asp Gly Ser
1               5                   10                  15

Tyr Leu Ala Glu Phe Leu Leu Glu Lys Gly Tyr Glu Val His Gly Ile
            20                  25                  30

Lys Arg Arg Ala Ser Ser Phe Asn Thr Glu Arg Val Asp His Ile Tyr
        35                  40                  45
```

Gln Asp Pro His Thr Cys Asn Pro Lys Phe His Leu His Tyr Gly Asp
    50                  55                  60

Leu Ser Asp Thr Ser Asn Leu Thr Arg Ile Leu Arg Glu Val Gln Pro
65                  70                  75                  80

Asp Glu Val Tyr Asn Leu Gly Ala Met Ser His Val Ala Val Ser Phe
                85                  90                  95

Glu Ser Pro Glu Tyr Thr Ala Asp Val Asp Ala Met Gly Thr Leu Arg
            100                 105                 110

Leu Leu Glu Ala Ile Arg Phe Leu Gly Leu Glu Lys Lys Thr Arg Phe
        115                 120                 125

Tyr Gln Ala Ser Thr Ser Glu Leu Tyr Gly Leu Val Gln Glu Ile Pro
    130                 135                 140

Gln Lys Glu Thr Thr Pro Phe Tyr Pro Arg Ser Pro Tyr Ala Val Ala
145                 150                 155                 160

Lys Leu Tyr Ala Tyr Trp Ile Thr Val Asn Tyr Arg Glu Ser Tyr Gly
                165                 170                 175

Met Tyr Ala Cys Asn Gly Ile Leu Phe Asn His Glu Ser Pro Arg Arg
            180                 185                 190

Gly Glu Thr Phe Val Thr Arg Lys Ile Thr Arg Ala Ile Ala Asn Ile
        195                 200                 205

Ala Gln Gly Leu Glu Ser Cys Leu Tyr Leu Gly Asn Met Asp Ser Leu
    210                 215                 220

Arg Asp Trp Gly His Ala Lys Asp Tyr Val Lys Met Gln Trp Met Met
225                 230                 235                 240

Leu Gln Gln Glu Gln Pro Glu Asp Phe Val Ile Ala Thr Gly Val Gln
                245                 250                 255

Tyr Ser Val Arg Gln Phe Val Glu Met Ala Ala Ala Gln Leu Gly Ile
            260                 265                 270

Lys Leu Arg Phe Glu Gly Thr Gly Val Glu Glu Lys Gly Ile Val Val
        275                 280                 285

Ser Val Thr Gly His Asp Ala Pro Gly Val Lys Pro Gly Asp Val Ile
    290                 295                 300

Ile Ala Val Asp Pro Arg Tyr Phe Arg Pro Ala Glu Val Glu Thr Leu
305                 310                 315                 320

Leu Gly Asp Pro Thr Lys Ala His Glu Lys Leu Gly Trp Lys Pro Glu
                325                 330                 335

Ile Thr Leu Arg Glu Met Val Ser Glu Met Val Ala Asn Asp Leu Glu
            340                 345                 350

Ala Ala Lys Lys His Ser Leu Leu Lys Ser His Gly Tyr Asp Val Ala
        355                 360                 365

Ile Ala Leu Glu Ser
    370

<210> SEQ ID NO 3
<211> LENGTH: 1260
<212> TYPE: DNA
<213> ORGANISM: Escherichia coli

<400> SEQUENCE: 3
atgctaacat cctttaaact tcattcattg aaaccttaca ctctgaaatc atcaatgatt    60
ttagagataa taacttatat attatgtttt ttttcaatga taattgcatt cgtcgataat   120
actttcagca taaaaatata taatatcact gctatagttt gcttattgtc actaatttta   180
cgtggcagac aagaaaatta atatataaaa aaccttattc ttccccttc tatattttta   240

```
ataggcttgc ttgatttaat ttggtattct gcgtttaaag tagataattc gccatttcgt    300
gctacttacc atagttattt aaatactgcc aaaatattta tatttggttc ttttattgtt    360
ttcttgacac taactagcca gctaaaatca aaaaagaga gtgtattata cactttgtat     420
tctctgtcat ttctaattgc tggatatgca atgtatatta atagcattca tgaaaatgac    480
cgcatttctt ttggtgtagg aacggcaaca ggagcagcat attcaacaat gctaataggg    540
atagttagtg gcgttgcgat tctttatact aagaaaaatc atcctttttt attttatta    600 aatagttgcg cggtacttta tgttctggcg ctaacacaaa ccagagcaac cctactcctg    660
ttccctataa tttgtgttgc tgcattaata gcttattata taaatcacc caagaaattc     720 acttcctcta ttgttctact aattgctata ttagctagca ttgttattat atttaataaa    780
ccaatacaga atcgctataa tgaagcatta aatgacttaa acagttatac caatgctaat    840
agtgttactt ccctaggtgc aagactggca atgtacgaaa ttggtttaaa tatattcata    900
aagtcacctt tttcatttag atcagcagag tcacgcgctg aaagtatgaa tttgttagtt    960
gcagaacaca ataggctaag aggggcattg gagttttcta acgtacatct acataatgag   1020
ataattgaag cagggtcact gaaaggtctg atgggaattt tttccacact tttcctctat   1080
ttttcactat tttatatagc atataaaaaa cgagctttgg gtttgttgat attaacgctt   1140
ggcattgtgg ggattggact cagtgatgtg atcatatggg cacgcagcat tccaattatc   1200
attatatccg ctatagtcct cttactcgtc attaataatc gtaacaatac aattaattaa   1260
```

<210> SEQ ID NO 4  
<211> LENGTH: 419  
<212> TYPE: PRT  
<213> ORGANISM: Escherichia coli

<400> SEQUENCE: 4

Met Leu Thr Ser Phe Lys Leu His Ser Leu Lys Pro Tyr Thr Leu Lys  
1               5                   10                  15

Ser Ser Met Ile Leu Glu Ile Ile Thr Tyr Ile Leu Cys Phe Phe Ser  
            20                  25                  30

Met Ile Ile Ala Phe Val Asp Asn Thr Phe Ser Ile Lys Ile Tyr Asn  
        35                  40                  45

Ile Thr Ala Ile Val Cys Leu Leu Ser Leu Ile Leu Arg Gly Arg Gln  
    50                  55                  60

Glu Asn Tyr Asn Ile Lys Asn Leu Ile Leu Pro Leu Ser Ile Phe Leu  
65                  70                  75                  80

Ile Gly Leu Leu Asp Leu Ile Trp Tyr Ser Ala Phe Lys Val Asp Asn  
                85                  90                  95

Ser Pro Phe Arg Ala Thr Tyr His Ser Tyr Leu Asn Thr Ala Lys Ile  
            100                 105                 110

Phe Ile Phe Gly Ser Phe Ile Val Phe Leu Thr Leu Thr Ser Gln Leu  
        115                 120                 125

Lys Ser Lys Lys Glu Ser Val Leu Tyr Thr Leu Tyr Ser Leu Ser Phe  
    130                 135                 140

Leu Ile Ala Gly Tyr Ala Met Tyr Ile Asn Ser Ile His Glu Asn Asp  
145                 150                 155                 160

Arg Ile Ser Phe Gly Val Gly Thr Ala Thr Gly Ala Ala Tyr Ser Thr  
                165                 170                 175

Met Leu Ile Gly Ile Val Ser Gly Val Ala Ile Leu Tyr Thr Lys Lys  
            180                 185                 190

Asn His Pro Phe Leu Phe Leu Leu Asn Ser Cys Ala Val Leu Tyr Val
    195                 200                 205

Leu Ala Leu Thr Gln Thr Arg Ala Thr Leu Leu Phe Pro Ile Ile
    210                 215                 220

Cys Val Ala Ala Leu Ile Ala Tyr Tyr Asn Lys Ser Pro Lys Lys Phe
225                 230                 235                 240

Thr Ser Ser Ile Val Leu Leu Ile Ala Ile Leu Ala Ser Ile Val Ile
                245                 250                 255

Ile Phe Asn Lys Pro Ile Gln Asn Arg Tyr Asn Glu Ala Leu Asn Asp
            260                 265                 270

Leu Asn Ser Tyr Thr Asn Ala Asn Ser Val Thr Ser Leu Gly Ala Arg
    275                 280                 285

Leu Ala Met Tyr Glu Ile Gly Leu Asn Ile Phe Ile Lys Ser Pro Phe
    290                 295                 300

Ser Phe Arg Ser Ala Glu Ser Arg Ala Glu Ser Met Asn Leu Leu Val
305                 310                 315                 320

Ala Glu His Asn Arg Leu Arg Gly Ala Leu Glu Phe Ser Asn Val His
                325                 330                 335

Leu His Asn Glu Ile Ile Glu Ala Gly Ser Leu Lys Gly Leu Met Gly
            340                 345                 350

Ile Phe Ser Thr Leu Phe Leu Tyr Phe Ser Leu Phe Tyr Ile Ala Tyr
    355                 360                 365

Lys Lys Arg Ala Leu Gly Leu Leu Ile Leu Thr Leu Gly Ile Val Gly
    370                 375                 380

Ile Gly Leu Ser Asp Val Ile Ile Trp Ala Arg Ser Ile Pro Ile Ile
385                 390                 395                 400

Ile Ile Ser Ala Ile Val Leu Leu Val Ile Asn Asn Arg Asn Asn
                405                 410                 415

Thr Ile Asn

<210> SEQ ID NO 5
<211> LENGTH: 2142
<212> TYPE: DNA
<213> ORGANISM: Campylobacter jejuni

<400> SEQUENCE: 5

```
atgttgaaaa aagagtattt aaaaaaccct tatttagttt tgtttgcgat gattgtatta      60
gcttatgttt ttagtgtatt ttgcaggttt tattgggttt ggtgggcaag tgagtttaac     120
gagtattttt tcaataatca attaatgatc atttcaaacg atggctatgc ttttgctgag     180
ggcgcaagag atatgatagc aggttttcat cagcctaatg atttgagtta ttatggatct     240
tctttatcta cgcttactta tggctttat aaaatcacac cttttttcttt tgaaagtatc     300
atttatata tgagtacttt tttatcttct ttggtggtga ttcctattat tttactagct     360
aatgaataca aacgcccttt aatgggcttt gtagctgctc ttttagcaag tgtagcaaac     420
agttattata atcgcactat gagtgggtat tatgatacgg atatgctggt aattgtttta     480
cctatgttta tttattttt tatggtaaga atgatttaa aaaagactt ttttttcattg     540
attgccttgc cattatttat aggaattat ctttggtggt atccttcaag ttatacttta     600
aatgtagctt taattggact ttttttaatt tatacactta ttttttcatag aaaagaaaag     660
attttttata tagctgtgat tttgtcttct cttactcttt caaatatagc atggttttat     720
caaagtgcca ttatagtaat acttttttgct ttatttgctt tagagcaaaa acgcttaaat     780
tttatgatta taggaatttt aggtagtgca actttgatat ttttgatttt aagtggtggg     840
```

```
gttgatccca tactttatca gcttaaattt tatatttta gaagcgatga aagtgcgaat    900
ttaacacagg gctttatgta ttttaatgtt aatcaaacca tacaagaagt tgaaaatgta    960
gattttagcg aatttatgcg aagaattagt ggtagtgaaa ttgttttctt gttttctttg   1020
tttggttttg tatggctttt gagaaaacat aaaagtatga ttatggcttt acctatattg   1080
gtgcttgggt ttttagcctt aaaaggagga cttagattta ccatttattc tgtacctgta   1140
atggctttag gatttggttt tttattgagc gagtttaagg ctatattggt taaaaaatat   1200
agccaattaa cttcaaatgt ttgtattgtt tttgcaacta ttttgacttt ggctccagta   1260
tttatccata tttacaacta taaagcgcca acagttttt ctcaaaatga agcatcatta   1320
ttaaatcaat taaaaaatat agccaataga gaagattatg tggtaacttg gtgggattat   1380
ggttatcctg tgcgttatta tagcgatgtg aaaactttag tagatggtgg aaagcattta   1440
ggtaaggata atttttccc ttctttttct ttaagtaaag atgaacaagc tgcagctaat   1500
atggcaagac ttagtgtaga atatacagaa aaaagctttt atgctccgca aaatgatatt   1560
ttaaaatcag acattttaca agccatgatg aaagattata atcaaagcaa tgtggattta   1620
tttctagctt cattatcaaa acctgatttt aaaatcgata caccaaaaac tcgtgatatt   1680
tatctttata tgcccgctag aatgtctttg attttttcta cggtggctag ttttttctttt   1740 attaatttag atacaggagt tttggataaa ccttttacct ttagcacagc ttatccactt   1800
gatgttaaaa atggagaaat ttatcttagc aacggagtgg ttttaagcga tgattttaga   1860
agttttaaaa taggtgataa tgtggtttct gtaaatagta tcgtagagat taattctatt   1920
aaacaaggtg aatacaaaat cactccaatc gatgataagg ctcagttta tatttttat   1980 ttaaaggata gtgctattcc ttacgcacaa tttattttaa tggataaaac catgtttaat   2040
agtgcttatg tgcaaatgtt tttttggga aattatgata agaatttatt tgacttggtg   2100
attaattcta gagatgctaa agttttaaa cttaaaattt aa                      2142
```

<210> SEQ ID NO 6
<211> LENGTH: 713
<212> TYPE: PRT
<213> ORGANISM: Campylobacter jejuni

<400> SEQUENCE: 6

```
Met Leu Lys Lys Glu Tyr Leu Lys Asn Pro Tyr Leu Val Leu Phe Ala
1               5                   10                  15

Met Ile Val Leu Ala Tyr Val Phe Ser Val Phe Cys Arg Phe Tyr Trp
            20                  25                  30

Val Trp Trp Ala Ser Glu Phe Asn Glu Tyr Phe Phe Asn Asn Gln Leu
        35                  40                  45

Met Ile Ile Ser Asn Asp Gly Tyr Ala Phe Ala Glu Gly Ala Arg Asp
    50                  55                  60

Met Ile Ala Gly Phe His Gln Pro Asn Asp Leu Ser Tyr Tyr Gly Ser
65                  70                  75                  80

Ser Leu Ser Thr Leu Thr Tyr Trp Leu Tyr Lys Ile Thr Pro Phe Ser
                85                  90                  95

Phe Glu Ser Ile Ile Leu Tyr Met Ser Thr Phe Leu Ser Ser Leu Val
            100                 105                 110

Val Ile Pro Ile Ile Leu Leu Ala Asn Glu Tyr Lys Arg Pro Leu Met
        115                 120                 125

Gly Phe Val Ala Ala Leu Leu Ala Ser Val Ala Asn Ser Tyr Tyr Asn
    130                 135                 140
```

```
Arg Thr Met Ser Gly Tyr Tyr Asp Thr Asp Met Leu Val Ile Val Leu
145                 150                 155                 160

Pro Met Phe Ile Leu Phe Phe Met Val Arg Met Ile Leu Lys Lys Asp
            165                 170                 175

Phe Phe Ser Leu Ile Ala Leu Pro Leu Phe Ile Gly Ile Tyr Leu Trp
        180                 185                 190

Trp Tyr Pro Ser Ser Tyr Thr Leu Asn Val Ala Leu Ile Gly Leu Phe
            195                 200                 205

Leu Ile Tyr Thr Leu Ile Phe His Arg Lys Glu Lys Ile Phe Tyr Ile
        210                 215                 220

Ala Val Ile Leu Ser Ser Leu Thr Leu Ser Asn Ile Ala Trp Phe Tyr
225                 230                 235                 240

Gln Ser Ala Ile Ile Val Ile Leu Phe Ala Leu Phe Ala Leu Glu Gln
            245                 250                 255

Lys Arg Leu Asn Phe Met Ile Ile Gly Ile Leu Gly Ser Ala Thr Leu
            260                 265                 270

Ile Phe Leu Ile Leu Ser Gly Gly Val Asp Pro Ile Leu Tyr Gln Leu
        275                 280                 285

Lys Phe Tyr Ile Phe Arg Ser Asp Glu Ser Ala Asn Leu Thr Gln Gly
290                 295                 300

Phe Met Tyr Phe Asn Val Asn Gln Thr Ile Gln Glu Val Glu Asn Val
305                 310                 315                 320

Asp Phe Ser Glu Phe Met Arg Arg Ile Ser Gly Ser Glu Ile Val Phe
            325                 330                 335

Leu Phe Ser Leu Phe Gly Phe Val Trp Leu Leu Arg Lys His Lys Ser
            340                 345                 350

Met Ile Met Ala Leu Pro Ile Leu Val Leu Gly Phe Leu Ala Leu Lys
            355                 360                 365

Gly Gly Leu Arg Phe Thr Ile Tyr Ser Val Pro Val Met Ala Leu Gly
        370                 375                 380

Phe Gly Phe Leu Leu Ser Glu Phe Lys Ala Ile Leu Val Lys Lys Tyr
385                 390                 395                 400

Ser Gln Leu Thr Ser Asn Val Cys Ile Val Phe Ala Thr Ile Leu Thr
            405                 410                 415

Leu Ala Pro Val Phe Ile His Ile Tyr Asn Tyr Lys Ala Pro Thr Val
            420                 425                 430

Phe Ser Gln Asn Glu Ala Ser Leu Leu Asn Gln Leu Lys Asn Ile Ala
        435                 440                 445

Asn Arg Glu Asp Tyr Val Val Thr Trp Trp Asp Tyr Gly Tyr Pro Val
        450                 455                 460

Arg Tyr Tyr Ser Asp Val Lys Thr Leu Val Asp Gly Gly Lys His Leu
465                 470                 475                 480

Gly Lys Asp Asn Phe Phe Pro Ser Phe Ser Leu Ser Lys Asp Glu Gln
            485                 490                 495

Ala Ala Ala Asn Met Ala Arg Leu Ser Val Glu Tyr Thr Glu Lys Ser
            500                 505                 510

Phe Tyr Ala Pro Gln Asn Asp Ile Leu Lys Ser Asp Ile Leu Gln Ala
            515                 520                 525

Met Met Lys Asp Tyr Asn Gln Ser Asn Val Asp Leu Phe Leu Ala Ser
        530                 535                 540

Leu Ser Lys Pro Asp Phe Lys Ile Asp Thr Pro Lys Thr Arg Asp Ile
545                 550                 555                 560
```

```
Tyr Leu Tyr Met Pro Ala Arg Met Ser Leu Ile Phe Ser Thr Val Ala
            565                 570                 575

Ser Phe Ser Phe Ile Asn Leu Asp Thr Gly Val Leu Asp Lys Pro Phe
        580                 585                 590

Thr Phe Ser Thr Ala Tyr Pro Leu Asp Val Lys Asn Gly Glu Ile Tyr
            595                 600                 605

Leu Ser Asn Gly Val Val Leu Ser Asp Asp Phe Arg Ser Phe Lys Ile
        610                 615                 620

Gly Asp Asn Val Val Ser Val Asn Ser Ile Val Glu Ile Asn Ser Ile
625                 630                 635                 640

Lys Gln Gly Glu Tyr Lys Ile Thr Pro Ile Asp Asp Lys Ala Gln Phe
                645                 650                 655

Tyr Ile Phe Tyr Leu Lys Asp Ser Ala Ile Pro Tyr Ala Gln Phe Ile
            660                 665                 670

Leu Met Asp Lys Thr Met Phe Asn Ser Ala Tyr Val Gln Met Phe Phe
        675                 680                 685

Leu Gly Asn Tyr Asp Lys Asn Leu Phe Asp Leu Val Ile Asn Ser Arg
    690                 695                 700

Asp Ala Lys Val Phe Lys Leu Lys Ile
705                 710

<210> SEQ ID NO 7
<211> LENGTH: 364
<212> TYPE: PRT
<213> ORGANISM: Haemophilus influenzae

<400> SEQUENCE: 7

Met Lys Leu Lys Thr Leu Ala Leu Ser Leu Leu Ala Ala Gly Val Leu
1               5                   10                  15

Ala Gly Cys Ser Ser His Ser Ser Asn Met Ala Asn Thr Gln Met Lys
            20                  25                  30

Ser Asp Lys Ile Ile Ile Ala His Arg Gly Ala Ser Gly Tyr Leu Pro
        35                  40                  45

Glu His Thr Leu Glu Ser Lys Ala Leu Ala Phe Ala Gln Gln Ala Asp
    50                  55                  60

Tyr Leu Glu Gln Asp Leu Ala Met Thr Lys Asp Gly Arg Leu Val Val
65                  70                  75                  80

Ile His Asp His Phe Leu Asp Gly Leu Thr Asp Val Ala Lys Lys Phe
                85                  90                  95

Pro His Arg His Arg Lys Asp Gly Arg Tyr Tyr Val Ile Asp Phe Thr
            100                 105                 110

Leu Lys Glu Ile Gln Ser Leu Glu Met Thr Glu Asn Phe Glu Thr Lys
        115                 120                 125

Asp Gly Lys Gln Ala Gln Val Tyr Pro Asn Arg Phe Pro Leu Trp Lys
    130                 135                 140

Ser His Phe Arg Ile His Thr Phe Glu Asp Glu Ile Glu Phe Ile Gln
145                 150                 155                 160

Gly Leu Glu Lys Ser Thr Gly Lys Lys Val Gly Ile Tyr Pro Glu Ile
                165                 170                 175

Lys Ala Pro Trp Phe His His Gln Asn Gly Lys Asp Ile Ala Ala Glu
            180                 185                 190

Thr Leu Lys Val Leu Lys Lys Tyr Gly Tyr Asp Lys Lys Thr Asp Met
        195                 200                 205

Val Tyr Leu Gln Thr Phe Asp Phe Asn Glu Leu Lys Arg Ile Lys Thr
    210                 215                 220
```

```
Glu Leu Leu Pro Gln Met Gly Met Asp Leu Lys Leu Val Gln Leu Ile
225                 230                 235                 240

Ala Tyr Thr Asp Trp Lys Glu Thr Gln Glu Lys Asp Pro Lys Gly Tyr
                245                 250                 255

Trp Val Asn Tyr Asn Tyr Asp Trp Met Phe Lys Pro Gly Ala Met Ala
            260                 265                 270

Glu Val Val Lys Tyr Ala Asp Gly Val Gly Pro Gly Trp Tyr Met Leu
        275                 280                 285

Val Asn Lys Glu Glu Ser Lys Pro Asp Asn Ile Val Tyr Thr Pro Leu
        290                 295                 300

Val Lys Glu Leu Ala Gln Tyr Asn Val Glu Val His Pro Tyr Thr Val
305                 310                 315                 320

Arg Lys Asp Ala Leu Pro Ala Phe Phe Thr Asp Val Asn Gln Met Tyr
                325                 330                 335

Asp Val Leu Leu Asn Lys Ser Gly Ala Thr Gly Val Phe Thr Asp Phe
            340                 345                 350

Pro Asp Thr Gly Val Glu Phe Leu Lys Gly Ile Lys
            355                 360

<210> SEQ ID NO 8
<211> LENGTH: 386
<212> TYPE: PRT
<213> ORGANISM: Neisseria meningitidis

<400> SEQUENCE: 8

Met Arg Lys Lys Leu Thr Ala Leu Val Leu Ser Ala Leu Pro Leu Ala
1               5                   10                  15

Ala Val Ala Asp Val Ser Leu Tyr Gly Glu Ile Lys Ala Gly Val Glu
            20                  25                  30

Gly Arg Asn Ile Gln Leu Gln Leu Thr Glu Gln Pro Ser Lys Ala Gln
        35                  40                  45

Gly Gln Thr Asn Asn Gln Val Lys Val Thr Lys Ala Lys Ser Arg Ile
    50                  55                  60

Arg Thr Lys Ile Ser Asp Phe Gly Ser Phe Ile Gly Phe Lys Gly Ser
65                  70                  75                  80

Glu Asp Leu Gly Glu Gly Leu Lys Ala Val Trp Gln Leu Glu Gln Asp
                85                  90                  95

Val Ser Val Ala Gly Gly Ala Thr Gln Trp Gly Asn Arg Glu Ser
            100                 105                 110

Phe Ile Gly Leu Ala Gly Glu Phe Gly Thr Leu Arg Ala Gly Arg Val
        115                 120                 125

Ala Asn Gln Phe Asp Asp Ala Ser Gln Ala Ile Asp Pro Trp Asp Ser
    130                 135                 140

Asn Asn Asp Val Ala Ser Gln Leu Gly Ile Phe Lys Arg His Asp Asp
145                 150                 155                 160

Met Pro Val Ser Val Arg Tyr Asp Ser Pro Asp Phe Ser Gly Phe Ser
                165                 170                 175

Gly Ser Val Gln Phe Val Pro Ala Gln Asn Ser Lys Ser Ala Tyr Thr
            180                 185                 190

Pro Ala Tyr Val Asp Glu Lys Gln Val Ser His Ala Val Val Gly
        195                 200                 205

Lys Pro Gly Ser Asp Val Tyr Tyr Ala Gly Leu Asn Tyr Lys Asn Gly
    210                 215                 220

Gly Phe Ala Gly Ser Tyr Ala Phe Lys Tyr Ala Lys His Ala Asn Glu
```

```
225                 230                 235                 240

Gly Arg Asp Ala Phe Phe Leu Phe Leu Leu Gly Ser Gly Ser Asp Glu
                245                 250                 255

Ala Lys Gly Thr Asp Pro Leu Lys Asn His Gln Val His Arg Leu Thr
            260                 265                 270

Gly Gly Tyr Glu Glu Gly Gly Leu Asn Leu Ala Leu Ala Ala Gln Leu
        275                 280                 285

Asp Leu Ser Glu Asn Ala Asp Lys Thr Lys Asn Ser Thr Thr Glu Ile
    290                 295                 300

Ala Ala Thr Ala Ser Tyr Arg Phe Gly Asn Ala Val Pro Arg Ile Ser
305                 310                 315                 320
Tyr Ala His Gly Phe Asp Phe Ile Glu Arg Gly Lys Lys Gly Glu Asn
                325                 330                 335

Thr Ser Tyr Asp Gln Ile Ile Ala Gly Val Asp Tyr Asp Phe Ser Lys
            340                 345                 350

Arg Thr Ser Ala Ile Val Ser Gly Ala Trp Leu Lys Arg Asn Thr Gly
        355                 360                 365

Ile Gly Asn Tyr Thr Gln Ile Asn Ala Ala Ser Val Gly Leu Arg His
    370                 375                 380

Lys Phe
385

<210> SEQ ID NO 9
<211> LENGTH: 560
<212> TYPE: PRT
<213> ORGANISM: Corynebacterium diphtheriae

<400> SEQUENCE: 9

Met Ser Arg Lys Leu Phe Ala Ser Ile Leu Ile Gly Ala Leu Leu Gly
1               5                   10                  15
Ile Gly Ala Pro Pro Ser Ala His Ala Gly Ala Asp Asp Val Val Asp
            20                  25                  30

Ser Ser Lys Ser Phe Val Met Glu Asn Phe Ser Ser Tyr His Gly Thr
        35                  40                  45

Lys Pro Gly Tyr Val Asp Ser Ile Gln Lys Gly Ile Gln Lys Pro Lys
    50                  55                  60

Ser Gly Thr Gln Gly Asn Tyr Asp Asp Asp Trp Lys Gly Phe Tyr Ser
65                  70                  75                  80

Thr Asp Asn Lys Tyr Asp Ala Ala Gly Tyr Ser Val Asp Asn Glu Asn
                85                  90                  95

Pro Leu Ser Gly Lys Ala Gly Gly Val Val Lys Val Thr Tyr Pro Gly
            100                 105                 110

Leu Thr Lys Val Leu Ala Leu Lys Val Asp Asn Ala Glu Thr Ile Lys
        115                 120                 125

Lys Glu Leu Gly Leu Ser Leu Thr Glu Pro Leu Met Glu Gln Val Gly
    130                 135                 140

Thr Glu Glu Phe Ile Lys Arg Phe Gly Asp Gly Ala Ser Arg Val Val
145                 150                 155                 160

Leu Ser Leu Pro Phe Ala Glu Gly Ser Ser Ser Val Glu Tyr Ile Asn
                165                 170                 175

Asn Trp Glu Gln Ala Lys Ala Leu Ser Val Glu Leu Glu Ile Asn Phe
            180                 185                 190

Glu Thr Arg Gly Lys Arg Gly Gln Asp Ala Met Tyr Glu Tyr Met Ala
        195                 200                 205
```

Gln Ala Cys Ala Gly Asn Arg Val Arg Arg Ser Val Gly Ser Ser Leu
    210                 215                 220

Ser Cys Ile Asn Leu Asp Trp Asp Val Ile Arg Asp Lys Thr Lys Thr
225                 230                 235                 240

Lys Ile Glu Ser Leu Lys Glu His Gly Pro Ile Lys Asn Lys Met Ser
                245                 250                 255

Glu Ser Pro Asn Lys Thr Val Ser Glu Lys Ala Lys Gln Tyr Leu
            260                 265                 270

Glu Glu Phe His Gln Thr Ala Leu Glu His Pro Glu Leu Ser Glu Leu
            275                 280                 285

Lys Thr Val Thr Gly Thr Asn Pro Val Phe Ala Gly Ala Asn Tyr Ala
    290                 295                 300

Ala Trp Ala Val Asn Val Ala Gln Val Ile Asp Ser Glu Thr Ala Asp
305                 310                 315                 320

Asn Leu Glu Lys Thr Thr Ala Ala Leu Ser Ile Leu Pro Gly Ile Gly
                325                 330                 335

Ser Val Met Gly Ile Ala Asp Gly Ala Val His His Asn Thr Glu Glu
            340                 345                 350

Ile Val Ala Gln Ser Ile Ala Leu Ser Ser Leu Met Val Ala Gln Ala
    355                 360                 365

Ile Pro Leu Val Gly Glu Leu Val Asp Ile Gly Phe Ala Ala Tyr Asn
370                 375                 380

Phe Val Glu Ser Ile Ile Asn Leu Phe Gln Val Val His Asn Ser Tyr
385                 390                 395                 400

Asn Arg Pro Ala Tyr Ser Pro Gly His Lys Thr Gln Pro Phe Leu His
                405                 410                 415

Asp Gly Tyr Ala Val Ser Trp Asn Thr Val Glu Asp Ser Ile Ile Arg
            420                 425                 430

Thr Gly Phe Gln Gly Glu Ser Gly His Asp Ile Lys Ile Thr Ala Glu
    435                 440                 445

Asn Thr Pro Leu Pro Ile Ala Gly Val Leu Leu Pro Thr Ile Pro Gly
450                 455                 460

Lys Leu Asp Val Asn Lys Ser Lys Thr His Ile Ser Val Asn Gly Arg
465                 470                 475                 480

Lys Ile Arg Met Arg Cys Arg Ala Ile Asp Gly Asp Val Thr Phe Cys
                485                 490                 495

Arg Pro Lys Ser Pro Val Tyr Val Gly Asn Gly Val His Ala Asn Leu
            500                 505                 510

His Val Ala Phe His Arg Ser Ser Glu Lys Ile His Ser Asn Glu
    515                 520                 525

Ile Ser Ser Asp Ser Ile Gly Val Leu Gly Tyr Gln Lys Thr Val Asp
    530                 535                 540

His Thr Lys Val Asn Ser Lys Leu Ser Leu Phe Glu Ile Lys Ser
545                 550                 555                 560

<210> SEQ ID NO 10
<211> LENGTH: 451
<212> TYPE: PRT
<213> ORGANISM: Clostridium tetani

<400> SEQUENCE: 10

Lys Asn Leu Asp Cys Trp Val Asp Asn Glu Glu Asp Ile Asp Val Ile
1               5                   10                  15

Leu Lys Lys Ser Thr Ile Leu Asn Leu Asp Ile Asn Asn Asp Ile Ile
            20                  25                  30

```
Ser Asp Ile Ser Gly Phe Asn Ser Val Ile Thr Tyr Pro Asp Ala
         35                  40                  45

Gln Leu Val Pro Gly Ile Asn Gly Lys Ala Ile His Leu Val Asn Asn
 50                  55                  60

Glu Ser Ser Glu Val Ile Val His Lys Ala Met Asp Ile Glu Tyr Asn
65                   70                  75                  80

Asp Met Phe Asn Asn Phe Thr Val Ser Phe Trp Leu Arg Val Pro Lys
                 85                  90                  95

Val Ser Ala Ser His Leu Glu Gln Tyr Gly Thr Asn Glu Tyr Ser Ile
            100                 105                 110

Ile Ser Ser Met Lys Lys His Ser Leu Ser Ile Gly Ser Gly Trp Ser
            115                 120                 125

Val Ser Leu Lys Gly Asn Asn Leu Ile Trp Thr Leu Lys Asp Ser Ala
        130                 135                 140

Gly Glu Val Arg Gln Ile Thr Phe Arg Asp Leu Pro Asp Lys Phe Asn
145                 150                 155                 160

Ala Tyr Leu Ala Asn Lys Trp Val Phe Ile Thr Ile Thr Asn Asp Arg
                165                 170                 175

Leu Ser Ser Ala Asn Leu Tyr Ile Asn Gly Val Leu Met Gly Ser Ala
            180                 185                 190

Glu Ile Thr Gly Leu Gly Ala Ile Arg Glu Asp Asn Asn Ile Thr Leu
        195                 200                 205

Lys Leu Asp Arg Cys Asn Asn Asn Asn Gln Tyr Val Ser Ile Asp Lys
210                 215                 220

Phe Arg Ile Phe Cys Lys Ala Leu Asn Pro Lys Glu Ile Glu Lys Leu
225                 230                 235                 240

Tyr Thr Ser Tyr Leu Ser Ile Thr Phe Leu Arg Asp Phe Trp Gly Asn
                245                 250                 255

Pro Leu Arg Tyr Asp Thr Glu Tyr Tyr Leu Ile Pro Val Ala Ser Ser
            260                 265                 270

Ser Lys Asp Val Gln Leu Lys Asn Ile Thr Asp Tyr Met Tyr Leu Thr
        275                 280                 285

Asn Ala Pro Ser Tyr Thr Asn Gly Lys Leu Asn Ile Tyr Tyr Arg Arg
290                 295                 300

Leu Tyr Asn Gly Leu Lys Phe Ile Ile Lys Arg Tyr Thr Pro Asn Asn
305                 310                 315                 320

Glu Ile Asp Ser Phe Val Lys Ser Gly Asp Phe Ile Lys Leu Tyr Val
                325                 330                 335

Ser Tyr Asn Asn Asn Glu His Ile Val Gly Tyr Pro Lys Asp Gly Asn
            340                 345                 350

Ala Phe Asn Asn Leu Asp Arg Ile Leu Arg Val Gly Tyr Asn Ala Pro
        355                 360                 365

Gly Ile Pro Leu Tyr Lys Lys Met Glu Ala Val Lys Leu Arg Asp Leu
    370                 375                 380

Lys Thr Tyr Ser Val Gln Leu Lys Leu Tyr Asp Asp Lys Asn Ala Ser
385                 390                 395                 400

Leu Gly Leu Val Gly Thr His Asn Gly Gln Ile Gly Asn Asp Pro Asn
                405                 410                 415

Arg Asp Ile Leu Ile Ala Ser Asn Trp Tyr Phe Asn His Leu Lys Asp
            420                 425                 430
```

```
Lys Ile Leu Gly Cys Asp Trp Tyr Phe Val Pro Thr Asp Glu Gly Trp
        435                 440                 445
Thr Asn Asp
    450
```